US009216966B2

(12) United States Patent
Gassman et al.

(10) Patent No.: US 9,216,966 B2
(45) Date of Patent: Dec. 22, 2015

(54) COMPOUNDS FOR ALZHEIMER'S DISEASE

(71) Applicant: John Manfredi, Salt Lake City, UT (US)

(72) Inventors: Andrew D. Gassman, Salt Lake City, UT (US); Christine Klein, Salt Lake City, UT (US); Leena Bhoite, Salt Lake City, UT (US); John Manfredi, Salt Lake City, UT (US); Rachel M. Slade, Salt Lake City, UT (US); Yevgeniya Klimova, Sandy, UT (US); Robert J. Halter, Salt Lake City, UT (US); Ashantai J. Yungai, Salt Lake City, UT (US); Warren S. Weiner, Phoenix, AZ (US); Ruth J. Walton, Bountiful, UT (US); Jon Adam Willardsen, Draper, UT (US); Mark B. Anderson, Norwell, MA (US); Kenton Zavitz, Salt Lake City, UT (US)

(73) Assignee: John Manfredi, Salt Lake City, UT (US)

( * ) Notice: Subject to any disclaimer, the term of this patent is extended or adjusted under 35 U.S.C. 154(b) by 0 days.

(21) Appl. No.: 13/801,348

(22) Filed: Mar. 13, 2013

(65) Prior Publication Data

US 2013/0261118 A1 Oct. 3, 2013

Related U.S. Application Data

(63) Continuation-in-part of application No. 13/447,115, filed on Apr. 13, 2012, now Pat. No. 9,034,871, which is a continuation-in-part of application No. 12/719,672, filed on Mar. 8, 2010, now abandoned, which is a continuation-in-part of application No. 11/696,526, filed on Apr. 4, 2007, now Pat. No. 7,678,823, which is a continuation of application No. PCT/US2005/035747, filed on Oct. 4, 2005, application No. 13/801,348, which is a continuation-in-part of application No. 13/464,538, filed on May 4, 2012, which is a continuation of application No. 12/295,922, filed as application No. PCT/US2007/065969 on Apr. 4, 2007, now abandoned.

(60) Provisional application No. 60/615,914, filed on Oct. 4, 2004, provisional application No. 60/616,162, filed on Oct. 4, 2004, provisional application No. 60/660,479, filed on Mar. 9, 2005, provisional application No. 60/660,278, filed on Mar. 10, 2005, provisional application No. 60/789,524, filed on Apr. 4, 2006.

(51) Int. Cl.
| | |
|---|---|
| A61K 31/405 | (2006.01) |
| A61K 31/427 | (2006.01) |
| A61K 31/341 | (2006.01) |
| A61K 31/4439 | (2006.01) |
| C07D 209/10 | (2006.01) |
| C07D 277/28 | (2006.01) |
| C07D 307/38 | (2006.01) |
| C07D 403/04 | (2006.01) |
| C07D 413/10 | (2006.01) |
| C07D 401/04 | (2006.01) |
| C07D 405/04 | (2006.01) |
| C07D 417/04 | (2006.01) |
| C07D 401/14 | (2006.01) |
| C07D 405/14 | (2006.01) |
| C07D 413/14 | (2006.01) |
| C07D 231/12 | (2006.01) |
| C07D 403/10 | (2006.01) |
| C07D 409/04 | (2006.01) |
| C07D 409/14 | (2006.01) |
| C07D 413/04 | (2006.01) |
| C07D 491/10 | (2006.01) |
| C07D 209/08 | (2006.01) |
| C07D 209/14 | (2006.01) |
| C07D 209/60 | (2006.01) |
| C07F 7/18 | (2006.01) |
| C07F 7/08 | (2006.01) |

(52) U.S. Cl.
CPC ............ *C07D 403/04* (2013.01); *C07D 209/08* (2013.01); *C07D 209/10* (2013.01); *C07D 209/14* (2013.01); *C07D 209/60* (2013.01); *C07D 231/12* (2013.01); *C07D 401/04* (2013.01); *C07D 401/14* (2013.01); *C07D 403/10* (2013.01); *C07D 405/04* (2013.01); *C07D 405/14* (2013.01); *C07D 409/04* (2013.01); *C07D 409/14* (2013.01); *C07D 413/04* (2013.01); *C07D 413/10* (2013.01); *C07D 413/14* (2013.01); *C07D 417/04* (2013.01); *C07D 491/10* (2013.01); *C07F 7/0812* (2013.01); *C07F 7/1856* (2013.01)

(58) Field of Classification Search
CPC .. C07D 209/10; C07D 222/28; C07D 307/38; A61K 31/405; A61K 31/427; A61K 31/341; A61K 31/4439
See application file for complete search history.

(56) References Cited

U.S. PATENT DOCUMENTS 3,736,323 A * 5/1973 Finizio et al. .................. 546/201
3,878,225 A 4/1975 Allen et al.
(Continued)

FOREIGN PATENT DOCUMENTS

DE 10015939 10/2001
EP 1224932 7/2000
(Continued)

OTHER PUBLICATIONS

Schule et al., 'SPG10 is a Rare Cause of Spastic Paraplegia in European Families', J Neurol Neurosurg Psychiatry 79:584-587, 2008.
(Continued)

*Primary Examiner* — Yong Chu
(74) *Attorney, Agent, or Firm* — Herbert L. Ley, III; Stoel Rives LLP

(57) ABSTRACT

The present disclosure relates to novel indole and tetrahydroindole core compounds useful for the treatment of disorders associated with a defect in vesicular transport (e.g., axonal transport).

15 Claims, 6 Drawing Sheets

(56) References Cited

U.S. PATENT DOCUMENTS

| | | | |
|---|---|---|---|
| 3,904,761 | A | 9/1975 | Novick et al. |
| 3,931,407 | A | 1/1976 | Allen et al. |
| 4,537,902 | A | 8/1985 | Cragoe, Jr. et al. |
| 5,124,482 | A | 6/1992 | Butler et al. |
| 6,387,916 | B1 | 5/2002 | Mayer et al. |
| 6,790,848 | B2 | 9/2004 | Briggs et al. |
| 7,057,052 | B2 | 6/2006 | Pirrung et al. |
| 7,678,823 | B2 | 3/2010 | Slade et al. |
| 2003/0130165 | A1 | 7/2003 | Reitz et al. |
| 2005/0054631 | A1 | 3/2005 | Jiang et al. |
| 2008/0249135 | A1 | 10/2008 | Slade et al. |
| 2009/0099179 | A1 | 4/2009 | Klein et al. |
| 2012/0225873 | A1 | 9/2012 | Slade et al. |

FOREIGN PATENT DOCUMENTS

| | | |
|---|---|---|
| EP | 1275646 | 1/2003 |
| WO | WO98/20864 | 5/1998 |
| WO | WO2006/041874 | 4/2006 |
| WO | WO2007/038684 | 4/2007 |
| WO | WO2007/115306 | 10/2007 |
| WO | WO2008/116926 | 10/2008 |

OTHER PUBLICATIONS

Martin et al., 'Cytoplasmic Dynein, The Dynactin Complex, and Kinesin are Interdependent and Essential for Fast Axonal Transport', Mol Diol Cell 10: 3717-3728, 1999.

Fuger et al., 'Spastic Paraplegia Mutation N256S in the Nueronal Microtuble Motor K1F5A Disrupts Azonal Transport in a *Drosphila* HSP Model', PLoS Genetics 8: e1003066, 2012.

Salinas et al., 'Hereditary Spastic Paraplegia: Clinical Features and Pathogenetic Mechanisms', Lancet Neurol 7: 1127-1138, 2008.

Tarrade et al., 'A Mutation of Soastin is Responsible for Swellings and Impairment of Transport in a Region of Azon Characterized by Changes in Microtuble Composition', Hum Mol Genet 15: 3544-3558, 2006.

Kasher et al., 'Direct Evidence for Axonal Transport Defects in a Novel Nouse Nodel of Mutant Spastin-Induced Hereditary Spastic Paraplegia (HSP) and Human HSP Patients', J Neurochem 110: 34-44, 2009.

Blackstone et al., 'Hereditary Spastic Paraplegias: Membrane Traffic and the Motor Pathway', Nat Rev Neurosci 12: 31.42, 2011.

Office Action dated Apr. 18, 2013 for U.S. Appl. No. 13/297,065.

Office Action dated Oct. 11, 2012 for U.S. Appl. No. 13/297,065.

Restriction Requirement dated Jun. 12, 2012 for U.S. Appl. No. 13/297,065.

Restriction Requirement dated Nov. 15, 2012 for U.S. Appl. No. 13/447,115.

Office Action dated Jan. 10, 2013 for U.S. Appl. No. 13/447,115.

Office Action dated Jul. 17, 2012 for U.S. Appl. No. 13/464,538.

Office Action dated Mar. 14, 2013 for U.S. Appl. No. 13/464,538.

Fink, 'Hereditary Spastic Paraplegia', Current Neurology and Neuroscience Reports, 6:65-76, 2006.

Fink, 'Hereditary Spastic Paraplegia Overview', GENEREVIEWS (online). Retrieved Apr. 12, 2013. Retrieved from the Internet: <URL:http://www.ncbi.nlm.nih.cov/books/NBK1509/?report=printable>. 2013.

Hurd et al., 'Kinesin Mutations Cause Motor Neuron Disease Phenotypes by Disrupting Fast Axonal Transport in *Drosophila*', Genetics, 144:1075-1085, 1996.

Orso et al., 'Disease-Related Phenotypes in a *Drosophila* Model of Hereditary Spastic Paraplegia are Ameliorated by Treatment with Vinblastine', J Clin Invest., 115:3026-3034, 2005.

Oslo, 'Editor—Chapter 27: Structure-Activity Relationship and Drug Design', Remington's Pharmaceutical Sciences (Sixteenth Edition), Mack Publishing, pp. 420-435, 1980.

Edvardson et al., 'Exome Sequencing and Disease-Network Analysis of a Single Family Implicate a Mutation in KIF1A in Hereditary Spastic Paraparesis', Gemone Res 21(5):658-664, 2011.

Klebe et al., 'KIF1A Missense Mutations in SPG30, an Autosomal Recessive Spastic Paraplegia: Distinct Phenotypes According to the Nature of the Mutations', Eur J Hum Genet 20(6):645-649, 2012.

Reid et al., 'A Kinesin Heavy Chain (KIF5A) Mutation in Hereditary Spastic Paraplegia (SPG10)', Am J Hum Genet 71(5):1189-1194, 2002.

Fischera et al., 'Evidence of Kinesin Heavy Chain (KIF5A) Involvement in Pure Hereditary Spastic Paraplegia', Neurology 63(6):1108-1110, 2004.

Goizet et al., 'Complicated Forms of Autosomal Dominant Hereditary Spastic Paraplegia are Frequent in SPG10', Hum Mutat 30(2):E376-385, 2009.

Blair et al., 'Mutation in KIF5A Can Also Cause Adult-Onset Hereditary Spastic Paraplegia', Neurogenetics 7(1):47-50, 2006.

Lo Giudice et al., 'A Missense Mutation in the Coiled-Coil Domain of the KIF5A Gene and Late-Onset Hereditary Spastic Paraplegia', Arch Neurol 63(2):284-287, 2006.

Crimella et al., 'Mutations in the Motor and Stalk Domains of KIF5A in Spastic Paraplegia Type 10 and in Axonal Charcot-Marie-Tooth Type 2', Clin Genet 82(2):157-164, 2012.

Zhao et al., 'Charcot-Marie-Tooth Disease Type 2A Caused by Mutation in a Microtubule Motor KIF1Bbeta', Cell 105(5):587-597, 2001.

Aulchenko et al., 'Genetic Variation in the KIF1B Locus Influences Susceptibility to Multiple Sclerosis', Nat Genet 40(12):1402-1403, 2008.

Munch et al., 'Heterozygous R11O1K Mutation of the DCTN1 Gene in a Family with ALS and FTD', Ann Neurol 58(5):777-780, 2005.

Munch et al., 'Point Mutations of the p150 Subunit of Dynactin (DCTN1) Gene in ALS', Neurology 63(4):724-726, 2004.

Weedon et al., 'Exome Sequencing Identifies a DYNC1H1 Mutation in a Large Pedigree with Dominate Axonal Charcot-Marie-Tooth Disease', Am J Hum Genet 89(2):308-312, 2011.

Harms et al., 'Mutations in the Tail Domain of DYNC1H1 Cause Dominant Spinal Muscular Atrophy', Neurology 78(22):1714-1720, 2012.

Puls et al., 'Mutant Dynactin in Motor Neuron Disease', Nat Benet 33(4):455-456, 2003.

Liu et al., 'Pathologies of Axonal Transport in Neurodegenerative Diseases', Translational Neuroscience 3(4):355-372, 2012.

Zhu et al., 'Alzheimer's Disease: An Intracellular Movement Disorder?', Trends in Molecular Medicine, vol. 11, No. 9, Sep. 2005.

Reid, 'The Hereditary Spastic Paraplegias', J Neurol 246:995-1003, 1999.

Extended European Search Report for EP 07760107.8, (2010).

GB Search Report for GB 1314198.1, (2014).

International Search Report for PCT/US2014/021331, (2008).

\* cited by examiner

COMPOUNDS FOR ALZHEIMER'S DISEASE

CROSS-REFERENCE TO RELATED APPLICATIONS

This application is a continuation-in-part of U.S. patent application Ser. No. 13/447,115 filed on Apr. 13, 2012, which is a continuation of U.S. patent application Ser. No. 12/719,672 filed on Mar. 8, 2010, abandoned, which is a continuation of U.S. patent application Ser. No. 11/696,526 filed on Apr. 4, 2007 and issued as U.S. Pat. No. 7,678,823, which is a continuation of International Patent Application PCT/US2005/035747 filed on Oct. 4, 2005, which claims the benefit of U.S. Provisional Application Ser. Nos. 60/615,914, filed on Oct. 4, 2004, 60/616,162, filed on Oct. 4, 2004, 60/660,479, filed on Mar. 9, 2005, and 60/660,278, filed on Mar. 10, 2005; this application is also a continuation-in-part of U.S. patent application Ser. No. 13/464,538 filed on May 4, 2012, which is a continuation of U.S. patent application Ser. No. 12/295,922, abandoned, filed on Oct. 3, 2008, which is a National Stage Entry of International Patent Application PCT/US2007/065969 filed on Apr. 4, 2007, which claims the benefit of U.S. Provisional Application Ser. No. 60/789,524, filed on Apr. 4, 2006; all of which are incorporated by reference herein in their entirety.

TECHNICAL FIELD OF THE INVENTION

The invention provides a method for the therapeutic treatment of neurodegenerative disorders. The invention further provides a method for prophylaxis against neurodegenerative disorders. The invention further provides pharmaceutical composition for use in the methods of the invention. The invention has utility for treating and preventing neurodegenerative disorders such as Alzheimer's disease, dementia, and mild cognitive impairment.

BACKGROUND OF THE INVENTION

Dementia is a brain disorder that seriously affects a person's ability to carry out normal daily activities. Among older people, Alzheimer's disease (AD) is the most common form of dementia and involves parts of the brain that control thought, memory, and language. Despite intensive research throughout the world, the causes of AD are still unknown and there is no cure. AD most commonly begins after the age of 60 with the risk increasing with age. Younger people can also get AD, but it is much less common. It is estimated that 3 percent of men and women ages 65 to 74 have AD. Almost half of those ages 85 and older may have the disease. AD is not a normal part of aging Alzheimer's disease is a complex disease that can be caused by genetic and environmental factors. In the United States alone, four million adults suffer from Alzheimer's disease (AD). Not only does Alzheimer's disease significantly impact the lives of countless families today, it threatens to become even more of a problem as the baby boom generation matures. The economic burden of AD in the United States is estimated to cost over $100 billion a year and the average lifetime cost per patient is estimated to be $174,000. Unfortunately, there is no cure available for AD.

In 1906, Dr. Alois Alzheimer, noticed changes in the brain tissue of a woman who had died of an unusual mental illness. In her brain tissue, he found abnormal clumps (now known as amyloid plaques) and tangled bundles of fibers (now known as neurofibrillary tangles) which, today, are considered the pathological hallmarks of AD. Other brain changes in people with AD have been discovered. For example, with AD, there is a loss of nerve cells in areas of the brain that are vital to memory and other mental abilities. Scientists have also found that there are lower levels of chemicals in the brain that carry complex messages back and forth between nerve cells. AD may disrupt normal thinking and memory by blocking these messages between nerve cells.

Plaques and tangles are found in the same brain regions that are affected by neuronal and synaptic loss. Neuronal and synaptic loss is universally recognized as the primary cause in decline of cognitive function. The number of tangles is more highly correlated with the cognitive decline than amyloid load in patients with AD (Albert *Proc. Natl. Acad. Sci. U.S.A.* 93:13547-13551 (1996)). The cellular, biochemical, and molecular events responsible for neuronal and synaptic loss in AD are not known. A number of studies have demonstrated that amyloid can be directly toxic to neurons (Iversen et al. *Biochem. J.* 311:1-16 (1995); Weiss et al. *J. Neurochem.* 62:372-375 (1994); Lorenzo et al. *Ann. N.Y. Acad. Sci.* 777: 89-95 (1996); Storey et al. *Neuropathol. Appl. Neurobiol.* 2:81-97 (1999), resulting in behavioral impairment. The toxicity of amyloid or tangles is potentially aggravated by activation of the complement cascade (Rogers et al. *Proc. Natl. Acad. Sci. U.S.A.* 21:10016-10020 (1992); Rozemuller et al. *Res. Immunol.* 6:646-9 (1992); Rogers et al. *Res. Immunol.* 6:624-30 (1992); Webster et al. *J. Neurochem.* 69(1):388-98 (1997)). This suggests involvement of an inflammatory process in AD and neuronal death seen in AD (Fagarasan et al. *Brain Res.* 723(1-2):231-4. (1996); Kalaria et al. *Neurodegeneration* 5(4):497-503 (1996); Kalaria et al. *Neurobiol Aging.* 17(5):687-93 (1996); Farlow *Am. J. Health Syst. Pharm.* 55 Suppl. 2:S5-10 (1998).

Evidence that amyloid β protein (Aβ) deposition causes some forms of AD was provided by genetic and molecular studies of some familial forms of AD (FAD). (See, e.g., Ii *Drugs Aging* 7(2):97-109 (1995); Hardy *Proc. Natl. Acad. Sci. U.S.A.* 94(6):2095-7 (1997); Selkoe *J. Biol. Chem.* 271 (31):18295-8 (1996)). The amyloid plaque buildup in AD patients suggests that abnormal processing of Aβ may be a cause of AD. Aβ is a peptide of 39 to 42 amino acids and forms the core of senile plaques observed in all Alzheimer cases. If abnormal processing is the primary cause of AD, then familial Alzheimer's disease (FAD) mutations that are linked (genetically) to FAD may induce changes that, in one way or another, foster Aβ deposition. There are 3 FAD genes known so far (Hardy et al. *Science* 282:1075-9 (1998); Ray et al. (1998)). Mutations in these FAD genes can result in increased Aβ deposition.

The first of the 3 FAD genes codes for the Aβ precursor, amyloid precursor protein (APP) (Selkoe *J. Biol. Chem.* 271 (31):18295-8 (1996)). Mutations in the APP gene are very rare, but all of them cause AD with 100% penetrance and result in elevated production of either total Aβ or Aβ$_{42}$, both in model transfected cells and transgenic animals. The other two FAD genes code for presenilin 1 and 2 (PS1, PS2) (Hardy *Proc. Natl. Acad. Sci. U.S.A.* 94(6):2095-7 (1997)). The presenilins contain 8 transmembrane domains and several lines of evidence suggest that they are involved in intracellular protein trafficking Other studies suggest that the presenilins function as proteases. Mutations in the presenilin genes are more common than in the APP gene, and all of them also cause FAD with 100% penetrance. Similar to APP mutants, studies have demonstrated that PS1 and PS2 mutations shift APP metabolism, resulting in elevated Aβ$_{42}$ production (in vitro and in vivo).

Cyclooxygenases (COX) are major Alzheimer's disease drug targets due to the epidemiological association of NSAID use, whose primary target are cyclooxygenases, with a reduced risk of developing Alzheimer's disease (see, e.g., Hoozemans et al. *Curr. Drug Targets* 4(6):461-8 (2003) and Pasinetti et al. *J. Neurosci. Res.* 54(1):1-6 (1998)). The epidemiological studies have indicated that chronic NSAID use appears to reduce the risk of acquiring Alzheimer's disease and/or delay the onset of the disease (see e.g., McGeer et al. *Neurology* 47(2):425-432 (1996); and Etminan et al. *BMJ.* 327(7407):128 (2003)). COX-2 selective inhibitors are attractive candidates for long-term drug use since they do not inhibit COX-1 and appear to be less toxic. In support of COX-2 as a target for the treatment for AD, a recent study was published reporting that in mouse models of AD, COX-2 overexpression was related to the neuropathology of AD (Xiang et al. *Neurobiol. Aging* 23:327-34 (2002)). However, recent clinical trials of specific NSAIDs have called into question the hypothesis the hypothesis that anti-inflammatory drugs are useful for the treatment or prevention of Alzheimer's disease. It was reported that rofecoxib, a COX-2 selective NSAID, at 25 mg daily, failed to show efficacy for treating AD. Naproxen, another NSAID, in the same trial failed to show efficacy in Alzheimer's treatment. See Aisen et al. *JAMA* 289:2819-26 (2003) and Reines et al. *Neurology* 62(1): 66-71 (2004). These authors concluded that the results with naproxen and rofecoxib do not support the use of NSAIDs for the treatment of AD. Celecoxib, a COX-2-selective NSAID, failed to show efficacy in several recent clinical trials for the treatment of AD. See Jhee et al., "A Double-Blind, Placebo-Controlled Pharmacokinetic (PK), Pharmacodynamic (PD) and Safety Study of Celecoxib Treatment for Four Weeks in Patients with Alzheimer's Disease (AD)," Abstract from 7th International Geneva/Springfield Symposium on Advances in Alzheimer's Therapy (2002); also published in *Clinical Research and Regulatory Affairs* 21(1): 49-66 (2004)) and Sainati et al. (Abstract from 6$^{th}$ International Stockholm/Springfield Symposium on Advances on Alzheimer's Therapy, Abstract Book 2000; 180). Conversely, it was reported recently that rofecoxib provides neuroprotection in an in vivo Alzheimer's disease excitotoxic model system (Scali et al. Neuroscience 117:909-919 (2003). However, rofecoxib, in a large prevention clinical trial, failed to prevent the development of Alzheimer's disease in patients having mild cognitive impairment. In fact, the results of this trial showed that 6.4% of patients taking rofecoxib developed AD as compared to 4.5% for those taking placebo (see e.g., Visser et al., abstract from Annual meeting of the American College of Neuropsychopharmacology San Juan, Puerto Rico, 2003; and Landers, *Wall Street Journal* 10 Dec. 2003). Thus, clinical trials have indicated that NSAIDs, as a general class of drugs, are not likely to be useful for treating and/or preventing Alzheimer's disease.

Of the five drugs currently being used in the US for the treatment of AD, four of them—tacrine (Cognex®), donepezil (Aricept®), rivastigmine (Exelon®), and galantamine (Reminyl®)—are inhibitors of acetylcholinesterase. Another drug, memantine, was recently approved for treating moderate-to-severe AD. More recently it was reported that memantine showed efficacy in treating mild-to-moderate AD. Memantine is a NMDA receptor antagonist.

The drugs currently used for treating AD, including memantine and the acetylcholine esterase inhibitors, are marginally efficacious and have undesirable side-effects. Thus, there is a large unmet need for better and safer drugs.

SUMMARY OF THE INVENTION

In general, the invention relates to compounds of Formulae I-XVI, pharmaceutically acceptable salts thereof, and pharmaceutical compositions containing the compounds and salts. The compounds of the invention can be used for the treatment and prophylaxis of neurodegenerative disorders, including Alzheimer's disease.

In a first aspect, the invention provides compounds of Formula I and II, pharmaceutically acceptable salts thereof, and pharmaceutical compositions having such compounds.

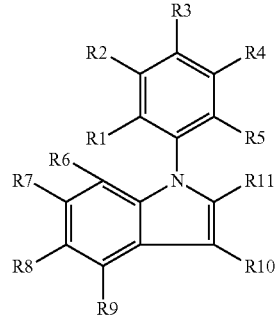

FORMULA I

According to the first aspect of the invention, compounds of Formula I have one or more of R1-R5 independently chosen from L-C(=O)OH, -L-CH=CHC(=O)OH, -L-C(=O)NH$_2$, -L-C(=O)NH(C$_{1-3}$ alkyl)$_2$, -L-S(=O)N(C$_{1-3}$ alkyl)$_2$, -L-S(=O)$_2$(C$_{1-3}$alkyl), -L-S(=O)$_2$NH$_2$, -L-S(=O)$_2$N(C$_{1-3}$ alkyl)$_2$, -L-S(=O)$_2$NH(C$_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N (R$_o$)$_2$, -L-sulfo, -L-(2,6 difluorophenol), -L-phosphono, and -L-tetrazolyl, and the others of R1-R5, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$ alkyl), —S(=O)$_2$NH$_2$, —S(=O)$_2$N (C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$;

R6-R10, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$ alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, ethylenedioxy, —C(=O)OCH$_2$CH$_3$ substituted furanyl, para-(C (=O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl or cycloalkyl ring;

R11 is an optionally substituted phenyl group;

R$_o$ is chosen from alkyl and haloalkyl; and

L can be saturated, partially saturated, or unsaturated, and is chosen from —(CH$_2$)$_n$—(CH$_2$)$_n$—, —(CH$_2$)$_n$C(=O) (CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, 3, 4, 5, 6, 7, and 8, and wherein each carbon can be optionally substituted with one or more C$_{1-3}$ alkyl or C$_{3-6}$ cycloalkyl.

The first aspect of the invention also includes compounds of Formula II.

FORMULA II

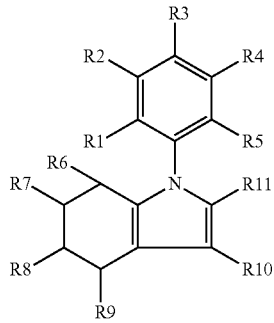

FORMULA III

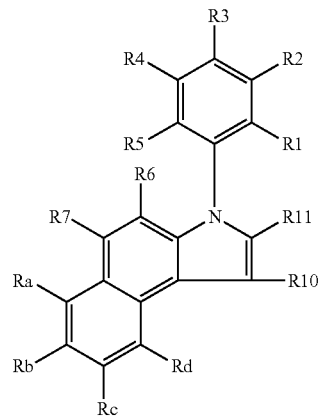

In the first aspect of the invention, compounds of Formula II are provided having one or more of R1-R5 independently chosen from -L-C(=O)OH, -L-CH=CHC(=O)OH, -L-C(=O)NH$_2$, -L-C(=O)NH(C$_{1-3}$ alkyl), -L-C(=O)N(C$_{1-3}$ alkyl)$_2$, -L-S(=O)$_2$NH$_2$, -L-S(=O)$_2$N(C$_{1-3}$ alkyl)$_2$, -L-S(=O)$_2$NH(C$_{1-3}$ alkyl), -L-C(=O)NHOH, -L-C(=O)CH$_2$NH$_2$, -LC(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl, and the others of R1-R5, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$ alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$; with the provision when R2 is —C(=O)OH, then R3 is not hydroxyl (or —O—C(=O)CH$_3$), —SH, —Cl, —NH$_2$, methoxy, and —NHC(=O)CH$_3$;

L can be saturated, partially saturated, or unsaturated, and is chosen from —(CH$_2$)$_n$—(CH$_2$)$_n$—, —(CH$_2$)$_n$C(=O)(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently selected from 0, 1, 2, 3, 4, 5, 6, 7, and 8, wherein each carbon can be optionally substituted with one or more C$_{1-3}$ alkyl or C$_{3-6}$ cycloalkyl;

R6-R10, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl or cycloalkyl ring;

R11 is an optionally substituted phenyl group; and

R$_o$ is chosen from haloalkyl and alkyl.

According to one embodiment of the first aspect of the invention, R8 and R9 in the compounds of Formula I are taken together to form a 6 member aryl ring as in Formula III.

According to one embodiment of the first aspect of the invention, compounds of Formula III are provided wherein Ra, Rb, Rc, and Rd are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$ alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); and the other variables can be defined as in one of the other embodiments of the first aspect of the invention.

According to one embodiment of the first aspect of the invention, R8 and R9 in the compounds of Formula II are taken together to form a 6 member aryl ring as in Formula IV.

FORMULA IV

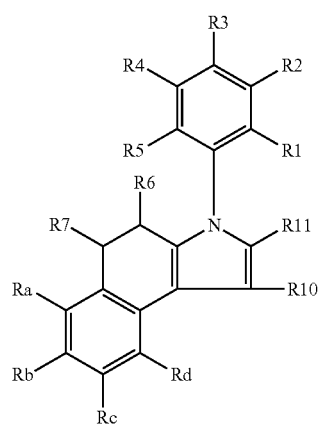

According to one embodiment of the first aspect of the invention, compounds of Formula IV are provided wherein Ra, Rb, Rc, and Rd are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$ alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); and the other variables can be defined as in one of the other embodiments of the first aspect of the invention.

In a second aspect, the invention provides compounds of Formula I and II, wherein R1-R5 are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$;

one or more of R6-R9 are chosen from -L-C(=O)OH, -L-CH=CHC(=O)OH, -L-C(=O)NH$_2$, -L-C(=O)NH(C$_{1-3}$ alkyl), -L-C(=O)N(C$_{1-3}$ alkyl)$_2$, -L-S(=O)$_2$(C$_{1-3}$alkyl), -L-S(=O)$_2$NH$_2$, -L-S(=O)$_2$N(C$_{1-3}$ alkyl)$_2$, -L-S(=O)$_2$NH(C$_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl; or two adjacent of R6-R9 can be taken together to form a 4-7 member substituted aryl or cycloalkyl ring wherein the substituent is chosen from -L-C(=O)OH, -L-CH=CHC(=O)OH, -L-C(=O)NH$_2$, -L-C(=O)NH(C$_{1-3}$ alkyl), -L-C(=O)N(C$_{1-3}$ alkyl)$_2$, -L-S(=O)$_2$(C$_{1-3}$alkyl), -L-S(=O)$_2$NH$_2$, -L-S(=O)$_2$N(C$_{1-3}$ alkyl)$_2$, -L-S(=O)$_2$NH(C$_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl; and the others of R6-R9, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$ alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$;

R10 is chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$ alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$;

R$_o$ is chosen from alkyl and haloalkyl;
R11 is an optionally substituted phenyl group; and
L is as defined above.

In a third aspect, the invention provides compounds of Formula I and II, wherein R1-R9 are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl or cycloalkyl ring;

R10 is chosen from -L-C(=O)OH, -L-CH=CHC(=O)OH, -L-C(=O)NH$_2$, -L-C(=O)NH(C$_{1-3}$ alkyl), -L-C(=O)N(C$_{1-3}$ alkyl)$_2$, -L-S(=O)$_2$(C$_{1-3}$alkyl), -L-S(=O)$_2$NH$_2$, -L-S(=O)$_2$N(C$_{1-3}$ alkyl)$_2$, -L-S(=O)$_2$NH(C$_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl;

R$_o$ is chosen from alkyl and haloalkyl; and
L is as defined above.

In a fourth aspect, the invention provides compounds of Formula I and II, wherein R1-R10 are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl or cycloalkyl ring;

R11 is a phenyl ring substituted with one or more substituents independently chosen from -L-C(=O)OH, -L-CH=CHC(=O)OH, -L-C(=O)NH$_2$, -L-C(=O)NH(C$_{1-3}$ alkyl), -L-C(=O)N(C$_{1-3}$ alkyl)$_2$, -L-S(=O)$_2$(C$_{1-3}$alkyl), -L-S(=O)$_2$NH$_2$, -L-S(=O)$_2$N(C$_{1-3}$ alkyl)$_2$, -L-S(=O)$_2$NH(C$_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl and the others are chosen from hydro, hydroxyl, halo, alkyl, alkoxy, haloalkyl, halo alkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$;

R$_o$ is chosen from alkyl and haloalkyl; and
L is as defined above.

In a fifth aspect, the invention provides compounds of Formula I and II, wherein R1-R9 and R11 are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl or cycloalkyl ring;

R10 is a phenyl ring substituted with one or more substituents independently chosen from -L-C(=O)OH, -L-CH=CHC(=O)OH, -L-C(=O)NH$_2$, -L-C(=O)NH(C$_{1-3}$ alkyl), -L-C(=O)N(C$_{1-3}$ alkyl)$_2$, -L-S(=O)$_2$(C$_{1-3}$alkyl), -L-S(=O)$_2$NH$_2$, -L-S(=O)$_2$N(C$_{1-3}$ alkyl)$_2$, -L-S(=O)$_2$NH(C$_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl;

R$_o$ is chosen from alkyl and haloalkyl; and

L is as defined above.

In a sixth aspect, the invention provides compounds of Formula I and II, wherein R1-R9 and R11 are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$ alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl or cycloalkyl ring;

R10 is -L-R12 wherein L is as defined above; and

R12 is a phenyl ring substituted with one or more substituents independently chosen from -L-C(=O)OH, -L-CH=CHC(=O)OH, -L-C(=O)NH$_2$, -L-C(=O)NH(C$_{1-3}$ alkyl), -L-C(=O)N(C$_{1-3}$ alkyl)$_2$, -L-S(=O)$_2$(C$_{1-3}$ alkyl), -L-S(=O)$_2$NH$_2$, -L-S(=O)$_2$N(C$_{1-3}$ alkyl)$_2$, -L-S(=O)$_2$NH(C$_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl;

R$_o$ is chosen from alkyl and haloalkyl; and

L is as defined above.

In a seventh embodiment, the invention provides compounds of Formula I and II, wherein R1-R10 are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)— phenyl, and —O—Si(CH$_3$)$_2$(C(CH$_3$)$_3$); two adjacent of R6-R9 can be taken together to form a 4-7 member optionally substituted aryl or cycloalkyl ring;

R11 is -L-R12 wherein L is as defined above; and

R12 is a phenyl ring substituted with one or more substituents independently chosen from -L-C(=O)OH, -L-CH=CHC(=O)OH, -L-C(=O)NH$_2$, -L-C(=O)NH(C$_{1-3}$ alkyl), -L-C(=O)N(C$_{1-3}$ alkyl)$_2$, -L-S(=O)$_2$(C$_{1-3}$ alkyl), -L-S(=O)$_2$NH$_2$, -L-S(=O)$_2$N(C$_{1-3}$ alkyl)$_2$, -L-S(=O)$_2$NH(C$_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl, and the others are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$;

R$_o$ is chosen from alkyl and haloalkyl; and

L is as defined above.

In an eighth embodiment, the invention provides compounds of Formula I and II, wherein R1-R9 are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)— phenyl, and —O—Si(CH$_3$)$_2$(C(CH$_3$)$_3$); two adjacent of R6-R9 can be taken together to form a 4-7 member optionally substituted aryl ring;

R10 and R11 are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —S(=O)$_2$(C$_{1-3}$ alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —NO$_2$, and -L-R12; and R12 is a phenyl ring substituted with one or more substituents independently chosen from -L-C(=O)OH, -L-CH=CHC(=O)OH, -L-C(=O)NH$_2$, -L-C(=O)NH(C$_{1-3}$ alkyl), -L-C(=O)N(C$_{1-3}$ alkyl)$_2$, -L-S(=O)$_2$(C$_{1-3}$alkyl), -L-S(=O)$_2$NH$_2$, -L-S(=O)$_2$N(C$_{1-3}$ alkyl)$_2$, -L-S(=O)$_2$NH(C$_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl;

R$_o$ is chosen from alkyl and haloalkyl; and

L is as defined above.

In a ninth aspect, the invention provides compounds of Formula V and VI,

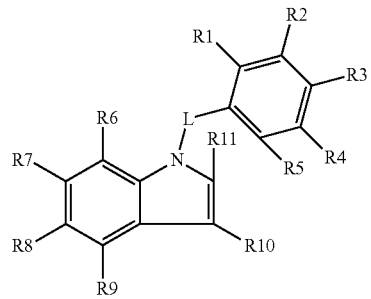

FORMULA V

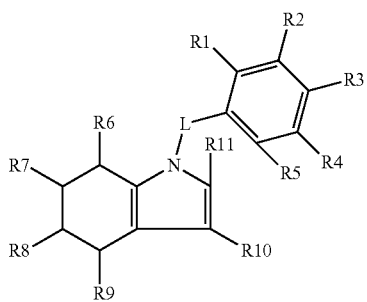

FORMULA VI wherein one or more of R1-R5 is independently chosen from -L-C(=O)OH, -L-CH=CHC(=O)OH, -L-C(=O)NH₂, -L-C(=O)NH(C₁₋₃ alkyl), -L-C(=O)N(C₁₋₃ alkyl)₂, -L-S(=O)₂(C₁₋₃alkyl), -L-S(=O)₂NH₂, -L-S(=O)₂N(C₁₋₃ alkyl)₂, -L-S(=O)₂NH(C₁₋₃ alkyl), -L-C(=O)NHOH, -L-C(=O)CH₂NH₂, -L-C(=O)CH₂OH, -L-C(=O)CH₂SH, -L-C(=O)NHCN, -L-NHC(=O)OR$_o$, -L-C(=O)NHR$_o$, -L-NH(C=O)NHR$_o$, -L-C(=O)N(R$_o$)₂, -L-NH(C=O)N(R$_o$)₂, -L-sulfo, -L-(2,6 difluorophenol), -L-phosphono, and -L-tetrazolyl; the others of R1-R5, independent of one another, are chosen from hydro, hydroxyl, halo, alkyl, alkoxy, haloalkyl, haloalkoxy, —N(C₁₋₃ alkyl)₂, —NH(C₁₋₃ alkyl), —C(=O)NH₂, —C(=O)NH(C₁₋₃ alkyl), —C(=O)N(C₁₋₃ alkyl)₂, —S(=O)₂(C₁₋₃alkyl), —S(=O)₂NH₂, —S(O)₂N(C₁₋₃ alkyl)₂, —S(=O)₂NH(C₁₋₃ alkyl), —CHF₂, —OCF₃, —OCHF₂, —SCF₃, —CF₃, —CN, —NH₂, and —NO₂;

R$_o$ is chosen from alkyl and haloalkyl;

L is as defined above;

R6-R10, independent of one another, are chosen from hydro, hydroxyl, halo, alkyl, alkoxy, haloalkyl, haloalkoxy, —N(C₁₋₃ alkyl)₂, —NH(C₁₋₃ alkyl), —C(=O)NH₂, —C(=O)NH(C₁₋₃ alkyl), —C(=O)N(C₁₋₃ alkyl)₂, —S(=O)₂(C₁₋₃alkyl), —S(=O)₂NH₂, —S(=O)₂N(C₁₋₃ alkyl)₂, —S(=O)₂NH(C₁₋₃ alkyl), —CHF₂, —OCF₃, —OCHF₂, —SCF₃, —CF₃, —CN, —NH₂, —NO₂, —C(=O)—N-morpholino, -cyclohexyl, -morpholino, -pyrrolidinyl, -piperazinyl, —(N-methyl)-piperazinyl, —OCH₂-phenyl, -pyridinyl, methylenedioxy, ethylenedioxy, —C(=O)OCH₂CH₃ substituted furanyl, para-(C(=O)OCH₂CH₃)-phenyl, and —O—Si(CH₃)₂(C(CH₃)₃); two adjacent of R6-R9 can be taken together to form a 4-7 member optionally substituted aryl or cycloalkyl ring; and R11 is an optionally substituted phenyl group.

In one embodiment of the ninth aspect of the invention, R8 and R9 in the compound of Formula V are taken together to form a 6 member aryl ring as in Formula VII.

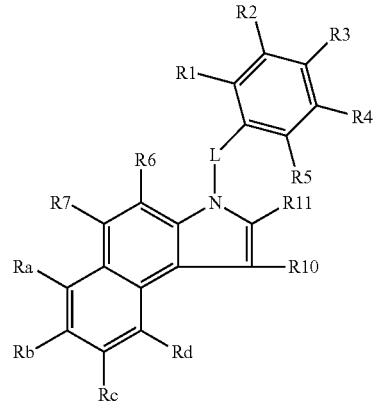

FORMULA VII

According to one embodiment of the ninth aspect of the invention, compounds of Formula VII are provided wherein Ra, Rb, Rc, and Rd are independently chosen from hydro, hydroxyl, halo, alkyl, alkoxy, haloalkyl, haloalkoxy, —N(C₁₋₃ alkyl)₂, —NH(C₁₋₃ alkyl), —C(=O)NH₂, —C(=O)NH(C₁₋₃ alkyl), —C(=O)N(C₁₋₃ alkyl)₂, —S(=O)₂(C₁₋₃ alkyl), —S(=O)₂NH₂, —S(=O)₂N(C₁₋₃ alkyl)₂, —S(=O)₂NH(C₁₋₃ alkyl), —CHF₂, —OCF₃, —OCHF₂, —SCF₃, —CF₃, —CN, —NH₂, —NO₂, —C(=O)—N-morpholino, -cyclohexyl, -morpholino, -pyrrolidinyl, -piperazinyl, —(N-methyl)-piperazinyl, —OCH₂-phenyl, -pyridinyl, methylenedioxy, ethylenedioxy, —C(=O)OCH₂CH₃ substituted furanyl, para-(C(=O)OCH₂CH₃)-phenyl, and —O—Si(CH₃)₂(C(CH₃)₃); and the other variables can be defined as in one of the other embodiments of the ninth aspect of the invention.

In one embodiment of the ninth aspect of the invention, R8 and R9 in the compounds of Formula VI are taken together to form a 6 member aryl ring as in Formula VIII.

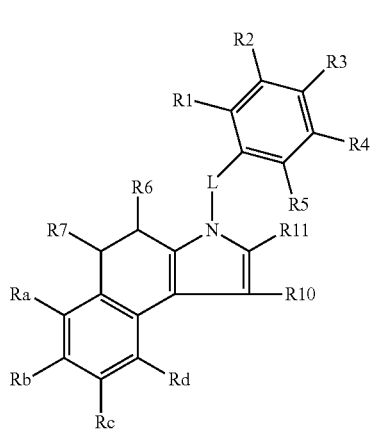

FORMULA VIII

According to one embodiment of the ninth aspect of the invention, compounds of Formula VIII are provided wherein Ra, Rb, Rc, and Rd are independently chosen from hydro, hydroxyl, halo, alkyl, alkoxy, haloalkyl, haloalkoxy, —N(C₁₋₃ alkyl)₂, —NH(C₁₋₃ alkyl), —C(=O)NH₂, —C(=O)NH(C₁₋₃ alkyl), —C(=O)N(C₁₋₃ alkyl)₂, —S(=O)₂(C₁₋₃ alkyl), —S(=O)₂NH₂, —S(=O)₂N(C₁₋₃ alkyl)₂, —S(=O)₂NH(C₁₋₃ alkyl), —CHF₂, —OCF₃, —OCHF₂, —SCF₃, —CF₃, —CN, —NH₂, —NO₂, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); and the other variables can be defined as in one of the other embodiments of the ninth aspect of the invention.

In a tenth aspect, the invention provides compounds of Formula IX and X:

FORMULA IX

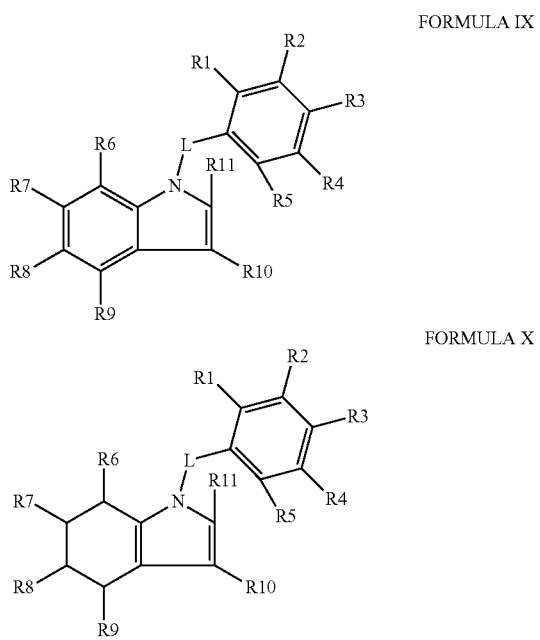

FORMULA X wherein one or more of R1-R11 are chosen from L-R12, -L-C(=O)OH, -L-CH=CHC(=O)OH, -L-C(=O)NH$_2$, -L-C(=O)NH(C$_{1-3}$ alkyl), -L-C(=O)N(C$_{1-3}$ alkyl)$_2$, -L-S(=O)$_2$(C$_{1-3}$ alkyl), -L-S(=O)$_2$NH$_2$, -L-S(=O)$_2$N(C$_{1-3}$ alkyl)$_2$, -L-S(=O)$_2$NH(C$_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl; wherein R12 is a phenyl ring substituted with one or more substituents independently chosen from -L-C(=O)OH, -L-CH=CHC(=O)OH, -L-C(=O)NH$_2$, -L-C(=O)NH(C$_{1-3}$ alkyl), -L-C(=O)N(C$_{1-3}$ alkyl)$_2$, -L-S(=O)$_2$(C$_{1-3}$ alkyl), -L-S(=O)$_2$NH$_2$, -L-S(=O)$_2$N(C$_{1-3}$ alkyl)$_2$, -L-S(=O)$_2$NH(C$_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl, and the others are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$;

R$_o$ is chosen from alkyl and haloalkyl;

L is as defined above; and the others of R1-R11 are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$—S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$; and two adjacent of R6-R9 can be taken together to form a 4-7 member optionally substituted aryl or cycloalkyl ring.

In one embodiment of the tenth aspect of the invention, R8 and R9 in the compounds of Formula IX are taken together to form a 6 member aryl ring as in Formula XI

FORMULA XI

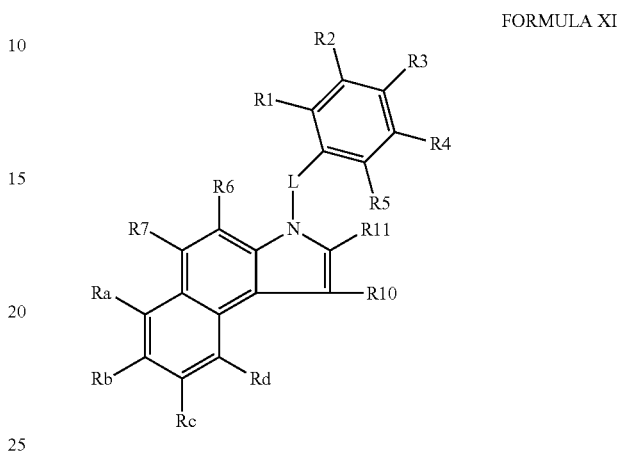

According to one embodiment of the tenth aspect of the invention, compounds of Formula XI are provided wherein Ra, Rb, Rc, and Rd are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$ alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); and the other variables can be defined as in one of the other embodiments of the tenth aspect of the invention.

In one embodiment of the tenth aspect of the invention, R8 and R9 in the compounds of Formula X are taken together to form a 6 member aryl ring as in Formula XII.

FORMULA XII

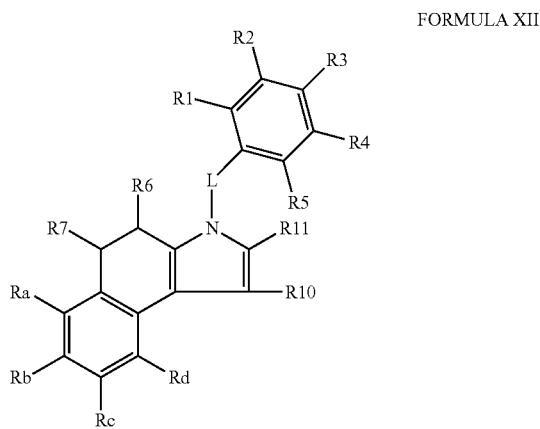

According to one embodiment of the tenth aspect of the invention, compounds of Formula XII are provided wherein Ra, Rb, Rc, and Rd are independently chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$ alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); and the other variables can be defined as in one of the other embodiments of the tenth aspect of the invention.

In an eleventh aspect, the invention provides compounds of Formula XIII and XIV:

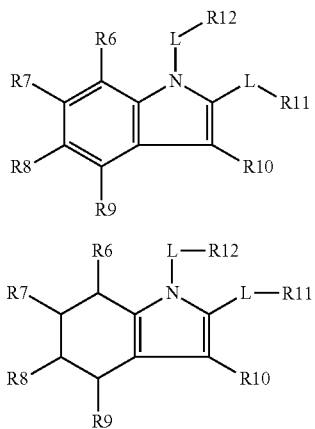

FORMULA XIII

FORMULA XIV wherein L is as defined above or is selected from an optionally substituted, saturated or partially saturated cyclopropyl, cyclobutyl, cyclopentyl, cyclohexyl, cycloheptyl, and $C_{1-12}$ alkyl;

R1-R10, independent of one another, are chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl or cycloalkyl ring;

R11 is chosen from L-C(=O)OH, -L-CH=CHC(=O)OH, -L-C(=O)NH$_2$, -L-C(=O)NH($C_{1-3}$ alkyl), -L-C(=O)N($C_{1-3}$ alkyl)$_2$, -L-S(=O)$_2$($C_{1-3}$alkyl), -L-S(=O)$_2$NH$_2$, -L-S(=O)$_2$N($C_{1-3}$ alkyl)$_2$, -L-S(=O)$_2$NH($C_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl;

R$_o$ is chosen from alkyl and haloalkyl; and

R12 is chosen from optionally substituted $C_{1-12}$ alkyl, phenyl, and $C_{3-7}$ cycloalkyl.

In one embodiment of the eleventh aspect of the invention, R8 and R9 in the compounds of Formula XIII are taken together to form a 6 member aryl ring as in Formula XV.

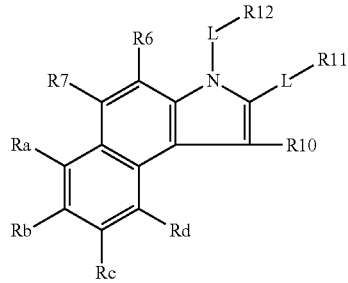

FORMULA XV

According to one embodiment of the eleventh aspect of the invention, compounds of Formula XV are provided wherein Ra, Rb, Rc, and Rd are independently chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); and the other variables can be defined as in one of the other embodiments of the eleventh aspect of the invention.

In one embodiment of the eleventh aspect of the invention, R8 and R9 in the compounds of Formula XIV are taken together to form a 6 member aryl ring as in Formula XVI.

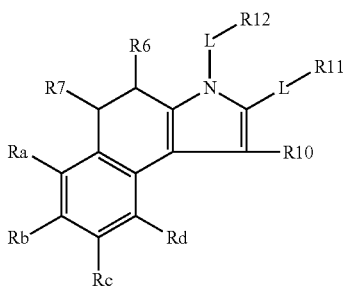

FORMULA XVI

According to one embodiment of the eleventh aspect of the invention, compounds of Formula XVI are provided wherein Ra, Rb, Rc, and Rd are independently chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$ alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); and the other variables can be defined as in one of the other embodiments of the eleventh aspect of the invention.

In a twelfth aspect, the invention provides compounds of Formula I and II, wherein one or more of R1-R5 is chosen from -L-C(=O)OH, -L-CH=CHC(=O)OH, -L-C(=O)NH$_2$, -L-C(=O)NH(C$_{1-3}$ alkyl), -L-C(=O)N(C$_{1-3}$ alkyl)$_2$, -L-S(=O)$_2$(C$_{1-3}$ alkyl), -L-S(=O)$_2$NH$_2$, -L-S(=O)$_2$N(C$_{1-3}$ alkyl)$_2$, -L-S(=O)$_2$NH(C$_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl, and the others of R1-R5, independent of one another, are chosen hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$ alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$;

R$_o$ is chosen from alkyl and haloalkyl;

R6-R10, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl, heterocyclic, or cycloalkyl ring;

R11 is an optionally substituted heterocyclic group; and

L can be saturated, partially saturated, or unsaturated, and is chosen from —(CH$_2$)$_n$—(CH$_2$)$_n$—, —(CH$_2$)$_n$C(=O)(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, 3, 4, 5, 6, 7, and 8, wherein each carbon can be optionally substituted with one or more C$_{1-3}$ alkyl or C$_{3-6}$ cycloalkyl.

In a thirteenth aspect, the invention provides compounds of Formula I and II, wherein R1-R5, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$NH$_2$, —S(=O)$_2$(C$_{1-3}$alkyl), —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$;

one or more of R6-R9 is independently chosen from -L-C(=O)OH, -L-CH=CHC(=O)OH, -L-C(=O)NH$_2$, -L-C(=O)NH(C$_{1-3}$ alkyl), -L-C(=O)N(C$_{1-3}$ alkyl)$_2$, -L-S(=O)$_2$(C$_{1-3}$alkyl), -L-S(=O)$_2$NH$_2$, -L-S(=O)$_2$N(C$_{1-3}$ alkyl)$_2$, -L-S(=O)$_2$NH(C$_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl; or two adjacent of R6-R9 can be taken together to form an optionally substituted 4-7 member aryl, heterocyclic, or cycloalkyl ring substituted with one or more substituents independently chosen from -L-C(=O)OH, -L-CH=CHC(=O)OH, -L-C(=O)NH$_2$, -L-C(=O)NH(C$_{1-3}$ alkyl), -L-C(=O)N(C$_{1-3}$ alkyl)$_2$, -L-S(=O)$_2$(C$_{1-3}$alkyl), -L-S(=O)$_2$NH$_2$, -L-S(=O)$_2$N(C$_{1-3}$ alkyl)$_2$, -L-S(=O)$_2$NH(C$_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl; and the others of R6-R9, independent of one another, are chosen from hydro, hydroxyl, halo, alkyl, alkoxy, haloalkyl, halo alkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(O)$_2$N(C$_{1-3}$ alkyl)$_2$, —S(=O)$_2$NH(C$_{1-3}$ alkyl), —CHF$_{25}$—OCF$_3$, —OCHF$_2$, —SCF$_3$, —CF$_3$, —CN, —NH$_2$, and —NO$_2$;

R$_o$ is chosen from alkyl and haloalkyl;

R11 is an optionally substituted heterocyclic group; and

L can be saturated, partially saturated, or unsaturated, and is chosen from —(CH$_2$)$_n$—(CH$_2$)$_n$—, —(CH$_2$)$_n$C(=O)(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently selected from 0, 1, 2, 3, 4, 5, 6, 7, and 8, wherein each carbon can be optionally substituted with one or more C$_{1-3}$ alkyl or C$_{3-6}$ cycloalkyl.

In a fourteenth aspect, the invention provides compounds of Formula I and II, wherein R1-R9 are independently chosen hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); two adjacent of R6-R9 can be taken together to form an optionally substituted C$_{4-7}$ member aryl, heterocyclic, or cycloalkyl ring;

R10 is chosen from -L-C(=O)OH, -L-CH=CHC(=O)OH, -L-C(=O)NH$_2$, -L-C(=O)NH(C$_{1-3}$ alkyl), -L-C(=O)N(C$_{1-3}$ alkyl)$_2$, -L-S(=O)$_2$(C$_{1-3}$alkyl), -L-S(=O)$_2$NH$_2$, -L-S(=O)$_2$N(C$_{1-3}$ alkyl)$_2$, -L-S(=O)$_2$NH(C$_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl;

R$_o$ is chosen from alkyl and haloalkyl;

R11 is an optionally substituted heterocyclic group; and

L can be saturated, partially saturated, or unsaturated, and is chosen from —(CH$_2$)$_n$—(CH$_2$)$_n$—, —(CH$_2$)$_n$C(=O)(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, 3, 4, 5, 6, 7, and 8, wherein each carbon can be optionally substituted with one or more C$_{1-3}$ alkyl or C$_{3-6}$ cycloalkyl.

In a fifteenth aspect, the invention provides compounds of Formula I and II, wherein R1-R10, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_{25}$—C(=O)NH(C$_{1-3}$ alkyl), —C(=O)N(C$_{1-3}$ alkyl)$_2$, —S(=O)$_2$(C$_{1-3}$ alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl, heterocyclic, or cycloalkyl ring;

R11 is a heterocyclic group with one or more substituents independently chosen from -L-C(=O)OH, -L-CH=CHC(=O)OH, -L-C(=O)NH$_2$, -L-C(=O)NH(C$_{1-3}$ alkyl), -L-C(=O)N(C$_{1-3}$ alkyl)$_2$, -L-S(=O)$_2$(C$_{1-3}$ alkyl), -L-S(=O)$_2$NH$_2$, -L-S(=O)$_2$N(C$_{1-3}$ alkyl)$_2$, -L-S(=O)$_2$NH(C$_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl;

R$_o$ is chosen from alkyl and haloalkyl; and

L can be saturated, partially saturated, or unsaturated, and is chosen from —(CH$_2$)$_n$—(CH$_2$)$_n$—, —(CH$_2$)$_n$C(=O)(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, 3, 4, 5, 6, 7, and 8, wherein each carbon can be optionally substituted with one or more C$_{1-3}$ alkyl or C$_{3-6}$ cycloalkyl.

In a sixteenth aspect, the invention provides compounds of Formula I and II, wherein R1-R9 and R11 independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$ alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl, heterocyclic, or cycloalkyl ring;

R10 is a heterocyclic group with one or more substituents independently chosen -L-C(=O)OH, -L-CH=CHC(=O)OH, -L-C(=O)NH$_2$, -L-C(=O)NH(C$_{1-3}$ alkyl), -L-C(=O)N(C$_{1-3}$ alkyl)$_2$, -L-S(=O)$_2$(C$_{1-3}$ alkyl), -L-S(=O)$_2$NH$_2$, -L-S(=O)$_2$N(C$_{1-3}$ alkyl)$_2$, -L-S(=O)$_2$NH(C$_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl;

R$_o$ is chosen from alkyl and haloalkyl; and

L can be saturated, partially saturated, or unsaturated, and is chosen from —(CH$_2$)$_n$—(CH$_2$)$_n$—, —(CH$_2$)$_n$C(=O)(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, 3, 4, 5, 6, 7, and 8, wherein each carbon can be optionally substituted with one or more C$_{1-3}$ alkyl or C$_{3-6}$ cycloalkyl.

In a seventeenth aspect, the invention provides compounds of Formula I and II, wherein R1-R9 and R11 independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$ alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl, heterocyclic, or cycloalkyl ring;

R10 is -L-R12;

R12 is a heterocyclic group with one or more substituents chosen from -L-C(=O)OH, -L-CH=CHC(=O)OH, -L-C(=O)NH$_2$, -L-C(=O)NH(C$_{1-3}$ alkyl), -L-C(=O)N(C$_{1-3}$ alkyl)$_2$, -L-S(=O)$_2$(C$_{1-3}$alkyl), -L-S(=O)$_2$NH$_2$, -L-S(=O)$_2$N(C$_{1-3}$ alkyl)$_2$, -L-S(=O)$_2$NH(C$_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl;

R$_o$ is chosen from alkyl and haloalkyl; and

L can be saturated, partially saturated, or unsaturated, and is chosen from —(CH$_2$)$_n$—(CH$_2$)$_n$—, —(CH$_2$)$_n$C(=O)(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, 3, 4, 5, 6, 7, and 8, wherein each carbon can be optionally substituted with one or more C$_{1-3}$ alkyl or C$_{3-6}$ cycloalkyl.

In an eighteenth embodiment, the invention provides compounds of Formula I and II, wherein R1-R9 and R11 independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$ alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl, heterocyclic, or cycloalkyl ring;

R10 is a heterocyclic group with one or more substituents independently chosen from -L-C(=O)OH, -L-CH=CHC(=O)OH, -L-C(=O)NH$_2$, -L-C(=O)NH(C$_{1-3}$ alkyl), -L-C(=O)N(C$_{1-3}$ alkyl)$_2$, -L-S(=O)$_2$(C$_{1-3}$ alkyl), -L-S(=O)$_2$NH$_2$, -L-S(=O)$_2$N(C$_{1-3}$ alkyl)$_2$, -L-S(=O)$_2$NH(C$_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl;

R$_o$ is chosen from alkyl and haloalkyl; and

L can be saturated, partially saturated, or unsaturated, and is chosen from —(CH$_2$)$_n$—(CH$_2$)$_n$—, —(CH$_2$)$_n$C(=O)(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, 3, 4, 5, 6, 7, and 8, wherein each carbon can be optionally substituted with one or more C$_{1-3}$ alkyl or C$_{3-6}$ cycloalkyl.

In a nineteenth aspect, the invention provides compounds of Formula I and II, wherein R1-R9, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$ alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl, heterocyclic, or cycloalkyl ring;

R10 and R11 are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$NH$_2$, —S(=O)$_2$(C$_{1-3}$alkyl), —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —NO$_2$, and -L-R12;

R12 is a heterocyclic group with one or more substituents independently chosen from -L-C(=O)OH, -L-CH=CHC(=O)OH, -L-C(=O)NH$_2$, -L-C(=O)NH(C$_{1-3}$ alkyl), -L-C(=O)N(C$_{1-3}$ alkyl)$_2$, -L-S(=O)$_2$(C$_{1-3}$alkyl), -L-S(=O)$_2$NH$_2$, -L-S(=O)$_2$N(C$_{1-3}$ alkyl)$_2$, -L-S(=O)$_2$NH(C$_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl;

R$_o$ is chosen from alkyl and haloalkyl; and

L can be saturated, partially saturated, or unsaturated, and is chosen from —(CH$_2$)$_n$—(CH$_2$)$_n$—, —(CH$_2$)$_n$C(=O)(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, 3, 4, 5, 6, 7, and 8, wherein each carbon can be optionally substituted with one or more C$_{1-3}$ alkyl or C$_{3-6}$ cycloalkyl.

In a twentieth aspect, the invention provides compounds of Formula V and VI,

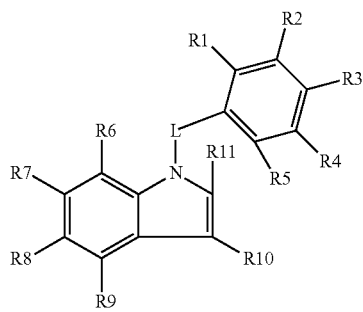

FORMULA V

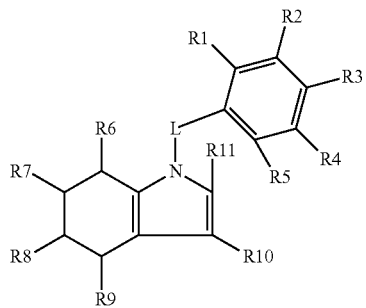

FORMULA VI wherein one or more of R1-R5 is independently chosen from -L-C(=O)OH, -L-CH=CHC(=O)OH, -L-C(=O)NH$_2$, -L-C(=O)NH(C$_{1-3}$ alkyl), -L-C(=O)N(C$_{1-3}$ alkyl)$_2$, -L-S(=O)$_2$(C$_{1-3}$alkyl), -L-S(=O)$_2$NH$_2$, -L-S(=O)$_2$N(C$_{1-3}$ alkyl)$_2$, -L-S(=O)$_2$NH(C$_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl, and the others of R1-R5, independent of one another, are chosen from hydro, hydroxyl, halo, alkyl, alkoxy, haloalkyl, halo alkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(O)$_2$N(C$_{1-3}$ alkyl)$_2$, —S(=O)$_2$NH(C$_{1-3}$ alkyl), —CHF$_{25}$—OCF$_3$, —OCHF$_2$, —SCF$_3$, —CF$_3$, —CN, —NH$_2$, and —NO$_2$;

R$_o$ is chosen from alkyl and haloalkyl;

R6-R10, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl, heterocyclic, or cycloalkyl ring;

R11 is an optionally substituted heterocyclic group; and

L can be saturated, partially saturated, or unsaturated, and is chosen from —(CH$_2$)$_n$—(CH$_2$)$_n$—, —(CH$_2$)$_n$C(=O)(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, 3, 4, 5, 6, 7, and 8, wherein each carbon can be optionally substituted with one or more C$_{1-3}$ alkyl or C$_{3-6}$ cycloalkyl.

In a twenty-first aspect, the invention provides compounds of Formula V and VI,

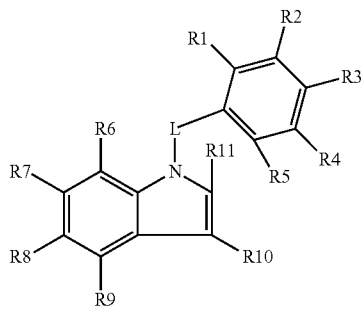

FORMULA V

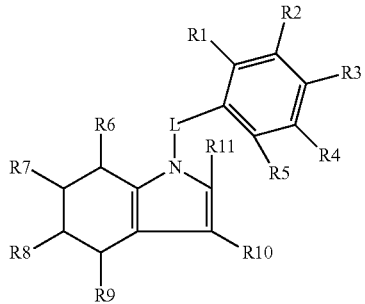

FORMULA VI wherein R1-R11, independent of one another, are chosen from -L-R12, -L-C(=O)OH, -L-CH=CHC(=O)OH, -L-C (=O)NH$_2$, -L-C(=O)NH(C$_{1-3}$ alkyl), -L-C(=O)N(C$_{1-3}$ alkyl)$_2$, -L-S(=O)$_2$(C$_{1-3}$alkyl), -L-S(=O)$_2$NH$_2$, -L-S(=O)$_2$N(C$_{1-3}$ alkyl)$_2$, -L-S(=O)$_2$NH(C$_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl;

R$_o$ is chosen from alkyl and haloalkyl;

R12 is a heterocyclic group with one or more substituents independently chosen -L-C(=O)OH, -L-CH=CHC(=O)OH, -L-C(=O)NH$_2$, -L-C(=O)NH(C$_{1-3}$ alkyl), -L-C(=O)N(C$_{1-3}$ alkyl)$_2$, -L-S(=O)$_2$(C$_{1-3}$ alkyl), -L-S(=O)$_2$NH$_2$, -L-S(=O)$_2$N(C$_{1-3}$ alkyl)$_2$, -L-S(=O)$_2$NH(C$_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl; and the others of R1-R11 are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl, heterocyclic, or cycloalkyl ring; and L can be saturated, partially saturated, or unsaturated, and is chosen from —(CH$_2$)$_n$—(CH$_2$)$_n$—, —(CH$_2$)$_n$C(=O)(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, 3, 4, 5, 6, 7, and 8, wherein each carbon can be optionally substituted with one or more C$_{1-3}$ alkyl or C$_{3-6}$ cycloalkyl.

In one embodiment of this twenty-first aspect, the invention includes analogs where the ring to which R1-R5 are attached is a 4-7 member heterocyclic ring instead a phenyl ring.

In another aspect of the invention, one or more of the carbon atoms of the indole core are replaced by a heteroatom independently —N—, —O—, and —S—.

In some embodiments of the invention, R$_o$ is independently chosen from methyl or ethyl.

Optionally substituted, when used herein without reference to further definition, refers to a substituent independently chosen from the group consisting of hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and NO$_2$.

Furthermore, the invention provides derivatives or analog of the compounds defined in first through twenty-first aspects of the invention, where the derivative or analog is chosen from an ester (e.g., methyl or ethyl ester), an amide, a carbamate, a urea, an amidine, or a combination thereof. Methods for generating an ester, an amide, a carbamate, a urea, an amidine, or a combination thereof, of the compounds of the first aspect through the twenty-first aspects are known to an ordinary artisan skilled in organic chemical synthesis.

As the skilled artisan readily recognizes, in some of the embodiments of the first twenty-one aspects of the invention, some of the compounds can have more than one -L- group, each of which is independent chosen.

In a twenty-second aspect, the invention provides a method of treating a neurodegenerative disorder, by identifying a patient in need of such treatment, and administering to the patient a therapeutically effective amount of a pharmaceutical composition having one or more compounds of Formulae I-XVI. Administration of a compound of Formulae I-XVI for at least 4 weeks, preferably at least 4 months, and more desirably at least 8 months, can provide an improvement or lessening in decline of cognitive function as characterized by cognition tests, biochemical disease marker progression, and/or plaque pathology. Cognition tests are those which are capable of measuring cognitive decline in a patient or group of patients. Examples of such cognition tests include the ADAS-cog (Alzheimer's Disease Assessment Scale, cognitive subscale) NPI (Neuropsychiatric Inventory), ADCS-ADL (Alzheimer's Disease Cooperative Study-Activities of Daily Living), CIBIC-plus (Clinician Interview Based Impression of Change), and CDR sum of boxes (Clinical Dementia Rating). It is preferred that the lessening in decline in cognitive function is at least 25% as compared to individuals treated with placebo, more preferably at least 40%, and even more desirably at least 60%. For example, an individual treated with placebo having probable mild-to-moderate Alzheimer's disease is expected to score approximately 5.5 points worse on the ADAS-cog test after a specified period of time of treatment (e.g., 1 year) whereas an individual treated with the composition of this aspect of the invention for the same period of time will score approximately 2.2 points worse on the ADAS-cog scale with a 60% decrease in decline or 3.3 points worse with a 40% decrease in decline in cognitive function when treated with the composition for the same specified period of time. Desirably, the oral dose is provided in capsule or tablet form. The pharmaceutical composition for use in the invention is formulated with one or more pharmaceutically acceptable excipients, salts, or carriers. The pharmaceutical composition for use in the invention is delivered orally, preferably in a tablet or capsule dosage form.

In a twenty-third aspect, the invention provides a method for prophylaxis against a neurodegenerative disorder, by identifying a patient in need of or desiring such treatment, and administering to the patient a prophylactically effective amount of a pharmaceutical composition having one or more compounds of Formulae I-XVI. Administration of a compound of Formulae I-XVI for at least 4 weeks, preferably at least 4 months, and more desirably at least 8 months, can delay the onset of the neurodegenerative disorder or slow the rate of onset of symptoms of the disorder. Patients having a predisposition to a neurodegenerative disorder or suspected of needing prophylaxis can be identified by any method known to the skilled artisan for diagnosis such neurodegenerative disorders.

In a twenty-fourth aspect, the invention provides a method of treating a disease characterized by abnormal amyloid precursor protein processing by (1) identifying a patient in need of such treatment, and (2) administering to the patient a therapeutically effective amount of a pharmaceutical composition having one or more compounds of Formulae I-XVI. Oral administration of the pharmaceutical composition for use in the method of this aspect the invention for at least 4 weeks, preferably at least 4 months, and more desirably at least 8 months, provides an improvement or lessening in decline of cognitive function as characterized by cognition tests, biochemical disease marker progression, and/or plaque pathology. Examples of biochemical disease markers include, for example, amyloid beta peptide (Aβ), Aβ$_{42}$, and tau. It is preferred that the lessening in decline in biochemical disease marker progression is at least 10% as compared to individuals treated with placebo, more preferably at least 20%, and more desirably at least 40%. It is preferred that the lessening in decline in cognitive function is at least 25% as compared to individuals treated with placebo, more preferably at least 40%, and even more desirably at least 60%. Desirably, the composition is provided as an oral dose, preferably in capsule or tablet form.

In a twenty-fifth aspect, the invention provides a method of prophylaxis or delaying the onset of a disease (or one or more symptoms thereof) characterized by abnormal amyloid precursor protein processing, by identifying a patient in need of such treatment and administering to the patient a prophylactically effective amount of a pharmaceutical composition having one or more compounds of Formulae I-XVI. Oral administration of the pharmaceutical composition for use in the method of this aspect the invention for at least 4 weeks, preferably at least 4 months, and more desirably at least 8 months, prevents or delays the onset of the disease (or symptoms thereof) characterized by abnormal amyloid precursor protein processing.

In a twenty-sixth aspect, the invention provides a method of treating Alzheimer's disease comprising administering to a patient in need of such treatment, a pharmaceutical composition having one or more compounds of Formulae I-XVI. Oral administration of the pharmaceutical composition for use in the method of this aspect of the invention for at least 4 weeks, preferably at least 4 months, and more desirably at least 8 months, provides an improvement or lessening in decline of cognitive function as characterized by cognition tests, biochemical disease marker progression, and/or plaque pathology. Desirably, the oral dose is provided in capsule or tablet form. According to this aspect of the invention, a patient in need of treatment is administered an Alzheimer's disease treating effective amount of a pharmaceutical composition having one or more compounds of Formulae I-XVI and one or more pharmaceutically acceptable salts, excipients and carriers. The method of this aspect of the invention involves identifying an individual likely to have mild-to-moderate Alzheimer's disease. An individual having probable mild-to-moderate Alzheimer's disease can be diagnosed by any method available to the ordinary artisan skilled in such diagnoses. For example, diagnosis can be according to DSM IV (TR) and/or meets NINCDS-ADRDA criteria for probable AD. According to this aspect of the invention, individuals with probable mild-to-moderate AD take an oral dose of a pharmaceutical composition for a specified period of time. Individuals undergoing such treatment are likely to see an improvement or lessening in decline of cognitive function, an improvement or lessening in decline in biochemical disease marker progression, and/or an improvement or lessening decline in plaque pathology. A lessening in decline in cognitive function can be assessed using a test of cognitive function like the ADAS-cog. For example, an individual treated with placebo having probable mild-to-moderate Alzheimer's disease is expected to score approximately 5.5 points worse on the ADAS-cog test after a specified period of time of treatment (e.g., 1 year) whereas an individual treated with the composition of this aspect of the invention for the same period of time will score approximately 2.2 points worse on the ADAS-cog scale with a 60% decrease in decline or 3.3 points worse with a 40% decrease in decline in cognitive function when treated with the composition for the same specified period of time. In a related aspect, the method involves identifying a patient having moderate-to-severe AD and administering to the patient an Alzheimer's disease treating effective amount of a compound of Formulae I-XVI.

In a twenty-seventh aspect, the invention provides a method of preventing the onset of Alzheimer's disease comprising administering to a patient in need of or desiring such treatment, a pharmaceutical composition having one or more compounds of Formulae I-XVI. Oral administration of the pharmaceutical composition for use in the method of this aspect of the invention for at least 4 weeks, preferably at least 4 months, and more desirably at least 8 months, delays the onset of decline of cognitive function, biochemical disease marker progression, and/or plaque pathology. According to this embodiment, an individual desiring or needing preventative treatment against the onset of AD is administered a pharmaceutical composition having one or more compounds of Formulae I-XVI. Desirably, the oral dose is provided in capsule or tablet form. The preventive treatment is preferably maintained as long as the individual continues to desire or need the treatment. Individuals needing or desiring preventative treatment against AD can be those having risk factors for developing AD. For example, risk factors for developing AD can be genetic factors or environmental factors. In one embodiment, the risk factor is age. Genetic risk factors can be assessed in a variety of ways, such as ascertaining the family medical history of the individual, or performing a genetic test to identify genes that confer a predisposition for developing AD. Additionally, risk factors can be assessed by monitoring genetic and biochemical markers.

The foregoing and other advantages and features of the invention, and the manner in which the same are accomplished, will become more readily apparent upon consideration of the following detailed description of the invention taken in conjunction with the accompanying examples, which illustrate preferred and exemplary embodiments.

DETAILED DESCRIPTION OF THE INVENTION

In general, the invention relates to the use of pharmaceutical compositions having one or more compounds of Formulae I-XVI as the active ingredient, for treating neurodegenerative disorders. When the pharmaceutical composition is administered, according to the treatment regimens of the invention, to an individual desiring or needing such treatment, it provides an improvement or lessening in decline of cognitive function, biochemical disease marker progression, and/or plaque pathology associated with neurodegenerative disorders such as AD. The composition of the invention is formulated with one or more pharmaceutically acceptable excipients, salts, or carriers. The pharmaceutical composition of the invention is delivered orally, preferably in a tablet or capsule dosage form. The pharmaceutical compositions can be used in methods for treating, preventing, and prophylaxis against neurodegenerative disorders such as Alzheimer's disease, and disease characterized by abnormal amyloid precursor protein processing.

The invention therefore provides compounds of Formulae I-XVI as described in the Summary of the Invention (and in more detail below) and pharmaceutical composition having such compounds. In one specific use, the compounds can be used for the treatment and/or prophylaxis of neurodegenerative disorders. The inventors have found that compounds of Formulae I-XVI as described in the summary have an Aβ$_{42}$ lowering effect in cell based assays.

Some of the compounds of Formulae I-XVI, for use in the invention may exist as single stereoisomers (i.e., essentially free of other stereoisomers), racemates, and/or mixtures of enantiomers and/or diastereomers. All such single stereoisomers, racemates and mixtures thereof are intended to be within the scope of the present invention. Preferably, the compounds that are optically active are used in optically pure form. Furthermore, some of the compound for use in the invention can exist as cis and trans geometric isomers all such isomers and mixtures thereof are intended to be within the scope of the present invention.

Additionally, the formulas are intended to cover solvated as well as unsolvated forms of the identified structures. For example, Formulae I-XVI includes compounds of the indicated structure in both hydrated and non-hydrated forms. Other examples of solvates include the structures in combination with isopropanol, ethanol, methanol, DMSO, ethyl acetate, acetic acid, or ethanolamine.

In addition to compounds of Formulae I-XVI, the invention includes pharmaceutically acceptable prodrugs, pharmaceutically active metabolites, and pharmaceutically acceptable salts of such compounds.

Prodrugs and active metabolites of compound may be identified using routine techniques known in the art. See, e.g., Bertolini, G et al., *J. Med. Chem.*, 40, 2011-2016 (1997); Shan, D. et al., *J. Pharm. Sci.*, 86 (7), 756-767; Bagshawe K., *Drug Dev. Res.*, 34, 220-230 (1995); Bodor N.; *Advance in Drug Res.*, 13, 224-331 (1984); Bundgaard, H., Design of Prodrugs (Elsevier Press 1985); and Larsen, I. K., Design and Application of Prodrugs, Drug Design and Development (Krogsgaard-Larsen et al., eds., Harwood Academic Publishers, 1991).

Compounds of the Invention

In general, the invention relates to compounds of Formulae I-XVI, pharmaceutically acceptable salts thereof, and pharmaceutical compositions containing the compounds and salts. The compounds of the invention can be used for the treatment and prophylaxis of neurodegenerative disorders, including Alzheimer's disease.

In a first aspect, the invention provides compounds of Formula I and II, pharmaceutically acceptable salts thereof, and pharmaceutical compositions having such compounds.

FORMULA I

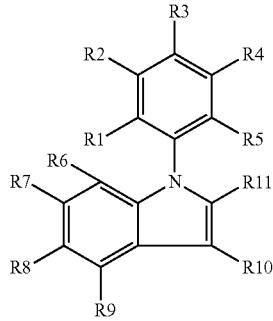

According to the first aspect of the invention, compounds of Formula I have one or more of R1-R5 independently chosen from L-C(=O)OH, -L-CH=CHC(=O)OH, -L-C(=O)NH$_2$, -L-C(=O)NH(C$_{1-3}$ alkyl), -L-C(=O)N(C$_{1-3}$ alkyl)$_2$, -L-S(=O)$_2$(C$_{1-3}$alkyl), -L-S(=O)$_2$NH$_2$, -L-S(=O)$_2$N(C$_{1-3}$ alkyl)$_2$, -L-S(=O)$_2$NH(C$_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl, and the others of R1-R5, independent of one another, are chosen from hydro, hydroxyl, halo, alkyl, alkoxy, haloalkyl, halo alkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$, with the provision that R3 is not hydroxyl;

R6-R10, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl or cycloalkyl ring;

R11 is an optionally substituted phenyl group;

R$_o$ is chosen from alkyl and haloalkyl; and

L can be saturated, partially saturated, or unsaturated, and is chosen from —(CH$_2$)$_n$—(CH$_2$)$_n$—, —(CH$_2$)$_n$C(=O)(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, 3, 4, 5, 6, 7, and 8, and wherein each carbon can be optionally substituted with one or more C$_{1-3}$ alkyl or C$_{3-6}$ cycloalkyl.

In one sub-embodiment, the compound is not 1-[4-(methylsulfonyl)phenyl]-2-phenyl-1H-Indole.

According to one embodiment of the first aspect of the invention, one or more of R1-R5 in the compounds of Formula I, are independently chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, —C(CH$_3$)$_2$C(=O)OH, —C(=O)NH$_2$, —C(=O)NHCH$_3$, —C(=O)N(CH$_3$)$_2$, —S(=O)$_2$(C$_{1-3}$alkyl), —S(=O)$_2$NH$_2$, —S(=O)$_2$NHCH$_3$, —S(=O)$_2$N(CH$_3$)$_2$, —C(=O)NH(C$_{1-3}$ alkyl), —C(=O)N(C$_{1-3}$ alkyl)$_2$, —S(=O)$_2$NH$_2$, —S(=O)$_2$N(C$_{1-3}$alkyl)$_2$, and the others of R1-R5, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$ alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$;

R6-R10, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$ alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$; two adjacent of R6-R9 can be taken together to form a 4-7 member optionally substituted aryl or cycloalkyl ring;

L is as defined above; and

R11 is an optionally substituted phenyl group.

In one sub-embodiment R3 is not hydroxyl.

According to another embodiment of this first aspect of the invention, in the compounds of Formula I, one of R1-R5 is chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, and —C(CH$_3$)$_2$C(=O)OH; and the others of R1-R5 independently are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$;

R6-R10, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$; two of R6-R9 can be taken together to form an optionally substituted C$_{4-7}$ aryl or cycloalkyl ring; and R11 is an optionally substituted phenyl.

According to one embodiment of the first aspect of the invention, in the compounds of Formula I, R1 is chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, —C(CH$_3$)$_2$C(=O)OH, —C(=O)NH$_2$, —C(=O)NHCH$_3$, —C(=O)N(CH$_3$)$_2$, —S(=O)$_2$(C$_{1-3}$ alkyl), —S(=O)$_2$NH$_2$, —S(=O)$_2$NHCH$_3$, —S(=O)$_2$N(CH$_3$)$_2$, —C(=O)NH(C$_{1-3}$alkyl), —C(=O)N(C$_{1-3}$alkyl)$_2$, —S(=O)$_2$NH$_2$, and —S(=O)$_2$N(C$_{1-3}$alkyl)$_2$.

According to one embodiment of the first aspect of the invention, in the compounds of Formula I, R1 is chosen from —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, —C(CH$_3$)$_2$C(=O)OH, —C(=O)NH$_2$, —C(=O)NHCH$_3$, —C(=O)N(CH$_3$)$_2$, —S(=O)$_2$(C$_{1-3}$ alkyl), —S(=O)$_2$NH$_2$, —S(=O)$_2$NHCH$_3$, —S(=O)$_2$N(CH$_3$)$_2$, —C(=O)NH(C$_{1-3}$ alkyl), —C(=O)N(C$_{1-3}$ alkyl)$_2$, —S(=O)$_2$NH$_2$, and —S(=O)$_2$N(C$_{1-3}$alkyl)$_2$.

According to another embodiment of the first aspect of the invention, in the compounds of Formula I, R1 is chosen from -L-C(=O)OH, -L-CH=CHC(=O)OH, -L-CH$_2$CH$_2$C(=O)OH, -L-CH$_2$CH$_2$CH$_2$C(=O)OH, -L-C(CH$_2$CH$_2$)C(=O)OH, -L-CH(CH$_3$)C(=O)OH, -L-CH(CH$_2$CH$_3$)C(=O)OH, -L-C(CH$_3$)(CH$_2$CH$_3$)C(=O)OH, -L-CH=C(CH$_3$)C(=O)OH, -L-C(CH$_2$CH$_3$)$_2$C(=O)OH, -L-CH$_2$C(=O)OH, -L-C(CH$_3$)$_2$C(=O)OH, -L-C(=O)NH$_2$, -L-C(=O)NHCH$_3$, -L-C(=O)N(CH$_3$)$_2$, -L-S(=O)$_2$(C$_{1-3}$alkyl), -L-S(=O)$_2$NH$_2$, -L-S(=O)$_2$NHCH$_3$, -L-S(=O)$_2$N(CH$_3$)$_2$, -L-C(=O)NH(C$_{1-3}$ alkyl), -L-C(=O)N(C$_{1-3}$alkyl)$_2$, -L-S(=O)$_2$NH$_2$, and -L-S(=O)$_2$N(C$_{1-3}$alkyl)$_2$, with the provision that if R1 is —COOH, or an ester thereof, then R10 is not —COOH, or an ester thereof.

According to one embodiment of the first aspect of the invention, in the compounds of Formula I, R2 is chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, —C(CH$_3$)$_2$C(=O)OH, —C(=O)NH$_2$, —C(=O)NHCH$_3$, —C(=O)N(CH$_3$)$_2$, —S(=O)$_2$(C$_{1-3}$ alkyl), —S(=O)$_2$NH$_2$, —S(=O)$_2$NHCH$_3$, —S(=O)$_2$N(CH$_3$)$_2$, —C(=O)NH(C$_{1-3}$alkyl), —C(=O)N(C$_{1-3}$alkyl)$_2$, —S(=O)$_2$NH$_2$, and —S(=O)$_2$N(C$_{1-3}$alkyl)$_2$.

According to yet another embodiment of the first aspect of the invention, in the compounds of Formula I, R2 is chosen from —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, —C(CH$_3$)$_2$C(=O)OH, —C(=O)NH$_2$, —C(=O)NHCH$_3$, —C(=O)N(CH$_3$)$_2$, —S(=O)$_2$(C$_{1-3}$ alkyl), —S(=O)$_2$NH$_2$, —S(=O)$_2$NHCH$_3$, —S(=O)$_2$N(CH$_3$)$_2$, —C(=O)NH(C$_{1-3}$alkyl), —C(=O)N(C$_{1-3}$alkyl)$_2$, —S(=O)$_2$NH$_2$, and —S(=O)$_2$N(C$_{1-3}$alkyl)$_2$.

According to another embodiment of the first aspect of the invention, in the compounds of Formula I, R2 is chosen from -L-C(=O)OH, -L-CH=CHC(=O)OH, -L-CH$_2$CH$_2$C(=O)OH, -L-CH$_2$CH$_2$CH$_2$C(=O)OH, -L-C(CH$_2$CH$_2$)C(=O)OH, -L-CH(CH$_3$)C(=O)OH, -L-CH(CH$_2$CH$_3$)C(=O)OH, -L-C(CH$_3$)(CH$_2$CH$_3$)C(=O)OH, -L-CH=C(CH$_3$)C(=O)OH, -L-C(CH$_2$CH$_3$)$_2$C(=O)OH, -L-CH$_2$C(=O)OH, -L-C(CH$_3$)$_2$C(=O)OH, -L-C(=O)NH$_2$, -L-C(=O)NHCH$_3$, -L-C(=O)N(CH$_3$)$_2$, -L-S(=O)$_2$(C$_{1-3}$ alkyl), -L-S(=O)$_2$NH$_2$, -L-S(=O)$_2$NHCH$_3$, -L-S(=O)$_2$N(CH$_3$)$_2$, -L-C(=O)NH(C$_{1-3}$ alkyl), -L-C(=O)N(C$_{1-3}$ alkyl)$_2$, -L-S(=O)$_2$NH$_2$, and -L-S(=O)$_2$N(C$_{1-3}$alkyl)$_2$, with the provision that when R2 is C(=O)OH, R3 is not OH or OC(=O)CH$_3$.

According to another embodiment of the first aspect of the invention, in the compounds of Formula I, R3 is chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, —C(CH$_3$)$_2$C(=O)OH, —C(=O)NH$_2$, —C(=O)NHCH$_3$, —C(=O)N(CH$_3$)$_2$, —S(=O)$_2$(C$_{1-3}$alkyl), —S(=O)$_2$NH$_2$, —S(=O)$_2$NHCH$_3$, —S(=O)$_2$N(CH$_3$)$_2$, —C(=O)NH(C$_{1-3}$alkyl), —C(=O)N(C$_{1-3}$ alkyl)$_2$, —S(=O)$_2$NH$_2$, and —S(=O)$_2$N(C$_{1-3}$ alkyl)$_2$.

According to still another embodiment of the first aspect of the invention, in the compounds of Formula I, R3 is chosen from -L-C(=O)OH, -L-CH=CHC(=O)OH, -L-CH$_2$CH$_2$C(=O)OH, -L-CH$_2$CH$_2$CH$_2$C(=O)OH, -L-C(CH$_2$CH$_2$)C(=O)OH, -L-CH(CH$_3$)C(=O)OH, -L-CH(CH$_2$CH$_3$)C(=O)OH, -L-C(CH$_3$)(CH$_2$CH$_3$)C(=O)OH, -L-CH=C(CH$_3$)C(=O)OH, -L-C(CH$_2$CH$_3$)$_2$C(=O)OH, -L-CH$_2$C(=O)OH, -L-C(CH$_3$)$_2$C(=O)OH, -L-C(=O)NH$_2$, -L-C(=O)NHCH$_3$, -L-C(=O)N(CH$_3$)$_2$, -L-S(=O)$_2$(C$_{1-3}$alkyl), -L-S(=O)$_2$NH$_2$, -L-S(=O)$_2$NHCH$_3$, -L-S(=O)$_2$N(CH$_3$)$_2$, -L-C(=O)NH(C$_{1-3}$ alkyl), -L-C(=O)N(C$_{1-3}$alkyl)$_2$, -L-S(=O)$_2$NH$_2$, and -L-S(=O)$_2$N(C$_{1-3}$ alkyl)$_2$.

The first aspect of the invention also includes compounds of Formula II.

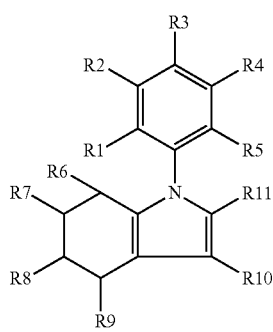

FORMULA II

In the first aspect of the invention, compounds of Formula II are provided having one or more of R1-R5 independently chosen from -L-C(=O)OH, -L-CH=CHC(=O)OH, -L-C(=O)NH$_2$, -L-C(=O)NHC$_{1-3}$ alkyl), -L-C(=O)N(C$_{1-3}$ alkyl)$_2$, -L-S(=O)$_2$NH$_2$, -L-S(=O)$_2$N(C$_{1-3}$ alkyl)$_2$, -L-S(=O)$_2$NH(C$_{1-3}$ alkyl), -L-C(=O)NHOH, -L-C(=O)CH$_2$NH$_2$, -LC(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl, and the others of R1-R5, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$ alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$;

L can be saturated, partially saturated, or unsaturated, and is chosen from —(CH$_2$)$_n$—(CH$_2$)$_n$—, —(CH$_2$)$_n$C(=O)(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently selected from 0, 1, 2, 3, 4, 5, 6, 7, and 8, wherein each carbon can be optionally substituted with one or more C$_{1-3}$ alkyl or C$_{3-6}$ cycloalkyl;

R6-R10, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$ alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl or cycloalkyl ring;

R11 is an optionally substituted phenyl group; and

R$_o$ is chosen from haloalkyl and alkyl.

In one sub-embodiment, when R2 is —C(=O)OH, then R3 is not hydroxyl (or —O—C(=O)CH$_3$), —SH, —Cl, —NH$_2$, methoxy, and —NHC(=O)CH$_3$;

In one sub-embodiment, the compound is not 4-(4,5-dihydro-2-phenyl-3H-benz[e]indol-3-yl)-2-hydroxy-benzoic acid, 4-(4,5-dihydro-2-phenyl-3H-benz[e]indol-3-yl)-benzoic acid, 4-(7-chloro-4,5-dihydro-2-phenyl-3H-benz[e]indol-3-yl)-2-hydroxy-benzoic acid, 2-hydroxy-4-(4,5,6,7-tetrahydro-2-phenyl-1H-indol-1-yl)-benzoic acid, 4-(4,5,6,7-tetrahydro-2-phenyl-1H-indol-1-yl)-benzoic acid, 3-(4,5-dihydro-2-phenyl-3H-benz[e]indol-3-yl)-benzamide, 4-(4,5-dihydro-2-phenyl-3H-benz[e]indol-3-yl)-benzamid e3-(4,5-dihydro-2-phenyl-1H-benz[g]indol-1-yl)-benzoic acid, 2-(4,5-dihydro-2-phenyl-1H-benz[g]indol-1-yl)-benzoic acid, or 3-[2-(4-bromophenyl)-4,5,6,7-tetrahydro-1H-indol-1-yl]-benzoic acid.

In one embodiment of the first aspect of the invention, one of R1-R5 in the compounds of Formula II is chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, —C(CH$_3$)$_2$C(=O)OH, —C(=O)NH$_2$, —C(=O)NHCH$_3$, —C(=O)N(CH$_3$)$_2$, —S(=O)$_2$NH$_2$, —S(=O)$_2$NHCH$_3$, —S(=O)$_2$N(CH$_3$)$_2$, —C(=O)NH(C$_{1-3}$alkyl), —C(=O)N(C$_{1-3}$ alkyl)$_2$, —S(=O)$_2$NH$_2$, and —S(=O)$_2$N(C$_{1-3}$ alkyl)$_2$, and the others of R1-R5, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$ alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$;

R6-R10, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$ alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$; two adjacent of R6-R9 can be taken together to form a 4-7 member optionally substituted aryl or cycloalkyl ring;

L is as defined above; and

R11 is an optionally substituted phenyl.

According to another embodiment of this first aspect of the invention, in the compounds of Formula II, one of R1-R5 is chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, and —C(CH$_3$)$_2$C(=O)OH; and the others of R1-R5 are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$ alkyl), —S(=O)$_2$NH$_2$, —S(=O)$_2$N(C$_{1-3}$ alkyl), —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$;

R6-R10, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$ alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$; two adjacent of R6-R9 can be taken together to form a 4-7 member optionally substituted aryl or cycloalkyl ring; and R11 is an optionally substituted phenyl.

According to another embodiment of the first aspect of the invention, in the compounds of Formula II, R1 is chosen from -L-C(=O)OH, -L-CH=CHC(=O)OH, -L-CH$_2$CH$_2$C(=O)OH, -L-CH$_2$CH$_2$CH$_2$C(=O)OH, -L-C(CH$_2$CH$_2$)C(=O)OH, -L-CH(CH$_3$)C(=O)OH, -L-CH(CH$_2$CH$_3$)C(=O)OH, -L-C(CH$_3$)(CH$_2$CH$_3$)C(=O)OH, -L-CH=C(CH$_3$)C(=O)OH, -L-C(CH$_2$CH$_3$)$_2$C(=O)OH, -L-CH$_2$C(=O)OH, -L-C(CH$_3$)$_2$C(=O)OH, -L-C(=O)NH$_2$, -L-C (=O)NHCH$_3$, -L-C(=O)N(CH$_3$)$_2$, -L-S(=O)$_2$(C$_{1-3}$ alkyl), -L-S(=O)$_2$NH$_2$, -L-S(=O)$_2$NHCH$_3$, -L-S(=O)$_2$N(CH$_3$)$_2$, -L-C(=O)NH(C$_{1-3}$ alkyl), -L-C(=O)N(C$_{1-3}$ alkyl)$_2$, -L-S(=O)$_2$NH$_2$, and -L-S(=O)$_2$N(C$_{1-3}$alkyl)$_2$. In one sub-embodiment, the compound is not 2-(4,5-dihydro-2-phenyl-1H-benz[g]indol-1-yl) benzoic acid (CAS No. 54670-19-8).

According to yet another embodiment of the first aspect of the invention, in the compounds of Formula II, R1 is chosen from —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, —C(CH$_3$)$_2$C(=O)OH, —C(=O)NH$_2$, —C(=O)NHCH$_3$, —C(=O)N(CH$_3$)$_2$, —S(=O)$_2$(C$_{1-3}$ alkyl), —S(=O)$_2$NH$_2$, —S(=O)$_2$NHCH$_3$, —S(=O)$_2$N(CH$_3$)$_2$, —C(=O)NH(C$_{1-3}$ alkyl), —C(=O)N(C$_{1-3}$ alkyl)$_2$, —S(=O)$_2$NH$_2$, and —S(=O)$_2$N(C$_{1-3}$alkyl)$_2$.

According to still another embodiment of the first aspect of the invention, in the compounds of Formula II, R2 is chosen from -L-C(=O)OH, -L-CH=CHC(=O)OH, -L-CH$_2$CH$_2$C(=O)OH, -L-CH$_2$CH$_2$CH$_2$C(=O)OH, -L-C(CH$_2$CH$_2$)C(=O)OH, -L-CH(CH$_3$)C(=O)OH, -L-CH(CH$_2$CH$_3$)C(=O)OH, -L-C(CH$_3$)(CH$_2$CH$_3$)C(=O)OH, -L-CH=C(CH$_3$)C(=O)OH, -L-C(CH$_2$CH$_3$)$_2$C(=O)OH, -L-CH$_2$C(=O)OH, -L-C(CH$_3$)$_2$C(=O)OH, -L-C(=O)NH$_2$, -L-C(=O)NHCH$_3$, -L-C(=O)N(CH$_3$)$_2$, -L-S(=O)$_2$(C$_{1-3}$alkyl), -L-S(=O)$_2$NH$_2$, -L-S(=O)$_2$NHCH$_3$, -L-S(=O)$_2$N(CH$_3$)$_2$, -L-C(=O)NH(C$_{1-3}$ alkyl), -L-C(=O)N(C$_{1-3}$alkyl)$_2$, -L-S(=O)$_2$NH$_2$, and -L-S(=O)$_2$N(C$_{1-3}$alkyl)$_2$. In one sub-embodiment, (1) if R2 is —C(=O)NH$_2$, —C(=O)NH(CH$_2$CH$_3$), —C(=O)N(CH$_2$CH$_3$)$_2$, then R3 is not —OH or if R3 is —OH then one or more R1 and R4-R9 has a substituent which is not hydro or a carbon, (2), if R2 is —C(=O)OH, then R3 is not —OH, —SH, —Cl, —NH$_2$, —OCH$_3$, —NHC(=O)CH$_3$, (3) R6 and R7 cannot be taken together to form a 6 member unsubstituted aryl ring, (4) R8 and R9 cannot be taken together to form a 6 member unsubstituted aryl ring, and/or (5) R11 is not para-bromo substituted phenyl.

According to another embodiment of the first aspect of the invention, in the compounds of Formula II, R2 is chosen from —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, —C(CH$_3$)$_2$C(=O)OH, —C(=O)NH$_2$, —C(=O)NHCH$_3$, —C(=O)N(CH$_3$)$_2$, —S(=O)$_2$(C$_{1-3}$ alkyl), —S(=O)$_2$NH$_2$, —S(=O)$_2$NHCH$_3$, —S(=O)$_2$N(CH$_3$)$_2$, —C(=O)NH(C$_{1-3}$ alkyl), —C(=O)N(C$_{1-3}$ alkyl)$_2$, —S(=O)$_2$NH$_2$, and —S(=O)$_2$N(C$_{1-3}$alkyl)$_2$.

According to still another embodiment of the first aspect of the invention, in the compounds of Formula II, R3 is chosen from -L-C(=O)OH, -L-CH=CHC(=O)OH, -L-CH$_2$CH$_2$C(=O)OH, -L-CH$_2$CH$_2$CH$_2$C(=O)OH, -L-C(CH$_2$CH$_2$)C(=O)OH, -L-CH(CH$_3$)C(=O)OH, -L-CH(CH$_2$CH$_3$)C(=O)OH, -L-C(CH$_3$)(CH$_2$CH$_3$)C(=O)OH, -L-CH=C(CH$_3$)C(=O)OH, -L-C(CH$_2$CH$_3$)$_2$C(=O)OH, -L-CH$_2$C(=O)OH, -L-C(CH$_3$)$_2$C(=O)OH, -L-C(=O)NH$_2$, -L-C(=O)NHCH$_3$, -L-C(=O)N(CH$_3$)$_2$, -L-S(=O)$_2$(C$_{1-3}$alkyl), -L-S(=O)$_2$NH$_2$, -L-S(=O)$_2$NHCH$_3$, -L-S(=O)$_2$N(CH$_3$)$_2$, -L-C(=O)NH(C$_{1-3}$ alkyl), -L-C(=O)N(C$_{1-3}$alkyl)$_2$, -L-S(=O)$_2$NH$_2$, and -L-S(=O)$_2$N(C$_{1-3}$alkyl)$_2$. In one sub-embodiment, if R3 is —C(=O)NH$_2$ then R2 is not hydroxyl or if R3 is —C(=O)NH$_2$ or —C(=O)OH then one or more of a 4-7 member aryl or cycloalkyl formed from two adjacent of R6-R9, R2, R3, R4, R5, R6, R7, R8, R9, R10 and R11, is substituted with one or more non-hydrogen substituents excluding R6-R9 attachments to form another ring system.

According to another embodiment of the first aspect of the invention, in the compounds of Formula II, R3 is chosen from —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_2$CH$_2$CH$_3$)C(=O)OH, —CH=C(CH$_3$)C(=O)OH, —C(CH$_2$CH$_3$)$_2$C(=O)OH, —CH$_2$C(=O)OH, —C(CH$_3$)$_2$C(=O)OH, —C(=O)NH$_2$, —C(=O)NHCH$_3$, —C(=O)N(CH$_3$)$_2$, —S(=O)$_2$(C$_{1-3}$ alkyl), —S(=O)$_2$NH$_2$, —S(=O)$_2$NHCH$_3$, —S(=O)$_2$N(CH$_3$)$_2$, —C(=O)NH(C$_{1-3}$alkyl), —C(=O)N(C$_{1-3}$alkyl)$_2$, —S(=O)$_2$NH$_2$, and —S(=O)$_2$N(C$_{1-3}$alkyl)$_2$.

According to another embodiment of the first aspect of the invention, in the compounds of Formula II, R4 is chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, —C(CH$_3$)$_2$C(=O)OH, —C(=O)NH$_2$, —C(=O)NHCH$_3$, —C(=O)N(CH$_3$)$_2$, —S(=O)$_2$(C$_{1-3}$alkyl), —S(=O)$_2$NH$_2$, —S(=O)$_2$NHCH$_3$, —S(=O)$_2$N(CH$_3$)$_2$, —C(=O)NH(C$_{1-3}$alkyl), —C(=O)N(C$_{1-3}$ alkyl)$_2$, —S(=O)$_2$NH$_2$, and —S(=O)$_2$N(C$_{1-3}$alkyl)$_2$.

According to yet another embodiment of the first aspect of the invention, in the compounds of Formula II, R5 is chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, —C(CH$_3$)$_2$C(=O)OH, —C(=O)NH$_2$, —C(=O)NHCH$_3$, —C(=O)N(CH$_3$)$_2$, —S(=O)$_2$(C$_{1-3}$alkyl), —S(=O)$_2$NH$_2$, —S(=O)$_2$NHCH$_3$, —S(=O)$_2$N(CH$_3$)$_2$, —C(=O)NH(C$_{1-3}$alkyl), —C(=O)N(C$_{1-3}$ alkyl)$_2$, —S(=O)$_2$NH$_2$, and —S(=O)$_2$N(C$_{1-3}$ alkyl)$_2$.

According to one embodiment of the first aspect of the invention, R8 and R9 in the compounds of Formula I are taken together to form a 6 member aryl ring as in Formula III.

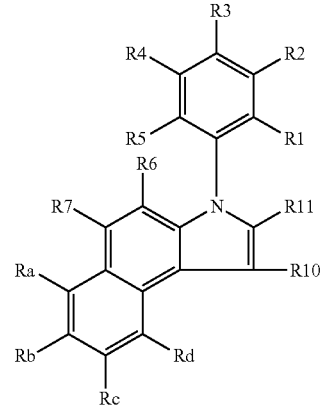

FORMULA III

According to one embodiment of the first aspect of the invention, compounds of Formula III are provided wherein Ra, Rb, Rc, and Rd are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)₂(C₁₋₃ alkyl), —S(=O)₂NH₂, —S(=O)₂N(C₁₋₃ alkyl)₂, —S(=O)₂NH(C₁₋₃ alkyl), —CHF₂, —OCF₃, —OCHF₂, —SCF₃, —CF₃, —CN, —NH₂, —NO₂, —C(=O)—N-morpholino, -cyclohexyl, -morpholino, -pyrrolidinyl, -piperazinyl, —(N-methyl)-piperazinyl, —OCH₂-phenyl, -pyridinyl, methylenedioxy, ethylenedioxy, —C(=O)OCH₂CH₃ substituted furanyl, para-(C(=O)OCH₂CH₃)-phenyl, and —O—Si(CH₃)₂(C(CH₃)₃); and the other variables can be defined as in one of the other embodiments of the first aspect of the invention.

According to one embodiment of the first aspect of the invention, R8 and R9 in the compounds of Formula II are taken together to form a 6 member aryl ring as in Formula IV.

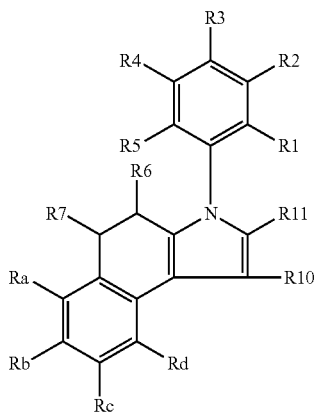

FORMULA IV

According to one embodiment of the first aspect of the invention, compounds of Formula IV are provided wherein Ra, Rb, Rc, and Rd are independently chosen from hydro, hydroxyl, halo, alkyl, alkoxy, haloalkyl, haloalkoxy, —N(C₁₋₃ alkyl)₂, —NH(C₁₋₃ alkyl), —C(=O)NH₂, —C(=O)NH(C₁₋₃ alkyl), —C(=O)N(C₁₋₃ alkyl)₂, —S(=O)₂(C₁₋₃ alkyl), —S(=O)₂NH₂, —S(=O)₂N(C₁₋₃ alkyl)₂, —S(=O)₂NH(C₁₋₃ alkyl), —CHF₂, —OCF₃, —OCHF₂, —SCF₃, —CF₃, —CN, —NH₂, —NO₂, —C(=O)—N-morpholino, -cyclohexyl, -morpholino, -pyrrolidinyl, -piperazinyl, —(N-methyl)-piperazinyl, —OCH₂-phenyl, -pyridinyl, methylenedioxy, ethylenedioxy, —C(=O)OCH₂CH₃ substituted furanyl, para-(C(=O)OCH₂CH₃)-phenyl, and —O—Si(CH₃)₂(C(CH₃)₃); and the other variables can be defined as in one of the other embodiments of the first aspect of the invention.

In a second aspect, the invention provides compounds of Formula I and II:

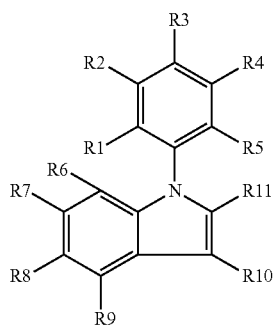

FORMULA I

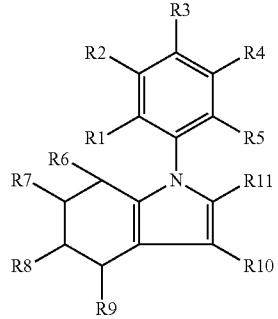

FORMULA II wherein R1-R5 are independently chosen from hydro, hydroxyl, halo, alkyl, alkoxy, haloalkyl, haloalkoxy, —N(C₁₋₃ alkyl)₂, —NH(C₁₋₃ alkyl), —C(=O)NH₂, —C(=O)NH(C₁₋₃ alkyl), —C(=O)N(C₁₋₃ alkyl)₂, —S(=O)₂(C₁₋₃alkyl), —S(=O)₂NH₂, —S(=O)₂N(C₁₋₃ alkyl)₂, —S(=O)₂NH(C₁₋₃ alkyl), —CHF₂, —OCF₃, —OCHF₂, —SCF₃, —CF₃, —CN, —NH₂, and —NO₂;

one or more of R6-R9 are chosen from -L-C(=O)OH, -L-CH=CHC(=O)OH, -L-C(=O)NH₂, -L-C(=O)NH(C₁₋₃ alkyl), -L-C(=O)N(C₁₋₃ alkyl)₂, -L-S(=O)₂(C₁₋₃alkyl), -L-S(=O)₂NH₂, -L-S(=O)₂N(C₁₋₃ alkyl)₂, -L-S(=O)₂NH(C₁₋₃ alkyl), -L-C(=O)NHOH, -L-C(=O)CH₂NH₂, -L-C(=O)CH₂OH, -L-C(=O)CH₂SH, -L-C(=O)NHCN, -L-NHC(=O)OR$_o$, -L-C(=O)NHR$_o$, -L-NH(C=O)NHR$_o$, -L-C(=O)N(R$_o$)₂, -L-NH(C=O)N(R$_o$)₂, -L-sulfo, -L-(2,6 difluorophenol), -L-phosphono, and -L-tetrazolyl; or two adjacent of R6-R9 can be taken together to form a 4-7 member substituted aryl or cycloalkyl ring wherein the substituent is chosen from -L-C(=O)OH, -L-CH=CHC(=O)OH, -L-C(=O)NH₂, -L-C(=O)NH (C₁₋₃ alkyl), -L-C(=O)N(C₁₋₃ alkyl)₂, -L-S(=O)₂(C₁₋₃ alkyl), -L-S(=O)₂NH₂, -L-S(=O)₂N(C₁₋₃ alkyl)₂, -L-S(=O)₂NH(C₁₋₃ alkyl), -L-C(=O)NHOH, -L-C(=O)CH₂NH₂, -L-C(=O)CH₂OH, -L-C(=O)CH₂SH, -L-C(=O)NHCN, -L-NHC(=O)OR$_o$, -L-C(=O)NHR$_o$, -L-NH(C=O)NHR$_o$, -L-C(=O)N(R$_o$)₂, -L-NH(C=O)N(R$_o$)₂, -L-sulfo, -L-(2,6 difluorophenol), -L-phosphono, and -L-tetrazolyl; and the others of R6-R9, independent of one another, are chosen from hydro, hydroxyl, halo, alkyl, alkoxy, haloalkyl, haloalkoxy, —N(C₁₋₃ alkyl)₂, —NH(C₁₋₃ alkyl), —C(=O)NH₂, —C(=O)NH(C₁₋₃ alkyl), —C(=O)N(C₁₋₃ alkyl)₂, —S(=O)₂(C₁₋₃ alkyl), —S(=O)₂NH₂, —S(=O)₂N (C₁₋₃ alkyl)₂, —S(=O)₂NH(C₁₋₃ alkyl), —CHF₂, —OCF₃, —OCHF₂, —SCF₃, —CF₃, —CN, —NH₂, and —NO₂;

R10 is chosen from hydro, hydroxyl, halo, alkyl, alkoxy, haloalkyl, haloalkoxy, —N(C₁₋₃ alkyl)₂, —NH(C₁₋₃ alkyl), —C(=O)NH₂, —C(=O)NH(C₁₋₃ alkyl), —C(=O)N(C₁₋₃ alkyl)₂, —S(=O)₂(C₁₋₃alkyl), —S(=O)₂NH₂, —S(=O)₂N (C₁₋₃ alkyl)₂, —S(=O)₂NH(C₁₋₃ alkyl), —CHF₂, —OCF₃, —OCHF₂, —SCF₃, —CF₃, —CN, —NH₂, and —NO₂;

R$_o$ is chosen from alkyl and haloalkyl;
R11 is an optionally substituted phenyl group; and
L is as defined above.

In one sub-embodiment, the compound is not 1,2-diphenyl-indole-4-acetic acid.

According to one embodiment of the second aspect of the invention, one of R6-R9 is chosen from —C(=O)OH, —CH=CHC(=O)OH, —CH₂CH₂C(=O)OH, —CH₂CH₂CH₂C(=O)OH, —C(CH₂CH₂)C(=O)OH, —CH(CH₃)C(=O)OH, —CH(CH₂CH₃)C(=O)OH, —C(CH₂CH₂CH₃)=O)OH, —CH=C(CH₃)C(=O)OH, —C(CH$_2$CH$_3$)$_2$C(=O)OH, —CH$_2$C(=O)OH, —C(CH$_3$)$_2$C(=O)OH, —C(=O)NH$_2$, —C(=O)NHCH$_3$, —C(=O)N(CH$_3$)$_2$, —S(=O)$_2$(C$_{1-3}$ alkyl), —S(=O)$_2$NH$_2$, —S(=O)$_2$NHCH$_3$, —S(=O)$_2$N(CH$_3$)$_2$, —C(=O)NH(C$_{1-3}$alkyl), —C(=O)N(C$_{1-3}$alkyl)$_2$, —S(=O)$_2$NH$_2$, and —S(=O)$_2$N(C$_{1-3}$alkyl)$_2$.

In another embodiment of this second aspect of the invention, one of R6-R9 is chosen from —C(=O)OH, —CH=CHC(=O)OH, —CH$_2$CH$_2$C(=O)OH, —CH$_2$CH$_2$CH$_2$C(=O)OH, —C(CH$_2$CH$_3$)C(=O)OH, —CH(CH$_3$)C(=O)OH, —CH(CH$_2$CH$_3$)C(=O)OH, —C(CH$_3$)(CH$_2$CH$_3$)=O)OH, —CH=C(CH$_3$)C(=O)OH, —C(CH$_2$CH$_3$)$_2$C(=O)OH, —CH$_2$C(=O)OH, and —C(CH$_3$)$_2$C(=O)OH; or two adjacent of R6-R9 can be taken together to form a 4-7 member aryl or cycloalkyl ring substituted with one or more substituents chosen from —C(=O)OH, —CH=CHC(=O)OH, —CH$_2$CH$_2$C(=O)OH, —CH$_2$CH$_2$CH$_2$C(=O)OH, —C(CH$_2$CH$_3$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, and —C(CH$_3$)$_2$C(=O)OH; and the others of R6-R9 are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$;

R1-R5 and R10, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$; and R11 is an optionally substituted phenyl.

In one embodiment of the second aspect of the invention, R6 is chosen from -L-C(=O)OH, -L-CH=CHC(=O)OH, -L-CH$_2$CH$_2$C(=O)OH, -L-CH$_2$CH$_2$CH$_2$C(=O)OH, -L-C(CH$_2$CH$_2$)C(=O)OH, -L-CH(CH$_3$)C(=O)OH, -L-CH(CH$_2$CH$_3$)C(=O)OH, -L-C(CH$_3$)(CH$_2$CH$_3$)C(=O)OH, -L-CH=C(CH$_3$)C(=O)OH, -L-C(CH$_2$CH$_3$)$_2$C(=O)OH, -L CH$_2$C(=O)OH, -L-C(CH$_3$)$_2$C(=O)OH, -L-C(=O)NH$_2$, -L-C(=O)NHCH$_3$, -L-C(=O)N(CH$_3$)$_2$, -L-S(=O)$_2$(C$_{1-3}$alkyl), -L-S(=O)$_2$NH$_2$, -L-S(=O)$_2$NHCH$_3$, -L-S(=O)$_2$N(CH$_3$)$_2$, -L-C(=O)NH(C$_{1-3}$ alkyl), -L-C(=O)N(C$_{1-3}$alkyl)$_2$, -L-S(=O)$_2$NH$_2$, and -L-S(=O)$_2$N(C$_{1-3}$alkyl)$_2$.

In one embodiment of the second aspect of the invention, R6 is chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, —C(CH$_3$)$_2$C(=O)OH, —C(=O)NH$_2$, —C(=O)NHCH$_3$, —C(=O)N(CH$_3$)$_2$, —S(=O)$_2$(C$_{1-3}$ alkyl), —S(=O)$_2$NH$_2$, —S(=O)$_2$NHCH$_3$, —S(=O)$_2$N(CH$_3$)$_2$, —C(=O)NH(C$_{1-3}$alkyl), —C(=O)N(C$_{1-3}$alkyl)$_2$, —S(=O)$_2$NH$_2$, and —S(=O)$_2$N(C$_{1-3}$alkyl)$_2$.

In one embodiment of the second aspect of the invention, R7 is chosen from -L-C(=O)OH, -L-CH=CHC(=O)OH, -L-CH$_2$CH$_2$C(=O)OH, -L-CH$_2$CH$_2$CH$_2$C(=O)OH, -L-C(CH$_2$CH$_2$)C(=O)OH, -L-CH(CH$_3$)C(=O)OH, -L-CH(CH$_2$CH$_3$)C(=O)OH, -L-C(CH$_3$)(CH$_2$CH$_3$)C(=O)OH, -L-CH=C(CH$_3$)C(=O)OH, -L-C(CH$_2$CH$_3$)$_2$C(=O)OH, -L CH$_2$C(=O)OH, -L-C(CH$_3$)$_2$C(=O)OH, -L-C(=O)NH$_2$, -L-C(=O)NHCH$_3$, -L-C(=O)N(CH$_3$)$_2$, -L-S(=O)$_2$(C$_{1-3}$alkyl), -L-S(=O)$_2$NH$_2$, -L-S(=O)$_2$NHCH$_3$, -L-S(=O)$_2$N(CH$_3$)$_2$, -L-C(=O)NH(C$_{1-3}$ alkyl), -L-C(=O)N(C$_{1-3}$alkyl)$_2$, -L-S(=O)$_2$NH$_2$, and -L-S(=O)$_2$N(C$_{1-3}$alkyl)$_2$.

In one embodiment of the second aspect of the invention, R7 is chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_2$CH$_2$CH$_3$)=O)OH, —CH=C(CH$_3$)C(=O)OH, —C(CH$_2$CH$_3$)$_2$C(=O)OH, —CH$_2$C(=O)OH, —C(CH$_3$)$_2$C(=O)OH, —C(=O)NH$_2$, —C(=O)NHCH$_3$, —C(=O)N(CH$_3$)$_2$, —S(=O)$_2$(C$_{1-3}$ alkyl), —S(=O)$_2$NH$_2$, —S(=O)$_2$NHCH$_3$, —S(=O)$_2$N(CH$_3$)$_2$, —C(=O)NH(C$_{1-3}$alkyl), —C(=O)N(C$_{1-3}$alkyl)$_2$, —S(=O)$_2$NH$_2$, and —S(=O)$_2$N(C$_{1-3}$alkyl)$_2$.

In one embodiment of the second aspect of the invention, R8 is chosen from -L-C(=O)OH, -L-CH=CHC(=O)OH, -L-CH$_2$CH$_2$C(=O)OH, -L-CH$_2$CH$_2$CH$_2$C(=O)OH, —C(CH$_2$CH$_2$)C(=O)OH, -L-CH(CH$_3$)C(=O)OH, -L-CH(CH$_2$CH$_3$)C(=O)OH, -L-C(CH$_3$)(CH$_2$CH$_3$)C(=O)OH, -L-CH=C(CH$_3$)C(=O)OH, -L-C(CH$_2$CH$_3$)$_2$C(=O)OH, -L CH$_2$C(=O)OH, -L-C(CH$_3$)$_2$C(=O)OH, -L-C(=O)NH$_2$, -L-C(=O)NHCH$_3$, -L-C(=O)N(CH$_3$)$_2$, -L-S(=O)$_2$(C$_{1-3}$alkyl), -L-S(=O)$_2$NH$_2$, -L-S(=O)$_2$NHCH$_3$, -L-S(=O)$_2$N(CH$_3$)$_2$, -L-C(=O)NH(C$_{1-3}$ alkyl), -L-C(=O)N(C$_{1-3}$alkyl)$_2$, -L-S(=O)$_2$NH$_2$, and -L-S(=O)$_2$N(C$_{1-3}$alkyl)$_2$.

In one embodiment of the second aspect of the invention, R8 is chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_2$CH$_2$CH$_3$)=O)OH, —CH=C(CH$_3$)C(=O)OH, —C(CH$_2$CH$_3$)$_2$C(=O)OH, —CH$_2$C(=O)OH, —C(CH$_3$)$_2$C(=O)OH, —C(=O)NH$_2$, —C(=O)NHCH$_3$, —C(=O)N(CH$_3$)$_2$, —S(=O)$_2$(C$_{1-3}$ alkyl), —S(=O)$_2$NH$_2$, —S(=O)$_2$NHCH$_3$, —S(=O)$_2$N(CH$_3$)$_2$, —C(=O)NH(C$_{1-3}$alkyl), —C(=O)N(C$_{1-3}$alkyl)$_2$, —S(=O)$_2$NH$_2$, and —S(=O)$_2$N(C$_{1-3}$alkyl)$_2$.

In one embodiment of the second aspect of the invention, R9 is chosen from -L-C(=O)OH, -L-CH=CHC(=O)OH, -L-CH$_2$CH$_2$C(=O)OH, -L-CH$_2$CH$_2$CH$_2$C(=O)OH, -L-C(CH$_2$CH$_2$)C(=O)OH, -L-CH(CH$_3$)C(=O)OH, -L-CH(CH$_2$CH$_3$)C(=O)OH, -L-C(CH$_3$)(CH$_2$CH$_3$)C(=O)OH, -L-CH=C(CH$_3$)C(=O)OH, -L-C(CH$_2$CH$_3$)$_2$C(=O)OH, -L CH$_2$C(=O)OH, -L-C(CH$_3$)$_2$C(=O)OH, -L-C(=O)NH$_2$, -L-C(=O)NHCH$_3$, -L-C(=O)N(CH$_3$)$_2$, -L-S(=O)$_2$(C$_{1-3}$alkyl), -L-S(=O)$_2$NH$_2$, -L-S(=O)$_2$NHCH$_3$, -L-S(=O)$_2$N(CH$_3$)$_2$, -L-C(=O)NH(C$_{1-3}$ alkyl), -L-C(=O)N(C$_{1-3}$alkyl)$_2$, -L-S(=O)$_2$NH$_2$, and -L-S(=O)$_2$N(C$_{1-3}$alkyl)$_2$.

In one embodiment of the second aspect of the invention, R9 is chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —C(CH$_3$)$_2$C(=O)OH, —C(=O)NH$_2$, —C(=O)NHCH$_3$, —C(=O)N(CH$_3$)$_2$, —S(=O)$_2$(C$_{1-3}$ alkyl), —S(=O)$_2$NH$_2$, —S(=O)$_2$NHCH$_3$, —S(=O)$_2$N(CH$_3$)$_2$, —C(=O)NH(C$_{1-3}$alkyl), —C(=O)N(C$_{1-3}$alkyl)$_2$, —S(=O)$_2$NH$_2$, and —S(=O)$_2$N(C$_{1-3}$alkyl)$_2$.

In one embodiment of the second aspect of the invention, R8 and R9 in the compounds of Formula I are taken together to form a 6 member aryl ring as in Formula III.

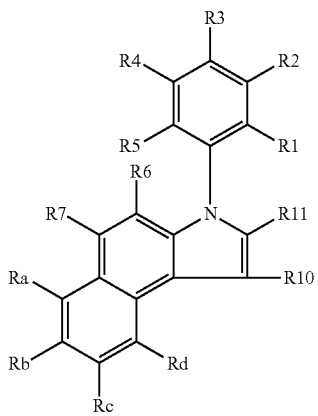

FORMULA III

According to one embodiment of the second aspect of the invention, compounds of Formula III are provided wherein Ra, Rb, Rc, and Rd are independently chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$ alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); and the other variables can be defined as in one of the other embodiments of the second aspect of the invention.

In one embodiment of the second aspect of the invention, R8 and R9 in the compounds of Formula II are taken together to form a 6 member aryl ring as in Formula IV.

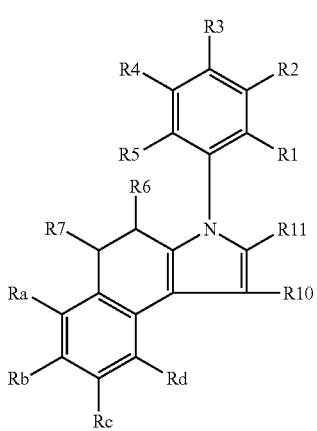

FORMULA IV

According to one embodiment of the second aspect of the invention, compounds of Formula IV are provided wherein Ra, Rb, Rc, and Rd are independently chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$ alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); and the other variables can be defined as in one of the other embodiments of the second aspect of the invention.

In a third aspect, the invention provides compounds of Formula I and II:

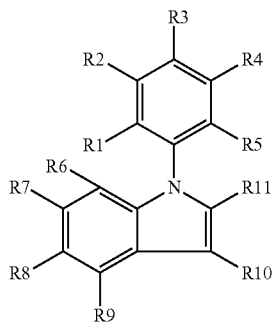

FORMULA I

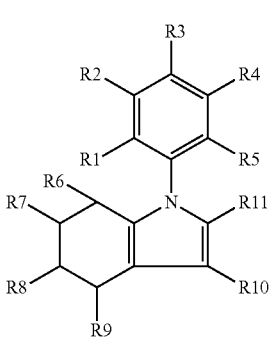

FORMULA II wherein R1-R9 are independently chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl or cycloalkyl ring;

R10 is chosen from L-C(=O)OH, -L-CH=CHC(=O)OH, -L-C(=O)NH$_2$, -L-C(=O)NH($C_{1-3}$ alkyl), -L-C(=O)N($C_{1-3}$ alkyl)$_2$, -L-S(=O)$_2$($C_{1-3}$alkyl), -L-S(=O)$_2$NH$_2$, -L-S(=O)$_2$N($C_{1-3}$ alkyl)$_2$, -L-S(=O)$_2$NH($C_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl;

R$_o$ is chosen from alkyl and haloalkyl; and

L is as defined above.

In one sub-embodiment, the compound is not 1-(O-carboxyphenyl)-2-phenyl-indole-3-carboxylic acid, or the methyl or ethyl ester thereof.

According to one embodiment of this aspect of the invention, R10 is chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_2$CH$_2$CH$_3$)C(=O)OH, —CH=C(CH$_3$)C(=O)OH, —C(CH$_2$CH$_3$)$_2$C(=O)OH, —CH$_2$C(=O)OH, —C(CH$_3$)$_2$C(=O)OH, —C(=O)NH$_2$, —C(=O)NHCH$_3$, —C(=O)N(CH$_3$)$_2$, —S(=O)$_2$(C$_{1-3}$ alkyl), —S(=O)$_2$NH$_2$, —S(=O)$_2$NHCH$_3$, —S(=O)$_2$N(CH$_3$)$_2$, —C(=O)NH(C$_{1-3}$ alkyl), —C(=O)N(C$_{1-3}$ alkyl)$_2$, —S(=O)$_2$NH$_2$, and —S(=O)$_2$N(C$_{1-3}$alkyl)$_2$.

In another embodiment of this third aspect of the invention, R10 is chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, and —C(CH$_3$)$_2$C(=O)OH; R1-R9 are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and NO$_2$; two adjacent of R6-R9 can be taken together to form a 4-7 member optionally substituted aryl or cycloalkyl ring; and R11 is an optionally substituted phenyl.

In one embodiment of the third aspect of the invention, R8 and R9 in the compounds of Formula I are taken together to form a 6 member aryl ring as in Formula III.

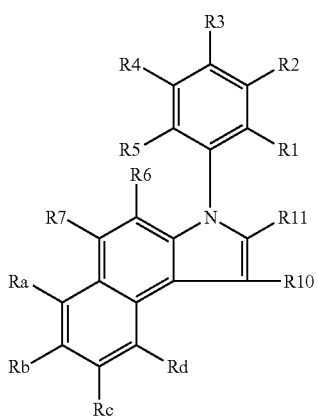

FORMULA III

According to one embodiment of the third aspect of the invention, compounds of Formula III are provided wherein Ra, Rb, Rc, and Rd are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$ (C$_{1-3}$ alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); and the other variables can be defined as in the other embodiments of the third aspect of the invention.

In one embodiment of the third aspect of the invention, R8 and R9 in the compounds of Formula II are taken together to form a 6 member aryl ring as in Formula IV

FORMULA IV

According to one embodiment of the third aspect of the invention, compounds of Formula IV are provided wherein Ra, Rb, Rc, and Rd are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$ alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); and the other variables can be defined as in one of the other embodiments of the third aspect of the invention.

In a fourth aspect, the invention provides compounds of Formula I and II:

FORMULA I

FORMULA II wherein R1-R10 are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl or cycloalkyl ring;

R11 is a phenyl ring substituted with one or more substituents independently chosen from L-C(=O)OH, -L-CH=CHC(=O)OH, -L-C(=O)NH$_2$, -L-C(=O)NH(C$_{1-3}$ alkyl), -L-C(=O)N(C$_{1-3}$ alkyl)$_2$, -L-S(=O)$_2$(C$_{1-3}$ alkyl), -L-S(=O)$_2$NH$_2$, -L-S(=O)$_2$N(C$_{1-3}$ alkyl)$_2$, -L-S(=O)$_2$NH(C$_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl and the others are chosen from hydro, hydroxyl, halo, alkyl, alkoxy, haloalkyl, halo alkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$;

R$_o$ is chosen from alkyl and haloalkyl; and

L is as defined above.

In one sub-embodiment, the compound is not 5-(4,5-dihydro-3-phenyl-3H-benz[e]indol-2-yl)-2-hydroxy-benzoic acid or 2-hydroxy-5-(4,5,6,7-tetrahydro-1-phenyl-1H-indol-2-yl)-benzoic acid.

According to one embodiment of the fourth aspect of the invention, one substituent on the phenyl of R11 is chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, —C(CH$_3$)$_2$C(=O)OH, —C(=O)NH$_2$, —C(=O)NHCH$_3$, —C(=O)N(CH$_3$)$_2$, —S(=O)$_2$(C$_{1-3}$ alkyl), —S(=O)$_2$NH$_2$, —S(=O)$_2$NHCH$_3$, —S(=O)$_2$N(CH$_3$)$_2$, —C(=O)NH(C$_{1-3}$alkyl), —C(=O)N(C$_{1-3}$alkyl)$_2$, —S(=O)$_2$NH$_2$, and —S(=O)$_2$N(C$_{1-3}$alkyl)$_2$.

In another embodiment of fourth aspect of the invention, R11 is a phenyl ring substituted with a substituent chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, and —C(CH$_3$)$_2$C(=O)OH; and the other substituents on the phenyl are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$ alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$;

R1-R10, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and NO$_2$; and two adjacent of R6-R9 can be taken together to form an optionally substituted 4-7 member aryl or cycloalkyl ring.

In one embodiment of the fourth aspect of the invention, R8 and R9 in the compounds of Formula I are taken together to form a 6 member aryl ring as in Formula III.

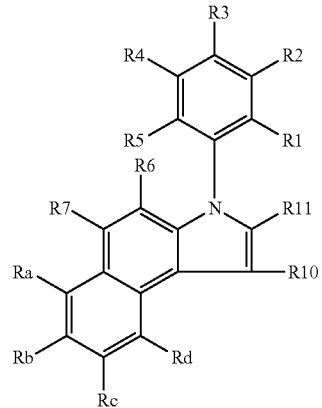

FORMULA III

According to one embodiment of the fourth aspect of the invention, compounds of Formula III are provided wherein Ra, Rb, Rc, and Rd are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$ alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); and the other variables can be defined as in one of the other embodiments of the fourth aspect of the invention.

In one embodiment of the fourth aspect of the invention, R8 and R9 in the compounds of Formula II are taken together to form a 6 member aryl ring as in Formula IV.

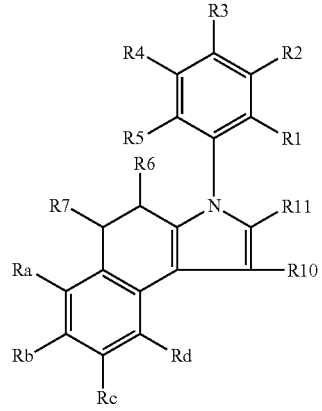

FORMULA IV

According to one embodiment of the fourth aspect of the invention, compounds of Formula IV are provided wherein Ra, Rb, Rc, and Rd are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$ alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); and the other variables can be defined as in the other embodiments of the fourth aspect of the invention.

In a fifth aspect, the invention provides compounds of Formula I and II:

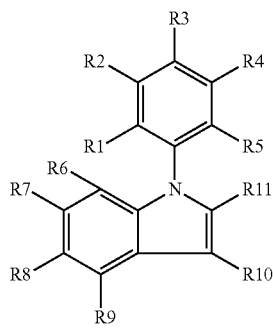

FORMULA I

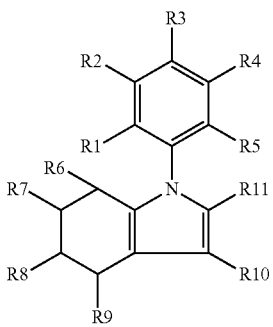

FORMULA II wherein R1-R9 and R11 are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$ alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl or cycloalkyl ring;

R10 is a phenyl ring substituted with one or more substituents independently chosen from -L-C(=O)OH, -L-CH=CHC(=O)OH, -L-C(=O)NH$_2$, -L-C(=O)NH(C$_{1-3}$ alkyl), -L-C(=O)N(C$_{1-3}$ alkyl)$_2$, -L-S(=O)$_2$(C$_{1-3}$alkyl), -L-S(=O)$_2$NH$_2$, -L-S(=O)$_2$N(C$_{1-3}$ alkyl)$_2$, -L-S(=O)$_2$NH(C$_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl;

R$_o$ is chosen from alkyl and haloalkyl; and
L is as defined above.

According to one embodiment of this fifth aspect of the invention, one substituent on the phenyl of R10 is chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, —C(CH$_3$)$_2$C(=O)OH, —C(=O)NH$_2$, —C(=O)NHCH$_3$, —C(=O)N(CH$_3$)$_2$, —S(=O)$_2$NH$_2$, —S(=O)$_2$NHCH$_3$, —S(=O)$_2$N(CH$_3$)$_2$, —C(=O)NH(C$_{1-3}$alkyl), —C(=O)N(C$_{1-3}$alkyl)$_2$, —S(=O)$_2$(C$_{1-3}$alkyl), —S(=O)$_2$NH$_2$, —S(=O)$_2$NH(C$_{1-3}$alkyl), and —S(=O)$_2$N(C$_{1-3}$alkyl)$_2$, and the others are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$ alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$.

In another embodiment of this fifth aspect of the invention, the phenyl group of R10 has a substituent chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, and —C(CH$_3$)$_2$C(=O)OH; and the other substituents are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$ alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and NO$_2$;

R1-R9, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$ alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and NO$_2$; two adjacent of R6-R9 can be taken together to form an optionally substituted 4-7 member aryl or cycloalkyl ring; and R11 is an optionally substituted phenyl.

In one embodiment of the fifth aspect of the invention, R8 and R9 in the compounds of Formula I are taken together to form a 6 member aryl ring as in Formula III.

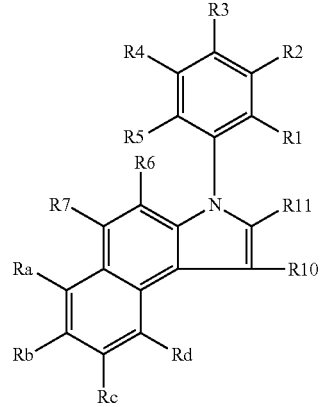

FORMULA III

According to one embodiment of the fifth aspect of the invention, compounds of Formula III are provided wherein Ra, Rb, Rc, and Rd are independently chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$ alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); and the other variables can be defined as in one of the other embodiments of the fifth aspect of the invention.

In one embodiment of the fifth aspect of the invention, R8 and R9 in the compounds of Formula II are taken together to form a 6 member aryl ring as in Formula IV.

FORMULA IV

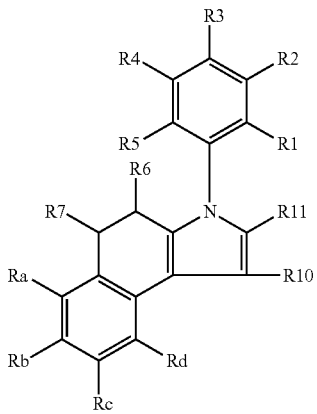

According to one embodiment of the fifth aspect of the invention, compounds of Formula IV are provided wherein Ra, Rb, Rc, and Rd are independently chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$ ($C_{1-3}$ alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); and the other variables can be defined as in one of the other embodiments of the fifth aspect of the invention.

In a sixth aspect, the invention provides compounds of Formula I and II:

FORMULA I

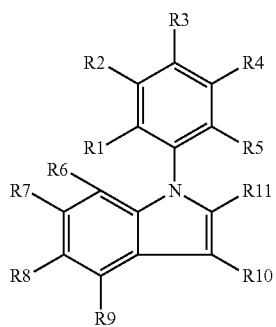

FORMULA II

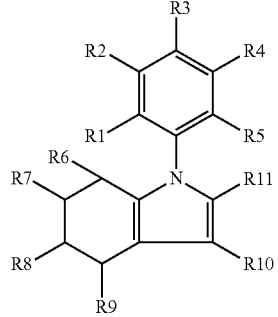

wherein R1-R9 and R11 are independently chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl or cycloalkyl ring;

R10 is -L-R12 wherein L is as defined above; and

R12 is a phenyl ring substituted with one or more substituents independently chosen from of L-C(=O)OH, -L-CH=CHC(=O)OH, -L-C(=O)NH$_2$, -L-C(=O)NH ($C_{1-3}$ alkyl), -L-C(=O)N($C_{1-3}$ alkyl)$_2$, -L-S(=O)$_2$ ($C_{1-3}$alkyl), -L-S(=O)$_2$NH$_2$, -L-S(=O)$_2$N($C_{1-3}$ alkyl)$_2$, -L-S(=O)$_2$NH($C_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl;

R$_o$ is chosen from alkyl and haloalkyl; and

L is as defined above.

According to one embodiment of the sixth aspect of the invention, one substituent on the phenyl of R12 is chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, —C(CH$_3$)$_2$C(=O)OH, —C(=O)NH$_2$, —C(=O)NHCH$_3$, —C(=O)N(CH$_3$)$_2$, —S(=O)$_2$NH$_2$, —S(=O)$_2$NHCH$_3$, —S(=O)$_2$N(CH$_3$)$_2$, —C(=O)NH($C_{1-3}$alkyl), —C(=O)N ($C_{1-3}$ alkyl)$_2$, —S(=O)$_2$($C_{1-3}$alkyl), —S(=O)$_2$NH$_2$, —S(=O)$_2$N($C_{1-3}$ alkyl), and —S(=O)$_2$N($C_{1-3}$ alkyl)$_2$, and the others are independently chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$ alkyl), —S(=O)$_2$NH$_2$, —S(=O)$_2$N($C_{1-3}$ alkyl)$_2$, —S(=O)$_2$NH ($C_{1-3}$ alkyl), —CHF$_2$, —OCF$_3$, —OCHF$_2$, —SCF$_3$, —CF$_3$, —CN, —NH$_2$, and —NO$_2$.

In another embodiment of this sixth aspect of the invention, one of the substituents of R12 is chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH₃)C(=O)OH, —CH(CH₂CH₃)C(=O)OH, —C(CH₃)(CH₂CH₃)C(=O)OH, —CH=C(CH₃)C(=O)OH, —C(CH₂CH₃)₂C(=O)OH, —CH₂C(=O)OH, and —C(CH₃)₂C(=O)OH; and the others are independently chosen from hydro, hydroxyl, halo, alkyl, alkoxy, haloalkyl, haloalkoxy, —N(C$_{1-3}$ alkyl)₂, —NH(C$_{1-3}$ alkyl), —C(=O)NH₂, —C(=O)NH(C$_{1-3}$ alkyl), —C(=O)N(C$_{1-3}$ alkyl)₂, —S(=O)₂(C$_{1-3}$ alkyl), —S(=O)₂NH₂, —S(=O)₂N(C$_{1-3}$ alkyl)₂, —S(=O)₂NH(C$_{1-3}$ alkyl), —CHF₂, —OCF₃, —OCHF₂, —SCF₃, —CF₃, —CN, —NH₂, and —NO₂;

R1-R9, and R11, independent of one another, are chosen from hydro, hydroxyl, halo, alkyl, alkoxy, haloalkyl, haloalkoxy, —N(C$_{1-3}$ alkyl)₂, —NH(C$_{1-3}$ alkyl), —C(=O)NH₂, —C(=O)NH(C$_{1-3}$ alkyl), —C(=O)N(C$_{1-3}$ alkyl)₂, —S(=O)₂(C$_{1-3}$ alkyl), —S(=O)₂NH₂, —S(=O)₂N(C$_{1-3}$ alkyl)₂, —S(=O)₂NH(C$_{1-3}$ alkyl), —CHF₂, —OCF₃, —OCHF₂, —SCF₃, —CF₃, —CN, —NH₂, and —NO₂; and two adjacent of R6-R9 can be taken together to form an optionally substituted 4-7 member aryl or cycloalkyl ring.

In one embodiment of the sixth aspect of the invention, R8 and R9 in the compounds of Formula I are taken together to form a 6 member aryl ring as in Formula III.

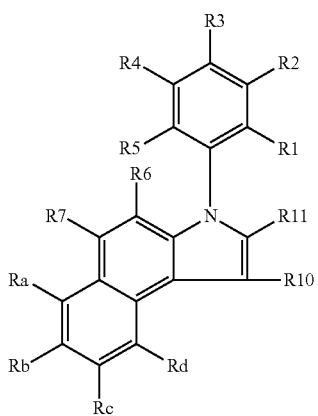

FORMULA III

According to one embodiment of the sixth aspect of the invention, compounds of Formula III are provided wherein Ra, Rb, Rc, and Rd are independently chosen from hydro, hydroxyl, halo, alkyl, alkoxy, haloalkyl, haloalkoxy, —N(C$_{1-3}$ alkyl)₂, —NH(C$_{1-3}$ alkyl), —C(=O)NH₂, —C(=O)NH(C$_{1-3}$ alkyl), —C(=O)N(C$_{1-3}$ alkyl)₂, —S(=O)₂ (C$_{1-3}$ alkyl), —S(=O)₂NH₂, —S(=O)₂N(C$_{1-3}$ alkyl)₂, —S(=O)₂NH(C$_{1-3}$ alkyl), —CHF₂, —OCF₃, —OCHF₂, —SCF₃, —CF₃, —CN, —NH₂, —NO₂, —C(=O)—N-morpholino, -cyclohexyl, -morpholino, -pyrrolidinyl, -piperazinyl, —(N-methyl)-piperazinyl, —OCH₂-phenyl, -pyridinyl, methylenedioxy, ethylenedioxy, —C(=O)OCH₂CH₃ substituted furanyl, para-(C(=O)OCH₂CH₃)-phenyl, and —O—Si(CH₃)₂(C(CH₃)₃); and the other variables can be defined as in one of the other embodiments of the sixth aspect of the invention.

In one embodiment of the sixth aspect of the invention, R8 and R9 in the compounds of Formula II are taken together to form a 6 member aryl ring as in Formula IV.

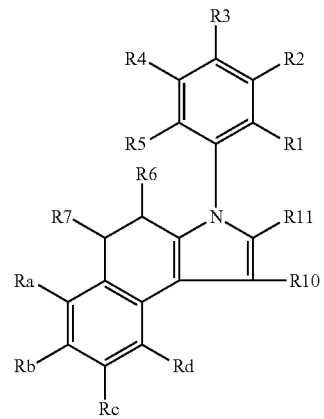

FORMULA IV

According to one embodiment of the sixth aspect of the invention, compounds of Formula IV are provided wherein Ra, Rb, Rc, and Rd are independently chosen from hydro, hydroxyl, halo, alkyl, alkoxy, haloalkyl, haloalkoxy, —N(C$_{1-3}$ alkyl)₂, —NH(C$_{1-3}$ alkyl), —C(=O)NH₂, —C(=O)NH(C$_{1-3}$ alkyl), —C(=O)N(C$_{1-3}$ alkyl)₂, —S(=O)₂ (C$_{1-3}$ alkyl), —S(=O)₂NH₂, —S(=O)₂N(C$_{1-3}$ alkyl)₂, —S(=O)₂NH(C$_{1-3}$ alkyl), —CHF₂, —OCF₃, —OCHF₂, —SCF₃, —CF₃, —CN, —NH₂, —NO₂, —C(=O)—N-morpholino, -cyclohexyl, -morpholino, -pyrrolidinyl, -piperazinyl, —(N-methyl)-piperazinyl, —OCH₂-phenyl, -pyridinyl, methylenedioxy, ethylenedioxy, —C(=O)OCH₂CH₃ substituted furanyl, para-(C(=O)OCH₂CH₃)-phenyl, and —O—Si(CH₃)₂(C(CH₃)₃); and the other variables can be defined as in one of the other embodiments of the sixth aspect of the invention.

In a seventh embodiment, the invention provides compounds of Formula I and II:

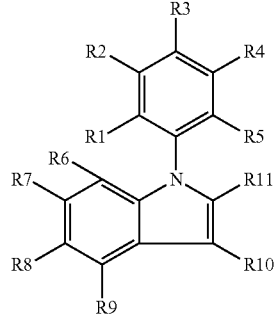

FORMULA I

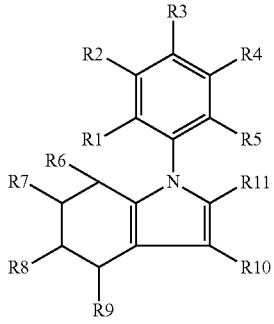

FORMULA II wherein R1-R10 are independently chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O) OCH$_2$CH$_3$)-phenyl, and —O—Si(CH$_3$)$_2$(C(CH$_3$)$_3$); two adjacent of R6-R9 can be taken together to form a 4-7 member optionally substituted aryl or cycloalkyl ring;

R11 is -L-R12 wherein L is as defined above; and

R12 is a phenyl ring substituted with one or more substituents independently chosen from -L-C(=O)OH, -L-CH=CHC(=O)OH, -L-C(=O)NH$_2$, -L-C(=O)NH ($C_{1-3}$ alkyl), -L-C(=O)N($C_{1-3}$ alkyl)$_2$, -L-S(=O)$_2$ ($C_{1-3}$alkyl), -L-S(=O)$_2$NH$_2$, -L-S(=O)$_2$N($C_{1-3}$ alkyl)$_2$, -L-S(=O)$_2$NH($C_{1-3}$ alkyl), -L-C(=O)NHOH, -L-C(=O) CH$_2$NH$_2$, -L-C(=O)CH$_2$OH, -L-C(=O)CH$_2$SH, -L-C (=O)NHCN, -L-NHC(=O)OR$_o$, -L-C(=O)NHR$_o$, -L-NH (C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl, and the others are independently chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, and —NO$_2$;

R$_o$ is chosen from alkyl and haloalkyl; and

L is as defined above.

According to one embodiment of this seventh aspect of the invention, one substituent on the phenyl of R12 is chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O) OH, —C(CH$_2$CH$_3$)$_2$C(=O)OH, —CH$_2$C(=O)OH, —C(CH$_3$)$_2$C(=O)OH, —C(=O)NH$_2$, —C(=O)NHCH$_3$, —C(=O)N(CH$_3$)$_2$, —S(=O)$_2$($C_{1-3}$ alkyl), —S(=O)$_2$NH$_2$, —S(=O)$_2$NHCH$_3$, —S(=O)$_2$N(CH$_3$)$_2$, —C(=O)NH ($C_{1-3}$alkyl), —C(=O)N($C_{1-3}$alkyl)$_2$, —S(=O)$_2$NH$_2$, -and —S(=O)$_2$N($C_{1-3}$alkyl)$_2$, and the others are independently chosen from hydro, hydroxyl, halo, alkyl, alkoxy, haloalkyl, haloalkoxy, —N($C_{1-3}$ alkyl)$_2$, —NH($C_{1-3}$ alkyl), —C(=O) NH$_2$, —C(=O)NH($C_{1-3}$ alkyl), —C(=O)N($C_{1-3}$ alkyl)$_2$, —S(=O)$_2$($C_{1-3}$ alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, and —NO$_2$.

In another embodiment of this seventh aspect of the invention, one substituent on the phenyl of R12 is chosen from —C(=O)OH, —CH=CHC(=O)OH, —CH$_2$CH$_2$C(=O) OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O) OH, —C(CH$_2$CH$_3$)$_2$C(=O)OH, —CH$_2$C(=O)OH, and —C(CH$_3$)$_2$C(=O)OH; and the others are independently chosen from hydro, hydroxyl, halo, alkyl, alkoxy, haloalkyl, haloalkoxy, —N($C_{1-3}$ alkyl)$_2$, —NH($C_{1-3}$ alkyl), —C(=O) NH$_2$, —C(=O)NH($C_{1-3}$ alkyl), —C(=O)N($C_{1-3}$ alkyl)$_2$, —S(=O)$_2$($C_{1-3}$ alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, and NO$_2$;

R1-R10, independent of one another, are chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$ alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, and NO$_2$; two adjacent of R6-R9 can be taken together to form an optionally substituted 4-7 member aryl or cycloalkyl ring; and R11 is an optionally substituted phenyl.

In one embodiment of the seventh aspect of the invention, R8 and R9 in the compounds of Formula I are taken together to form a 6 member aryl ring as in Formula III

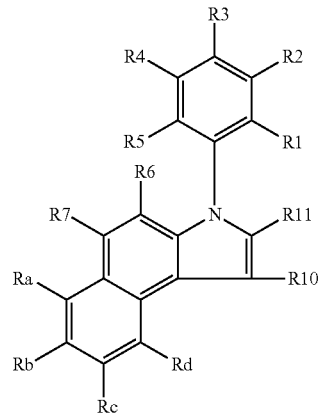

FORMULA III

According to one embodiment of the seventh aspect of the invention, compounds of Formula III are provided wherein Ra, Rb, Rc, and Rd are independently chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$ alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O) OCH$_2$CH$_3$)-phenyl, and —O—Si(CH$_3$)$_2$(C(CH$_3$)$_3$); and the other variables can be defined as in one of the other embodiments of the seventh aspect of the invention.

In one embodiment of the seventh aspect of the invention, R8 and R9 in the compounds of Formula II are taken together to form a 6 member aryl ring as in Formula IV.

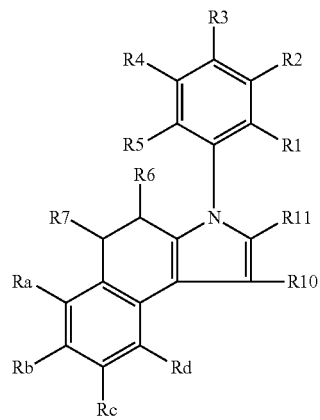

FORMULA IV

According to one embodiment of the seventh aspect of the invention, compounds of Formula IV are provided wherein Ra, Rb, Rc, and Rd are independently chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$ alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); and the other variables can be defined as in one of the other embodiments of the seventh aspect of the invention.

In an eighth embodiment, the invention provides compounds of Formula I and II:

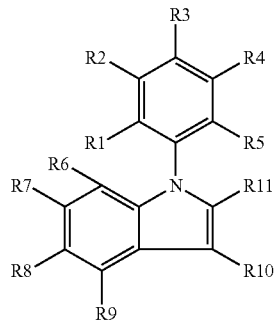

FORMULA I

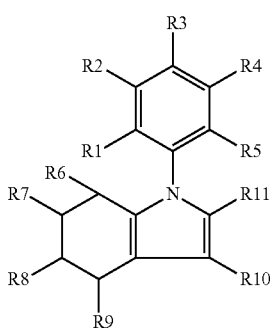

FORMULA II wherein R1-R9 are independently chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl ring;

R10 and R11 are independently chosen from hydro, hydroxyl, halo, alkyl, alkoxy, haloalkyl, haloalkoxy, —N($C_{1-3}$ alkyl)$_2$, —NH($C_{1-3}$ alkyl), —S(=O)$_2$($C_{1-3}$ alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, —NO$_2$, and L-R12; and R12 is a phenyl ring substituted with one or more substituents independently chosen from L-C(=O)OH, -L-CH=CHC(=O)OH, -L-C(=O)NH$_2$, -L-C(=O)NH($C_{1-3}$ alkyl), -L-C(=O)N($C_{1-3}$ alkyl)$_2$, -L-S(=O)$_2$($C_{1-3}$ alkyl), -L-S(=O)$_2$NH$_2$, -L-S(=O)$_2$N($C_{1-3}$ alkyl)$_2$, -L-S(=O)$_2$NH($C_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl;

R$_o$ is chosen from alkyl and haloalkyl; and

L is as defined above.

According to one embodiment of the eighth of the invention, R12 is present and one substituent on the phenyl of R12 is chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, —C(CH$_3$)$_2$C(=O)OH, —C(=O)NH$_2$, —C(=O)NHCH$_3$, —C(=O)N(CH$_3$)$_2$, —S(=O)$_2$NH$_2$, —S(=O)$_2$NHCH$_3$, —S(=O)$_2$N(CH$_3$)$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$NH($C_{1-3}$ alkyl), and —S(=O)$_2$N($C_{1-3}$ alkyl)$_2$, and the others are independently chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, and —NO$_2$.

In another embodiment of the eighth aspect of the invention, R12 is present and one substituent on the phenyl of R12 is chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, and —C(CH$_3$)$_2$C(=O)OH; and the others are independently chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$ alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, and —NO$_2$;

R1-R9, independent of one another, are chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, and —NO$_2$; two adjacent of R6-R9 can be taken together to form an optionally substituted 4-7 member aryl or cycloalkyl ring.

In one embodiment of the eighth aspect of the invention, R8 and R9 in the compounds of Formula I are taken together to form a 6 member aryl ring as in Formula III.

FORMULA III

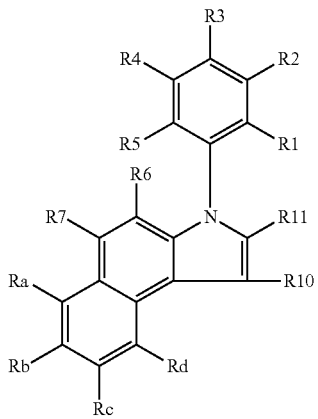

According to one embodiment of the eighth aspect of the invention, compounds of Formula III are provided wherein Ra, Rb, Rc, and Rd are independently chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$ alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); and the other variables can be defined as in one of the other embodiments of the eighth aspect of the invention.

In one embodiment of the eighth aspect of the invention, R8 and R9 in the compounds of Formula II are taken together to form a 6 member aryl ring as in Formula IV.

FORMULA IV

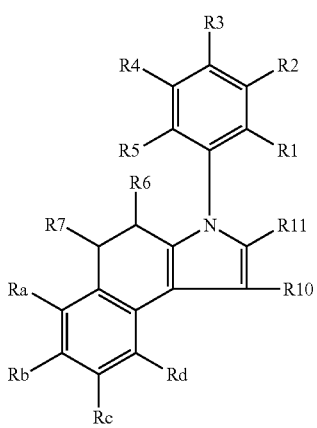

According to one embodiment of the eighth aspect of the invention, compounds of Formula IV are provided wherein Ra, Rb, Rc, and Rd are independently chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$ alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); and the other variables can be defined as in one of the other embodiments of the eighth aspect of the invention.

In a ninth aspect, the invention provides compounds of Formula V and VI:

FORMULA V

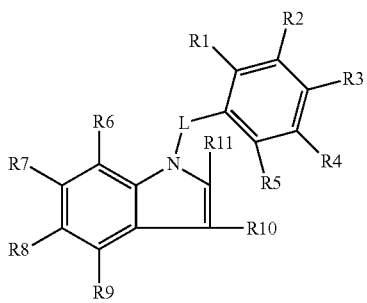

FORMULA VI

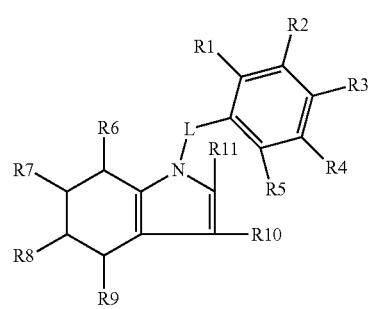

wherein one or more of R1-R5 is independently chosen from -L-C(=O)OH, -L-CH=CHC(=O)OH, -L-C(=O)NH$_2$, -L-C(=O)NH($C_{1-3}$ alkyl), -L-C(=O)N($C_{1-3}$ alkyl)$_2$, -L-S(=O)$_2$($C_{1-3}$alkyl), -L-S(=O)$_2$NH$_2$, -L-S(=O)$_2$N($C_{1-3}$ alkyl)$_2$, -L-S(=O)$_2$NH($C_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl; the others of R1-R5, independent of one another, are chosen from hydro, hydroxyl, halo, alkyl, alkoxy, haloalkyl, halo alkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, and —NO$_2$;

R$_o$ is chosen from alkyl and haloalkyl;

L is as defined above;

R6-R10, independent of one another, are chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$ alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl or cycloalkyl ring; and R11 is an optionally substituted phenyl group.

In one sub-embodiment, R3 is not hydroxyl

According to one embodiment of this ninth aspect of the invention, one of R1-R5 is chosen from —C(=O)OH, —CH$_2$CH$_2$C(=O)OH,
—CH$_2$CH$_2$C(=O)OH, —CH$_2$CH$_2$CH$_2$C(=O)OH, —C(CH$_2$CH$_2$)C(=O)OH,
—CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, —C(CH$_3$)$_2$C(=O)OH, —C(=O)NH$_2$, —C(=O)NHCH$_3$, —C(=O)N(CH$_3$)$_2$, —S(=O)$_2$(C$_{1-3}$ alkyl), —S(=O)$_2$NH$_2$, —S(=O)$_2$NHCH$_3$, —S(=O)$_2$N(CH$_3$)$_2$, —C(=O)NH(C$_{1-3}$ alkyl), —C(=O)N(C$_{1-3}$ alkyl)$_2$, —S(=O)$_2$NH$_2$, —S(=O)$_2$NH(C$_{1-3}$ alkyl), and —S(=O)$_2$N(C$_{1-3}$alkyl)$_2$, and the others are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$ alkyl), —S(=O)$_2$NH$_2$, —S(=O)$_2$N(C$_{1-3}$ alkyl)$_2$, —S(=O)$_2$NH (C$_{1-3}$ alkyl), —CHF$_2$, —OCF$_3$, —OCHF$_2$, —SCF$_3$, —CF$_3$, —CN, —NH$_2$, and —NO$_2$.

In another embodiment of this ninth aspect of the invention, L is a bond, one of R1-R5 is chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, C(CH$_3$)(CH$_2$CH$_3$)=O)OH, —CH=C(CH$_3$)C(=O)OH, —C(CH$_2$CH$_3$)$_2$C(=O)OH, —CH$_2$C(=O)OH, and —C(CH$_3$)$_2$C(=O)OH; and the others are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O) NH$_2$, —C(=O)NH(C$_{1-3}$ alkyl), —C(=O)N(C$_{1-3}$ alkyl)$_2$, —S(=O)$_2$(C$_{1-3}$ alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$;

R6-R9, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and NO$_2$; or two adjacent of R6-R9 can be taken together to form an optionally substituted 4-7 member aryl or cycloalkyl ring.

In one embodiment of the ninth aspect of the invention, R8 and R9 in the compound of Formula V are taken together to form a 6 member aryl ring as in Formula VII.

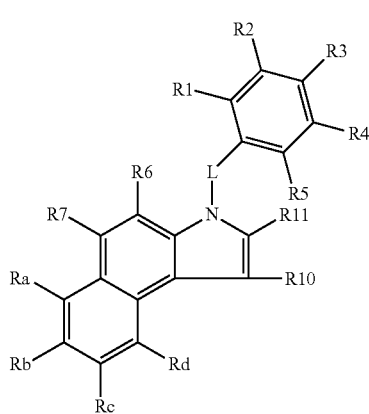

FORMULA VII

According to one embodiment of the ninth aspect of the invention, compounds of Formula VII are provided wherein Ra, Rb, Rc, and Rd are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$ alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O) OCH$_2$CH$_3$)-phenyl, and —O—Si(CH$_3$)$_2$(C(CH$_3$)$_3$); and the other variables can be defined as in one of the other embodiments of the ninth aspect of the invention.

In one embodiment of the ninth aspect of the invention, R8 and R9 in the compounds of Formula VI are taken together to form a 6 member aryl ring as in Formula VIII.

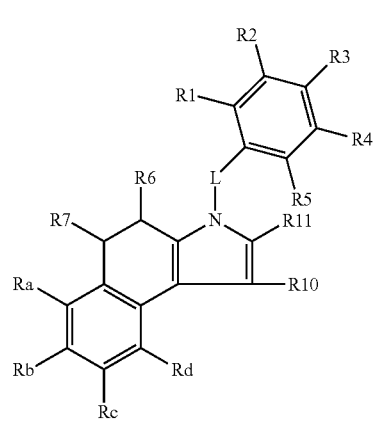

FORMULA VIII

According to one embodiment of the ninth aspect of the invention, compounds of Formula VIII are provided wherein Ra, Rb, Rc, and Rd are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O) OCH$_2$CH$_3$)-phenyl, and —O—Si(CH$_3$)$_2$(C(CH$_3$)$_3$); and the other variables can be defined as in one of the other embodiments of the ninth aspect of the invention.

In a tenth aspect, the invention provides compounds of Formula IX and X:

FORMULA IX

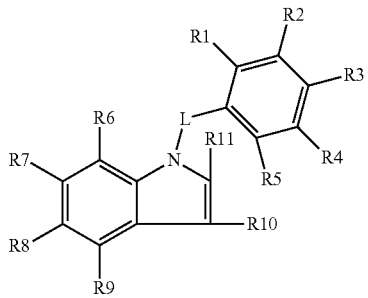

FORMULA X

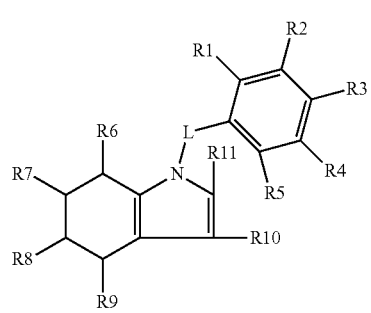

wherein one or more of R1-R11 are chosen from -L-R12, -L-C(=O)OH, -L-CH=CHC(=O)OH, -L-C(=O)NH$_2$, -L-C(=O)NH(C$_{1-3}$ alkyl), -L-C(=O)N(C$_{1-3}$ alkyl)$_2$, -L-S(=O)$_2$(C$_{1-3}$alkyl), -L-S(=O)$_2$NH$_2$, -L-S(=O)$_2$N(C$_{1-3}$ alkyl)$_2$, -L-S(=O)$_2$NH(C$_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl; wherein R12 is a phenyl ring substituted with one or more substituents independently chosen from -L-C(=O)OH, -L-CH=CHC(=O)OH, -L-C(=O)NH$_2$, -L-C(=O)NH(C$_{1-3}$ alkyl), -L-C(=O)N(C$_{1-3}$ alkyl)$_2$, -L-S(=O)$_2$(C$_{1-3}$ alkyl), -L-S(=O)$_2$NH$_2$, -L-S(=O)$_2$N(C$_{1-3}$ alkyl)$_2$, -L-S(=O)$_2$NH(C$_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl, and the others are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$;

R$_o$ is chosen from alkyl and haloalkyl;

L is as defined above; and the others of R1-R11 are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$; and two adjacent of R6-R9 can be taken together to form a 4-7 member optionally substituted aryl or cycloalkyl ring.

In another embodiment of this tenth aspect of the invention, L is a bond, R12 is present and one substituents on the phenyl of R12 is chosen from —C(=O)OH, —CH=CHC(=O)OH, —CH$_2$CH$_2$C(=O)OH, —CH$_2$CH$_2$CH$_2$C(=O)OH, —C(CH$_2$CH$_3$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, and —C(CH$_3$)$_2$C(=O)OH; and the others are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$;

R1-R9, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$ alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and NO$_2$; and two adjacent of R6-R9 can be taken together to form an optionally substituted 4-7 member aryl or cycloalkyl ring.

In one embodiment of the tenth aspect of the invention, R8 and R9 in the compounds of Formula IX are taken together to form a 6 member aryl ring as in Formula XI

FORMULA XI

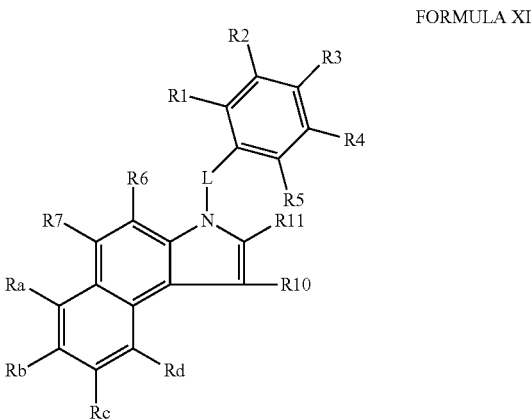

According to one embodiment of the tenth aspect of the invention, compounds of Formula XI are provided wherein Ra, Rb, Rc, and Rd are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$ alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); and the other variables can be defined as in one of the other embodiments of the tenth aspect of the invention.

In one embodiment of the tenth aspect of the invention, R8 and R9 in the compounds of Formula X are taken together to form a 6 member aryl ring as in Formula XII.

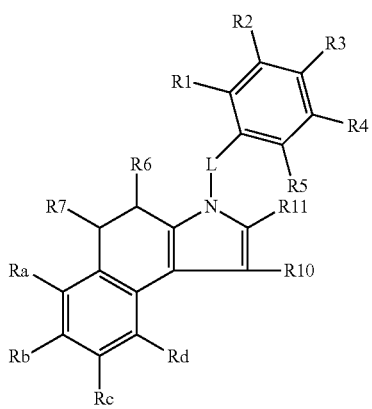

FORMULA XII

According to one embodiment of the tenth aspect of the invention, compounds of Formula XII are provided wherein Ra, Rb, Rc, and Rd are independently chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$ alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); and the other variables can be defined as in one of the other embodiments of the tenth aspect of the invention.

In an eleventh aspect, the invention provides compounds of Formula XIII and XIV:

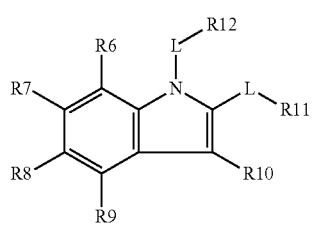

Formula XIII

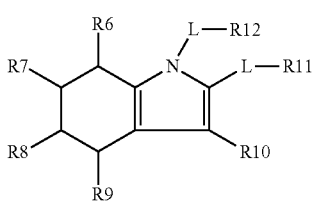

Formula XIV wherein L is as defined above or is selected from an optionally substituted, saturated or partially saturated cyclopropyl, cyclobutyl, cyclopentyl, cyclohexyl, cycloheptyl, and $C_{1-12}$ alkyl;

R1-R10, independent of one another, are chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$ alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl or cycloalkyl ring;

R11 is chosen from L-C(=O)OH, -L-CH=CHC(=O)OH, -L-C(=O)NH$_2$, -L-C(=O)NH($C_{1-3}$ alkyl), -L-C(=O)N($C_{1-3}$ alkyl)$_2$, -L-S(=O)$_2$($C_{1-3}$alkyl), -L-S(=O)$_2$NH$_2$, -L-S(=O)$_2$N($C_{1-3}$ alkyl)$_2$, -L-S(=O)$_2$NH($C_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl;

R$_o$ is chosen from alkyl and haloalkyl; and

R12 is chosen from optionally substituted $C_{1-12}$ alkyl, phenyl, and $C_{3-7}$ cycloalkyl.

In one embodiment of the eleventh aspect of the invention, R8 and R9 in the compounds of Formula XIII are taken together to form a 6 member aryl ring as in Formula XV.

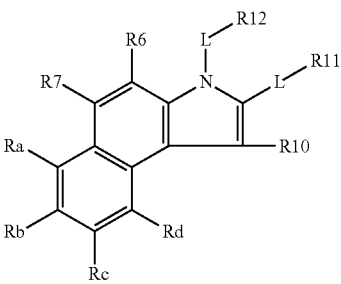

FORMULA XV

According to one embodiment of the eleventh aspect of the invention, compounds of Formula XV are provided wherein Ra, Rb, Rc, and Rd are independently chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); and the other variables can be defined as in one of the other embodiments of the eleventh aspect of the invention.

In one embodiment of the eleventh aspect of the invention, R8 and R9 in the compounds of Formula XIV are taken together to form a 6 member aryl ring as in Formula XVI.

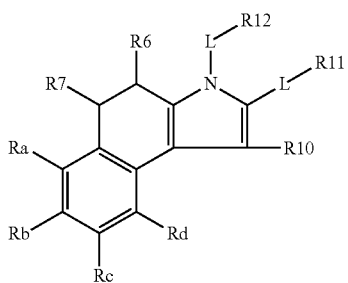

FORMULA XVI

According to one embodiment of the eleventh aspect of the invention, compounds of Formula XVI are provided wherein Ra, Rb, Rc, and Rd are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$ alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); and the other variables can be defined as in one of the other embodiments of the eleventh aspect of the invention.

In a twelfth aspect, the invention provides compounds of Formula I and II pharmaceutically acceptable salts thereof, and pharmaceutical compositions having such compounds:

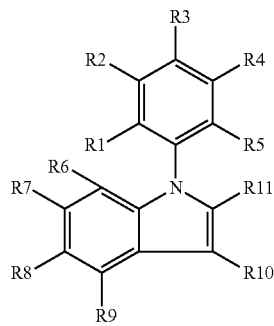

FORMULA I

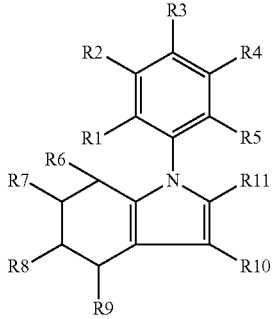

FORMULA II wherein one or more of R1-R5 is chosen from -L-C(=O)OH, -L-CH=CHC(=O)OH, -L-C(=O)NH$_2$, -L-C(=O)NH(C$_{1-3}$ alkyl), -L-C(=O)N(C$_{1-3}$ alkyl)$_2$, -L-S(=O)$_2$(C$_{1-3}$ alkyl), -L-S(=O)$_2$NH$_2$, -L-S(=O)$_2$N(C$_{1-3}$ alkyl)$_2$, -L-S(=O)$_2$NH(C$_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl, and the others of R1-R5, independent of one another, are chosen hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$ alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$;

R$_o$ is chosen from alkyl and haloalkyl;

R6-R10, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$ alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl, heterocyclic, or cycloalkyl ring;

R11 is an optionally substituted heterocyclic group; and

L can be saturated, partially saturated, or unsaturated, and is chosen from —(CH$_2$)$_n$—(CH$_2$)$_n$—, —(CH$_2$)$_n$C(=O)(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, 3, 4, 5, 6, 7, and 8, wherein each carbon can be optionally substituted with one or more C$_{1-3}$ alkyl or C$_{3-6}$ cycloalkyl.

In one embodiment of the twelfth aspect of the invention, one of R1-R5 in the compounds of Formulae I and II, is chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, —C(CH$_3$)$_2$C(=O)OH, —C(=O)NH$_2$, —C(=O)NHCH$_3$, —C(=O)N(CH$_3$)$_2$, —S(=O)$_2$(C$_{1-3}$alkyl), —S(=O)$_2$NH$_2$, —S(=O)$_2$NHCH$_3$, —S(=O)$_2$N(CH$_3$)$_2$, —C(=O)NH(C$_{1-3}$ alkyl), —C(=O)N(C$_{1-3}$ alkyl)$_2$, —S(=O)$_2$NH$_2$, —S(=O)$_2$N(C$_{1-3}$ alkyl)$_2$, and the others of R1-R5, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$;

R6-R10, independent of one another, are chosen hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$; two adjacent of R6-R9 can be taken together to form a 4-7 member optionally substituted aryl or cycloalkyl ring;

L is —(CH$_2$)$_n$—(CH$_2$)$_n$—, with n independently 0, 1, 2, or 3; and

R11 is an optionally substituted heterocyclic group.

In another embodiment of this twelfth aspect of the invention, one of R1-R5 is chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, and —C(CH$_3$)$_2$C(=O)OH; and the others of R1-R5 are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$ alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$;

R6-R10 are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and NO$_2$; two of R6-R9 can be taken together to form an optionally substituted C$_{4-7}$ member aryl, heterocyclic, or cycloalkyl ring; and R11 is an optionally substituted heterocyclic group.

In one embodiment of this aspect of the invention the heterocyclic group is chosen from thienyl (thiophenyl), benzo[b]thienyl, naphtho[2,3-b]thienyl, thianthrenyl, furyl (furanyl), isobenzofuranyl, chromenyl, xanthenyl, phenoxanthinyl, pyrrolyl, 2H-pyrrolyl, imidazolyl, pyrazolyl, pyridyl (pyridinyl), 2-pyridyl, 3-pyridyl, 4-pyridyl, pyrazinyl, pyrimidinyl, pyridazinyl, tetrahydrofuranyl, pyranyl, piperidinyl, piperazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, quinuclidinyl, morpholinyl, cinnolinyl, pteridinyl, carbazolyl, beta-carbolinyl, phenanthridinyl, acrindinyl, perimidinyl, phenanthrolinyl, phenazinyl, isothiazolyl, phenothiazinyl, oxazolyl, isoxazolyl, furazanyl, phenoxazinyl, 1,4-dihydroquinoxaline-2,3-dione, 7 aminoisocoumarin, pyrido[1,2-a]pyrimidin-4-one, pyrazolo[1,5-a]pyrimidinyl, pyrazolo[1,5-a]pyrimidin-3-yl, 1,2-benzoisoxazol-3-yl, benzimidazolyl, 2-oxindolyl and 2 oxobenzimidazolyl. In one sub-embodiment of this embodiment, the heterocyclic group is chosen from pyridinyl, isoxazolyl, furanyl, thiazolyl, pyrimidinyl, pyrrolyl, thiophenyl, triazolyl, benzo[1,3]dioxolyl, and benzofuranyl.

In a thirteenth aspect, the invention provides compounds of Formula I and II:

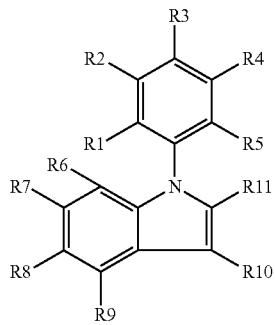

FORMULA I

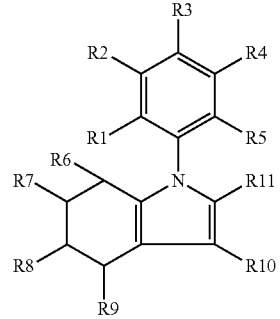

FORMULA II wherein R1-R5, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$NH$_2$, —S(=O)$_2$(C$_{1-3}$ alkyl), —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$;

one or more of R6-R9 is independently chosen from -L-C(=O)OH, -L-CH=CHC(=O)OH, -L-C(=O)NH$_2$, -L-C(=O)NH(C$_{1-3}$ alkyl), -L-C(=O)N(C$_{1-3}$ alkyl)$_2$, -L-S(=O)$_2$(C$_{1-3}$alkyl), -L-S(=O)$_2$NH$_2$, -L-S(=O)$_2$N(C$_{1-3}$ alkyl)$_2$, -L-S(=O)$_2$NH(C$_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl; or two adjacent of R6-R9 can be taken together to form an optionally substituted 4-7 member aryl, heterocyclic, or cycloalkyl ring substituted with one or more substituents independently chosen from -L-C(=O)OH, -L-CH=CHC(=O)OH, -L-C(=O)NH$_2$, -L-C(=O)NH(C$_{1-3}$ alkyl), -L-C(=O)N(C$_{1-3}$ alkyl)$_2$, -L-S(=O)$_2$(C$_{1-3}$alkyl), -L-S(=O)$_2$NH$_2$, -L-S(=O)$_2$N(C$_{1-3}$ alkyl)$_2$, -L-S(=O)$_2$NH(C$_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl; and the others of R6-R9, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$;

R$_o$ is chosen from alkyl and haloalkyl;

R11 is an optionally substituted heterocyclic group; and

L can be saturated, partially saturated, or unsaturated, and is chosen from —(CH$_2$)$_n$—(CH$_2$)$_n$—, —(CH$_2$)$_n$C(=O)(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently selected from 0, 1, 2, 3, 4, 5, 6, 7, and 8, wherein each carbon can be optionally substituted with one or more C$_{1-3}$ alkyl or C$_{3-6}$ cycloalkyl.

In one embodiment of the thirteenth aspect of the invention, one of R6-R9 is chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, —C(CH$_3$)$_2$C(=O)OH, —C(=O)NH$_2$, —C(=O)NHCH$_3$, —C(=O)N(CH$_3$)$_2$, —S(=O)$_2$(C$_{1-3}$ alkyl), —S(=O)$_2$NH$_2$, —S(=O)$_2$NHCH$_3$, —S(=O)$_2$N(CH$_3$)$_2$, —C(=O)NH(C$_{1-3}$alkyl), —C(=O)N(C$_{1-3}$alkyl)$_2$, —S(=O)$_2$NH$_2$, and —S(=O)$_2$N(C$_{1-3}$alkyl)$_2$; or two adjacent of R6-R9 can be taken together to form an optionally substituted 4-7 member aryl, heterocyclic, or cycloalkyl ring substituted with one or more substituents chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, —C(CH$_3$)$_2$C(=O)OH, —C(=O)NH$_2$, —C(=O)NHCH$_3$, —C(=O)N(CH$_3$)$_2$, —S(=O)$_2$(C$_{1-3}$ alkyl), —S(=O)$_2$NH$_2$, —S(=O)$_2$NHCH$_3$, —S(=O)$_2$N(CH$_3$)$_2$, —C(=O)NH(C$_{1-3}$ alkyl), —C(=O)N(C$_{1-3}$ alkyl)$_2$, —S(=O)$_2$NH$_2$, and —S(=O)$_2$N(C$_{1-3}$alkyl)$_2$; and the others of R6-R9, independent of one another, are chosen from hydro, hydroxyl, halo, alkyl, alkoxy, haloalkyl, haloalkoxy, —N(C$_{1-3}$ alkyl)$_2$, 3 alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$;

R1-R5, and R10, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$ alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$;

R11 is an optionally substituted heterocyclic group.

In another embodiment of this thirteenth aspect of the invention, one of R6-R9 is chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, and —C(CH$_3$)$_2$C(=O)OH; or two adjacent of R6-R9 can be taken together to form an optionally substituted 4-7 member aryl, heterocyclic, or cycloalkyl ring substituted with one or more substituents chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, and —C(CH$_3$)$_2$C(=O)OH;

and the others of R6-R9 independently are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$ alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$;

R1-R5, and R10, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and NO$_2$; and R11 is an optionally substituted heterocyclic group.

In one embodiment of this aspect of the invention the heterocyclic group is chosen from thienyl (thiophenyl), benzo[b]thienyl, naphtho[2,3-b]thienyl, thianthrenyl, furyl (furanyl), isobenzofuranyl, chromenyl, xanthenyl, phenoxanthinyl, pyrrolyl, 2H-pyrrolyl, imidazolyl, pyrazolyl, pyridyl (pyridinyl), 2-pyridyl, 3-pyridyl, 4-pyridyl, pyrazinyl, pyrimidinyl, pyridazinyl, tetrahydrofuranyl, pyranyl, piperidinyl, piperazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, quinuclidinyl, morpholinyl, cinnolinyl, pteridinyl, carbazolyl, beta-carbolinyl, phenanthridinyl, acrindinyl, perimidinyl, phenanthrolinyl, phenazinyl, isothiazolyl, phenothiazinyl, oxazolyl, isoxazolyl, furazanyl, phenoxazinyl, 1,4-dihydroquinoxaline-2,3-dione, 7 aminoisocoumarin, pyrido[1,2-a]pyrimidin-4-one, pyrazolo[1,5-a]pyrimidinyl, pyrazolo[1,5-a]pyrimidin-3-yl, 1,2-benzoisoxazol-3-yl, benzimidazolyl, 2-oxindolyl and 2 oxobenzimidazolyl. In one sub-embodiment of this embodiment, the heterocyclic group is chosen from pyridinyl, isoxazolyl, furanyl, thiazolyl, pyrimidinyl, pyrrolyl, thiophenyl, triazolyl, benzo[1,3]dioxolyl, and benzofuranyl.

In a fourteenth aspect, the invention provides compounds of Formula I and II:

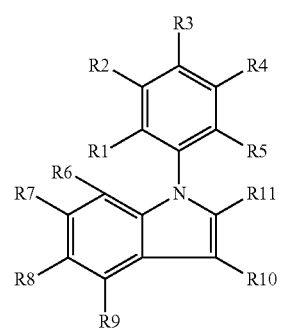

FORMULA I

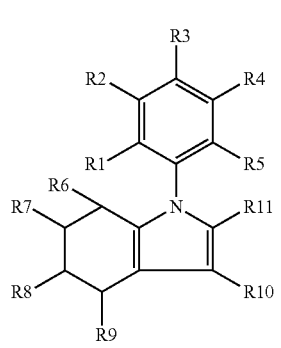

FORMULA II wherein R1-R9 are independently chosen hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); two adjacent of R6-R9 can be taken together to form an optionally substituted C$_{4-7}$ member aryl, heterocyclic, or cycloalkyl ring;

R10 is chosen from -L-C(=O)OH, -L-CH=CHC(=O)OH, -L-C(=O)NH$_2$, -L-C(=O)NH(C$_{1-3}$ alkyl), -L-C(=O)N(C$_{1-3}$ alkyl)$_2$, -L-S(=O)$_2$(C$_{1-3}$alkyl), -L-S(=O)$_2$NH$_2$, -L-S(=O)$_2$N(C$_{1-3}$ alkyl)$_2$, -L-S(=O)$_2$NH(C$_{1-3}$ alkyl), -L-C (=O)NHOH, -L-C(=O)CH₂NH₂, -L-C(=O)CH₂OH, -L-C(=O)CH₂SH, -L-C(=O)NHCN, -L-NHC(=O)OR_o, -L-C(=O)NHR_o, -L-NH(C=O)NHR_o, -L-C(=O)N(R_o)₂, -L-NH(C=O)N(R_o)₂, -L-sulfo, -L-(2,6 difluorophenol), -L-phosphono, and -L-tetrazolyl;

R_o is chosen from alkyl and haloalkyl;

R11 is an optionally substituted heterocyclic group; and

L can be saturated, partially saturated, or unsaturated, and is chosen from —(CH₂)_n—(CH₂)_n—, —(CH₂)_nC(=O)(CH₂)_n—, —(CH₂)_nNH(CH₂)_n—, —(CH₂)_nO(CH₂)_n—, and —(CH₂)_nS(CH₂)_n—, where each n is independently chosen from 0, 1, 2, 3, 4, 5, 6, 7, and 8, wherein each carbon can be optionally substituted with one or more C₁₋₃ alkyl or C₃₋₆ cycloalkyl;

In one embodiment of the fourteenth aspect of the invention, R10 is chosen from —C(=O)OH, —CH=CHC(=O)OH, —CH₂CH₂C(=O)OH, —CH₂CH₂CH₂C(=O)OH, —C(CH₂CH₂)C(=O)OH, —CH(CH₃)C(=O)OH, —CH(CH₂CH₃)C(=O)OH, —C(CH₃)(CH₂CH₃)C(=O)OH, —CH=C(CH₃)C(=O)OH, —C(CH₂CH₃)₂C(=O)OH, —CH₂C(=O)OH, —C(CH₃)₂C(=O)OH, —C(=O)NH₂, —C(=O)NHCH₃, —C(=O)N(CH₃)₂, —S(=O)₂(C₁₋₃ alkyl), —S(=O)₂NH₂, —S(=O)₂NHCH₃, —S(=O)₂N(CH₃)₂, —C(=O)NH(C₁₋₃alkyl), —C(=O)N(C₁₋₃alkyl)₂, —S(=O)₂NH₂, and —S(=O)₂N(C₁₋₃ alkyl)₂; and R11 is an optionally substituted heterocyclic group.

In another embodiment of this third aspect of the invention, R10 is chosen from —C(=O)OH, —CH=CHC(=O)OH, —CH₂CH₂C(=O)OH, —CH₂CH₂CH₂C(=O)OH, —C(CH₂CH₂)C(=O)OH, —CH(CH₃)C(=O)OH, —CH(CH₂CH₃)C(=O)OH, —C(CH₃)(CH₂CH₃)C(=O)OH, —CH=C(CH₃)C(=O)OH, —C(CH₂CH₃)₂C(=O)OH, —CH₂C(=O)OH, and —C(CH₃)₂C(=O)OH; and R11 is an optionally substituted heterocyclic group.

In one embodiment of this aspect of the invention the heterocyclic group is chosen from thienyl (thiophenyl), benzo[b]thienyl, naphtho[2,3-b]thienyl, thianthrenyl, furyl (furanyl), isobenzofuranyl, chromenyl, xanthenyl, phenoxanthinyl, pyrrolyl, 2H-pyrrolyl, imidazolyl, pyrazolyl, pyridyl (pyridinyl), 2-pyridyl, 3-pyridyl, 4-pyridyl, pyrazinyl, pyrimidinyl, pyridazinyl, tetrahydrofuranyl, pyranyl, piperidinyl, piperazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, quinuclidinyl, morpholinyl, cinnolinyl, pteridinyl, carbazolyl, beta-carbolinyl, phenanthridinyl, acrindinyl, perimidinyl, phenanthrolinyl, phenazinyl, isothiazolyl, phenothiazinyl, oxazolyl, isoxazolyl, furazanyl, phenoxazinyl, 1,4-dihydroquinoxaline-2,3-dione, 7 aminoisocoumarin, pyrido[1,2-a]pyrimidin-4-one, pyrazolo[1,5-a]pyrimidinyl, pyrazolo[1,5-a]pyrimidin-3-yl, 1,2-benzoisoxazol-3-yl, benzimidazolyl, 2-oxindolyl and 2 oxobenzimidazolyl. In one sub-embodiment of this embodiment, the heterocyclic group is chosen from pyridinyl, isoxazolyl, furanyl, thiazolyl, pyrimidinyl, pyrrolyl, thiophenyl, triazolyl, benzo[1,3]dioxolyl, and benzofuranyl.

In a fifteenth aspect, the invention provides compounds of Formula I and II:

FORMULA I

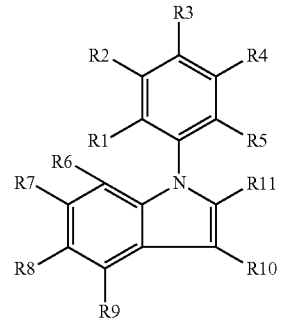

FORMULA II

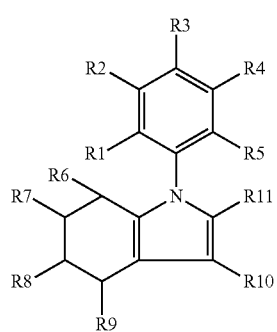

wherein R1-R10, independent of one another, are chosen from hydro, hydroxyl, halo, alkyl, alkoxy, haloalkyl, haloalkoxy, —N(C₁₋₃ alkyl)₂, —NH(C₁₋₃ alkyl), —C(=O)NH₂, —C(=O)NH(C₁₋₃ alkyl), —C(=O)N(C₁₋₃ alkyl)₂, —S(=O)₂(C₁₋₃ alkyl), —S(=O)₂NH₂, —S(=O)₂N(C₁₋₃ alkyl)₂, —S(=O)₂NH(C₁₋₃ alkyl), —CHF₂, —OCF₃, —OCHF₂, —SCF₃, —CF₃, —CN, —NH₂, —NO₂, —C(=O)—N-morpholino, -cyclohexyl, -morpholino, -pyrrolidinyl, -piperazinyl, —(N-methyl)-piperazinyl, —OCH₂-phenyl, -pyridinyl, methylenedioxy, ethylenedioxy, —C(=O)OCH₂CH₃ substituted furanyl, para-(C(=O)OCH₂CH₃)-phenyl, and —O—Si(CH₃)₂(C(CH₃)₃); two adjacent of R6-R9 can be taken together to form a 4-7 member optionally substituted aryl, heterocyclic, or cycloalkyl ring;

R11 is a heterocyclic group with one or more substituents independently chosen from -L-C(=O)OH, -L-CH=CHC(=O)OH, -L-C(=O)NH₂, -L-C(=O)NH(C₁₋₃ alkyl), -L-C(=O)N(C₁₋₃ alkyl)₂, -L-S(=O)₂(C₁₋₃ alkyl), -L-S(=O)₂NH₂, -L-S(=O)₂N(C₁₋₃ alkyl)₂, -L-S(=O)₂NH(C₁₋₃ alkyl), -L-C(=O)NHOH, -L-C(=O)CH₂NH₂, -L-C(=O)CH₂OH, -L-C(=O)CH₂SH, -L-C(=O)NHCN, -L-NHC(=O)OR_o, -L-C(=O)NHR_o, -L-NH(C=O)NHR_o, -L-C(=O)N(R_o)₂, -L-NH(C=O)N(R_o)₂, -L-sulfo, -L-(2,6 difluorophenol), -L-phosphono, and -L-tetrazolyl;

R_o is chosen from alkyl and haloalkyl; and

L can be saturated, partially saturated, or unsaturated, and is chosen from —(CH₂)_n—(CH₂)_n—, —(CH₂)_nC(=O)(CH₂)_n—, —(CH₂)_nNH(CH₂)_n—, —(CH₂)_nO(CH₂)_n—, and —(CH₂)_nS(CH₂)_n—, where each n is independently chosen from 0, 1, 2, 3, 4, 5, 6, 7, and 8, wherein each carbon can be optionally substituted with one or more C₁₋₃ alkyl or C₃₋₆ cycloalkyl.

In one embodiment of the fifteenth aspect of the invention, one substituent on the heterocyclic group of R11 is chosen from —C(=O)OH, —CH=CHC(=O)OH, —CH₂CH₂C(=O)OH, —CH₂CH₂CH₂C(=O)OH, —C(CH₂CH₂)C(=O)OH, —CH(CH₃)C(=O)OH, —CH(CH₂CH₃)C(=O)OH, —C(CH₃)(CH₂CH₃)C(=O)OH, —CH=C(CH₃)C(=O)OH, —C(CH₂CH₃)₂C(=O)OH, —CH₂C(=O)OH, —C(CH₃)₂C(=O)OH, —C(=O)NH₂, —C(=O)NHCH₃, —C(=O)N(CH₃)₂, —S(=O)₂(C₁₋₃ alkyl), —S(=O)₂NH₂, —S(=O)₂NHCH₃, —S(=O)₂N(CH₃)₂, —C(=O)NH(C₁₋₃alkyl), —C(=O)N(C₁₋₃alkyl)₂, —S(=O)₂NH₂, and —S(=O)₂N(C₁₋₃alkyl)₂.

In another embodiment of this fifteenth aspect of the invention, one of the substituents on the heterocyclic group of R11 is chosen from —C(=O)OH, —CH=CHC(=O)OH, —CH₂CH₂C(=O)OH, —CH₂CH₂CH₂C(=O)OH, —C(CH₂CH₂)C(=O)OH, —CH(CH₃)C(=O)OH, —CH(CH₂CH₃)C(=O)OH, —C(CH₃)(CH₂CH₃)C(=O)OH, —CH=C(CH₃)C(=O)OH, —C(CH₂CH₃)₂C(=O)OH, —CH₂C(=O)OH, and —C(CH₃)₂C(=O)OH.

In one embodiment of this aspect of the invention the heterocyclic group is chosen from thienyl (thiophenyl), benzo[b]thienyl, naphtho[2,3-b]thienyl, thianthrenyl, furyl (furanyl), isobenzofuranyl, chromenyl, xanthenyl, phenoxanthinyl, pyrrolyl, 2H-pyrrolyl, imidazolyl, pyrazolyl, pyridyl (pyridinyl), 2-pyridyl, 3-pyridyl, 4-pyridyl, pyrazinyl, pyrimidinyl, pyridazinyl, tetrahydrofuranyl, pyranyl, piperidinyl, piperazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, quinuclidinyl, morpholinyl, cinnolinyl, pteridinyl, carbazolyl, beta-carbolinyl, phenanthridinyl, acrindinyl, perimidinyl, phenanthrolinyl, phenazinyl, isothiazolyl, phenothiazinyl, oxazolyl, isoxazolyl, furazanyl, phenoxazinyl, 1,4-dihydroquinoxaline-2,3-dione, 7 aminoisocoumarin, pyrido[1,2-a]pyrimidin-4-one, pyrazolo[1,5-a]pyrimidinyl, pyrazolo[1,5-a]pyrimidin-3-yl, 1,2-benzoisoxazol-3-yl, benzimidazolyl, 2-oxindolyl and 2 oxobenzimidazolyl. In one sub-embodiment of this embodiment, the heterocyclic group is chosen from pyridinyl, isoxazolyl, furanyl, thiazolyl, pyrimidinyl, pyrrolyl, thiophenyl, triazolyl, benzo[1,3]dioxolyl, and benzofuranyl.

In a sixteenth aspect, the invention provides compounds of Formula I and II:

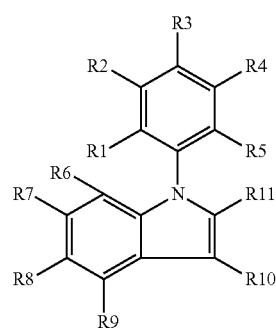

FORMULA I

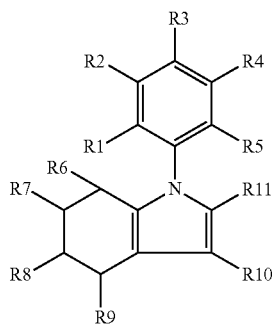

FORMULA II wherein R1-R9 and R11 independent of one another, are chosen from hydro, hydroxyl, halo, alkyl, alkoxy, haloalkyl, haloalkoxy, —N(C₁₋₃ alkyl)₂, —NH(C₁₋₃ alkyl), —C(=O)NH₂, —C(=O)NH(C₁₋₃ alkyl), —C(=O)N(C₁₋₃ alkyl)₂, —S(=O)₂(C₁₋₃ alkyl), —S(=O)₂NH₂, —S(=O)₂N(C₁₋₃ alkyl)₂, —S(=O)₂NH(C₁₋₃ alkyl), —CHF₂, —OCF₃, —OCHF₂, —SCF₃, —CF₃, —CN, —NH₂, —NO₂, —C(=O)—N-morpholino, -cyclohexyl, -morpholino, -pyrrolidinyl, -piperazinyl, —(N-methyl)-piperazinyl, —OCH₂-phenyl, -pyridinyl, methylenedioxy, ethylenedioxy, —C(=O)OCH₂CH₃ substituted furanyl, para-(C(=O)OCH₂CH₃)-phenyl, and —O—Si(CH₃)₂(C(CH₃)₃); two adjacent of R6-R9 can be taken together to form a 4-7 member optionally substituted aryl, heterocyclic, or cycloalkyl ring;

R10 is a heterocyclic group with one or more substituents independently chosen L-C(=O)OH, -L-CH=CHC(=O)OH, -L-C(=O)NH₂, -L-C(=O)NH(C₁₋₃ alkyl), -L-C(=O)N(C₁₋₃ alkyl)₂, -L-S(=O)₂(C₁₋₃ alkyl), -L-S(=O)₂NH₂, -L-S(=O)₂N(C₁₋₃ alkyl)₂, -L-S(=O)₂NH(C₁₋₃ alkyl), -L-C(=O)NHOH, -L-C(=O)CH₂NH₂, -L-C(=O)CH₂OH, -L-C(=O)CH₂SH, -L-C(=O)NHCN, -L-NHC(=O)OR₀, -L-C(=O)NHR₀, -L-NH(C=O)NHR₀, -L-C(=O)N(R₀)₂, -L-NH(C=O)N(R₀)₂, -L-sulfo, -L-(2,6 difluorophenol), -L-phosphono, and -L-tetrazolyl;

R₀ is chosen from alkyl and haloalkyl; and

L can be saturated, partially saturated, or unsaturated, and is chosen from —(CH₂)ₙ—(CH₂)ₙ—, —(CH₂)ₙC(=O)(CH₂)ₙ—, —(CH₂)ₙNH(CH₂)ₙ—, —(CH₂)ₙO(CH₂)ₙ—, and —(CH₂)ₙS(CH₂)ₙ—, where each n is independently chosen from 0, 1, 2, 3, 4, 5, 6, 7, and 8, wherein each carbon can be optionally substituted with one or more C₁₋₃ alkyl or C₃₋₆ cycloalkyl.

In one embodiment of the sixteenth aspect of the invention, one substituent on the heterocyclic group of R10 is chosen from —C(=O)OH, —CH=CHC(=O)OH, —CH₂CH₂C(=O)OH, —CH₂CH₂CH₂C(=O)OH, —C(CH₂CH₂)C(=O)OH, —CH(CH₃)C(=O)OH, —CH(CH₂CH₃)C(=O)OH, —C(CH₃)(CH₂CH₃)C(=O)OH, —CH=C(CH₃)C(=O)OH, —C(CH₂CH₃)₂C(=O)OH, —CH₂C(=O)OH, —C(CH₃)₂C(=O)OH, —C(=O)NH₂, —C(=O)NHCH₃, —C(=O)N(CH₃)₂, —S(=O)₂(C₁₋₃alkyl), —S(=O)₂NH₂, —S(=O)₂NHCH₃, —S(=O)₂N(CH₃)₂, —C(=O)NH(C₁₋₃ alkyl), —C(=O)N(C₁₋₃ alkyl)₂, —S(=O)₂NH₂, and —S(=O)₂N(C₁₋₃alkyl)₂.

In another embodiment of this sixteenth aspect of the invention, one substituent on the heterocyclic group of R10 is chosen from —C(=O)OH, —CH=CHC(=O)OH, —CH₂CH₂C(=O)OH, —CH₂CH₂CH₂C(=O)OH, —C(CH₂CH₂)C(=O)OH, —CH(CH₃)C(=O)OH, —CH(CH₂CH₃)C(=O)OH, —C(CH₃)(CH₂CH₃)C(=O)OH, —CH=C(CH₃)C(=O)OH, —C(CH₂CH₃)₂C(=O)OH, —CH₂C(=O)OH, and —C(CH₃)₂C(=O)OH.

In one embodiment of this aspect of the invention the heterocyclic group is chosen from thienyl (thiophenyl), benzo[b]thienyl, naphtho[2,3-b]thienyl, thianthrenyl, furyl (furanyl), isobenzofuranyl, chromenyl, xanthenyl, phenoxanthinyl, pyrrolyl, 2H-pyrrolyl, imidazolyl, pyrazolyl, pyridyl (pyridinyl), 2-pyridyl, 3-pyridyl, 4-pyridyl, pyrazinyl, pyrimidinyl, pyridazinyl, tetrahydrofuranyl, pyranyl, piperidinyl, piperazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, quinuclidinyl, morpholinyl, cinnolinyl, pteridinyl, carbazolyl, beta-carbolinyl, phenanthridinyl, acrindinyl, perimidinyl, phenanthrolinyl, phenazinyl, isothiazolyl, phenothiazinyl, oxazolyl, isoxazolyl, furazanyl, phenoxazinyl, 1,4-dihydroquinoxaline-2, 3-dione, 7 aminoisocoumarin, pyrido[1,2-a]pyrimidin-4-one, pyrazolo[1,5-a]pyrimidinyl, pyrazolo[1,5-a]pyrimidin-3-yl, 1,2-benzoisoxazol-3-yl, benzimidazolyl, 2-oxindolyl and 2 oxobenzimidazolyl. In one sub-embodiment of this embodiment, the heterocyclic group is chosen from pyridinyl, isoxazolyl, furanyl, thiazolyl, pyrimidinyl, pyrrolyl, thiophenyl, triazolyl, benzo[1,3]dioxolyl, and benzofuranyl.

In a seventeenth aspect, the invention provides compounds of Formula I and II:

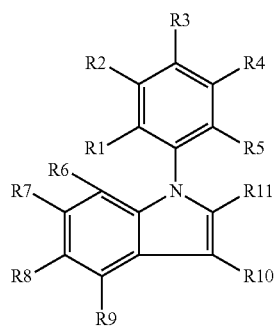

FORMULA I

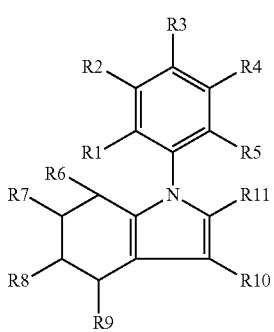

FORMULA II wherein R1-R9 and R11 independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(═O)NH$_2$, —C(═O)NH(C$_{1-3}$ alkyl), —C(═O)N(C$_{1-3}$ alkyl)$_2$, —S(═O)$_2$(C$_{1-3}$alkyl), —S(═O)$_2$NH$_2$, —S(═O)$_2$N(C$_{1-3}$ alkyl)$_2$, —S(═O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(═O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(═O)OCH$_2$CH$_3$ substituted furanyl, para-(C(═O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl, heterocyclic, or cycloalkyl ring;

R10 is L-R12;

R12 is a heterocyclic group with one or more substituents chosen from -L-C(═O)OH, -L-CH═CHC(═O)OH, -L-C(═O)NH$_2$, -L-C(═O)NH(C$_{1-3}$ alkyl), -L-C(═O)N(C$_{1-3}$ alkyl)$_2$, -L-S(═O)$_2$(C$_{1-3}$alkyl), -L-S(═O)$_2$NH$_2$, -L-S(═O)$_2$N(C$_{1-3}$ alkyl)$_2$, -L-S(═O)$_2$NH(C$_{1-3}$ alkyl), -L-C(═O)NHOH, -L-C(═O)CH$_2$NH$_2$, -L-C(═O)CH$_2$OH, -L-C(═O)CH$_2$SH, -L-C(═O)NHCN, -L-NHC(═O)OR$_o$, -L-C(═O)NHR$_o$, -L-NH(C═O)NHR$_o$, -L-C(═O)N(R$_o$)$_2$, -L-NH(C═O)N(R$_o$)$_2$, -L-sulfo, -L-(2,6 difluorophenol), -L-phosphono, and -L-tetrazolyl;

R$_o$ is chosen from alkyl and haloalkyl; and

L can be saturated, partially saturated, or unsaturated, and is chosen from —(CH$_2$)$_n$—(CH$_2$)$_n$—, —(CH$_2$)$_n$C(═O)(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, 3, 4, 5, 6, 7, and 8, wherein each carbon can be optionally substituted with one or more C$_{1-3}$ alkyl or C$_{3-6}$ cycloalkyl.

In one embodiment of the seventeenth aspect of the invention, one substituent on the heterocyclic group of R12 is chosen from —C(═O)OH, —CH═CHC(═O)OH, —CH$_2$CH$_2$C(═O)OH, —CH$_2$CH$_2$CH$_2$C(═O)OH, —C(CH$_2$CH$_2$)C(═O)OH, —CH(CH$_3$)C(═O)OH, —CH(CH$_2$CH$_3$)C(═O)OH, —C(CH$_3$)(CH$_2$CH$_3$)C(═O)OH, —CH═C(CH$_3$)C(═O)OH, —C(CH$_2$CH$_3$)$_2$C(═O)OH, —CH$_2$C(═O)OH, —C(CH$_3$)$_2$C(═O)OH, —C(═O)NH$_2$, —C(═O)NHCH$_3$, —C(═O)N(CH$_3$)$_2$, —S(═O)$_2$(C$_{1-3}$alkyl), —S(═O)$_2$NH$_2$, —S(═O)$_2$NHCH$_3$, —S(═O)$_2$N(CH$_3$)$_2$, —C(═O)NH(C$_{1-3}$ alkyl), —C(═O)N(C$_{1-3}$ alkyl)$_2$, —S(═O)$_2$NH$_2$, and —S(═O)$_2$N(C$_{1-3}$alkyl)$_2$.

In another embodiment of this seventeenth aspect of the invention, one of the substituent on the heterocyclic group of R12 is chosen from —C(═O)OH, —CH═CHC(═O)OH, —CH$_2$CH$_2$C(═O)OH, —CH$_2$CH$_2$CH$_2$C(═O)OH, —C(CH$_2$CH$_2$)C(═O)OH, —CH(CH$_3$)C(═O)OH, —CH(CH$_2$CH$_3$)C(═O)OH, —C(CH$_3$)(CH$_2$CH$_3$)C(═O)OH, —CH═C(CH$_3$)C(═O)OH, —C(CH$_2$CH$_3$)$_2$C(═O)OH, —CH$_2$C(═O)OH, and —C(CH$_3$)$_2$C(═O)OH.

In one embodiment of this aspect of the invention the heterocyclic group is chosen from thienyl (thiophenyl), benzo[b]thienyl, naphtho[2,3-b]thienyl, thianthrenyl, furyl (furanyl), isobenzofuranyl, chromenyl, xanthenyl, phenoxanthinyl, pyrrolyl, 2H-pyrrolyl, imidazolyl, pyrazolyl, pyridyl (pyridinyl), 2-pyridyl, 3-pyridyl, 4-pyridyl, pyrazinyl, pyrimidinyl, pyridazinyl, tetrahydrofuranyl, pyranyl, piperidinyl, piperazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, quinuclidinyl, morpholinyl, cinnolinyl, pteridinyl, carbazolyl, beta-carbolinyl, phenanthridinyl, acrindinyl, perimidinyl, phenanthrolinyl, phenazinyl, isothiazolyl, phenothiazinyl, oxazolyl, isoxazolyl, furazanyl, phenoxazinyl, 1,4-dihydroquinoxaline-2, 3-dione, 7 aminoisocoumarin, pyrido[1,2-a]pyrimidin-4-one, pyrazolo[1,5-a]pyrimidinyl, pyrazolo[1,5-a]pyrimidin-3-yl, 1,2-benzoisoxazol-3-yl, benzimidazolyl, 2-oxindolyl and 2 oxobenzimidazolyl. In one sub-embodiment of this embodiment, the heterocyclic group is chosen from pyridinyl, isoxazolyl, furanyl, thiazolyl, pyrimidinyl, pyrrolyl, thiophenyl, triazolyl, benzo[1,3]dioxolyl, and benzofuranyl.

In an eighteenth embodiment, the invention provides compounds of Formula I and II:

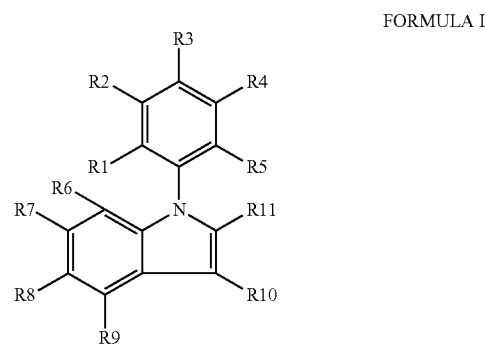

FORMULA I

-continued

FORMULA II

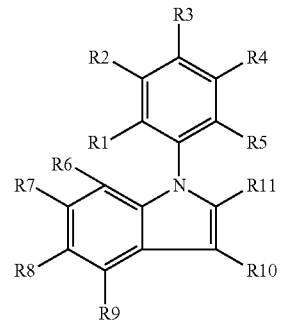

wherein R1-R9 and R11 independent of one another, are chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$ alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl, heterocyclic, or cycloalkyl ring;

R10 is a heterocyclic group with one or more substituents independently chosen from -L-C(=O)OH, -L-CH=CHC(=O)OH, -L-C(=O)NH$_2$, -L-C(=O)NH($C_{1-3}$ alkyl), -L-C(=O)N($C_{1-3}$ alkyl)$_2$, -L-S(=O)$_2$($C_{1-3}$ alkyl), -L-S(=O)$_2$NH$_2$, -L-S(=O)$_2$N($C_{1-3}$ alkyl)$_2$, -L-S(=O)$_2$NH($C_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl;

R$_o$ is chosen from alkyl and haloalkyl; and

L can be saturated, partially saturated, or unsaturated, and is chosen from —(CH$_2$)$_n$—(CH$_2$)$_n$—, —(CH$_2$)$_n$C(=O)(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, 3, 4, 5, 6, 7, and 8, wherein each carbon can be optionally substituted with one or more $C_{1-3}$ alkyl or $C_{3-6}$ cycloalkyl.

In one embodiment of the eighteenth aspect of the invention, one substituent on the heterocyclic group of R10 is chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, —C(CH$_3$)$_2$C(=O)OH, —C(=O)NH$_2$, —C(=O)NHCH$_3$, —C(=O)N(CH$_3$)$_2$, —S(=O)$_2$($C_{1-3}$ alkyl), —S(=O)$_2$NH$_2$, —S(=O)$_2$NHCH$_3$, —S(=O)$_2$N(CH$_3$)$_2$, —C(=O)NH($C_{1-3}$ alkyl), —C(=O)N($C_{1-3}$ alkyl)$_2$, —S(=O)$_2$NH$_2$, and —S(=O)$_2$N($C_{1-3}$alkyl)$_2$.

In another embodiment of the eighteenth aspect of the invention, one substituent on the heterocyclic group of R10 is chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, and —C(CH$_3$)$_2$C(=O)OH.

In one embodiment of this aspect of the invention the heterocyclic group is chosen from thienyl (thiophenyl), benzo[b]thienyl, naphtho[2,3-b]thienyl, thianthrenyl, furyl (furanyl), isobenzofuranyl, chromenyl, xanthenyl, phenoxanthinyl, pyrrolyl, 2H-pyrrolyl, imidazolyl, pyrazolyl, pyridyl (pyridinyl), 2-pyridyl, 3-pyridyl, 4-pyridyl, pyrazinyl, pyrimidinyl, pyridazinyl, tetrahydrofuranyl, pyranyl, piperidinyl, piperazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, quinuclidinyl, morpholinyl, cinnolinyl, pteridinyl, carbazolyl, beta-carbolinyl, phenanthridinyl, acrindinyl, perimidinyl, phenanthrolinyl, phenazinyl, isothiazolyl, phenothiazinyl, oxazolyl, isoxazolyl, furazanyl, phenoxazinyl, 1,4-dihydroquinoxaline-2,3-dione, 7 aminoisocoumarin, pyrido[1,2-a]pyrimidin-4-one, pyrazolo[1,5-a]pyrimidinyl, pyrazolo[1,5-a]pyrimidin-3-yl, 1,2-benzoisoxazol-3-yl, benzimidazolyl, 2-oxindolyl and 2 oxobenzimidazolyl. In one sub-embodiment of this embodiment, the heterocyclic group is chosen from pyridinyl, isoxazolyl, furanyl, thiazolyl, pyrimidinyl, pyrrolyl, thiophenyl, triazolyl, benzo[1,3]dioxolyl, and benzofuranyl.

In a nineteenth aspect, the invention provides compounds of Formula I and II:

FORMULA I

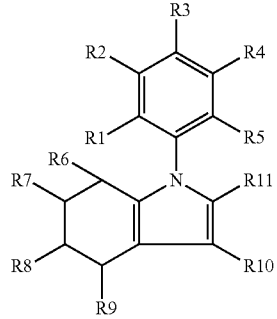

FORMULA II

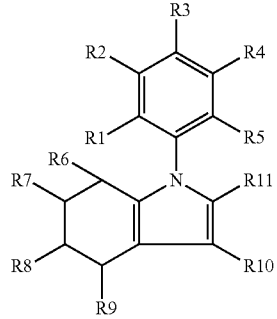

wherein R1-R9, independent of one another, are chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$ alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl, heterocyclic, or cycloalkyl ring;

R10 and R11 are independently chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$NH$_2$, —S(=O)$_2$($C_{1-3}$alkyl), —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, —NO$_2$, and -L-R12;

R12 is a heterocyclic group with one or more substituents independently chosen from -L-C(=O)OH, -L-CH=CHC(=O)OH, -L-C(=O)NH$_2$, -L-C(=O)NH($C_{1-3}$ alkyl), -L-C(=O)N($C_{1-3}$ alkyl)$_2$, -L-S(=O)$_2$($C_{1-3}$alkyl), -L-S(=O)$_2$NH$_2$, -L-S(=O)$_2$N($C_{1-3}$ alkyl)$_2$, -L-S(=O)$_2$NH($C_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl;

R$_o$ is chosen from alkyl and haloalkyl; and

L can be saturated, partially saturated, or unsaturated, and is chosen from —(CH$_2$)$_n$—(CH$_2$)$_n$—, —(CH$_2$)$_n$C(=O)(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, 3, 4, 5, 6, 7, and 8, wherein each carbon can be optionally substituted with one or more $C_{1-3}$ alkyl or $C_{3-6}$ cycloalkyl.

In one embodiment of the nineteenth aspect of the invention, R12 is present and has one or more substituents independently chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, —C(CH$_3$)$_2$C(=O)OH, —C(=O)NH$_2$, —C(=O)NHCH$_3$, —C(=O)N(CH$_3$)$_2$, —S(=O)$_2$($C_{1-3}$alkyl), —S(=O)$_2$NH$_2$, —S(=O)$_2$NHCH$_3$, —S(=O)$_2$N(CH$_3$)$_2$, —C(=O)NH($C_{1-3}$alkyl), —C(=O)N($C_{1-3}$alkyl)$_2$, —S(=O)$_2$NH$_2$, and —S(=O)$_2$N($C_{1-3}$alkyl)$_2$.

In another embodiment of this nineteenth aspect of the invention, R12 is present and has one substituent chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, and —C(CH$_3$)$_2$C(=O)OH.

In one embodiment of this aspect of the invention the heterocyclic group is chosen from thienyl (thiophenyl), benzo[b]thienyl, naphtho[2,3-b]thienyl, thianthrenyl, furyl (furanyl), isobenzofuranyl, chromenyl, xanthenyl, phenoxanthinyl, pyrrolyl, 2H-pyrrolyl, imidazolyl, pyrazolyl, pyridyl (pyridinyl), 2-pyridyl, 3-pyridyl, 4-pyridyl, pyrazinyl, pyrimidinyl, pyridazinyl, tetrahydrofuranyl, pyranyl, piperidinyl, piperazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, quinuclidinyl, morpholinyl, cinnolinyl, pteridinyl, carbazolyl, beta-carbolinyl, phenanthridinyl, acrindinyl, perimidinyl, phenanthrolinyl, phenazinyl, isothiazolyl, phenothiazinyl, oxazolyl, isoxazolyl, furazanyl, phenoxazinyl, 1,4-dihydroquinoxaline-2,3-dione, 7 aminoisocoumarin, pyrido[1,2-a]pyrimidin-4-one, pyrazolo[1,5-a]pyrimidinyl, pyrazolo[1,5-a]pyrimidin-3-yl, 1,2-benzoisoxazol-3-yl, benzimidazolyl, 2-oxindolyl and 2 oxobenzimidazolyl. In one sub-embodiment of this embodiment, the heterocyclic group is chosen from pyridinyl, isoxazolyl, furanyl, thiazolyl, pyrimidinyl, pyrrolyl, thiophenyl, triazolyl, benzo[1,3]dioxolyl, and benzofuranyl.

In a twentieth aspect, the invention provides compounds of Formula V and VI:

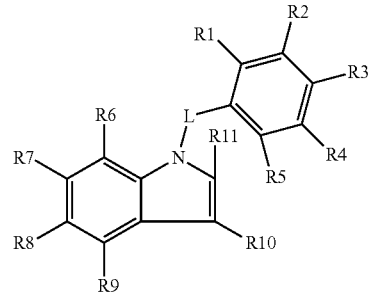

FORMULA V

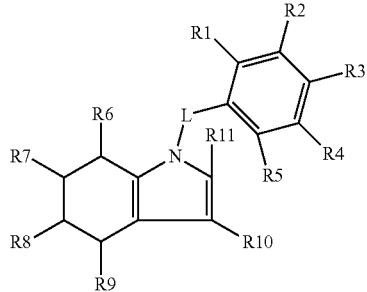

FORMULA VI wherein one or more of R1-R5 is independently chosen from -L-C(=O)OH, -L-CH=CHC(=O)OH, -L-C(=O)NH$_2$, -L-C(=O)NH($C_{1-3}$ alkyl), -L-C(=O)N($C_{1-3}$ alkyl)$_2$, -L-S(=O)$_2$($C_{1-3}$alkyl), -L-S(=O)$_2$NH$_2$, -L-S(=O)$_2$N($C_{1-3}$ alkyl)$_2$, -L-S(=O)$_2$NH($C_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl, and the others of R1-R5, independent of one another, are chosen from hydro, hydroxyl, halo, alkyl, alkoxy, haloalkyl, halo alkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, and —NO$_2$;

R$_o$ is chosen from alkyl and haloalkyl;

R6-R10, independent of one another, are chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl, heterocyclic, or cycloalkyl ring;

R11 is an optionally substituted heterocyclic group; and

L can be saturated, partially saturated, or unsaturated, and is chosen from —(CH$_2$)$_n$—(CH$_2$)$_n$—, —(CH$_2$)$_n$C(=O)(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, 3, 4, 5, 6, 7, and 8, wherein each carbon can be optionally substituted with one or more C$_{1-3}$ alkyl or C$_{3-6}$ cycloalkyl.

In one embodiment of the twentieth aspect of the invention, one of R1-R5 in the compounds of Formulae I and II, is chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, —C(CH$_3$)$_2$C(=O)OH, —C(=O)NH$_2$, —C(=O)NHCH$_3$, —C(=O)N(CH$_3$)$_2$, —S(=O)$_2$(C$_{1-3}$alkyl), —S(=O)$_2$NH$_2$, —S(=O)$_2$NHCH$_3$, —S(=O)$_2$N(CH$_3$)$_2$, —C(=O)NH(C$_{1-3}$alkyl), —C(=O)N(C$_{1-3}$ alkyl)$_2$, —S(=O)$_2$NH$_2$, and —S(=O)$_2$N(C$_{1-3}$ alkyl)$_2$, and the others of R1-R5, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$;

R6-R10, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$; two adjacent of R6-R9 can be taken together to form a 4-7 member optionally substituted aryl or cycloalkyl ring;

L is —(CH$_2$)$_n$—(CH$_2$)$_n$—, with n independently 0, 1, 2, or 3; and

R11 is an optionally substituted heterocyclic group.

In another embodiment of this twentieth of the invention, L is a bond, one of R1-R5 is chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, and —C(CH$_3$)$_2$C(=O)OH; and the others of R1-R5 independently are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$ alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$;

R6-R10, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$ alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and NO$_2$; two of R6-R9 can be taken together to form an optionally substituted 4-7 member aryl, heterocyclic, or cycloalkyl ring; and R11 is an optionally substituted heterocyclic group.

In one embodiment of this aspect of the invention the heterocyclic group is chosen from thienyl (thiophenyl), benzo[b]thienyl, naphtho[2,3-b]thienyl, thianthrenyl, furyl (furanyl), isobenzofuranyl, chromenyl, xanthenyl, phenoxanthinyl, pyrrolyl, 2H-pyrrolyl, imidazolyl, pyrazolyl, pyridyl (pyridinyl), 2-pyridyl, 3-pyridyl, 4-pyridyl, pyrazinyl, pyrimidinyl, pyridazinyl, tetrahydrofuranyl, pyranyl, piperidinyl, piperazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, quinuclidinyl, morpholinyl, cinnolinyl, pteridinyl, carbazolyl, beta-carbolinyl, phenanthridinyl, acrindinyl, perimidinyl, phenanthrolinyl, phenazinyl, isothiazolyl, phenothiazinyl, oxazolyl, isoxazolyl, furazanyl, phenoxazinyl, 1,4-dihydroquinoxaline-2,3-dione, 7 aminoisocoumarin, pyrido[1,2-a]pyrimidin-4-one, pyrazolo[1,5-a]pyrimidinyl, pyrazolo[1,5-a]pyrimidin-3-yl, 1,2-benzoisoxazol-3-yl, benzimidazolyl, 2-oxindolyl and 2 oxobenzimidazolyl. In one sub-embodiment of this embodiment, the heterocyclic group is chosen from pyridinyl, isoxazolyl, furanyl, thiazolyl, pyrimidinyl, pyrrolyl, thiophenyl, triazolyl, benzo[1,3]dioxolyl, and benzofuranyl.

In a twenty-first aspect, the invention provides compounds of Formula V and VI:

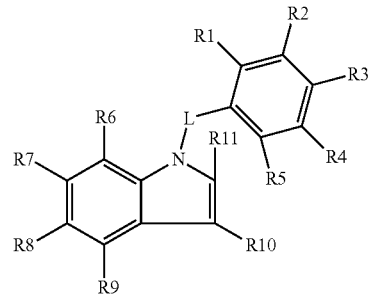

FORMULA V

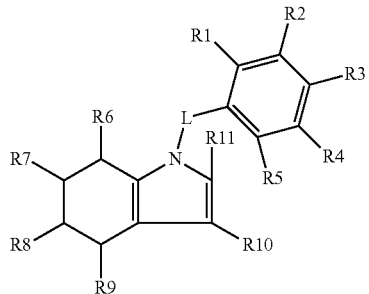

FORMULA VI wherein R1-R11, independent of one another, are chosen from -L-R12, -L-C(=O)OH, -L-CH=CHC(=O)OH, -L-C(=O)NH$_2$, -L-C(=O)NH(C$_{1-3}$ alkyl), -L-C(=O)N(C$_{1-3}$ alkyl)$_2$, -L-S(=O)$_2$(C$_{1-3}$alkyl), -L-S(=O)$_2$NH$_2$, -L-S(=O)$_2$N(C$_{1-3}$ alkyl)$_2$, -L-S(=O)$_2$NH(C$_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl;

R$_o$ is chosen from alkyl and haloalkyl;

R12 is a heterocyclic group with one or more substituents independently chosen -L-C(=O)OH, -L-CH=CHC(=O)OH, -L-C(=O)NH$_2$, -L-C(=O)NH(C$_{1-3}$ alkyl), -L-C(=O)N(C$_{1-3}$ alkyl)$_2$, -L-S(=O)$_2$(C$_{1-3}$ alkyl), -L-S(=O)$_2$NH$_2$, -L-S(=O)$_2$N(C$_{1-3}$ alkyl)$_2$, -L-S(=O)$_2$NH(C$_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl; and the others of R1-R11 are independently chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl, heterocyclic, or cycloalkyl ring; and L can be saturated, partially saturated, or unsaturated, and is chosen from —(CH$_2$)$_n$—(CH$_2$)$_n$—, —(CH$_2$)$_n$C(=O)(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, 3, 4, 5, 6, 7, and 8, wherein each carbon can be optionally substituted with one or more $C_{1-3}$ alkyl or $C_{3-6}$ cycloalkyl.

In one embodiment of the twenty-first aspect of the invention, R12 is present and has one or more substituents independently chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, —C(CH$_3$)$_2$C(=O)OH, —C(=O)NH$_2$, —C(=O)NHCH$_3$, —C(=O)N(CH$_3$)$_2$, —S(=O)$_2$($C_{1-3}$alkyl), —S(=O)$_2$NH$_2$, —S(=O)$_2$NHCH$_3$, —S(=O)$_2$N(CH$_3$)$_2$, —C(=O)NH($C_{1-3}$alkyl), —C(=O)N($C_{1-3}$ alkyl)$_2$, —S(=O)$_2$NH$_2$, and —S(=O)$_2$N($C_{1-3}$ alkyl)$_2$.

In another embodiment of this twenty-first aspect of the invention, L is a bond, R12 is present and has one substituent chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, and —C(CH$_3$)$_2$C(=O)OH.

In one embodiment of this twenty-first aspect, the invention includes analogs where the ring to which R1-R5 are attached is a 4-7 member heterocyclic ring instead a phenyl ring.

In one embodiment of this aspect of the invention the heterocyclic group is chosen from thienyl (thiophenyl), benzo[b]thienyl, naphtho[2,3-b]thienyl, thianthrenyl, furyl (furanyl), isobenzofuranyl, chromenyl, xanthenyl, phenoxanthinyl, pyrrolyl, 2H-pyrrolyl, imidazolyl, pyrazolyl, pyridyl (pyridinyl), 2-pyridyl, 3-pyridyl, 4-pyridyl, pyrazinyl, pyrimidinyl, pyridazinyl, tetrahydrofuranyl, pyranyl, piperidinyl, piperazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, quinuclidinyl, morpholinyl, cinnolinyl, pteridinyl, carbazolyl, beta-carbolinyl, phenanthridinyl, acrindinyl, perimidinyl, phenanthrolinyl, phenazinyl, isothiazolyl, phenothiazinyl, oxazolyl, isoxazolyl, furazanyl, phenoxazinyl, 1,4-dihydroquinoxaline-2,3-dione, 7 aminoisocoumarin, pyrido[1,2-a]pyrimidin-4-one, pyrazolo[1,5-a]pyrimidinyl, pyrazolo[1,5-a]pyrimidin-3-yl, 1,2-benzoisoxazol-3-yl, benzimidazolyl, 2-oxindolyl and 2 oxobenzimidazolyl. In one sub-embodiment of this embodiment, the heterocyclic group is chosen from pyridinyl, isoxazolyl, furanyl, thiazolyl, pyrimidinyl, pyrrolyl, thiophenyl, triazolyl, benzo[1,3]dioxolyl, and benzofuranyl.

In another aspect of the invention, one or more of the carbon atoms of the indole core are replaced by a heteroatom independently —N—, —O—, and —S—. In one embodiment, the substituents are as in any one of the other aspects and/or sub-embodiments of the invention.

In another aspect of the invention, the core indole group is replaced with a group chosen from 5,7-Dihydro-6H-pyrrolo[2,3-h]cinnoline; 5,7-Dihydro-6H-pyrrolo[2,3-h]quinazoline; 4,5-Dihydro-3H-3,6,7-triaza-cyclopenta[α]naphthalene; 5,7-Dihydro-6H-pyrrolo[3,2-f]quinoxaline; 5,7-Dihydro-6H-pyrrolo[3,2-f]phthalazine; 5,7-Dihydro-6H-pyrrolo[2,3-h]quinoline; 5,7-Dihydro-6H-pyrrolo[3,2-f]pyrrolo[2,3-h]quinazoline; 4,5-Dihydro-3H-pyrrolo[3,2-f]iso quino line; 4,5-Dihydro-3H-pyrrolo[3,2-f]quinoline; and 5,7-Dihydro-6H-pyrrolo[2,3-h]iso quino line. In one embodiment, the substituents are as in any one of the other aspects and/or sub-embodiments of the invention.

In some aspects of the invention, L is substituted with one or more substituents independently chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, and —C(CH$_3$)$_2$C(=O)OH, in lieu of having one of said substituents elsewhere in the compounds of Formulae I-XVI.

In some embodiments, of the first through twenty-first aspects of the invention, if a position in Formulae I-XVI is not specified then it can be specified as in one of the other embodiments of that aspect of the invention. Alternatively, the position can be substituted with one or more substituents independently chosen from the list of optional substituents below.

Optionally substituted, when used herein without reference to further definition, refers to a substituent independently chosen from the group consisting of hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$ alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, and NO$_2$.

Furthermore, the invention provides derivatives or analog of the compounds defined in first through twenty-first aspects of the invention, where the derivative or analog is chosen from an ester (e.g., methyl or ethyl ester), an amide, a carbamate, a urea, an amidine, or a combination thereof. Methods for generating an ester, an amide, a carbamate, a urea, an amidine, or a combination thereof, of the compounds of the first aspect through the twenty-first aspects are known to an ordinary artisan skilled in organic chemical synthesis.

As the skilled artisan readily recognizes, in some of the embodiments of the first twenty-one aspects of the invention, some of the compounds can have more than one -L- group, each of which is independent chosen.

Methods of Prevention and Treatment

In some aspects, the invention provides methods for treating and/or preventing neurodegenerative disorders like AD and MCI, and lowering Aβ$_{42}$ in an individual in need of such treatment. It is believed that by lowering the amounts of Aβ$_{42}$ in an individual by administering an Aβ$_{42}$ lowering effective amount of a composition described herein, that Alzheimer's disease and mild cognitive impairment can be treated or prevented. Generally, the invention relates to the idea that compounds of Formulae I-XVI can be used to lower Aβ$_{42}$ levels. Thus, diseases characterized by increased levels of Aβ$_{42}$, can be treated or prevented with the methods of the invention which are designed to lower $A\beta_{42}$, prevent an increase in $A\beta_{42}$, and/or reduce the rate of increase of $A\beta_{42}$.

The invention is based on the fact that the inventors have discovered that compounds of Formulae I-XVI lower $A\beta_{42}$ levels in in vitro APP processing assays. Furthermore, compounds of Formulae I-XVI, in general, have negligible levels of COX inhibition and therefore are thought to essentially be devoid of the deleterious side-effects associated with COX inhibition. Thus, a preferred embodiment of the invention is the use of a pharmaceutical composition having one or more compounds of Formulae I-XVI, where the compound lowers $A\beta_{42}$ levels and does not substantial inhibit the cyclooxygenases. Preferred compounds of Formulae I-XVI for use in the invention are those that have little or negligible COX-1 and/or COX-2 inhibition at 1 μM, more preferred are those that little or negligible COX-1 and/or COX-2 inhibition at 10 μM, and more preferred are those that little or negligible COX-1 and/or COX-2 inhibition at 100 μM compound. COX-1 and COX-2 inhibition can be determined with a COX inhibitor screening kit from e.g., Cayman Chemical, Ann Arbor, Mich. (Cat. #560131).

In one embodiment of the invention, a method for lowering $A\beta_{42}$ protein levels, in an individual in need of such treatment, is provided that includes the step of administering an effective amount of a compound of Formulae I-XVI as described above.

While not wishing to be bound by theory, it is believed that the compound of Formulae I-XVI acts in vivo to treat and/or prevent Alzheimer's disease and MCI by lowering the amount of $A\beta_{42}$ that is present or would be present in the absence of such treatment. Amyloid β polypeptides are derived from amyloid precursor proteins (APPs). A variety of amyloid β polypeptides are known including $A\beta_{34}$, $A\beta_{37}$, $A\beta_{38}$, $A\beta_{39}$, and $A\beta_{40}$. Increased $A\beta_{42}$ levels are associated with Alzheimer's disease and MCI. Thus, by lowering the amounts of $A\beta_{42}$, a treatment is provided for combating Alzheimer's disease and/or MCI.

In another embodiment, the invention relates to a method of preventing Alzheimer's disease. According to this embodiment, a method for preventing Alzheimer's disease is provided which comprises administering, to an individual in need of such treatment, a composition comprising a compound having Formulae I-XVI. The method of this embodiment is useful for preventing the symptoms of Alzheimer's disease, the onset of Alzheimer's disease, and/or the progression of the disease.

In another embodiment, the invention provides a method of treating a neurodegenerative disorder, by identifying a patient in need of such treatment, and administering to the patient a therapeutically effective amount of a pharmaceutical composition having one or more compounds of Formulae I-XVI. Administration of a compound of Formulae I-XVI for at least 4 weeks, preferably at least 4 months, and more desirably at least 8 months, can provide an improvement or lessening in decline of cognitive function as characterized by cognition tests, biochemical disease marker progression, and/or plaque pathology. It is preferred that the lessening in decline in cognitive function is at least 25% as compared to individuals treated with placebo, more preferably at least 40%, and even more desirably at least 60%. For example, an individual treated with placebo having probable mild-to-moderate Alzheimer's disease is expected to score approximately 5.5 points worse on the ADAS-cog test after a specified period of time of treatment (e.g., 1 year) whereas an individual treated with the composition of this aspect of the invention for the same period of time will score approximately 2.2 points worse on the ADAS-cog scale with a 60% decrease in decline or 3.3 points worse with a 40% decrease in decline in cognitive function when treated with the composition for the same specified period of time. The pharmaceutical composition for use in the invention is formulated with one or more pharmaceutically acceptable excipients, salts, or carriers. The pharmaceutical composition for use in the invention is delivered orally, preferably in a tablet or capsule dosage form.

In yet another embodiment, the invention provides a method for prophylaxis against a neurodegenerative disorder, by identifying a patient in need of or desiring such treatment, and administering to the patient a prophylactically effective amount of a pharmaceutical composition having one or more compounds of Formulae I-XVI. Preferred compounds for use in this embodiment of the invention include those in Tables 1-6. Administration of a compound of Formulae I-XVI for at least 4 weeks, preferably at least 4 months, and more desirably at least 8 months, can delay the onset of the neurodegenerative disorder or slow the rate of onset of symptoms of the disorder. Patients having a predisposition to a neurodegenerative disorder or suspected of needing prophylaxis can be identified by any method known to the skilled artisan for diagnosis of such neurodegenerative disorders.

In still another embodiment, the invention provides a method of treating a disease characterized by abnormal amyloid precursor protein processing by (1) identifying a patient in need of such treatment, and (2) administering to the patient a therapeutically effective amount of a pharmaceutical composition having one or more compounds of Formulae I-XVI. Examples of biochemical disease markers include, for example, amyloid beta peptide (Aβ), $A\beta_{42}$, and tau.

In another embodiment, the invention provides a method of prophylaxis or delaying the onset of a disease (or one or more symptoms thereof) characterized by abnormal amyloid precursor protein processing, by identifying a patient in need of such treatment and administering to the patient a prophylactically effective amount of a pharmaceutical composition having one or more compounds of Formulae I-XVI. Oral administration of the pharmaceutical composition for use in the method of this aspect the invention for at least 4 weeks, preferably at least 4 months, and more desirably at least 8 months, prevents or delays the onset of the disease (or symptoms thereof) characterized by abnormal amyloid precursor protein processing.

In another embodiment, the invention provides a method of treating Alzheimer's disease comprising administering to a patient in need of such treatment, a pharmaceutical composition having one or more compounds of Formulae I-XVI. Oral administration of the pharmaceutical composition for use in the method of this aspect of the invention for at least 4 weeks, preferably at least 4 months, and more desirably at least 8 months, provides an improvement or lessening in decline of cognitive function as characterized by cognition tests, biochemical disease marker progression, and/or plaque pathology. Desirably, the oral dose is provided in capsule or tablet form. According to this aspect of the invention, a patient in need of treatment is administered an Alzheimer's disease treating effective amount of a pharmaceutical composition having one or more compounds of Formulae I-XVI and one or more pharmaceutically acceptable salts, excipients and carriers. The method of this aspect of the invention involves identifying an individual likely to have mild-to-moderate Alzheimer's disease. An individual having probable mild-to-moderate Alzheimer's disease can be diagnosed by any method available to the ordinary artisan skilled in such diagnoses. For example, diagnosis can be according to DSM IV (TR) and/or meets NINCDS-ADRDA criteria for probable AD. According to this aspect of the invention, individuals with probable mild-to-moderate AD take an oral dose of a pharmaceutical composition for a specified period of time. Individuals undergoing such treatment are likely to see an improvement or lessening in decline of cognitive function, an improvement or lessening in decline in biochemical disease marker progression, and/or an improvement or lessening of decline in plaque pathology. A lessening in decline in cognitive function can be assessed using tests of cognitive function like the ADAS-cog. For example, an individual treated with placebo having probable mild-to-moderate Alzheimer's disease is expected to score approximately 5.5 points worse on the ADAS-cog test after a specified period of time of treatment (e.g., 1 year) whereas an individual treated with the composition of this aspect of the invention for the same period of time will score approximately 2.2 points worse on the ADAS-cog scale with a 60% decrease in decline or 3.3 points worse with a 40% decrease in decline in cognitive function when treated with the composition for the same specified period of time. In a related aspect, the method involves identifying a patient having moderate-to-severe AD and administering to the patient an Alzheimer's disease treating effective amount of a compound of Formulae I-XVI.

In another embodiment, the invention provides a method of preventing the onset of Alzheimer's disease comprising administering to a patient in need of or desiring such treatment, a pharmaceutical composition having one or more compounds of Formulae I-XVI. Administration of the pharmaceutical composition for use in the method of this aspect of the invention for at least 4 weeks, preferably at least 4 months, and more desirably at least 8 months, delays the onset of decline of cognitive function, biochemical disease marker progression, and/or plaque pathology. According to this embodiment, an individual desiring or needing preventative treatment against the onset of AD is administered a pharmaceutical composition having one or more compounds of Formulae I-XVI. The preventative treatment is preferably maintained as long as the individual continues to desire or need the treatment. Individuals needing or desiring preventative treatment against AD can be those having risk factors for developing AD. For example, risk factors for developing AD can be genetic factors or environmental factors. In one embodiment, the risk factor is age. Genetic risk factors can be assessed in a variety of ways, such as ascertaining the family medical history of the individual, or performing a genetic test to identify genes that confer a predisposition for developing AD. Additionally, risk factors can be assessed by monitoring genetic and biochemical markers. The method of this embodiment involves evaluating risk factors for cognitive decline. Evaluation of risk factors can include genetic testing for predisposing genes, alleles, and polymorphisms. Risk factors also refer to environmental factors like stroke, brain injury, age, and diet. Depending on the risk factor or factors associated with a particular patient a particular treatment regimen is selected for treating cognitive decline. For example, mutations in a Familial Alzheimer's disease gene are a risk factor. Another risk factor for cognitive decline is age. Head trauma is another risk factor for cognitive decline. Based on the patient's risk factors, a physician will prescribe a particular therapeutic treatment or prophylactic treatment suitable for the patient.

In still another embodiment, the invention provides a method of lowering $A\beta_{42}$ levels to a greater extent than inhibiting COX-1, COX-2, or a combination thereof. In particular, the method of this embodiment comprises administering to a patient in need of treatment an effective amount of one or more compounds of Formulae I-XVI. The method of this embodiment involves the lowering of $A\beta_{42}$ levels while not substantial affecting the activity of COX-1, COX-2, or both COX-1, and COX-2. Thus, the amount of the composition administered is effective for lowering $A\beta_{42}$ levels and does not substantially inhibit COX-1, COX-2, or both COX-1 and COX-2. For example, the effective amount can be above the ED50 (the dose therapeutically effective in 50% of the population) for $A\beta_{42}$ lowering, and below the ED50 for COX inhibition. Another example is a sufficiently small amount of compound so that inhibition of at least one COX activity is negligible and $A\beta_{42}$ levels are reduced. The method of this embodiment can be used to treat and/or prevent Alzheimer's disease. The method of this embodiment can also be used to treat and/or prevent MCI and other neurodegenerative disorders.

According to a preferred embodiment, the invention provides a method of lowering $A\beta_{42}$ levels to a greater extent than inhibiting COX-1, COX-2, or a combination thereof. In particular, the method of this embodiment comprises administering, to a patient in need of treatment, an effective amount of one or more compounds of Formulae I-XVI, wherein the effective amount of compound is capable of lowering $A\beta_{42}$, while not substantially affecting or inhibiting the activity of at least one isoform of COX. Thus, the method of this embodiment involves the lowering of $A\beta_{42}$ levels while not substantially inhibiting the activity of COX-1, COX-2, or both COX-1 and COX-2. The method of this embodiment can be used to treat and/or prevent Alzheimer's disease, MCI, and/or other neurodegenerative disorders. In one aspect of this embodiment, the effective amount of compound having Formulae I-XVI reduce $A\beta_{42}$ levels or production of $A\beta_{42}$ by at least 1, 2, 5, 10, 15, 20, 25, 30, 40, or 50 or more percent while inhibiting COX-1, COX-2, or both COX-1 and COX-2 by less than 1, 2, 5, 10, 15, 20, 25, 30, 40, 50, 60, 70, 80, or 90 percent. In a preferred aspect of this embodiment, the effective amount of compound according to Formulae I-XVI lower $A\beta_{42}$ by at least 5 percent while not substantially inhibiting COX-1, COX-2, or both COX-1 and COX-2 activity or levels. In another preferred aspect of this embodiment, the effective amount of the compound having Formulae I-XVI that is administered to an individual is such that it lowers $A\beta_{42}$ levels, and does not inhibit COX activity to a significant extent, e.g., the amount administered is below the in vivo IC50 value for COX-1, COX-2 or both COX-1 and COX-2 and above the in vivo IC50 value for $A\beta_{42}$ lowering activity. As used in this context, IC50 refers to the amount of compound sufficient to inhibit COX activity by 50% (COX-1, COX-2, or both COX-1 and COX-2) or reduce $A\beta_{42}$ levels by 50%. An "effective amount" according to this preferred aspect of this embodiment, can also be viewed in terms of ED50 parameters, binding constants, dissociation constants, and other pharmacological parameters, e.g., the amount administered is below the ED50 value for COX-1, COX-2 or both COX-1 and COX-2 and above the ED50 value for $A\beta_{42}$. It is noted that the effective amount of the compound does not necessarily have to be above an IC50 or ED50 for $A\beta_{42}$ lowering and below the IC50 or ED50 for COX inhibition. That is, the "effective amount" can be at some intermediate value such that $A\beta_{42}$ levels are lowered to a greater extent than inhibition of COX-1, COX-2 or both COX-1 and COX-2.

The skilled artisan readily recognizes that the compounds and pharmaceutical compositions can be used to treat other disease besides those listed herein.

Patient Population

In one aspect of the invention, any individual having, or suspected of having, a neurodegenerative disorder, such as Alzheimer's disease, may be treated using the compositions and methods of the present invention. Individuals who would particularly benefit from the compositions and methods of the invention include those individuals diagnosed as having mild to moderate Alzheimer's disease according to a medically-accepted diagnosis, such as, for example the NINCDS-ADRDA criteria. Progression of the disease may be followed by medically accepted measure of cognitive function, such as, for example, the Mini-Mental State Exam (MMSE; see Mohs et al. *Int. Psychogeriatr.* 8:195-203 (1996)); ADAS-Cog (Alzheimer Disease Assessment Scale-Cognitive; see Galasko et al. *Alzheimer Dis Assoc Disord,* 11 suppl 2:S33-9 (1997)); Behavioral Pathology in Alzheimer's Disease Rating Scale (BEHAVE-AD); Blessed Test; CANTAB—Cambridge Neuropsychological Test Automated Battery; CERAD (The Consortium to Establish a Registry for Alzheimer's Disease) Clinical and Neuropsychological Tests (includes MMSE); Clock Draw Test; Cornell Scale for Depression in Dementia (CSDD); Geriatric Depression Scale (GDS); Neuropsychiatric Inventory (NPI); the 7 Minute Screen; the Alzheimer's Disease Cooperative Study Activities of Daily Living scale (ADCS-ADL; see McKhann et al. *Neurology* 34:939-944 (1984)); the DSM-IV (Diagnostic and Statistical Manual of Mental Disorders—Fourth Edition (DSM-IV), published by the American Psychiatric Association, Washington D.C., 1994); or the NINCDS-ADRDA criteria (see Folstein et al. *J. Psychiatr. Res.* 12:189-198 (1975)). Individuals diagnosed as having probable AD can be identified as having a mild-to-moderate form of the disease by an accepted measure of cognitive function such as the MMSE. In addition, methods that allow for evaluating different regions of the brain and estimating plaque and tangle frequencies can be used. These methods are described by Braak et al. *Acta Neuropathol* 82:239-259 (1991); Khachaturian *Arch. Neuro.* 42:1097-1105 (1985); Mirra et al. (1991) *Neurology* 41:479-486; and Mirra et al. *Arch Pathol Lab Med* 117:132-144 (1993). The severity of AD is generally determined by one of the initial tests provided above. For example, MMSE scores of 26-19 indicate mild AD, while scores from 18-10 indicate moderate AD.

Diagnoses of Alzheimer's disease based on these tests are recorded as presumptive or probable, and may optionally be supported by one or more additional criteria. For example, a diagnosis of Alzheimer's disease may be supported by evidence of a family history of AD; non-specific changes in EEG, such as increased slow-wave activity; evidence of cerebral atrophy on CT with progression documented by serial observation; associated symptoms such as depression, insomnia, incontinence, delusions, illusions, hallucinations, catastrophic verbal, emotional or physical outbursts, sexual disorders, weight loss, and/or attendant neurologic abnormalities, such as increased muscle tone, myoclonus or gait disorder, etc.

Additionally, amyloid deposits, generally associated with AD, may be detected through the use of positron emission tomography (PET) using an amyloid-specific tracer such as Pittsburgh Compound-B (PIB). See Klunk et al., *Ann. Neurol.* 55(3):306-309 (2004). Increased amyloid deposits in the frontal, parietal, temporal and occipital cortices, and in the striatum, relative to normal brain tissue, as visualized, for example by PIB, support a diagnosis of AD. Generally, a greater number and density of amyloid deposits indicates more advanced AD.

The invention encompasses the treatment of an individual preferably having mild to moderate AD, to the extent that individual has AD, whether or not one or more non-AD neurodegenerative diseases or conditions are previously, concurrently or subsequently diagnosed.

The compounds and methods of the present invention are useful for individuals who have received prior medication for AD, as well as individuals who have received no prior medication for AD, and is useful for individuals currently receiving medication for AD other than a compound of Formulae I-XVI, and for individuals not receiving medication for AD other than a compound of Formulae I-XVI.

Individuals of any age may be treated by the methods of the invention, with the pharmaceutical compositions of the invention; however, the invention encompasses a preferred embodiment for treating or preventing Alzheimer's disease in individuals between the ages of 45 and 105. In various embodiments, individuals treated by the therapeutic or prophylactic methods of the invention may be from 55 to 70 years of age, 60 to 80 years of age, 55 to 65 years of age, 60 to 75 years of age, 65 to 80 years of age, 55 to 60 years of age, 60 to 65 years of age, 65 to 70 years of age, 70 to 75 years of age, 75 to 80 years of age, or 80 years old and older.

In yet another embodiment, the invention provides a method of slowing cognitive decline in an individual suspected of having mild cognitive impairment (MCI) comprising administering to the individual an effective amount of a compound of Formulae I-XVI. Mild cognitive impairment is a clinical condition between normal aging and Alzheimer's disease characterized by memory loss greater than expected for the particular age of the individual yet the individual does not meet the currently accepted definition for probable Alzheimer's disease. See, e.g., Petersen et al. *Arch. Neurol.* 58:1985-1992 (2001); Petersen *Nature Rev.* 2:646-653 (2003); and Morris et al. *J. Mol. Neuro.* 17:101-118 (2001). Thus, according to this embodiment an individual suspected of having or diagnosed with MCI is treated twice daily with a composition having a compound of Formulae I-XVI per dose for at least 4 weeks, at least 4 months, preferably at least 8 months, and more desirably at least 1 year. Typically, patients having MCI first complain of or have a loss of memory. Preferably an individual associated with the patient can corroborate the memory deficit. Furthermore, general cognition is not sufficiently impaired to cause concern about more widespread cognitive disorder and although daily living activities may be affected that are not significantly impaired and the patients are not demented. Individuals having or suspected of having MCI that are treated according to this embodiment can expect to slow cognitive decline and/or progression to probable AD.

Thus, in one embodiment, the invention provides a method of treating an individual known or suspected of having Alzheimer's disease comprising administering an effective amount of a compound of Formulae I-XVI. In a specific embodiment, the individual is diagnosed as having mild to moderate Alzheimer's disease. In another specific embodiment, the individual is diagnosed by a cognitive test as having mild to moderate AD. In another specific embodiment, the cognitive test is the Mini-Mental State Exam (MMSE). In another specific embodiment, the individual has a score on the MMSE of from 26 to 19, inclusive. In another specific embodiment, the individual has a score on the MMSE of from 18 to 10, inclusive. In another specific embodiment, the individual has a score on the MMSE of 26 to 10, inclusive.

In other embodiments, the invention provides a method of treating an individual known or suspected of having Alzheimer's disease comprising administering an effective amount of a compound of Formulae I-XVI, wherein the individual is concurrently taking a second drug for the treatment of Alzheimer's disease. In a further embodiment, the individual has been diagnosed as having mild to moderate Alzheimer's disease. In a specific embodiment, said second drug is an acetylcholinesterase (AChE) inhibitor. In a more specific embodiment, said AChE inhibitor is Galanthamine (galantamine, Reminyl); E2020 (Donepezil, Aricept); Physostigmine; Tacrine (tetrahydroaminoacridine, THA); Rivastigmine; Phenserine; Metrifonate (Promem); or Huperazine, or a combination of any of the foregoing. In another embodiment, the second drug is a drug other than an acetylcholinesterase inhibitor. In a preferred embodiment, the method or compositions of the invention are used in patients or individuals undergoing therapy with Aricept. The invention also encompasses methods of treating patients refractory to, or who no longer show improvement with, conventional AD therapy.

In another embodiment, the individual is concurrently taking a non-drug substance for the treatment of Alzheimer's disease. In a specific embodiment, said non-drug substance is an anti-oxidant. In another specific example, said anti-oxidant is vitamin C or vitamin E. In another specific embodiment, vitamin C is taken in a dose of 500-1000 mg per dose of a compound of Formulae I-XVI. In another specific embodiment, vitamin E is taken in a dose of 400-800 IU per dose of a compound of Formulae I-XVI. In this regard, the invention encompasses the use of one or more such anti-oxidants as an adjunct to therapy for Alzheimer's disease, and not primarily as a nutritional supplement.

In another embodiment, the invention provides a method of treating an individual diagnosed as having mild to moderate Alzheimer's disease comprising administering an effective amount of a compound of Formulae I-XVI, wherein the individual has, prior to taking a compound of Formulae I-XVI, taken a second drug for the treatment of Alzheimer's disease. In a specific embodiment, the second drug is an acetylcholinesterase (AChE) inhibitor. In a more specific embodiment, the ACE inhibitor is Galanthamine (galantamine, Reminyl); E2020 (Donepezil, Aricept); Physostigmine; Tacrine (tetrahydroaminoacridine, THA); Rivastigmine; Phenserine; Metrifonate (Promem); or Huperazine, or a combination of any of the foregoing. In another embodiment, the second drug is a drug other than an acetylcholinesterase inhibitor.

In another embodiment, the individual has, prior to taking a compound of Formulae I-XVI, taken a non-drug substance for the treatment of Alzheimer's disease. In a specific embodiment, said non-drug substance is an anti-oxidant. In a specific example, the anti-oxidant is vitamin C or vitamin E. In another specific embodiment, the vitamin C is taken in a dose of 500-1000 mg per dose. In another specific embodiment, the vitamin E is taken in a dose of 400-800 IU per dose. In this regard, the invention encompasses the use of one or more such anti-oxidants as an adjunct to therapy for Alzheimer's disease, and not primarily as a nutritional supplement.

The invention further provides a combination therapy strategy for preventing Alzheimer's disease and MCI. According to this aspect of the invention, an individual in need of treatment is administered a compound of Formulae I-XVI, and a compound chosen from NSAIDs (non-steroidal anti-inflammatory drugs), COX-2 inhibitors (cyclooxygenase-2), β-secretase inhibitors, R-flurbiprofen, γ-secretase inhibitors, acetylcholine esterase inhibitors, and NMDA antagonists. Preferably the combination therapy involves treating the individual in need of treatment with a compound of Formulae I-XVI in combination with an acetylcholine esterase inhibitor or an NMDA receptor antagonist. Preferred acetylcholine esterase inhibitors for combination therapy are tacrine, donepezil, rivastigmine, and galantamine. Preferred NMDA receptor antagonists for combination therapy are memantine, adamantane, amantadine, an adamantane derivative, dextromethorphan, dextrorphan, dizocilpine, ibogaine, ketamine, and remacemide. The acetylcholine esterase inhibitor or NMDA receptor antagonists is preferably formulated in a combination dosage form with a compound of Formulae I-XVI.

The treatment regime used in the combination therapy can involve administration of a composition comprising the combination of active ingredients, the concomitant administration of separate compositions, each comprising at least one active ingredient. Furthermore, the administration of the active ingredients can be performed at different times and/or different routes. For example, a composition comprising at least one active ingredient can be administered in the morning, and a composition comprising at least one different active ingredient can be administered in the evening. Another example would involve the administration of a composition having at least one active ingredient orally while the second composition is administered intravenously.

While not wishing to be bound by theory, it is believed that the compounds of Formulae I-XVI are capable of slowing the rate of death of neurons. Accordingly, it is also believed that the compounds of Formulae I-XVI acts in vivo to treat and/or prevent Alzheimer's disease and MCI by slowing the rate of death of neurons that is present or would be present in the absence of such treatment.

The skilled artisan readily recognizes that the invention includes the use of compounds of Formulae I-XVI, pharmaceutically acceptable salts, metabolites and prodrugs thereof in each of the described embodiments.

DEFINITIONS

As used herein, the term "alkyl" refers to a saturated aliphatic hydrocarbon including straight chain and branched chain groups. Preferably, the alkyl group has 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc. up to and including 20 carbon atoms). More preferably, it is a medium size alkyl having 1 to 10 carbon atoms. Even more preferably, it is a lower alkyl having 1 to 6 carbon atoms, and even more preferably 1 to 4 carbon atoms. The alkyl group may be substituted or unsubstituted. When substituted, the substituent group(s) is preferably one or more individually selected from cycloalkyl, aryl, heteroaryl, heteroalicyclic, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, C-carboxy, O-carboxy, cyanato, isocyanato, thiocyanato, isothiocyanato, nitro, silyl, and amino.

As used herein, the term "halo" refers to chloro, fluoro, bromo, and iodo.

As used herein, the term "hydro" refers to a hydrogen atom (—H group).

As used herein, the term "hydroxy" refers to an —OH group.

As used herein, the term "alkoxy" refers to both an —O-alkyl and an —O-cycloalkyl group, as defined herein. Lower alkoxy refers to —O-lower alkyl groups.

As used herein, the term "aryloxy" refers to both an —O-aryl and an —O-heteroaryl group, as defined herein.

As used herein, the term "mercapto" group refers to an —SH group.

As used herein, the term "alkylthio" group refers to both an S-alkyl and an —S-cycloalkyl group, as defined herein.

As used herein, the term "arylthio" group refers to both an —S-aryl and an —S-heteroaryl group, as defined herein.

As used herein, the term "carbonyl" group refers to a —C(=O)R" group, where R" is selected from the group consisting of hydro, alkyl, cycloalkyl, aryl, heteroaryl (bonded through a ring carbon) and heterocyclic (bonded through a ring carbon), as defined herein.

As used herein, the term "aldehyde" group refers to a carbonyl group where R" is hydro.

As used herein, the term "cycloketone" refer to a cycloalkyl group in which one of the carbon atoms which form the ring has a "=O" bonded to it; i.e. one of the ring carbon atoms is a —C(=O)-group.

As used herein, the term "thiocarbonyl" group refers to a —C(=S)R" group, with R" as defined herein.

As used herein, the term "O-carboxy" group refers to a R"C(=O)O-group, with R" as defined herein.

As used herein, the term "C-carboxy" group refers to a —C(=O)OR" groups with R" as defined herein.

As used herein, the term "ester" is a C-carboxy group, as defined herein, wherein R" is any of the listed groups other than hydro.

As used herein, the term "C-carboxy salt" refers to a —C(=O)O⁻M⁺ group wherein M⁺ is selected from the group consisting of lithium, sodium, magnesium, calcium, potassium, barium, iron, zinc and quaternary ammonium.

As used herein, the term "acetyl" group refers to a —C(=O)CH$_3$ group.

As used herein, the term "carboxyalkyl" refers to —(CH$_2$)$_r$C(=O)OR" wherein r is 1-6 and R" is as defined above.

As used herein, the term "carboxyalkyl salt" refers to a —(CH$_2$)$_r$C(=O)O⁻M⁺ wherein M⁺ is selected from the group consisting of lithium, sodium, potassium, calcium, magnesium, barium, iron, zinc and quaternary ammonium.

As used herein, the term "carboxylic acid" refers to a C-carboxy group in which R" is hydro.

As used herein, the term "haloalkyl" refers to an alkyl group substituted with 1 to 6 halo groups, preferably haloalkyl is a —CX$_3$ group wherein X is a halo group. The halo groups can be independently selected.

As used herein, the term "trihalomethanesulfonyl" refers to a X$_3$CS(=O)$_2$— group with X as defined above.

As used herein, the term "cyano" refers to a —C≡N group.

As used herein, the term "cyanato" refers to a —CNO group.

As used herein, the term "isocyanato" refers to a —NCO group.

As used herein, the term "thiocyanato" refers to a —CNS group.

As used herein, the term "isothiocyanato" refers to a —NCS group.

As used herein, the term "sulfinyl" refers to a —S(=O)R" group, with R" as defined herein.

As used herein, the term "sulfonyl" refers to a —S(=O)$_2$R" group, with R" as defined herein.

As used herein, the term "sulfonamido" refers to a —S(=O)$_2$ NR$^{17}$R$^{18}$, with R$^{17}$ and R$^{18}$ as defined herein.

As used herein, the term "trihalomethanesulfonamido" refers to a X$_3$CS(=O)$_2$ NR$^{17}$-group with X and R$^{17}$ as defined herein.

As used herein, the term "O-carbamyl" refers to a —OC(=O)NR$^{17}$R$^{18}$ group with R$^{17}$ and R$^{18}$ as defined herein.

As used herein, the term "N-carbamyl" refers to a R$^{18}$OC(=O)NR$^{17}$— group, with R$^{17}$ and R$^{18}$ as defined herein.

As used herein, the term "O-thiocarbamyl" refers to a —OC(=S)NR$^{17}$R$^{18}$ group with R$^{17}$ and R$^{18}$ as defined herein.

As used herein, the term "N-thiocarbamyl" refers to a R$^{17}$OC(=S)NR$^{18}$— group, with R$^{17}$ and R$^{18}$ as defined herein.

As used herein, the term "amino" refers to an —NR$^{17}$R$^{18}$ group, with R$^{17}$ and R$^{18}$ both being hydro.

As used herein, the term "C-amido" refers to a —C(=O)NR$^{17}$R$^{18}$ group with R$^{17}$ and R$^{18}$ as defined herein. An "N-amido" refers to a R$^{17}$C(=O)NR$^{18}$— group with R$^{17}$ and R$^{18}$ as defined herein.

As used herein, the term "nitro" refers to a —NO$_2$ group.

As used herein, the term "quaternary ammonium" refers to a —NR$^{17}$R$^{18}$R$^{19}$ group wherein R$^{17}$, R$^{18}$, and R$^{19}$ are independently selected from the group consisting of hydro and unsubstituted lower alkyl.

As used herein, the term "methylenedioxy, ethylenedioxy" refers to a —OCH$_2$O— group wherein the oxygen atoms are bonded to adjacent ring carbon atoms.

As used herein, the term "ethylenedioxy" refers to a —OCH$_2$CH$_2$O— group wherein the oxygen atoms are bonded to adjacent ring carbon atoms.

As used herein, the term "cycloalkyl" refers to an all-carbon monocyclic or fused ring (i.e., rings which share an adjacent pair of carbon atoms) group wherein one or more of the rings does not have a completely conjugated pi-electron system. Examples, without limitation, of cycloalkyl groups are cyclopropane, cyclobutane, cyclopentane, cyclopentene, cyclohexane, adamantane, cyclohexadiene, cycloheptane and, cycloheptatriene. A cycloalkyl group may be substituted or unsubstituted. When substituted, the substituent group(s) is preferably one or more individually selected from alkyl, aryl, heteroaryl, heterocyclic, hydroxy, alkoxy, aryloxy, mercapto, alkylthio, arylthio, cyano, halo, carbonyl, thiocarbonyl, carboxy, O-carbamyl, N-carbamyl, C-amido, N-amido, nitro, and amino.

As used herein, the term "heterocycle" or heterocyclic" refers to a saturated or partially saturated 3-7 membered monocyclic, or 7-10 membered bicyclic ring system, which consists of carbon atoms and from one to four heteroatoms independently selected from the group consisting of O, N, and S, wherein the nitrogen and sulfur heteroatoms can be optionally oxidized, the nitrogen can be optionally quaternized, and including any bicyclic group in which any of the above-defined heterocyclic rings is fused to a benzene ring, and wherein the heterocyclic ring can be substituted on carbon or on a nitrogen atom if the resulting compound is stable. Non-limiting saturated or partially saturated heterocyclic groups include tetrahydrofuranyl, pyranyl, piperidinyl, piperazinyl, pyrrolidinyl, imidazolidinyl, imidazolinyl, indolinyl, isoindolinyl, quinuclidinyl, morpholinyl, isochromanyl, chromanyl, pyrazolidinyl, pyrazolinyl, tetronoyl and tetramoyl groups. Example of "heterocycles" or "heterocyclic" rings also include, but are not limited to, morpholino, piperidyl, piperazinyl, pyrrolidinyl, thiomorpholino, homopiperazinyl, imidazolyl, imidazolidinyl, pyrazolidinyl, dioxanyl and dioxolanyl. "Heterocycle" can include heteroaryls when the pi-electron system of a heterocycle is completely conjugated.

As used herein, the term "aryl" refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, the substituted group(s) is preferably one or more selected from halo, trihalomethyl, alkyl, hydroxy, alkoxy, aryloxy, mercapto, alkylthio, arylthio, cyano, nitro, carbonyl, thiocarbonyl, C-carboxy, O-carboxy, O-carbamyl, N-carbamyl, O-thiocarbamyl, N-thiocarbamyl, C-amido, N-amido, sulfinyl, sulfonyl, S-sulfonamido, N-sulfonamido, trihalomethanesulfonamido, and amino.

As used herein, the term "heteroaryl" refers to groups having 5 to 14 ring atoms; 6, 10 or 14 pi electrons shared in a cyclic array; and containing carbon atoms and 1, 2 or 3 oxygen, nitrogen or sulfur heteroatoms. Non-limiting heteroaryl groups include thienyl (thiophenyl), benzo[b]thienyl, naphtho[2,3-b]thienyl, thianthrenyl, furyl (furanyl), isobenzofuranyl, chromenyl, xanthenyl, phenoxanthinyl, pyrrolyl, including without limitation 2H-pyrrolyl, imidazolyl, pyrazolyl, pyridyl (pyridinyl), including without limitation 2-pyridyl, 3-pyridyl, and 4-pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, beta-carbolinyl, phenanthridinyl, acrindinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7 aminoisocoumarin, pyrido[1,2-a]pyrimidin-4-one, pyrazolo[1,5-a]pyrimidinyl, including without limitation pyrazolo[1,5-a]pyrimidin-3-yl, 1,2-benzoisoxazol-3-yl, benzimidazolyl, 2-oxindolyl and 2 oxobenzimidazolyl. Where the heteroaryl group contains a nitrogen atom in a ring, such nitrogen atom may be in the form of an N-oxide, e.g., a pyridyl N oxide, pyrazinyl N-oxide and pyrimidinyl N-oxide. When substituted, the substituted group(s) is preferably one or more selected from alkyl, cycloalkyl, halo, trihalomethyl, hydroxy, alkoxy, aryloxy, mercapto, alkylthio, arylthio, cyano, nitro, carbonyl, thiocarbonyl, sulfonamido, carboxy, sulfinyl, sulfonyl, O-carbamyl, N-carbamyl, O-thiocarbamyl, N-thiocarbamyl, C-amido, N-amido, and amino.

As used herein, the term "preventing an increase in a symptom" refers to both not allowing a symptom to increase or worsen, as well as reducing the rate of increase in the symptom. For example, a symptom can be measured as the amount of particular disease marker, i.e., a protein. In another example the symptom can be cognitive decline. Preventing an increase, according to the definition provided herein, means that the amount of symptom (e.g., protein or cognitive decline) does not increase or that the rate at which it increases is reduced.

As used herein, the term "treating Alzheimer's disease" refers to a slowing of or a reversal of the progress of the disease. Treating Alzheimer's disease includes treating a symptom and/or reducing the symptoms of the disease.

As used herein, the term "preventing Alzheimer's disease" refers to a slowing of the disease or of the onset of the disease or the symptoms thereof. Preventing Alzheimer's disease can include stopping the onset of the disease or symptoms thereof.

As used herein, the term "$A\beta_{42}$ lowering" refers to the capability to reduce the amount of $A\beta_{42}$ present and/or being produced. Levels of $A\beta_{42}$ can be determined with an ELISA assay configured to detect $A\beta_{42}$. Methods of determining $A\beta_{42}$ levels are described in the examples and references cited therein.

As used herein, the term "unit dosage form" refers to a physically discrete unit, such as a capsule or tablet suitable as a unitary dosage for a human patient. Each unit contains a predetermined quantity of a compound of Formulae I-XVI, which was discovered or believed to produce the desired pharmacokinetic profile which yields the desired therapeutic effect. The dosage unit is composed of a compound of Formulae I-XVI in association with at least one pharmaceutically acceptable carrier, salt, excipient, or combination thereof.

As used herein, the term "dose" or "dosage" refers the amount of active ingredient that an individual takes or is administered at one time. For example, an 800 mg dose of a compound of Formulae I-XVI refers to, in the case of a twice-daily dosage regimen, a situation where the individual takes 800 mg of a compound of Formulae I-XVI twice a day, e.g., 800 mg in the morning and 800 mg in the evening. The 800 mg of a compound of Formulae I-XVI dose can be divided into two or more dosage units, e.g., two 400 mg dosage units of a compound of Formulae I-XVI in tablet form or two 400 mg dosage units of a compound of Formulae I-XVI in capsule form.

"A pharmaceutically acceptable prodrug" is a compound that may be converted under physiological conditions or by solvolysis to the specified compound or to a pharmaceutically acceptable salt of such compound.

"A pharmaceutically active metabolite" is intended to mean a pharmacologically active product produced through metabolism in the body of a specified compound or salt thereof. Metabolites of a compound may be identified using routine techniques known in the art and their activities determined using tests such as those described herein.

"A pharmaceutically acceptable salt" is intended to mean a salt that retains the biological effectiveness of the free acids and bases of the specified compound and that is not biologically or otherwise undesirable. A compound for use in the invention may possess a sufficiently acidic, a sufficiently basic, or both functional groups, and accordingly react with any of a number of inorganic or organic bases, and inorganic and organic acids, to form a pharmaceutically acceptable salt. Exemplary pharmaceutically acceptable salts include those salts prepared by reaction of the compounds of the present invention with a mineral or organic acid or an inorganic base, such as salts including sulfates, pyrosulfates, bisulfates, sulfites, bisulfites, phosphates, monohydrophosphates, dihydrophosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4 dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, gamma-hydroxybutyrates, glycollates, tartrates, methanesulfonates, propanesulfonates, naphthalene-1-sulfonates, naphthalene-2-sulfonates, and mandelates.

Preparation of the Compounds of the Invention

Representative synthetic schemes and experimental descriptions for the compounds of Formulae I-XVI for use in the methods of the invention are given in the Examples below.

Dosages, Formulations, and Route of Administration

The active compounds of this invention are typically administered in combination with a pharmaceutically acceptable carrier through any appropriate routes such as parenteral, oral, or topical administration, in a therapeutically (or prophylactically) effective amount according to the methods set forth above. A preferred route of administration for use in the invention is oral administration.

Generally, the toxicity profile and therapeutic efficacy of the therapeutic agents can be determined by standard pharmaceutical procedures in suitable cell models or animal models. As is known in the art, the LD50 represents the dose lethal to about 50% of a tested population. The ED50 is a parameter indicating the dose therapeutically effective in about 50% of a tested population. Both LD50 and ED50 can be determined in cell models and animal models. In addition, the IC50 may also be obtained in cell models and animal models, which stands for the circulating plasma concentration that is effective in achieving about 50% of the maximal inhibition of the symptoms of a disease or disorder. Such data may be used in designing a dosage range for clinical trials in humans. Typically, as will be apparent to skilled artisans, the dosage range for human use should be designed such that the range centers around the ED50 and/or IC50, but remains significantly below the LD50 dosage level, as determined from cell or animal models.

Typically, the compounds and compositions for use in the invention can be effective at an amount of from about 0.05 mg to about 4000 mg per day, preferably from about 0.1 mg to about 2000 mg per day. However, the amount can vary with the body weight of the patient treated and the state of disease conditions. The active ingredient may be administered at once, or may be divided into a number of smaller doses to be administered at predetermined intervals of time.

In the case of combination therapy, a therapeutically effective amount of another therapeutic compound can be administered in a separate pharmaceutical composition, or alternatively included in the pharmaceutical composition according to the present invention. The pharmacology and toxicology of other therapeutic compositions are known in the art. See e.g., Physicians Desk Reference, Medical Economics, Montvale, N.J.; and The Merck Index, Merck & Co., Rahway, N.J. The therapeutically effective amounts and suitable unit dosage ranges of such compounds used in the art can be equally applicable in the present invention.

It should be understood that the dosage ranges set forth above are exemplary only and are not intended to limit the scope of this invention. The therapeutically effective amount for each active compound can vary with factors including but not limited to the activity of the compound used, stability of the active compound in the patient's body, the severity of the conditions to be alleviated, the total weight of the patient treated, the route of administration, the ease of absorption, distribution, and excretion of the active compound by the body, the age and sensitivity of the patient to be treated, and the like, as will be apparent to a skilled artisan. The amount of administration can also be adjusted as the various factors change over time.

The active compounds can also be administered parenterally in the form of solution or suspension, or in lyophilized form capable of conversion into a solution or suspension form before use. In such formulations, diluents or pharmaceutically acceptable carriers such as sterile water and physiological saline buffer can be used. Other conventional solvents, pH buffers, stabilizers, anti-bacterial agents, surfactants, and antioxidants can all be included. For example, useful components include sodium chloride, acetate, citrate or phosphate buffers, glycerin, dextrose, fixed oils, methyl parabens, polyethylene glycol, propylene glycol, sodium bisulfate, benzyl alcohol, ascorbic acid, and the like. The parenteral formulations can be stored in any conventional containers such as vials and ampules.

Routes of topical administration include nasal, bucal, mucosal, rectal, or vaginal applications. For topical administration, the active compounds can be formulated into lotions, creams, ointments, gels, powders, pastes, sprays, suspensions, drops and aerosols. Thus, one or more thickening agents, humectants, and stabilizing agents can be included in the formulations. Examples of such agents include, but are not limited to, polyethylene glycol, sorbitol, xanthan gum, petrolatum, beeswax, or mineral oil, lanolin, squalene, and the like. A special form of topical administration is delivery by a transdermal patch. Methods for preparing transdermal patches are disclosed, e.g., in Brown, et al., *Annual Review of Medicine,* 39:221-229 (1988), which is incorporated herein by reference.

Subcutaneous implantation for sustained release of the active compounds may also be a suitable route of administration. This entails surgical procedures for implanting an active compound in any suitable formulation into a subcutaneous space, e.g., beneath the anterior abdominal wall. See, e.g., Wilson et al., *J. Clin. Psych.* 45:242-247 (1984). Hydrogels can be used as a carrier for the sustained release of the active compounds. Hydrogels are generally known in the art. They are typically made by crosslinking high molecular weight biocompatible polymers into a network that swells in water to form a gel like material. Preferably, hydrogels are biodegradable or biosorbable. For purposes of this invention, hydrogels made of polyethylene glycols, collagen, or poly(glycolic-co-L-lactic acid) may be useful. See, e.g., Phillips et al., *J. Pharmaceut. Sci.* 73:1718-1720 (1984).

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

Soft gelatin capsules can be prepared in which capsules contain a mixture of the active ingredient and vegetable oil or non-aqueous, water miscible materials such as, for example, polyethylene glycol and the like. Hard gelatin capsules may contain granules of the active ingredient in combination with a solid, pulverulent carrier, such as, for example, lactose, saccharose, sorbitol, mannitol, potato starch, corn starch, amylopectin, cellulose derivatives, or gelatin.

Tablets for oral use are typically prepared in the following manner, although other techniques may be employed. The solid substances are ground or sieved to a desired particle size, and the binding agent is homogenized and suspended in a suitable solvent. The active ingredient and auxiliary agents are mixed with the binding agent solution. The resulting mixture is moistened to form a uniform suspension. The moistening typically causes the particles to aggregate slightly, and the resulting mass is gently pressed through a stainless steel sieve having a desired size. The layers of the mixture are then dried in controlled drying units for determined length of time to achieve a desired particle size and consistency. The granules of the dried mixture are gently sieved to remove any powder. To this mixture, disintegrating, anti-friction, and anti-adhesive agents are added. Finally, the mixture is pressed into tablets using a machine with the appropriate punches and dies to obtain the desired tablet size. The operating parameters of the machine may be selected by the skilled artisan.

If the compound for use in the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound for use in the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium. These substituents may optionally be further substituted with a substituent selected from such groups.

EXAMPLES

Example 1

Tablets

| Ingredient | Amount | Preferred Ranges |
| --- | --- | --- |
| Compound of Formulae I-XVI | 400 mg | +50% to −50% |
| Microcrystalline Cellulose | 392 mg | +50% to −50% |
| Colloidal Silicon Dioxide | 4 mg | +50% to −50% |
| Magnesium Stearate | 4 mg | +50% to −50% |

The tablets are prepared using art known procedures.

Example 2

Coated Tablets

| Ingredient | Amount | Preferred Ranges |
| --- | --- | --- |
| Compound of Formulae I-XVI | 400 mg | +50% to −50% |
| Microcrystalline Cellulose | 392 mg | +50% to −50% |
| Colloidal Silicon Dioxide | 4 mg | +50% to −50% |
| Magnesium Stearate | 4 mg | +50% to −50% |
| Coated with | | |
| Lactose monohydrate | | |
| Hydroxyl propyl methyl cellulose | | |
| Titanium dioxide | | |
| Tracetin/glycerol triacetate | | |
| Iron oxide | | |

The coated tablets are produced using art known procedures.

Example 3

Capsules

| Ingredient | Amount | Preferred Ranges |
| --- | --- | --- |
| Compound of Formulae I-XVI | 400 mg | +50% to −50% |
| Microcrystalline Cellulose | 392 mg | +50% to −50% |
| Colloidal Silicon Dioxide | 4 mg | +50% to −50% |
| Magnesium Stearate | 4 mg | +50% to −50% |
| Encapsulated in gelatin | | |

The capsules are produced using art known procedures.

Example 4

Tablets

| Ingredient | Amount | Preferred Ranges |
| --- | --- | --- |
| Compound of Formulae I-XVI | 200 mg | +50% to −50% |
| Microcrystalline Cellulose | 196 mg | +50% to −50% |
| Colloidal Silicon Dioxide | 2 mg | +50% to −50% |
| Magnesium Stearate | 2 mg | +50% to −50% |

Example 5

Treatment of Alzheimer's Disease with a Compound of Formulae I-XVI

The compounds of Formulae I-XVI can be administered twice daily as tablets containing 400 mg of active ingredient or as a capsule containing 400 mg of the active ingredient. A higher dose can be administered to the patient in need of such treatment which can involve the patient taking e.g., a 800 mg dose of a compound of Formulae I-XVI in the morning and a 800 mg dose of a compound of Formulae I-XVI in the evening. Typically, for the treatment of mild-to-moderate Alzheimer's disease, an individual is diagnosed by a doctor as having the disease using a suitable combination of observations. One criterion indicating a likelihood of mild-to-moderate Alzheimer's disease is a score of about 15 to about 26 on the MMSE test. Another criteria indicating mild-to-moderate Alzheimer's disease is a decline in cognitive function. Compounds of Formulae I-XVI can also be administered in liquid dosage forms (or any other appropriate route of administration). The dosages can also be divided or modified, and taken with or without food. For example, the 400 mg dose can be divided into two 200 mg tablets or capsules.

Depending on the stage of the disease, the compound (i.e., Formulae I-XVI) can also be administered twice daily in liquid, capsule, or tablet dosage forms where the dose has various amounts (i.e., 850 mg, 750 mg, 700 mg, 650 mg, 600 mg, 550 mg, 500 mg, 450 mg, 350 mg, 300 mg, 250 mg, 200 mg, 150 mg, and 100 mg). Again, the dosages can also be divided or modified, and taken with or without food. The doses can be taken during treatment with other medications for treating Alzheimer's disease or symptoms thereof. For example, the compound can be administered in the morning as a tablet containing 400 mg of active ingredient (i.e., a compound of Formulae I-XVI) and an acetylcholine esterase inhibitor (i.e., tacrine (Cognex®), donepezil (Aricept®), rivastigmine (Exelon®), and galantamine (Reminyl®)), and/or an NMDA antagonist (i.e., memantine). It may be desirable to lower the amount of acetylcholine esterase inhibitor (and/or NMDA antagonist) and/or the compound of Formulae I-XVI to avoid adverse side effects associated with higher doses of these compounds. Alternatively, the acetylcholine esterase inhibitor (and/or NMDA antagonist) and compound of Formulae I-XVI can be co-formulated into a single dosage form, i.e., liquid, tablet, capsule, etc.

Patients having mild-to-moderate Alzheimer's disease undergoing the treatment regimen of this example with a compound of Formulae I-XVI in doses of about 20 mg to 1600 mg per day can experience a lessening in decline of cognitive function (as measured by the ADAS-cog or CDR sum of boxes), plaque pathology, and/or biochemical disease marker progression.

Example 6

Detection of Amyloid Beta with Biosource ELISA Kit (Camarillo, Calif.)

The present invention provides compositions and methods for lowering $A\beta_{42}$ levels. To test whether compounds and compositions are capable of modulating $A\beta$ levels, a sandwich enzyme-linked immunosorbent assay (ELISA) is employed to measure secreted $A\beta$ ($A\beta 42$ and/or $A\beta \tilde{4}0$ levels). In this example, H4 cells expressing wide type APP695 are seeded at 200,000 cells/per well in 6 well plates, and incubated at 37° C. with 5% $CO_2$ overnight. Cells are treated with 1.5 ml medium containing vehicle (DMSO) or a test compound at 1.25 μM, 2.5 μM, 5.0 μM and 10.0 μM (as well as other concentration if desirable) concentration for 24 hours or 48 hours. The supernatant from treated cells is collected into eppendorf tubes and frozen at −80° C. for future analysis.

The amyloid peptide standard is reconstituted and frozen samples are thawed. The samples and standards are diluted with appropriate diluents and the plate is washed 4 times with Working Wash Buffer and patted dry on a paper towel. 100 μL per well of peptide standards, controls, and dilutions of samples to be analyzed is added. The plate is incubated for 2 hours while shaking on an orbital plate shaker at RT. The plate is then washed 4 times with Working Wash Buffer and patted dry on a paper towel. Detection Antibody Solution is poured into a reservoir and 100 μL/well of Detection Antibody Solution is immediately added to the plate. The plate is incubated at RT for 2 hours while shaking and then washed four times with Working Wash Buffer and patted dry on a paper towel. Secondary Antibody Solution is then poured into a reservoir and 100 μL/well of Secondary Antibody Solution is immediately added to the plate. The plate is incubated at RT for 2 hours with shaking, washed 5 times with Working Wash Buffer, and patted dry on a paper towel.

100 μL of stabilized chromogen is added to each well and the liquid in the wells begins to turn blue. The plate is incubated for 30 minutes at room temperature and in the dark. 100 μL of stop solution is added to each well and the plate is tapped gently to mix resulting in a change of solution color from blue to yellow. The absorbance of each well is read at 450 nm having blanked the plate reader against a chromogen blank composed of 100 μL each of stabilized chromogen and stop solution. The plate is read within 2 hours of adding the stop solution. The absorbance of the standards is plotted against the standard concentration and the concentrations of unknown samples and controls are calculated.

Example 7

Synthesis of Compounds

General: Chemicals were purchased from standard commercial vendors and used as received unless otherwise noted. "Degassed" means reduced pressure then nitrogen gas for three cycles. Abbreviations are consistent with those in the ACS Style Guide, plus: satd (saturated), DCM (dichloromethane), pRPLC (preparative HPLC), "dry" glassware means oven/desiccator dried. Solvents were ACS grade unless otherwise noted. Analytical TLC plates (Silica Gel 60 F254, EM Science, Gibbstown, N.J., or Merck #5715) were used to follow the course of reactions, and the MPLC system used for purifications was from Isco (Foxy Jr fraction collector, UA-6 detector), using Isco silica gel flash columns (10 or 40 g). $^1$H NMR spectra in $CDCl_3$, $CD_3OD$, and/or d6-DMSO were recorded on either a Varian Mercury 400 MHz or Brucker ARX-300 MHz instrument and chemical shifts are expressed in parts per million (ppm, δ) relative to TMS as the internal standard. Mass spectra were obtained on a Thermo Finnigan LCQ-Deca (injection volume 5 μl, XTerra MS-$C_{18}$ 3.5 μm 2.1×50 mm column, XTerra MS-$C_{18}$ 5 μm 2.1×20 mm guard column), ESI source, analytical HPLC was performed on an HP1050 (injection volume 5 μl, XTerra RP-$C_{18}$ 5 μm 4.6×250 mm column, with an XTerra MS-$C_{18}$ 5 μm 2.1×20 mm guard column), and preparative HPLC was performed on an Agilent 1100 Prep-LC with various columns and conditions depending on the compound. GCMS was performed on either an Agilent Technology 6890N or Shimadzu QP5000/17A instrument. Yields are unoptimized.

1-(2-Oxo-2-phenyl-ethyl)-3,4-dihydro-1H-naphthalen-2-one (3)

A solution of phenacylbromide (5.21 g, 26.1 mmol) in toluene (16 mL) was added over 15 minutes to a boiling, stirred solution of 1-(3,4-dihydro-2-naphthyl)pyrrolidine (5.21 g, 26.2 mmol) in toluene (17 mL). The reaction was refluxed 3 hours, diluted with water (15 mL) and refluxed for 4 hours then cooled. The layers were separated and the aqueous phase was extracted with toluene and dried over $MgSO_4$ and concentrated. The material was purified by MPLC using a gradient from 0 to 20% ethyl acetate/hexanes to afford 4.85 g (70% yield) title product as a yellow oil.

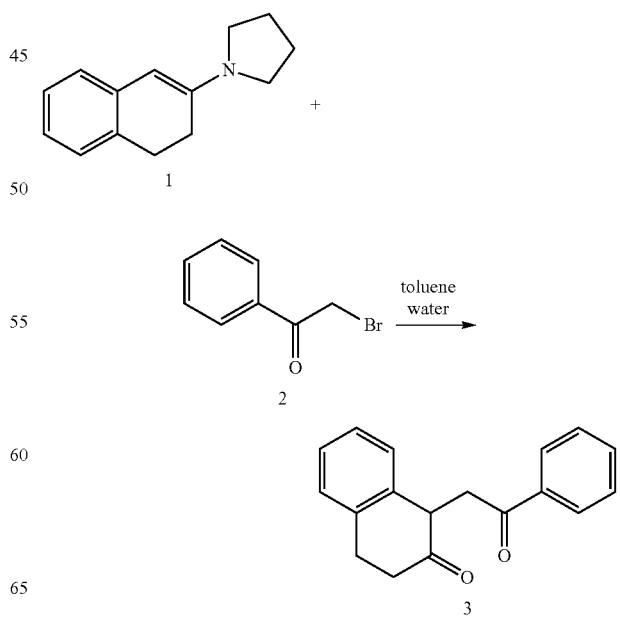

-continued

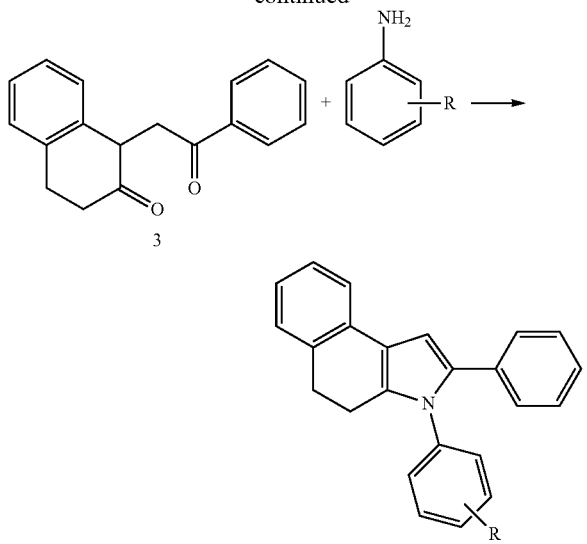

(4) R = 3-COOH, 4-OH
(5) R = 4-CH$_2$CH$_2$COOH
(6) R = 4-CH$_2$COOH
(7) R = 3-OH
(8) R = 4-OH
(9) R = 3-COOH
(10) R = 3-CH$_2$COOH
(11) R = 3-CH$_2$CH$_2$COOH
(12) R = 4-CH$_2$CH$_2$CH$_2$COOH

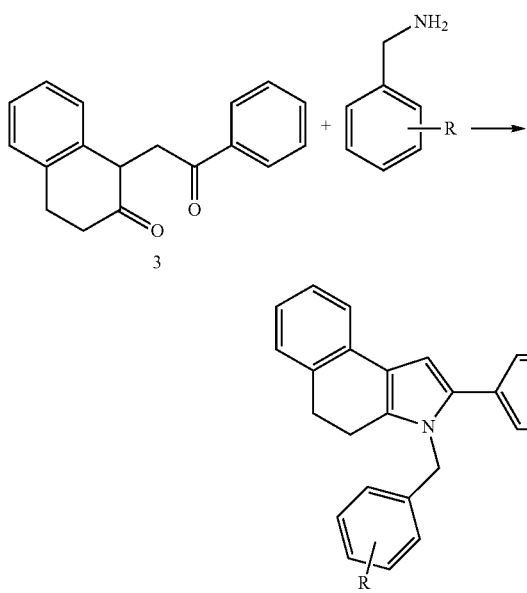

(13) R = 4-COOH
(14) R = 4-OH

Compounds 4-14 were prepared in the same way. Compound 4 is given as an example.

[2-Hydroxy-5-(2-phenyl-4,5-dihydro-benzo[e]indol-3-yl)-phenyl]-methanediol (4)

A mixture of 3 (2.41 g, 9.1 mmol), 5-aminosalicylic acid (1.40 g, 9.1 mmol) and glacial acetic acid (9 mL) was heated under reflux for 2 hours. After cooling, the precipitate was filtered and washed with acetic acid and water. The solid was recrystallized from acetic acid to afford 1.75 g (50% yield) title product as a yellow solid; MS m/z 380 (M$^-$–H) 9.92 min; $^1$H NMR (DMSO-d$_6$) δ 2.63 (t, 2H), 2.94 (t, 2H), 4.89 (s, 1H), 7.16 (m, 13H).

3-[4-(2-Phenyl-4,5-dihydro-benzo[e]indol-3-yl)-phenyl]-propionic acid (5)

MS m/z 392 (M$^-$–H) 6.99 min; $^1$H NMR (CDCl$_3$) δ 2.7 (d, 8H), 7.18 (m, 15H).

[4-(2-Phenyl-4,5-dihydro-benzo[e]indol-3-yl)-phenyl]-acetic acid (6)

MS m/z 380 (M$^+$+H) 6.90 min; $^1$H NMR (CDCl$_3$) δ 2.75 (d, 2H), 3.74 (d, 2H), 7.40 (m, 17H).

3-(2-Phenyl-4,5-dihydro-benzo[e]indol-3-yl)-phenol (7)

MS m/z 336 (M$^-$–H), 6.97 min, 338 (M$^+$+H) 6.95 min; $^1$H NMR (CDCl$_3$) δ 2.75 (d, 4H), 7.08 (m, 15H).

4-(2-Phenyl-4,5-dihydro-benzo[e]indol-3-yl)-phenol (8)

MS m/z 336 (M$^-$–H) 6.85 min, 338 (M$^+$+H) 6.86 min; $^1$H NMR (CDCl$_3$) δ 2.60 (s, 2H), 2.87 (s, 2H), 3.89 (s, 2H), 6.91 (m, 13H).

3-(2-Phenyl-4,5-dihydro-benzo[e]indol-3-yl)-benzoic acid (9)

MS m/z 364 (M$^-$–H) 6.97 min, 366 (M$^+$+H) 6.97 min; $^1$H NMR (CDCl$_3$) δ 2.66 (t, 2H), 2.94 (t, 2H), 7.12 (m, 15H).

[3-(2-Phenyl-4,5-dihydro-benzo[e]indol-3-yl)-phenyl]-acetic acid (10)

MS m/z 378 (M$^-$–H) 6.92 min; $^1$H NMR (DMSO-d$_6$) δ 2.50 (s, 1H), 3.29 (s, 4H), 3.68 (s, 2H), 7.35 (m, 14H).

3-[3-(2-Phenyl-4,5-dihydro-benzo[e]indol-3-yl)-phenyl]-propionic acid (11)

MS m/z 392 (M$^-$–H) 7.33 min; $^1$H NMR (CDCl$_3$) δ 2.12 (t, 3H), 2.47 (t, 4H) 2.80 (t, 2H), 7.08 (m, 14H).

4-[4-(2-Phenyl-4,5-dihydro-benzo[e]indol-3-yl)-phenyl]-butyric acid (12)

MS m/z 406 (M$^-$–H) 8.22 min; $^1$H NMR(C$_6$D$_6$) δ 1.99 (m, 10H), 7.07 (m, 15H).

4-(2-Phenyl-4,5-dihydro-benzo[e]indol-3-ylmethyl)-benzoic acid (13)

MS m/z 378 (M$^-$–H) 6.81 min, 380 (M$^+$+H) 6.81 min; β 2.66 (t, 2H), 2.98 (t, 2H), 6.61 (s, 2H), 7.22 (m, 15H).

4-(2-Phenyl-4,5-dihydro-benzo[e]indol-3-ylmethyl)-phenol (14)

MS m/z 352 (M$^+$+H) 6.83 min; $^1$H NMR (CDCl$_3$) δ 2.68 (t, 2H), 2.97 (t, 2H), 5.09 (s, 2H), 7.21 (m, 15H).

3-[3-(2-Phenyl-benzo[e]indol-3-yl)-phenyl]-propionic acid (15)

MS m/z 390 (M$^-$–H) 7.45 min; $^1$H NMR (CDCl$_3$) δ 2.15 (m, 4H), 7.07 (m, 15H).

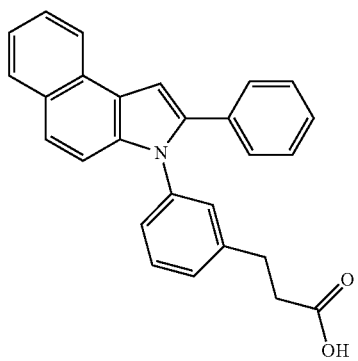
Example 8
The following synthetic routes can be employed to make the compounds of Formulae I-XVI (e.g., those in the Tables below).
Route A: Allen, et al, J. Med. Chem. 1976, 19(2), 318-325.
Route C: Allen, et al, J. Med. Chem. 1976, 19(2), 318-325.
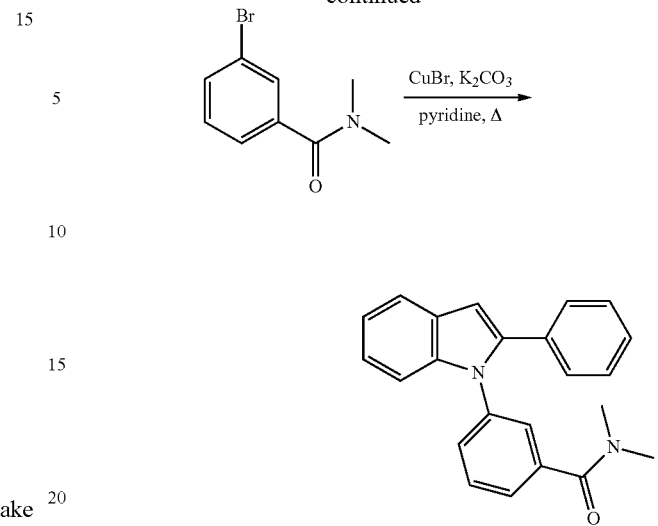
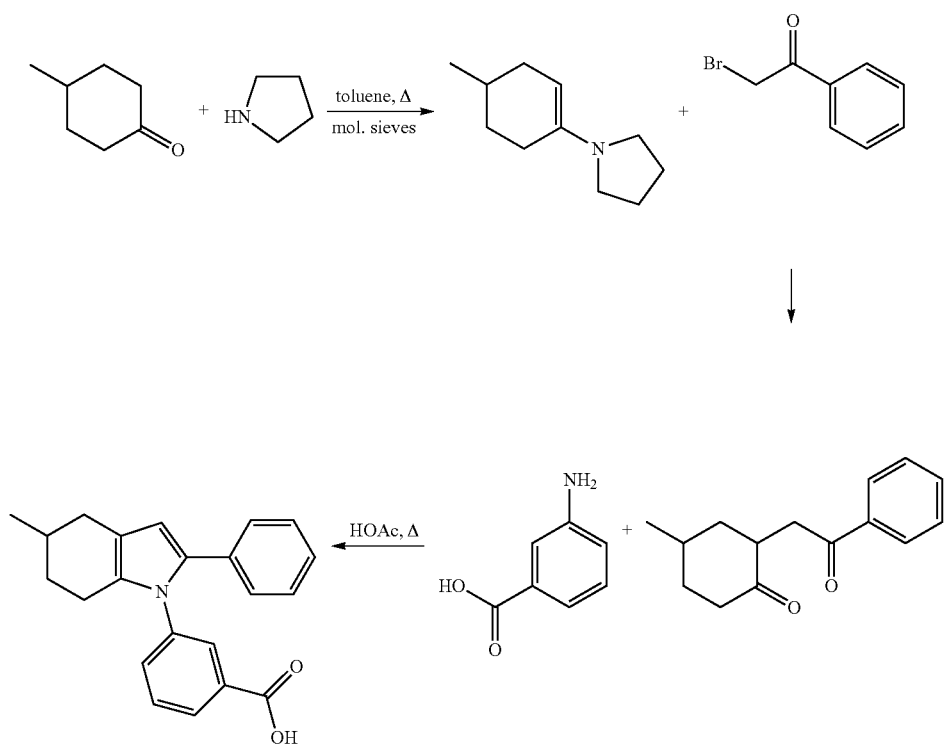
Route B: Murakami, et al, Chem. Pharm. Bull. 1995, 43(8), 1281-1286.
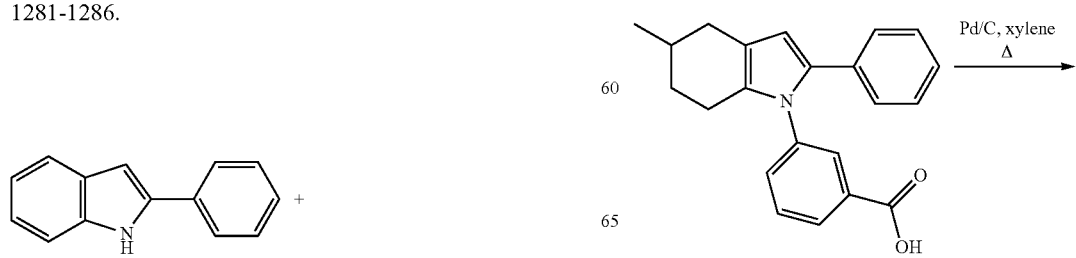

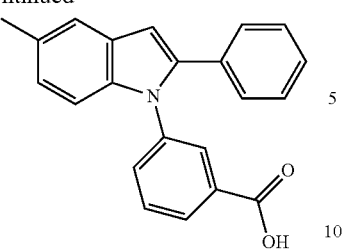
Compounds 16-90 below in Table 1, can be prepared in a similar manner as described for Compounds 4-14.
TABLE 1
| | product structure | SM ketone | alpha-bromo ketone | aniline | synth. route |
|---|---|---|---|---|---|
| 16 | | | | | A |
| 17 | | | | | A, C |
| 18 | | | | | A |
| 19 | | | | | A, C |

TABLE 1-continued
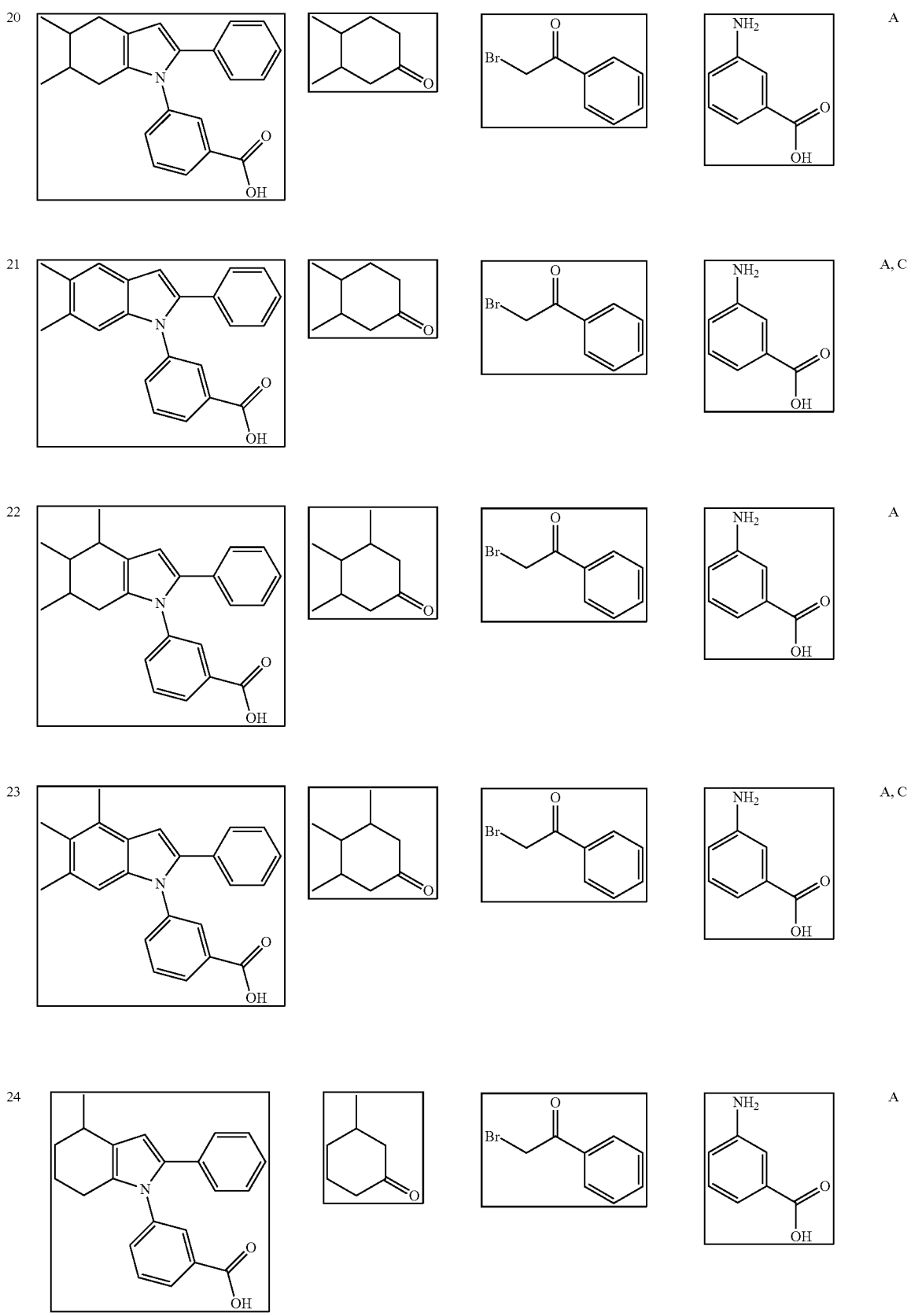

TABLE 1-continued

| | | | | | |
|---|---|---|---|---|---|
| 25 | | | | | A, C |
| 26 | | | | | A |
| 27 | | | | | A, C |
| 28 | | | | | A |
| 29 | | | | | A, C |
| 30 | | | | | A |

TABLE 1-continued
| 31 | 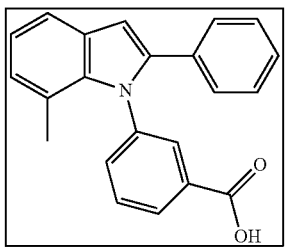 | 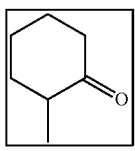 | 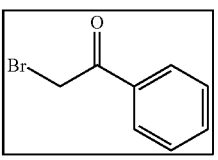 | 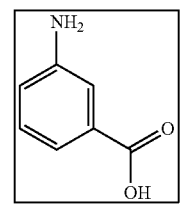 | A, C |
| 32 | 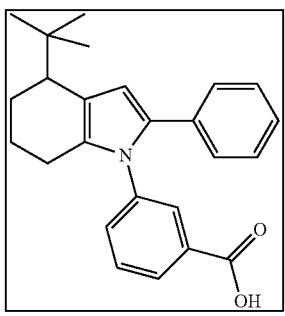 [SMILES: CC(C)(C)C1CCCc2c1cc(-c1ccccc1)n2-c1cccc(C(=O)O)c1] | 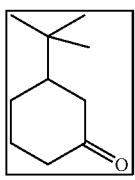 | 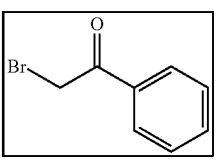 | 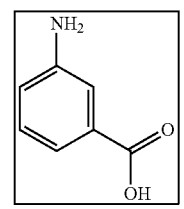 | A |
| 33 | 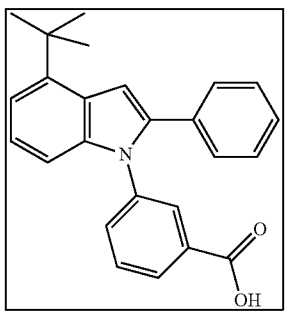 [SMILES: CC(C)(C)c1cccc2c1cc(-c1ccccc1)n2-c1cccc(C(=O)O)c1] | 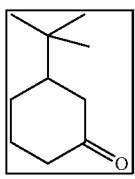 | 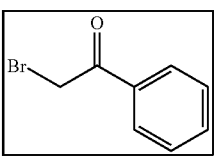 | 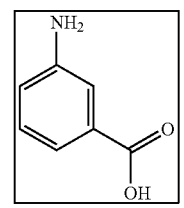 | A, C |
| 34 | 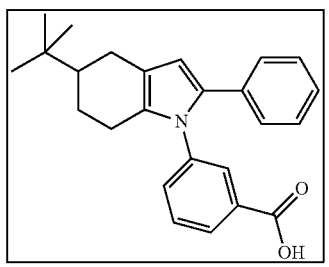 [SMILES: CC(C)(C)C1CCc2c(cc(-c3ccccc3)n2-c2cccc(C(=O)O)c2)C1] | 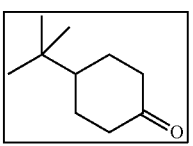 | 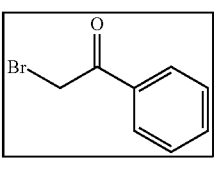 | 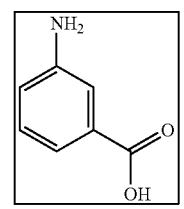 | A |
| 35 | 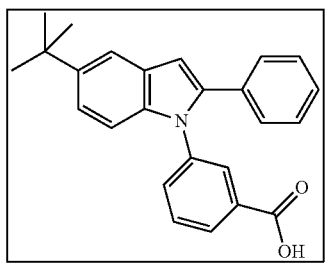 [SMILES: CC(C)(C)c1ccc2c(c1)cc(-c1ccccc1)n2-c1cccc(C(=O)O)c1] | 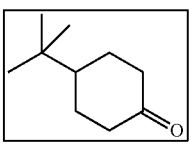 | 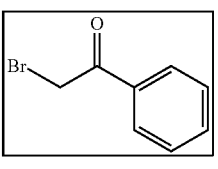 | 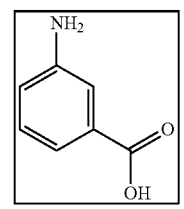 | A, C |

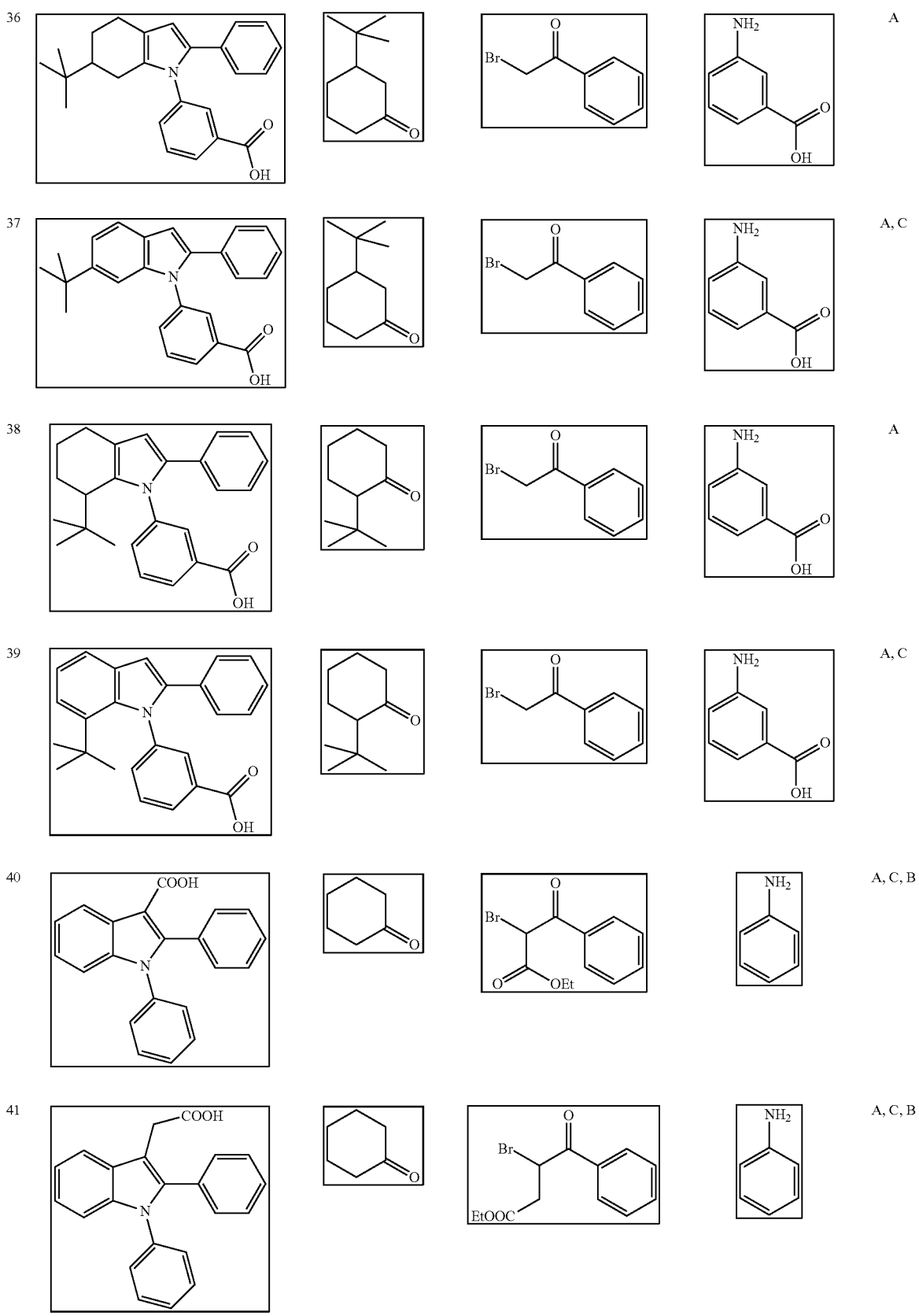

TABLE 1-continued
| 42 | 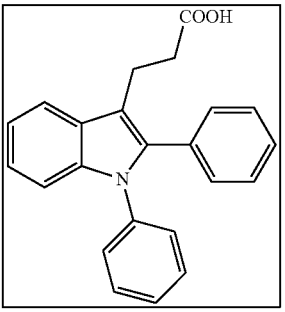 [SMILES: O=C(O)CCc1c(-c2ccccc2)n(-c2ccccc2)c2ccccc12] | 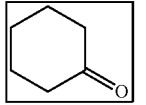 | 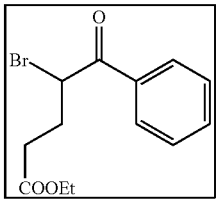 [SMILES: CCOC(=O)CCC(Br)C(=O)c1ccccc1] | 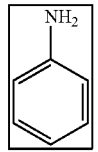 | A, C, B |
| --- | --- | --- | --- | --- | --- |
| 43 | 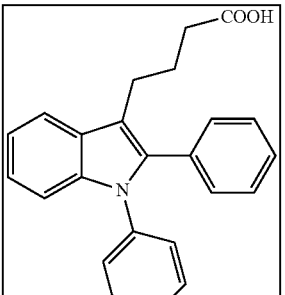 | 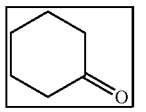 | 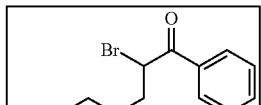 | 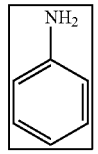 | A, C, B |
| 44 | 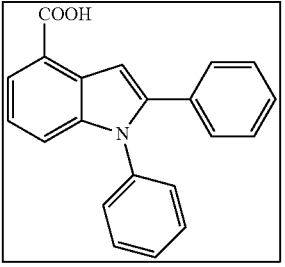 [SMILES: O=C(O)c1cccc2c1cc(-c1ccccc1)n2-c1ccccc1] | 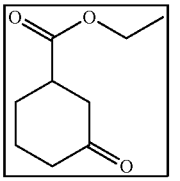 | 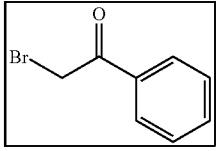 | 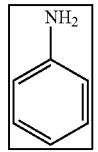 | A, C, B |
| 46 | 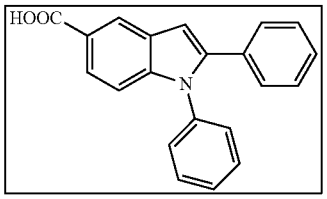 [SMILES: O=C(O)c1ccc2c(c1)cc(-c1ccccc1)n2-c1ccccc1] | 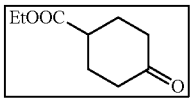 [SMILES: CCOC(=O)C1CCC(=O)CC1] | 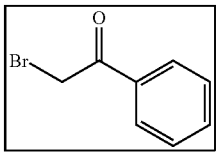 | 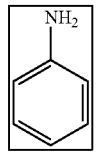 | A, C, B |
| 47 | 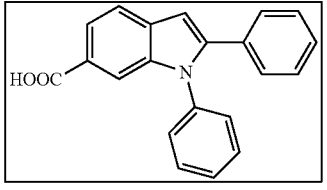 [SMILES: O=C(O)c1ccc2cc(-c3ccccc3)n(-c3ccccc3)c2c1] | 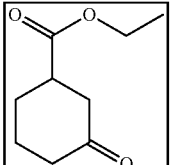 | 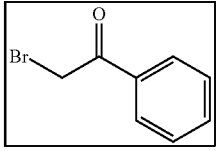 | 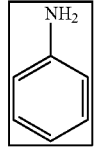 | A, C, B |
| 48 | 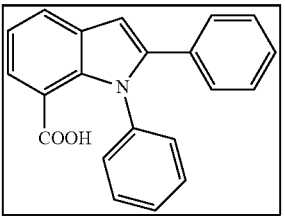 [SMILES: O=C(O)c1cccc2cc(-c3ccccc3)n(-c3ccccc3)c12] | 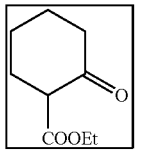 [SMILES: CCOC(=O)C1CCCCC1=O] | 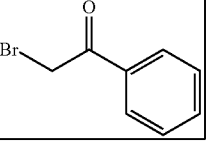 | 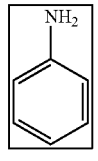 | A, C, B |

TABLE 1-continued
| | | | | | |
|---|---|---|---|---|---|
| 49 | 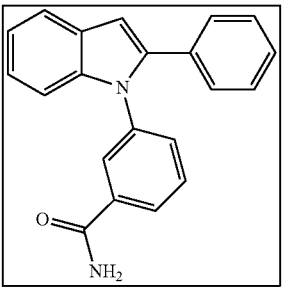 [SMILES: NC(=O)c1cccc(-n2c(-c3ccccc3)cc3ccccc32)c1] | 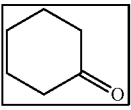 | 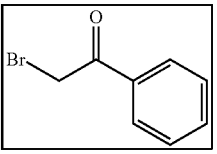 | 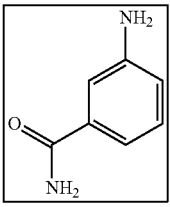 | A, C, B |
| 50 | 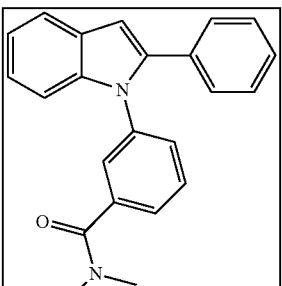 | 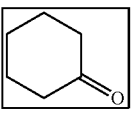 | 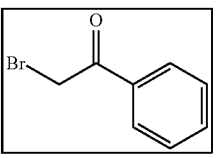 | 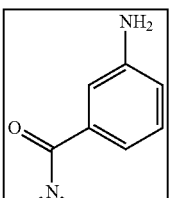 | A, C |
| 51 | 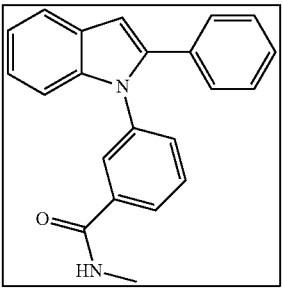 [SMILES: CNC(=O)c1cccc(-n2c(-c3ccccc3)cc3ccccc32)c1] | 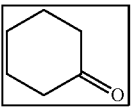 | 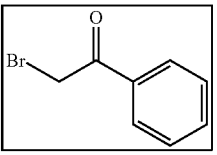 | 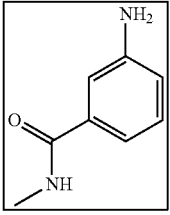 | A, C |
| 52 | 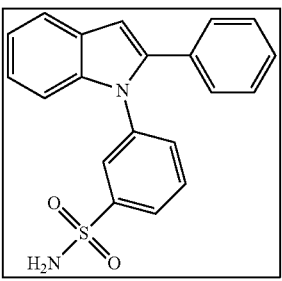 [SMILES: NS(=O)(=O)c1cccc(-n2c(-c3ccccc3)cc3ccccc32)c1] | 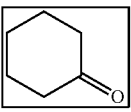 | 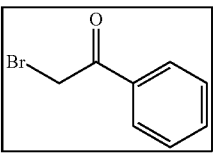 | 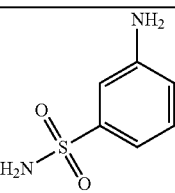 | A, C |
| 53 | 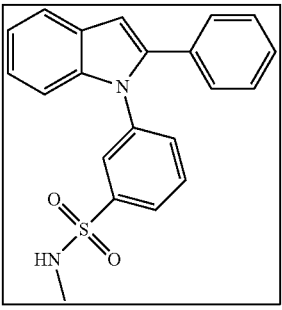 [SMILES: CNS(=O)(=O)c1cccc(-n2c(-c3ccccc3)cc3ccccc32)c1] | 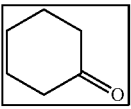 | 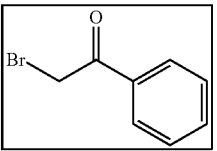 | 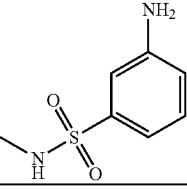 | A, C |

TABLE 1-continued
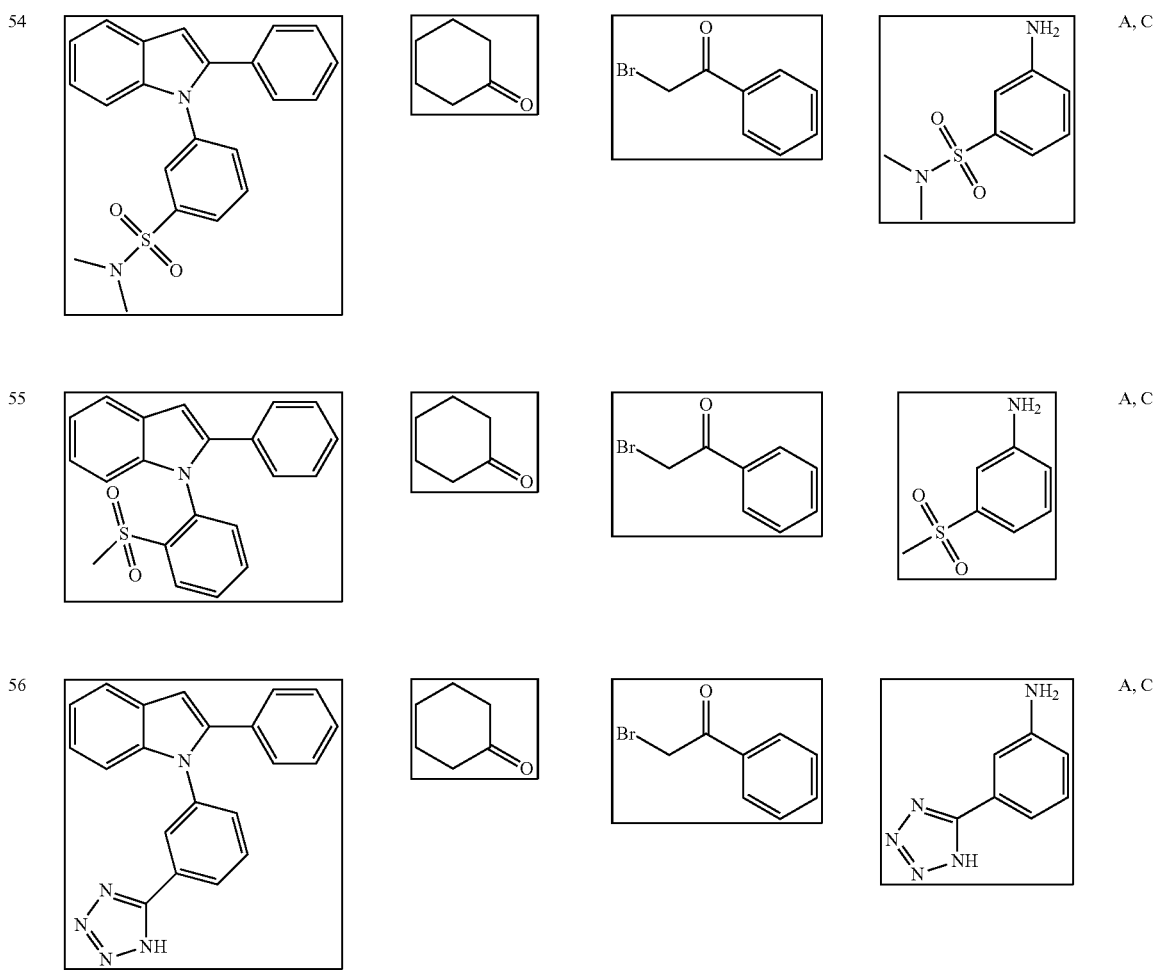
| product structure | SM ketone/enamine | alpha-bromo ketone | aniline | synth. route |
|---|---|---|---|---|
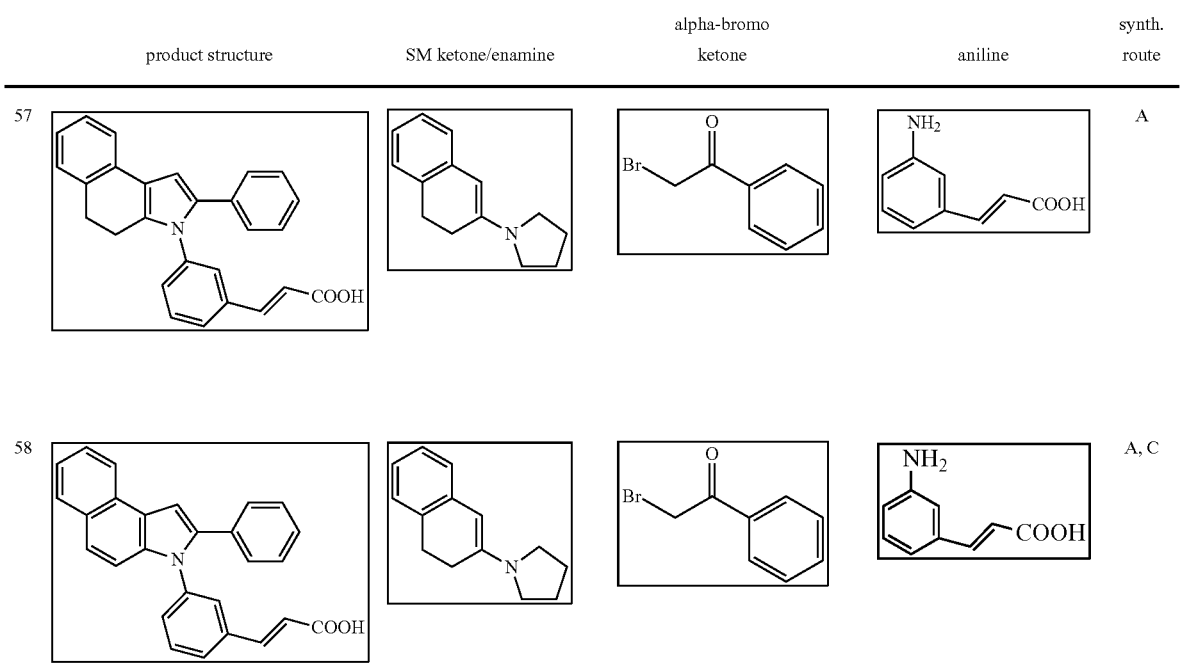

TABLE 1-continued
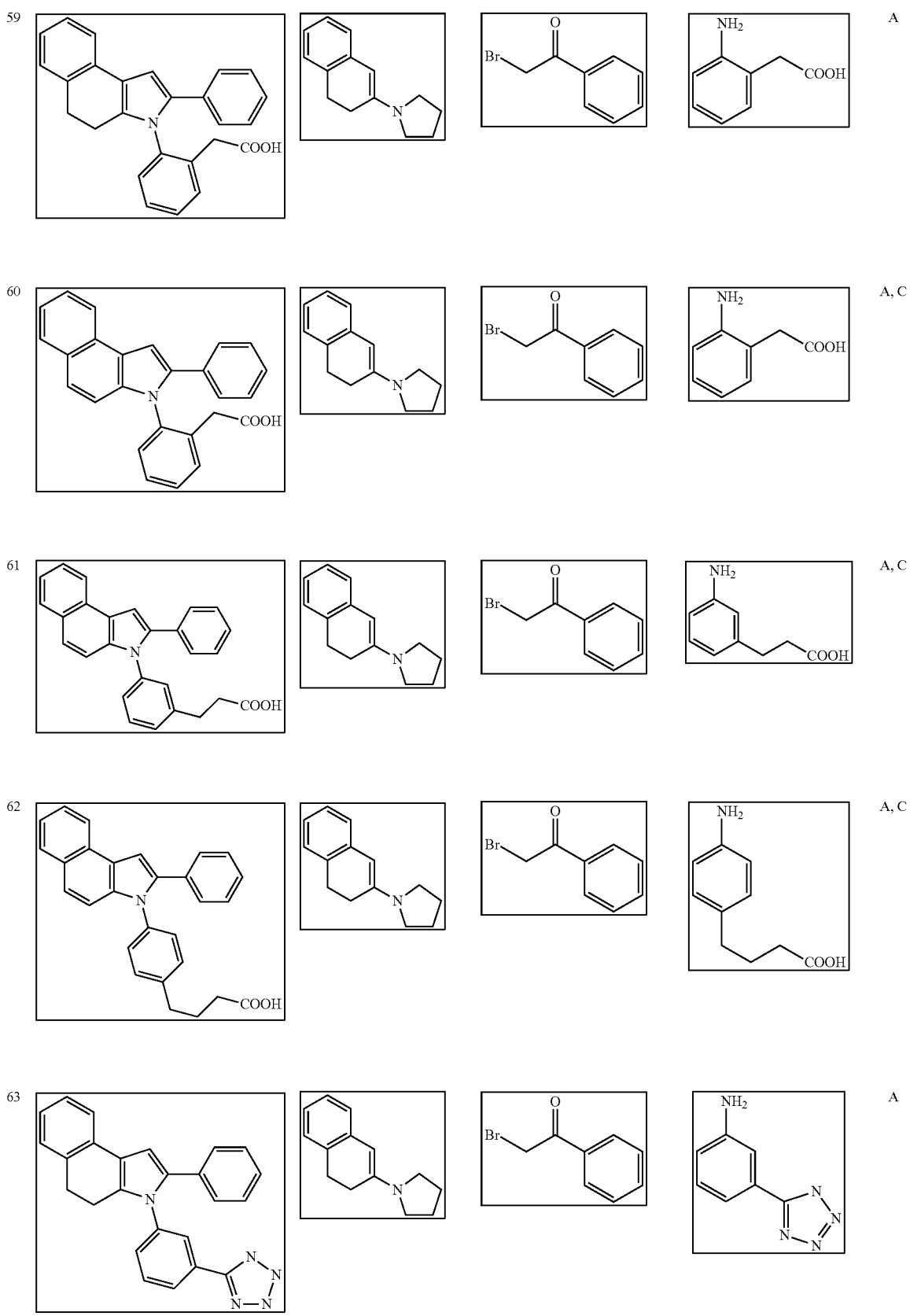

TABLE 1-continued
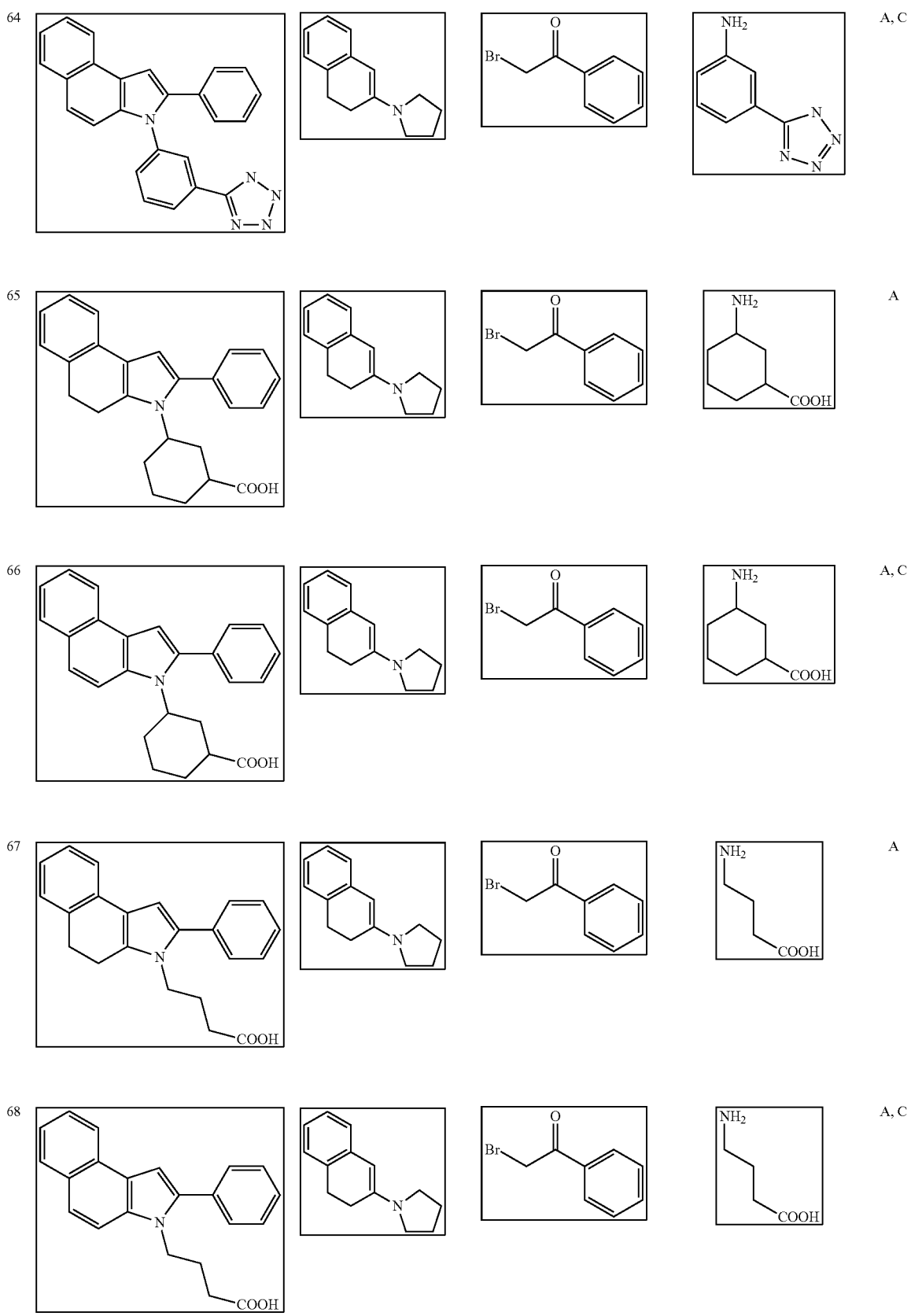

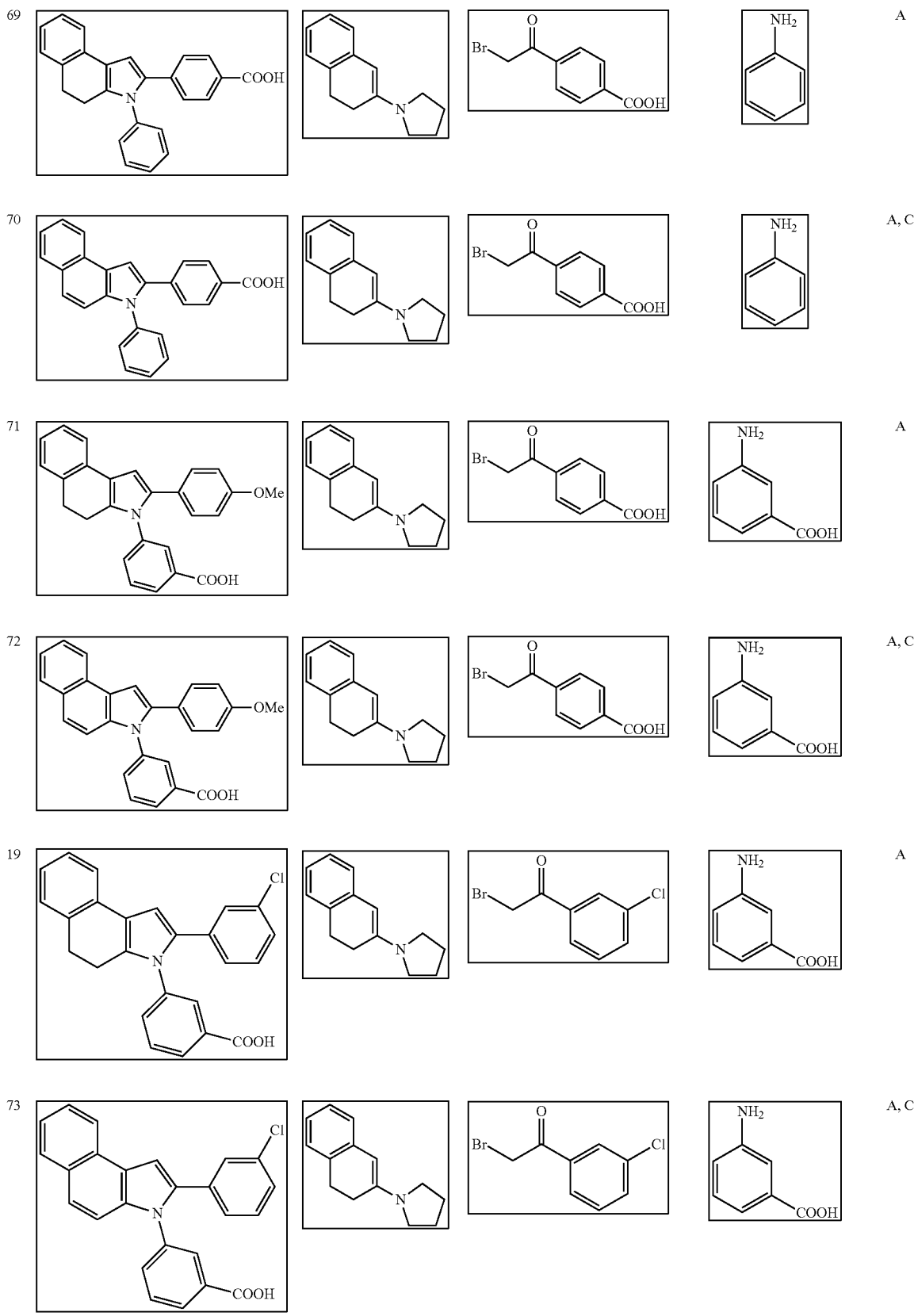

TABLE 1-continued
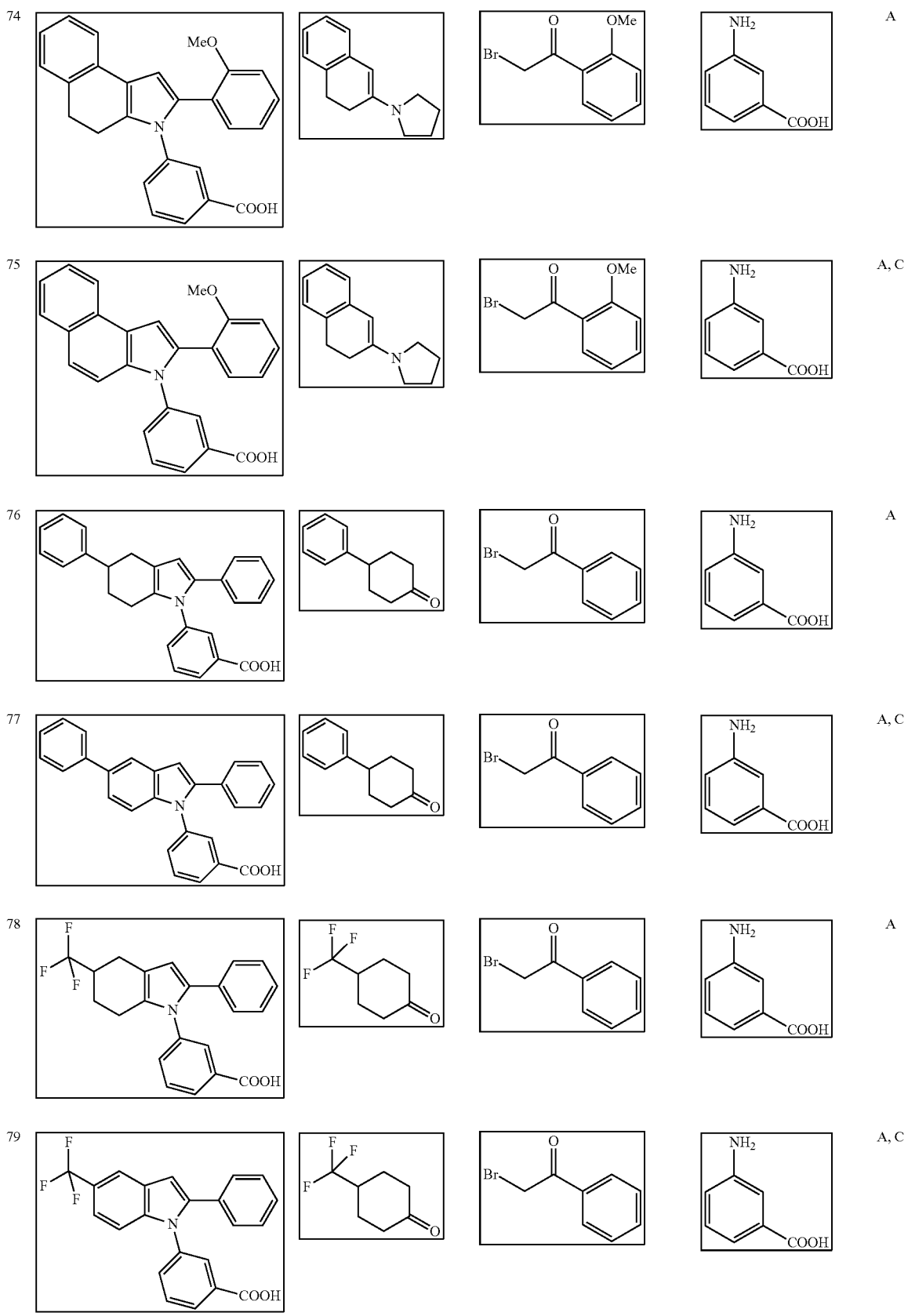

TABLE 1-continued

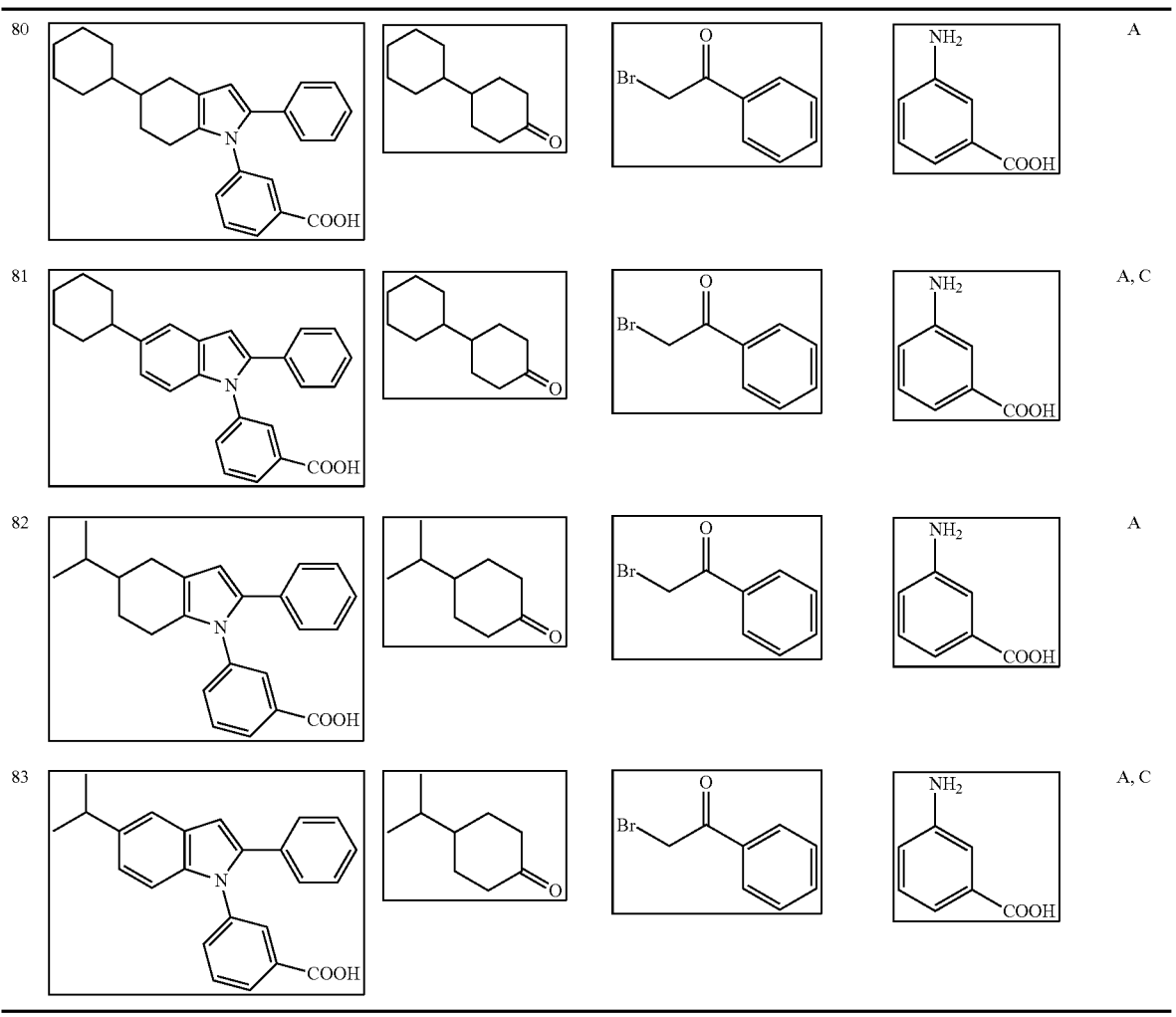

Example 9

Synthesis of Compound 34

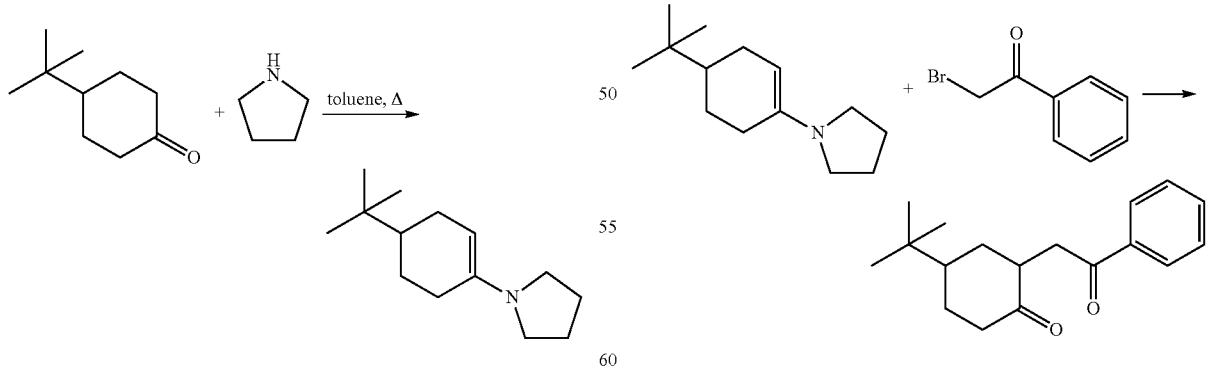

1-(4-tert-butylcyclohex-1-enyl) pyrrolidine 4-tert-butyl-2-(2-oxo-2-phenylethyl)-cyclohexanone A 50 mL round-bottomed flask containing 4-tert-butylcyclohexanone (6.01 gm) in anhydrous toluene (20 mL) was fitted with a Dean-Stark trap containing 3A molecular sieves, reflux condenser and a heating mantle. Pyrrolidine (6.00 mL) was added, and the solution heated to reflux for 18 hr. The solvent was evaporated and the crude product was used directly for the next reaction.

To a 250-mL round-bottomed flask containing 3.3 mL of 1-(4-tert-butylcyclohex-1-enyl) pyrrolidine was added 100 mL anhydrous DMF, under nitrogen. The flask was fitted with an addition funnel containing 2-bromoacetophenone (4.12 gm) in 35 mL anhydrous DMF, which was dripped into the enamine solution over 60 min. This solution was stirred at ambient temperature for 10 hr, then 90 mL water was added to the solution and it was stirred for another 11 hr, under nitrogen. The solution was then extracted twice with ethyl acetate and water, the organic layers combined and further washed with water (3×), dried over sodium sulfate, filtered and rotovapped down to give a yellow oil. The oil was purified by MPLC using 10% ethyl acetate/hexanes.

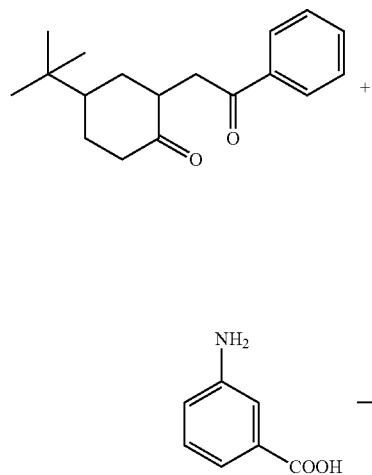

3-(5-tert-butyl-2-phenyl-4,5,6,7-tetrahydroindol-1-yl) benzoic acid (Compound 34)

A solution of 4-tert-butyl-2-(2-oxo-2-phenylethyl)-cyclohexanone (0.219 gm) in glacial acetic acid (3.0 mL) in a 25-mL round-bottomed flask, under nitrogen, was fitted with a heating mantle and reflux condenser. To this solution was added 3-aminobenzoic acid (0.138 gm), which was then heated at 110 C for 3 hr. The solution was cooled to ambient temperature, 8 mL water was added, and the suspension was stirred 18 hr under nitrogen. The solid was filtered, washed with water, and recrystallized in acetonitrile to provide 0.123 gm of the pure product.

Example 10

Analytical data for compounds of Formulae I and II. These compounds were synthesized via the indicated synthetic route. Aβ42 IC50 (uM) refers to IC50 value for Aβ42 lowering in e.g., the assay described in Example 6.

TABLE 2

| Compound Number | product structure | 1H NMR, δ | MS | name | Syn. route used |
|---|---|---|---|---|---|
| 17 | | CDCl3; 8.1 (m, 2H); 7.7 (m, 1H); 7.5 (t, 1H); 7.4 (m, 1H); 7.2-7.3 (m, 8H, ArH); 6.8 (s, 1H). | pos. mode 314 (M + H); neg. mode 312 (M − H) | 3-(2-phenylindol-1-yl) benzoic acid | A, C |
| 34 | | CDCl3/d3-MeOD; 8.0 (m, 2H); 7.4 (t, 1H); 7.2 (m, 1H); 7.0-7.2 (m, 5H, ArH); 6.2 (s, 1H); 2.7 (m, 1H); 2.5 (s, 1H); 2.4 (m, 2H); 2.0 (m, 1H); 1.5 (m, 1H); 1.4 (m, 1H); 0.9 (s, 9H). | pos. mode 374 (M + H); neg. mode 372 (M − H) | 3-(5-tert-Butyl-2-phenyl-4,5,6,7-tetrahydro-indol-1-yl) benzoic acid | A |

TABLE 2-continued

| Compound Number | product structure | 1H NMR, δ | MS | name | Syn. route used |
|---|---|---|---|---|---|
| 85 | | CDCl3; 7.2 (m, 1H); 6.9-7.1 (m, 8H, ArH); 6.2 (s, 1H); 2.9 (t, 2H); 2.7 (m, 1H); 2.5 (m, 3H); 2.4 (m, 2H); 2.0 (m, 1H); 1.5 (m, 1H); 1.4 (m, 1H); 0.9 (s, 9H). | pos. mode 402 (M + H); neg. mode 400 (M − H) | 3-[3-(5-tert-Butyl-2-phenyl-4,5,6,7-tetrahydro-indol-1-yl)-phenyl] propionic acid | A |
| 63 | | DMSO-d6; 7.0-8.4 (13H, ArH); 6.9 (1H), 2.9 (2H, CH2), 2.5 (2H, CH2). | pos. mode 342 (M + H); neg. mode 340 (M − H) | 2-phenyl-3-[3-(2H-tetrazol-5-yl)-phenyl]-4,5-dihydro-3H-benzo[e]indole | A |
| 69 | | DMSO-d6; 6.8-7.9 (14H, ArH), 3.0 (2H, CH2) 2.7 (2H, CH2). | neg. mode 364 (M − 1) | 4-(3-phenyl-4,5-dihydro-3H-benzo[e]indol-2-yl)benzoic acid | A |
| 86 | | CDCl3; 7.0-7.2 (m, 9H, ArH); 6.2 (s, 1H); 2.6 (m, 4H); 2.4 (m, 4H); 2.0 (m, 3H); 1.8 (s, 3H). | neg. mode 358 (M − H) | 4-[4-(2-phenyl-4,5,6,7-tetrahydro-indol-1-yl)-phenyl] butyric acid | A |
| 87 | | DMSO-d6; 7.2-8.4 (16H, ArH). | pos. mode 364 (M + 1); neg. mode 362 (M − 1) | 3-(2-phenylbenzo[e]indol-3-yl)benzoic acid | A, C |

TABLE 2-continued

| Compound Number | product structure | 1H NMR, δ | MS | name | Syn. route used |
|---|---|---|---|---|---|
| 88 | | CDCl3; 7.3 (t, 1H); 6.9-7.1 (m, 8H, ArH); 6.2 (s, 1H); 2.9 (t, 2H); 2.7 (m, 1H); 2.5 (m, 3H); 2.4 (m, 1H); 2.2 (m, 1H); 1.9 (m, 2H); 1.4 (m, 1H); 1.0 (d, 3H). | pos. mode 360 (M + H); neg. mode 358 (M − H) | 3-[3-(5-methyl-2-phenyl-4,5,6,7-tetrahydro-indol-1-yl)-phenyl] propionic acid | A |
| 89 | | DMSO-d6; 7.2-8.4 (16H, ArH); 2.7 (2H, CH2); 2.3 (2H, CH2); 1.9 (2H, CH2). | pos. mode 406 (M + 1); neg. mode 404 (M − 1) | 4-[4-(2-phenyl-benzo[e]indol-3-yl)-phenyl] butyric acid | A, C |
| 90 | | CDCl3; 7.3 (t, 1H); 6.9-7.2 (m, 8H, ArH); 6.2 (s, 1H); 2.9 (t, 2H); 2.6 (br. s, 2H); 2.5 (t, 2H); 2.4 (br. s, 2H); 1.8 (br. s, 4H). | pos. mode 346 (M + H) | 3-[3-(2-phenyl-4,5,6,7-tetrahydro-indol-1-yl)-phenyl] propionic acid | A |
| 66 | | CDCl3; 7.1-8.4 (11H, ArH), 6.4 (1H, ArH), 4.4 (1H, CH) 1.4-2.7 (9H, CH2). | pos. mode 372 (M + 1) | 3-(2-phenylbenzo[e]indol-3-yl) cyclohexane-carboxylic acid | A, C |

TABLE 2-continued

| Compound Number | product structure | 1H NMR, δ | MS | name | Syn. route used |
|---|---|---|---|---|---|
| 67 | | CD3OD-d4; 7.1-8.2 (10H, ArH), 4.0 (2H, CH2), 3.0 (2H, CH2), 2.9 (2H, CH2), 2.1 (2H, CH2), 1.9 (2H, CH2). | pos. mode 332 (M + 1) | 4-(2-phenyl-4,5-dihydrobenzo[e]indol-3-yl)butyric acid | A |
| 68 | | CD3OD-d4; 7.1-8.2 (12H, ArH) 4.4 (2H, CH2) 2.1 (2H, CH2) 1.9 (2H, CH2). | pos. mode 330 (M + 1) | 4-(2-phenyl-benzo[e]indol-3-yl)butyric acid | A, C |
| 71 | | DMSO-d6; 7.0-7.9(14H, ArH), 6.3 (1H, ArH), 3.0 (1H, CH), 2.8 (1H, CH2), 2.7 (2H, CH2), 2.4 (1H, CH2), 1.9 (2H, CH2). | pos. mode 394 (M + 1) | 3-(2,5-diphenyl-4,5,6,7-tetrahydro-indol-1-yl)benzoic acid | A |
| 91 | | CDCl3; 8.0 (m, 1H); 7.9 (m, 1H); 7.4 (t, 1H); 7.0-7.3 (m, 6H, ArH); 6.2 (s, 1H); 2.6 (m, 1H); 2.5 (br. s, 1H); 2.4 (m, 1H); 2.1 (m, 1H); 1.9 (m, 2H); 1.4 (m, 1H); 1.0 (d, 3H). | pos. mode 332 (M + H) | 3-(4-methyl-2-phenyl-4,5,6,7-tetrahydro-indol-1-yl)benzoic acid | A |

TABLE 2-continued

| Compound Number | product structure | 1H NMR, δ | MS | name | Syn. route used |
|---|---|---|---|---|---|
| 92 | | acetone-d6; 7.5 (m, 5H); 7.2 (m, 7H); 7.0 (t, 1H); 6.8 (s, 1H); 3.2 (s, 2H, CH2); 2.9 (m, 2H); 2.6 (m, 1H); 2.4 (m, 1H). | pos. mode 380 (M + H) | [2-(2-phenyl-4,5-dihydrobenzo[e]indol-3-yl)-phenyl] acetic acid | A |

Example 11

The following synthetic routes can be used to make the compounds of Formulae I-XVI.

Synthetic Routes for Heteroaromatics

Route A: Allen, et al, J. Med. Chem. 1976, 19(2), 318-325.

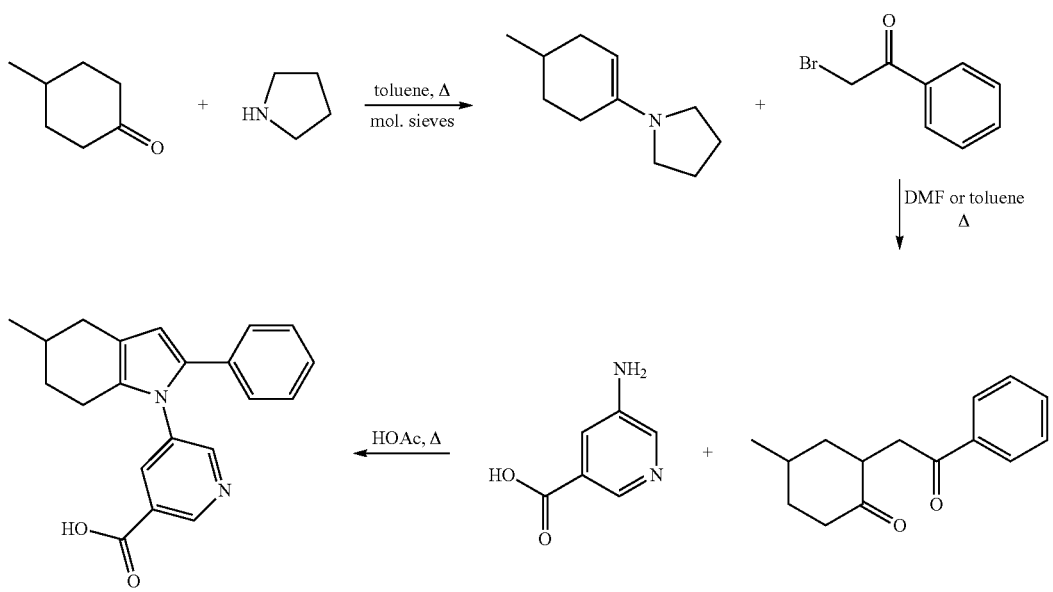

Route B: Murakami, et al, Chem. Pharm. Bull. 1995, 43(8), 1281-1286.

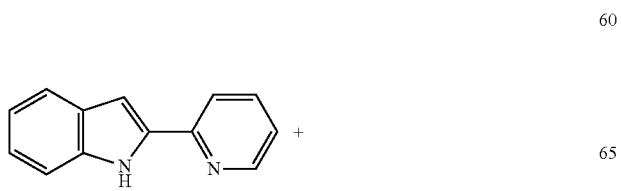

-continued

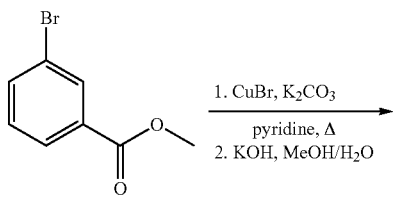

-continued

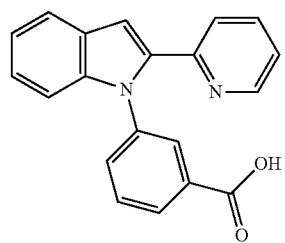

Route C: Allen, et al, J. Med. Chem. 1976, 19(2), 318-325.
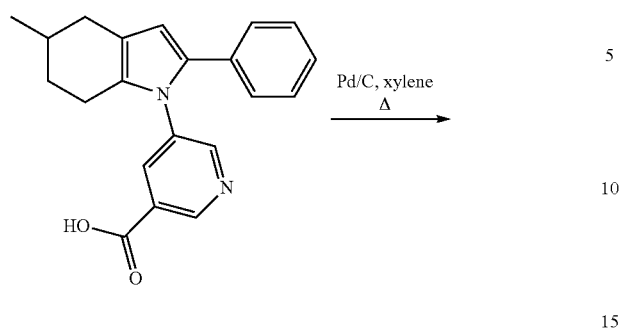
Compounds for Heteroaromatics
Heteroaromatic N-Alkylated Analogs:
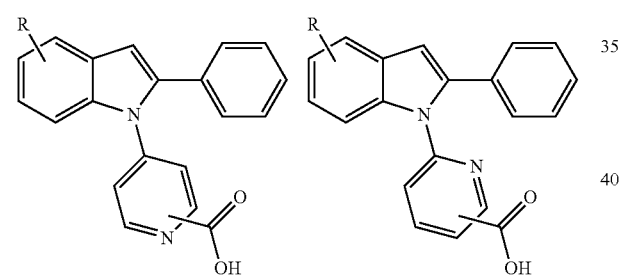
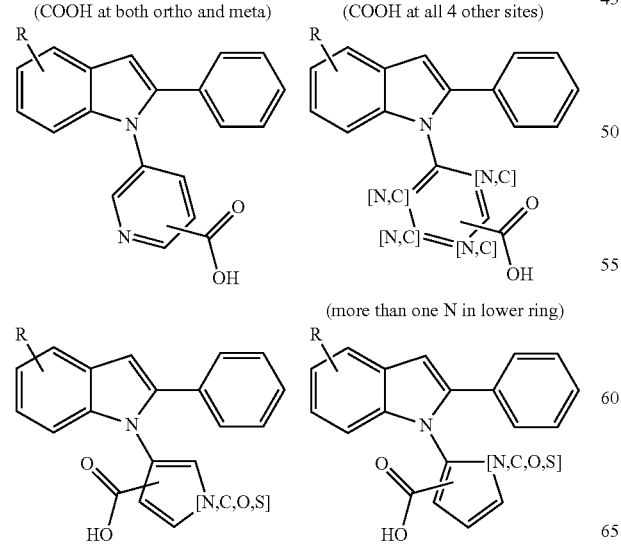
also, all of the above with a partially saturated ring (4,5,6,7-tetrahydroindoles):
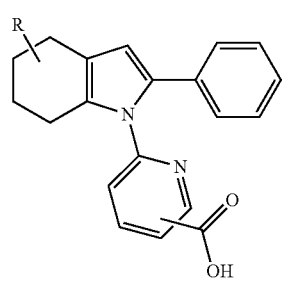
(etc, as above)
rearranging the acid group placement:
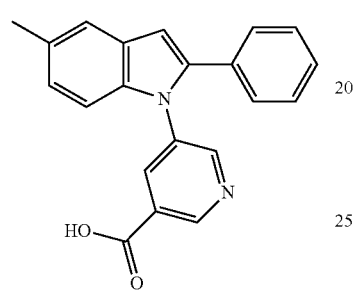
(n = 0-3)
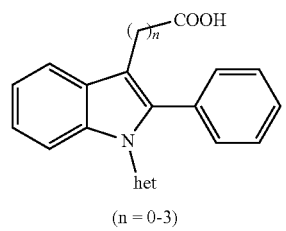
(COOH at C4, C5, C6, C7)
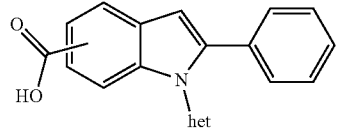
(o, m, and p)
placing the heterocycle at the indole C-1 or C-2 position:
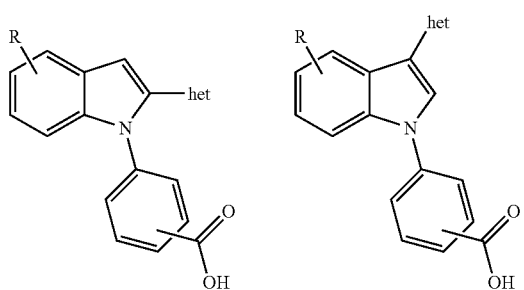

changing the acid group moiety:
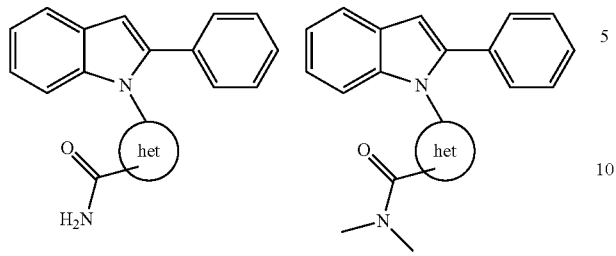
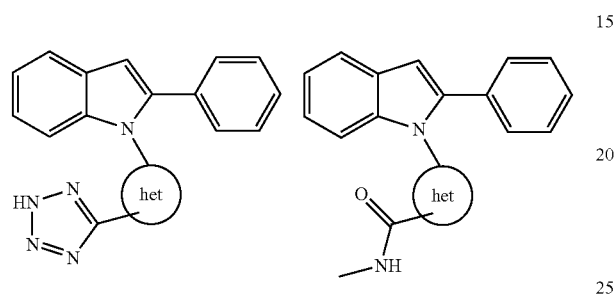
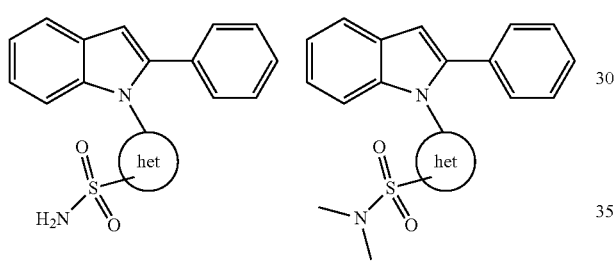
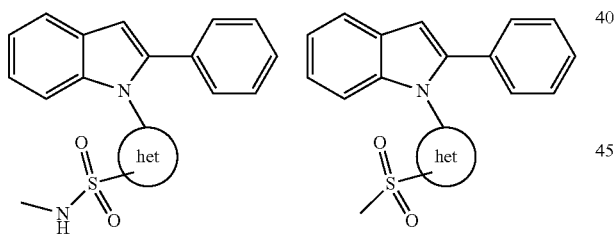
Compounds of Formulae I-XVI include, but are not limited to:
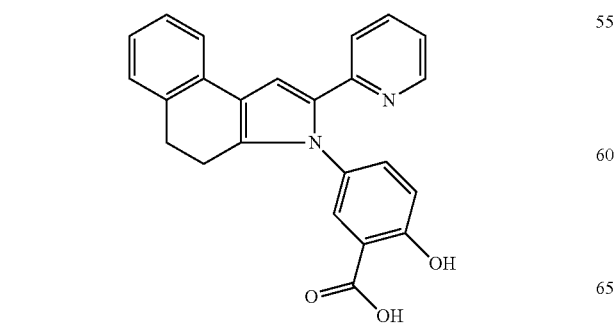
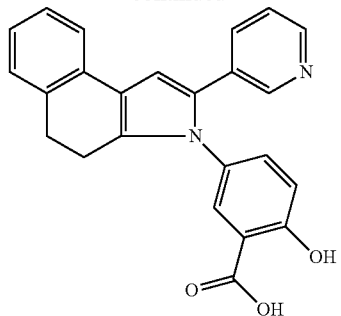
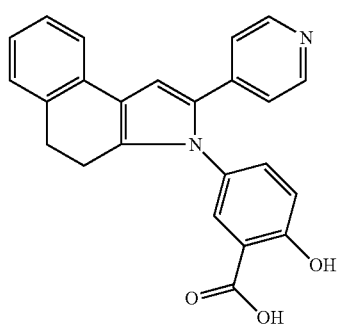
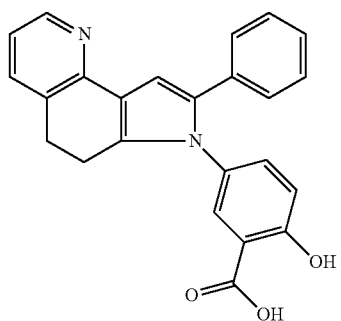
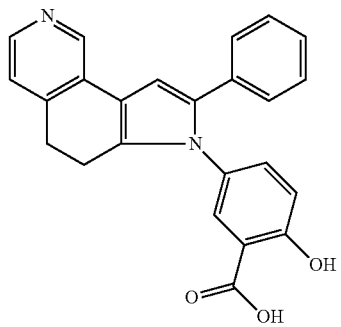
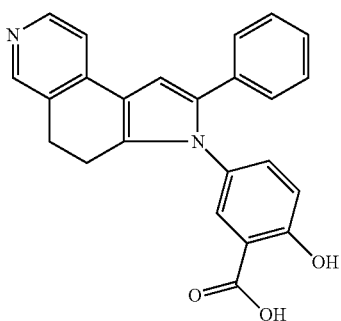

145
-continued
146
-continued
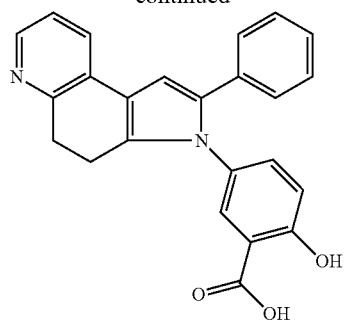
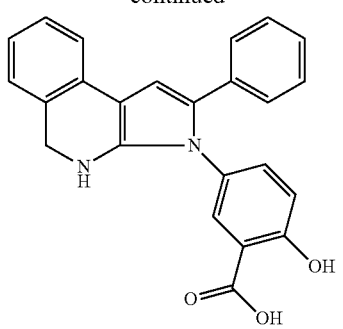

147
-continued
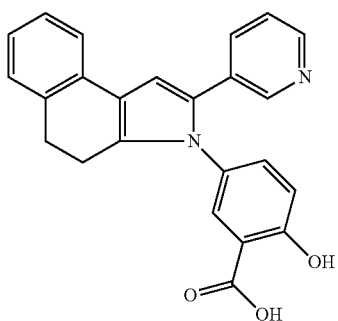
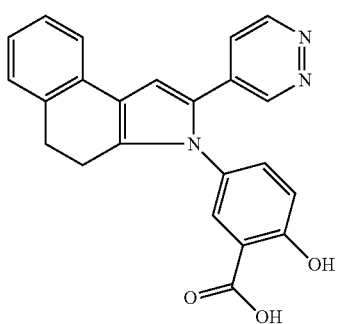
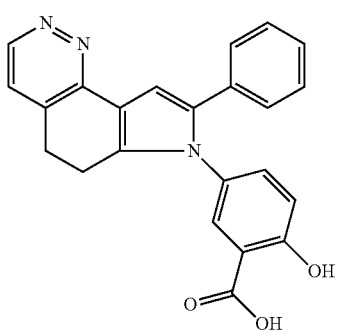
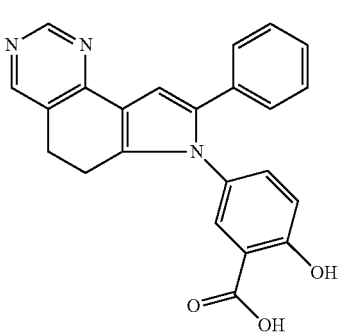
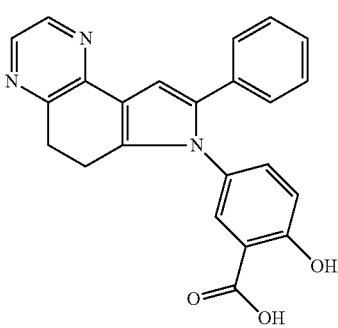
148
-continued
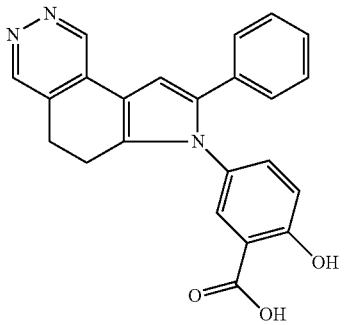
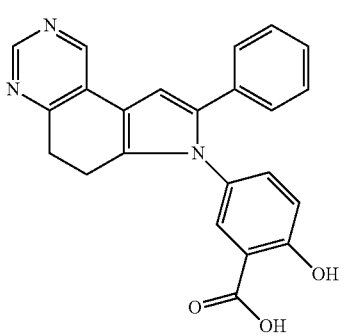
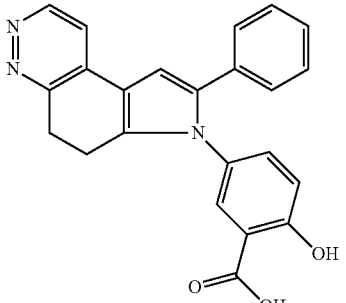
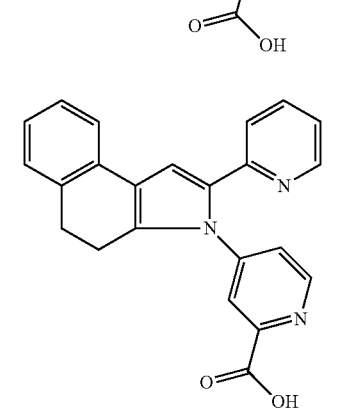
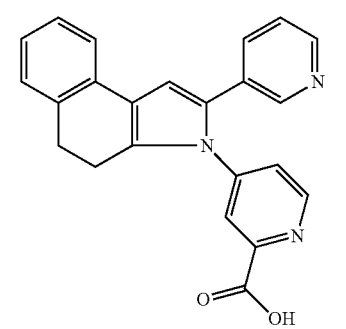

149
-continued
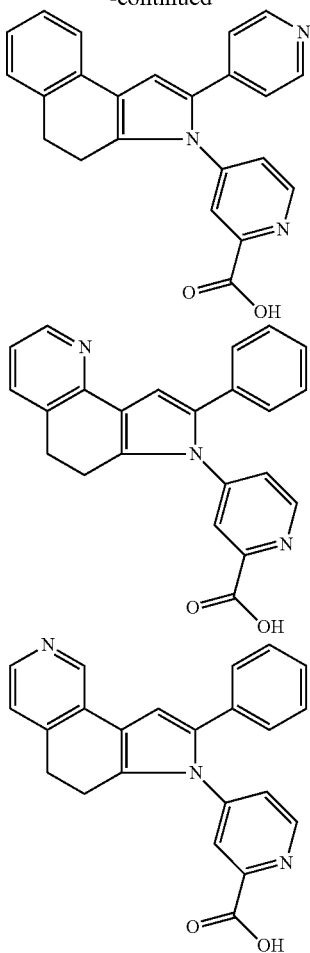
150
-continued
TABLE 3
| | Exemplary Compounds of the Invention | | | |
|---|---|---|---|---|
| product structure | SM ketone | alpha-bromo ketone | aniline | synth. route |
| 93 | | | | A |
| 94 | | | | A, C |

TABLE 3-continued
Exemplary Compounds of the Invention
| # | product structure | SM ketone | alpha-bromo ketone | aniline | synth. route |
|---|---|---|---|---|---|
| 95 | 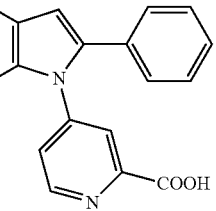 | 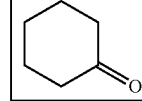 | 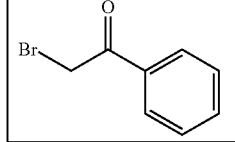 | 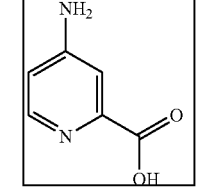 | A |
| 96 | 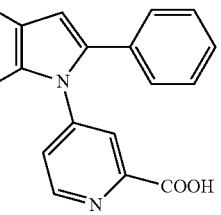 | 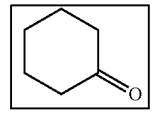 | 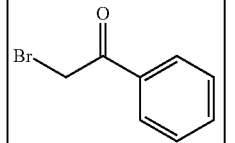 | 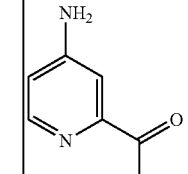 | A, C |
| 97 | 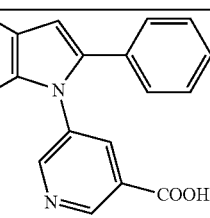 | 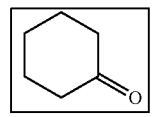 | 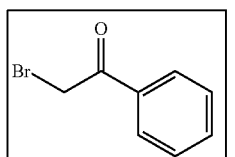 | 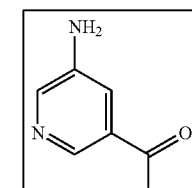 | A |
| 98 | 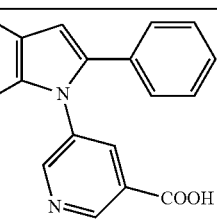 | 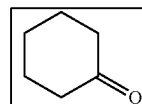 | 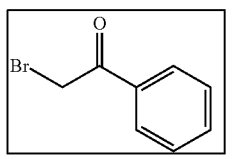 | 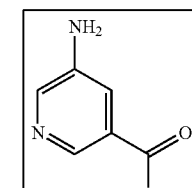 | A, C |
| 99 | 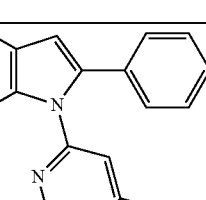 | 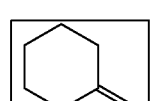 | 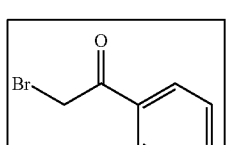 | 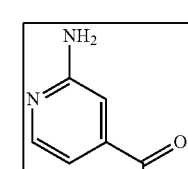 | A |
| 100 | 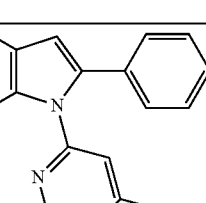 | 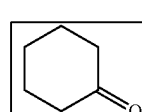 | 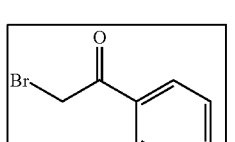 | 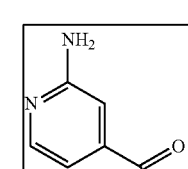 | A, C |

TABLE 3-continued

Exemplary Compounds of the Invention

| product structure | SM ketone | alpha-bromo ketone | aniline | synth. route |
|---|---|---|---|---|
| 101 | cyclohexanone | 2-bromo-1-phenylethanone | 4-amino-nicotinic acid | A |
| 102 | cyclohexanone | 2-bromo-1-phenylethanone | 4-amino-nicotinic acid | A, C |
| 103 | cyclohexanone | 2-bromo-1-phenylethanone | 2-aminopyrimidine-4-carboxylic acid | A |
| 104 | cyclohexanone | 2-bromo-1-phenylethanone | 2-aminopyrimidine-4-carboxylic acid | A, C |
| 105 | cyclohexanone | 2-bromo-1-phenylethanone | 5-amino-1H-pyrrole-2-carboxylic acid | A |
| 106 | cyclohexanone | 2-bromo-1-phenylethanone | 5-amino-1H-pyrrole-2-carboxylic acid | A, C |

US 9,216,966 B2

155                                                                                     156

TABLE 3-continued

Exemplary Compounds of the Invention

| product structure | SM ketone | alpha-bromo ketone | aniline | synth. route |
|---|---|---|---|---|
| 107 | cyclohexanone | 2-bromo-1-phenylethanone | 4-amino-furan-2-carboxylic acid | A |
| 108 | cyclohexanone | 2-bromo-1-phenylethanone | 4-amino-furan-2-carboxylic acid | A, C |
| 109 | cyclohexanone | ethyl 2-bromo-3-oxo-3-phenylpropanoate | 3-aminopyridine | A, C |
| 110 | cyclohexanone | ethyl 3-bromo-4-oxo-4-phenylbutanoate | 3-aminopyridine | A, C |
| 111 | cyclohexanone | ethyl 4-bromo-5-oxo-5-phenylpentanoate | 3-aminopyridine | A, C |

TABLE 3-continued

Exemplary Compounds of the Invention

| product structure | SM ketone | alpha-bromo ketone | aniline | synth. route |
|---|---|---|---|---|
| 112 | cyclohexanone | EtOOC-(CH2)2-CHBr-C(O)-Ph | 3-aminopyridine | A, C |
| 113 | ethyl 3-oxocyclohexanecarboxylate | 2-bromo-1-phenylethanone | 3-aminopyridine | A, C |
| 114 | ethyl 4-oxocyclohexanecarboxylate | 2-bromo-1-phenylethanone | 3-aminopyridine | A, C |
| 115 | ethyl 3-oxocyclohexanecarboxylate | 2-bromo-1-phenylethanone | 3-aminopyridine | A, C |
| 116 | ethyl 2-oxocyclohexanecarboxylate | 2-bromo-1-phenylethanone | 3-aminopyridine | A, C |
| 117 | cyclohexanone | 4-(2-bromoacetyl)benzoic acid | 3-aminopyridine | A, C |

TABLE 3-continued

Exemplary Compounds of the Invention

| product structure | SM ketone | alpha-bromo ketone | aniline | synth. route |
|---|---|---|---|---|
| 118 | cyclohexanone | 2-bromo-1-(3-carboxyphenyl)ethanone | 3-aminopyridine | A, C |
| 119 | cyclohexanone | 2-bromo-1-(2-carboxyphenyl)ethanone | 3-aminopyridine | A, C |
| 120 | cyclohexanone | 2-bromo-1-phenylethanone | 3-aminobenzoic acid | A, C, B |
| 121 | cyclohexanone | 2-bromo-1-phenylethanone | 3-aminobenzoic acid | A, C, B |
| 122 | cyclohexanone | 2-bromo-1-phenylethanone | 3-aminobenzoic acid | A, C, B |

TABLE 3-continued

Exemplary Compounds of the Invention

| product structure | SM ketone | alpha-bromo ketone | aniline | synth. route |
|---|---|---|---|---|
| 123 | cyclohexanone | 1-bromo-1-phenylpropan-2-one | 3-aminobenzoic acid | A, C |
| 124 | cyclohexanone | 1-bromo-1-phenylpropan-2-one | 3-aminobenzoic acid | A, C |
| 125 | cyclohexanone | 1-bromo-1-phenylpropan-2-one | 3-aminobenzoic acid | A, C |
| 126 | cyclohexanone | 2-bromo-1-phenylethan-1-one | 5-aminonicotinamide | A, C |

TABLE 3-continued

Exemplary Compounds of the Invention

| product structure | SM ketone | alpha-bromo ketone | aniline | synth. route |
|---|---|---|---|---|
| 127 | cyclohexanone | bromoacetophenone | 5-amino-N,N-dimethylnicotinamide | A, C |
| 128 | cyclohexanone | bromoacetophenone | 5-amino-N-methylnicotinamide | A, C |
| 129 | cyclohexanone | bromoacetophenone | 5-aminopyridine-3-sulfonamide | A, C |
| 130 | cyclohexanone | bromoacetophenone | 5-amino-N-methylpyridine-3-sulfonamide | A, C |

TABLE 3-continued
Exemplary Compounds of the Invention
| product structure | SM ketone | alpha-bromo ketone | aniline | synth. route |
|---|---|---|---|---|
| 131 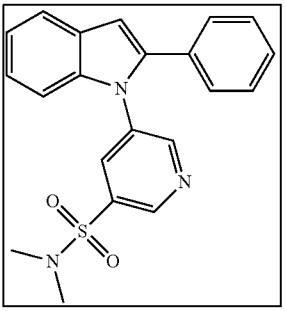 [SMILES: CN(C)S(=O)(=O)c1cncc(-n2c(-c3ccccc3)cc3ccccc32)c1] | 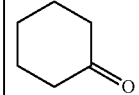 | 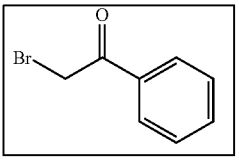 | 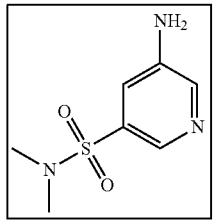 | A, C |
| 132 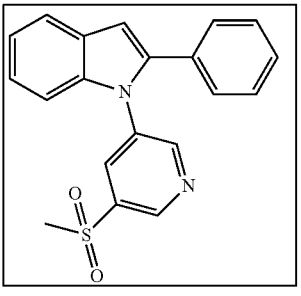 [SMILES: CS(=O)(=O)c1cncc(-n2c(-c3ccccc3)cc3ccccc32)c1] | 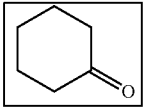 | 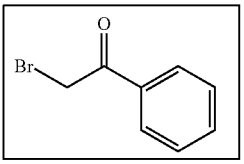 | 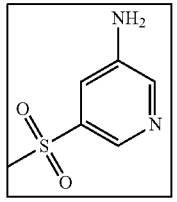 | A, C |
TABLE 4
Exemplary Compounds of the Invention
| Compound Number | product structure | ketone/diketone SM | a-bromo ketone SM | aniline |
|---|---|---|---|---|
| 133 | 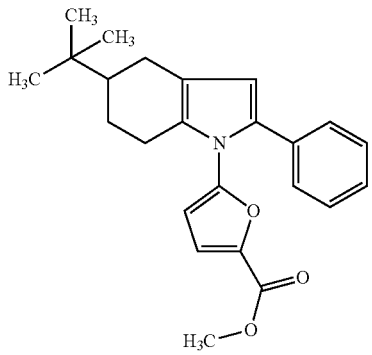 [SMILES: COC(=O)c1ccc(-n2c(-c3ccccc3)cc3c2CCC(C(C)(C)C)C3)o1] | 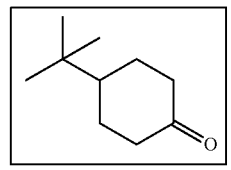 | 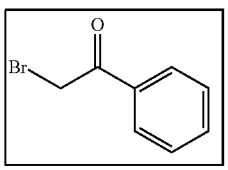 | 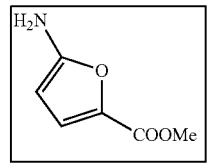 |

TABLE 4-continued

Exemplary Compounds of the Invention

| Compound Number | product structure | ketone/diketone SM | a-bromo ketone SM | aniline |
|---|---|---|---|---|
| 134 | | | | |
| 135 | | | | |
| 136 | | | | |
| 137 | | | | |

TABLE 4-continued

Exemplary Compounds of the Invention

| Compound Number | product structure | ketone/diketone SM | a-bromo ketone SM | aniline |
|---|---|---|---|---|
| 138 | | | | |
| 139 | | | | |
| 140 | | | | |
| 141 | | | | |

TABLE 4-continued

Exemplary Compounds of the Invention

| Compound Number | product structure | ketone/diketone SM | a-bromo ketone SM | aniline |
|---|---|---|---|---|
| 142 | | | | |
| 143 | | | | |
| 144 | | | | |
| 145 | | | | |

TABLE 4-continued

Exemplary Compounds of the Invention

| Compound Number | product structure | ketone/diketone SM | a-bromo ketone SM | aniline |
|---|---|---|---|---|
| 146 | | | | |
| 147 | | | | |
| 148 | | | | |

TABLE 5

Analytical data for the Compounds in Table 4

| Compound Number | 1H NMR, δ | MS | Name | Synth. route |
|---|---|---|---|---|
| 133 | CDCl3; 7.1-7.3 (m, 6H, ArH); 6.2 (s, 1H); 6.0 (d, 1H); 3.9 (s, 3H); 2.6 (m, 3H); 2.3 (m, 1H); 2.0 (m, 1H); 1.3-1.5 (m, 2H); 1.0 (s, 9H). | pos. mode 378 (M + H). | 5-(5-tertButyl-2-phenyl-4,5,6,7-tetrahydroindol-1-yl) furan-2-carboxylic acid methyl ester | A |
| 134 | DMSO - d6; 6.6-8.4(14H, ArH), | pos. mode 370 (M + 1) | 3-(2-thiophen-3-yl-benzo[e]indol-3-yl) benzoic acid | A, C |
| 135 | DMSO - d6; 6.6-8.4(13H, ArH), 2.9(2H, CH2), 2.6(2H, CH2) | pos. mode 396 (M + 1); 394 (M − 1). | 3-[3-(2H-tetrazol-5-yl)-phenyl]-2-thiophen-3-yl-3H benzo[e]indole | A, C |
| 136 | CDCl3; 7.1-7.3 (m, 6H, ArH); 6.2 (s, 1H); 6.0 (d, 1H); 2.6 (m, 2H); 2.4-2.5 (m, 2H); 2.0 (m, 1H); 1.5 (m, 2H); 1.0 (s, 9H). | pos. mode 364 (M + H); neg. mode 362 (M − H) | 5-(5-tertButyl-2-phenyl-4,5,6,7-tetrahydroindol-1-yl) furan-2-carboxylic acid | A |
| 137 | DMSO - d6; 7.1-8.5 (14H, ArH/NH); 5.8 (1H); 2.9 (2H, CH2); 2.6 (2H, CH2). | pos. mode 430 (M + 1); neg. mode 429 (M − 1). | 2-benzofuran-2-yl-3-[3-(2H-tetrazol-5-yl)-phenyl]-4,5-dihydro-3H-benzo[e]indole | A |
| 138 | DMSO - d6; 7.0-8.2 (15H, ArH/NH); 6.3 (1H); 2.9 (2H, CH2); 2.6 (2H, CH2). | pos. mode 457 (M + 1); neg mode 455 (M − 1). | 2-(3-phenylisoxazol-5-yl)-3-[3-(2H-tetrazol-5-yl)-phenyl]-4,5-dihydro-3H-benzo[e]indole | A |
| 139 | DMSO d6; 7.0-8.1 (14H, ArH); 6.2 (1H); 2.9 (2H, CH2); 2.6 (2H, CH2). | pos. mode 433 (M + 1); neg. mode 431 (M − 1). | 3-(2-phenylisoxazol-5-yl)-4,5-dihydrobenzo[e]indol-3-yl] benzoic acid | A |
| 140 | DMSO - d6; 7.3-8.8 (15H, ArH). | pos. mode 365 (M + 1). | 3-(2-pyridin-3-yl-benzo[e]indol-3-yl) benzoic acid | A, C |
| 141 | DMSO - d6; 7.0-8.6 (13H, ArH), 2.9 (2H, CH2), 2.6 (2H, CH2). | pos. mode 367 (M + 1). | 3-(2-pyridin-3-yl-4,5-dihydrobenzo[e]indol-3-yl) benzoic acid | A |
| 142 | DMSO - d6; 7.2-8.5(15H, ArH). | pos. mode 365 (M + 1). | 3-(2-pyridin-2-yl-benzo[e]indol-3-yl) benzoic acid | A, C |
| 143 | DMSO - d6; 6.9-8.5 (13H, ArH), 2.9 (2H, CH2), 2.6 (2H, CH2). | pos. mode 367 (M + 1); 365 (M + 1). | 3-(2-pyridin-2-yl-4,5-dihydrobenzo[e]indol-3-yl) benzoic acid | A |
| 144 | DMSO - d6; 7.1-8.2 (16H, ArH). | pos. mode 404 (M + 1). | 3-(2-benzofuran-2-yl-benzo[e]indol-3-yl) benzoic acid | A, C |
| 145 | DMSO - d6; 7.0-8.1 (14H, ArH), 2.9 (2H, CH2), 2.6 (2H, CH2). | pos. mode 406 (M + 1). | 3-(2-benzofuran-2-yl-4,5-dihydrobenzo[e]indol-3-yl) benzoic acid | A |
| 146 | DMSO - d6; 7.0-8.6 (14H, ArH), 2.9 (2H, CH2), 2.6 (2H, CH2). | pos. mode 391 (M + 1). | 2-pyridin-2-yl-3-[3-(2H-tetrazol-5-yl)-phenyl]-4,5-dihydro-3H-benzo[e]indole | A |
| 147 | DMSO - d6; 7.4-8.6(16H, ArH). | pos. mode 389 (M + 1). | 2-pyridin-3-yl-3-[3-(2H-tetrazol-5-yl)-phenyl]-3H-benzo[e]indole | A, C |
| 148 | DMSO - d6; 7.2-8.4 (16H, ArH). | pos. mode 389 (M + 1). | 2-pyridin-2-yl-3-[3-(2H-tetrazol-5-yl)-phenyl]-3H-benzo[e]indole | A, C |

Compounds of Formulae I and II, e.g., those disclosed in Table 4 and 5, are capable of modulating APP processing and lower Aβ42 in the cell based assay described in Example 6. Compounds 138 and 139 have an Aβ42 lowering IC50 of 1004 and 204, respectively.

Example 12

More Compounds of the Invention

Additional compounds of the invention, synthesized according to the above described routes are given below along with relevant characterization data. These compounds exemplify the compounds of the invention including those of aspects 1-21 of the invention.

TABLE 6
Compounds of the Invention and Starting Materials
| product structure | ketone SM | α-bromo ketone SM | aniline/amine |
|---|---|---|---|
|  | 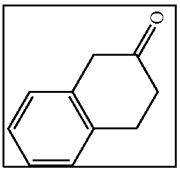 | 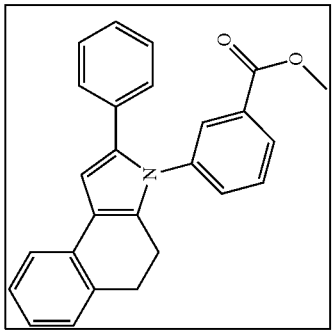 | 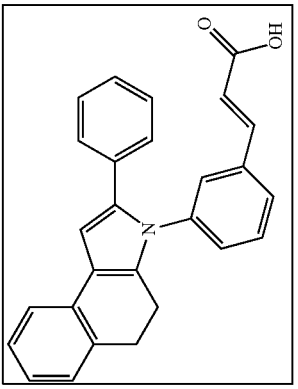 |
| 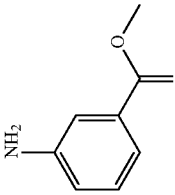 | 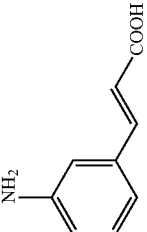 | 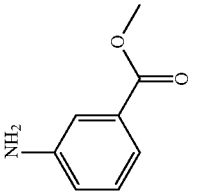 | 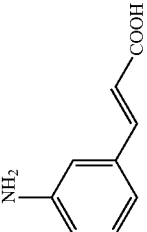 |
| 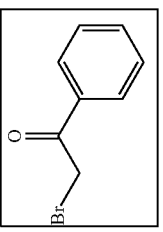 |  | 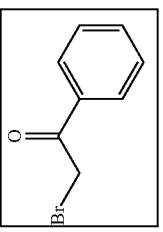 | 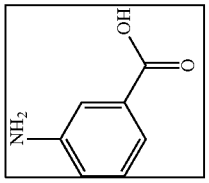 |

TABLE 6-continued

Compounds of the Invention and Starting Materials

| product structure | ketone SM | α-bromo ketone SM | aniline/amine |
|---|---|---|---|

TABLE 6-continued

Compounds of the Invention and Starting Materials

| product structure | ketone SM | α-bromo ketone SM | aniline/amine |
|---|---|---|---|

TABLE 6-continued

Compounds of the Invention and Starting Materials

| product structure | ketone SM | α-bromo ketone SM | aniline/amine |
|---|---|---|---|

TABLE 6-continued

Compounds of the Invention and Starting Materials

| product structure | ketone SM | α-bromo ketone SM | aniline/amine |
|---|---|---|---|

TABLE 6-continued

Compounds of the Invention and Starting Materials

| product structure | ketone SM | α-bromo ketone SM | aniline/amine |
|---|---|---|---|

TABLE 6-continued
Compounds of the Invention and Starting Materials
| product structure | ketone SM | α-bromo ketone SM | aniline/amine |
|---|---|---|---|
| 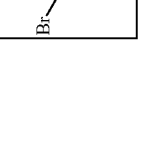 | 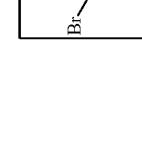 | 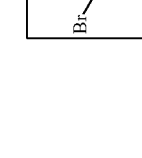 |  |
| 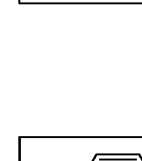 |  | 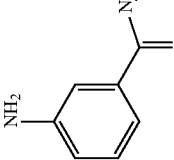 | 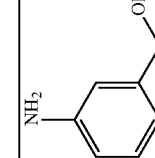 |
| 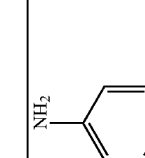 | 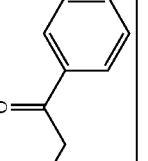 | | |

TABLE 6-continued

Compounds of the Invention and Starting Materials

| ketone SM | α-bromo ketone SM | aniline/amine | product structure |
|---|---|---|---|

TABLE 6-continued

Compounds of the Invention and Starting Materials

| product structure | ketone SM | α-bromo ketone SM | aniline/amine |
|---|---|---|---|
| 193 | | | |
| 194 | | | |

TABLE 6-continued
Compounds of the Invention and Starting Materials
| product structure | ketone SM | α-bromo ketone SM | aniline/amine |
|---|---|---|---|
| 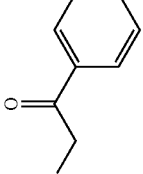 | 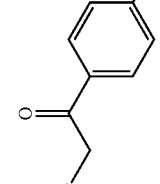 | 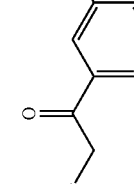 | 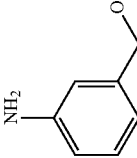 |
| 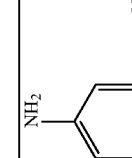 | 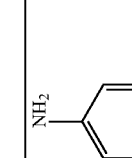 | 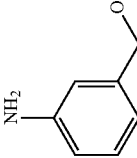 | 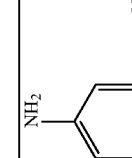 |
| 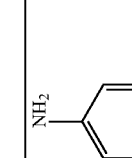 | 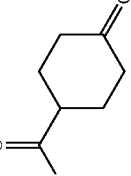 | 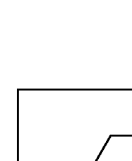 |  |

TABLE 6-continued

Compounds of the Invention and Starting Materials

| product structure | ketone SM | α-bromo ketone SM | aniline/amine |
|---|---|---|---|
| (3-(cyclohexyl)-2-phenyl-4,5-dihydrobenzo[g]indol-3-yl)propanoic acid structure | 2-tetralone | α-bromoacetophenone | 2-amino-2-cyclohexylpropanoic acid derivative |
| similar benzo[g]indole structure with cyclohexyl and propanoic acid | 2-tetralone | α-bromoacetophenone | 2-amino-2-cyclohexylpropanoic acid derivative |
| 4-methyl-tetrahydroindole with phenyl and 3-(carboxyethyl)phenyl | 3-methylcyclohexanone | α-bromoacetophenone | 3-aminophenylpropanoic acid |

TABLE 6-continued

Compounds of the Invention and Starting Materials

| product structure | ketone SM | α-bromo ketone SM | aniline/amine |
|---|---|---|---|

TABLE 6-continued

Compounds of the Invention and Starting Materials

| product structure | ketone SM | α-bromo ketone SM | aniline/amine |
|---|---|---|---|

TABLE 6-continued

Compounds of the Invention and Starting Materials

| product structure | ketone SM | α-bromo ketone SM | aniline/amine |
|---|---|---|---|

TABLE 6-continued
Compounds of the Invention and Starting Materials
| product structure | ketone SM | α-bromo ketone SM | aniline/amine |
|---|---|---|---|
| 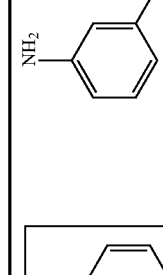 | 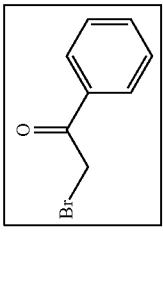 | 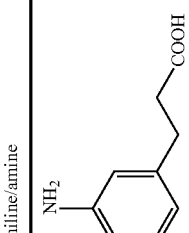 | 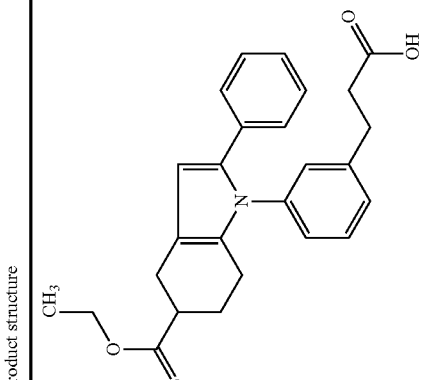 |
| 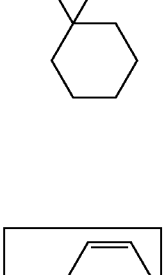 | 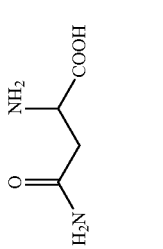 | 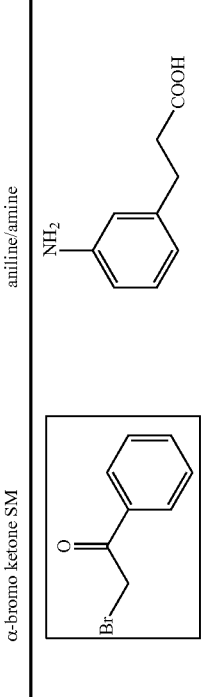 | 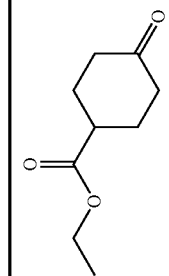 |
| 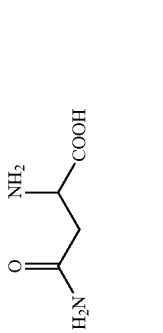 | 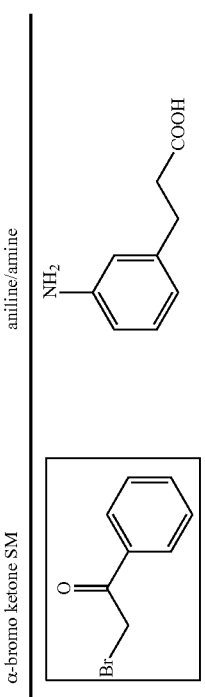 | 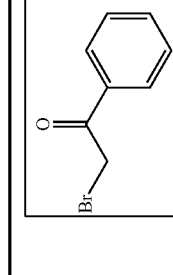 | 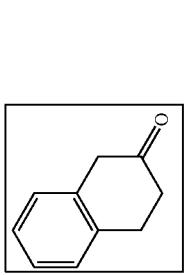 |

TABLE 6-continued

Compounds of the Invention and Starting Materials

| product structure | ketone SM | α-bromo ketone SM | aniline/amine |
|---|---|---|---|

TABLE 6-continued

Compounds of the Invention and Starting Materials

| product structure | ketone SM | α-bromo ketone SM | aniline/amine |
|---|---|---|---|

TABLE 6-continued

Compounds of the Invention and Starting Materials

| product structure | ketone SM | α-bromo ketone SM | aniline/amine |

TABLE 6-continued

Compounds of the Invention and Starting Materials

TABLE 6-continued
Compounds of the Invention and Starting Materials
| product structure | ketone SM | α-bromo ketone SM | aniline/amine |
|---|---|---|---|
| 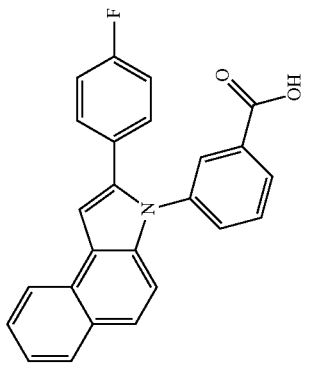 | 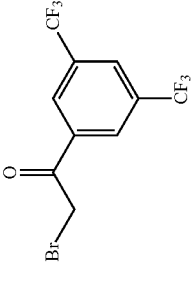 | 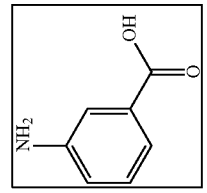 | 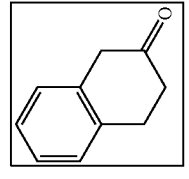 |
| 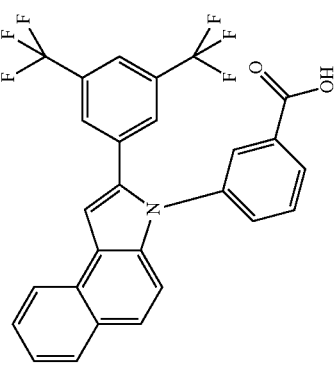 | 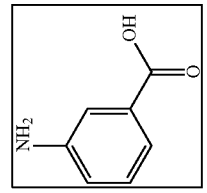 | 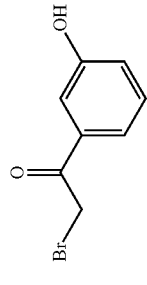 | 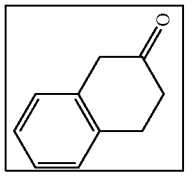 |
| 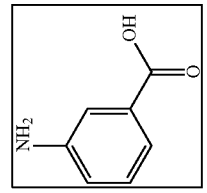 | 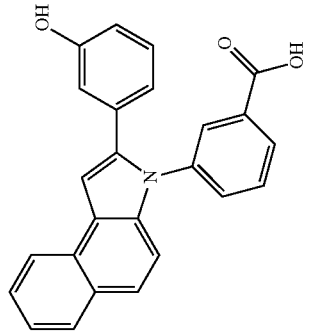 | 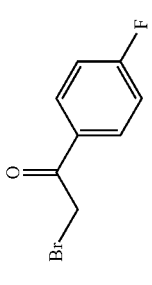 | 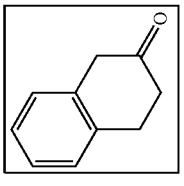 |

TABLE 6-continued
Compounds of the Invention and Starting Materials
| ketone SM | α-bromo ketone SM | aniline/amine |
|---|---|---|
| 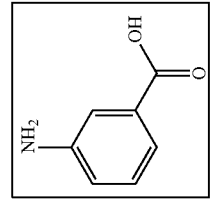 | 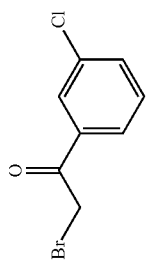 | 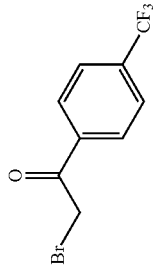 |
| 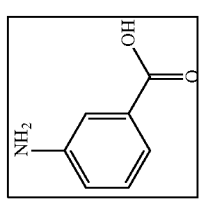 | 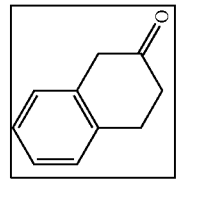 | 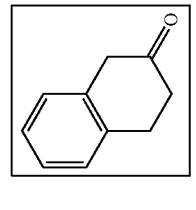 |
| 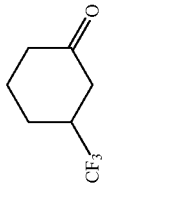 | 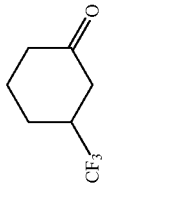 | 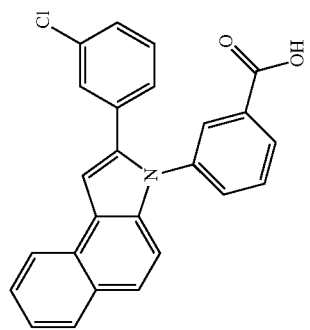 |
product structure
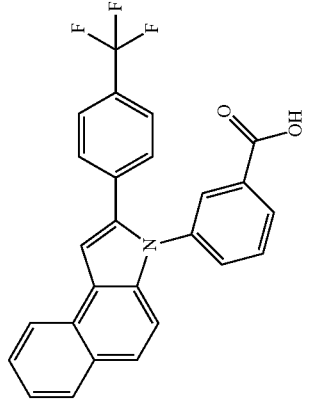
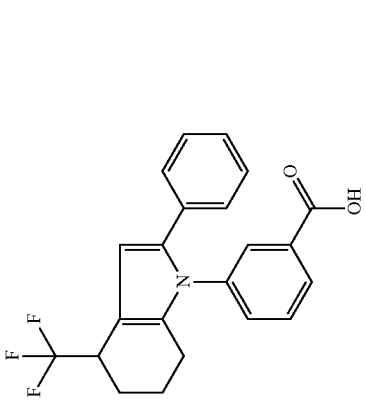

TABLE 6-continued
Compounds of the Invention and Starting Materials
| product structure | ketone SM | α-bromo ketone SM | aniline/amine |
|---|---|---|---|
| 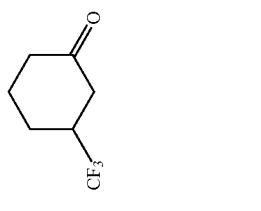 | 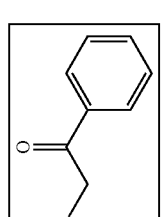 | 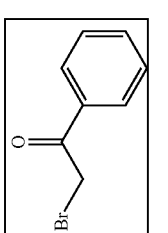 | 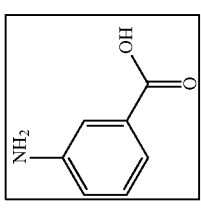 |
| 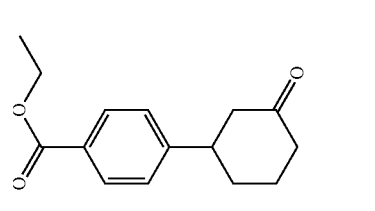 | | | |

TABLE 6-continued

Compounds of the Invention and Starting Materials

TABLE 6-continued

Compounds of the Invention and Starting Materials

TABLE 6-continued

Compounds of the Invention and Starting Materials

US 9,216,966 B2
TABLE 6-continued
Compounds of the Invention and Starting Materials
| product structure | ketone SM | α-bromo ketone SM | aniline/amine |
|---|---|---|---|
| 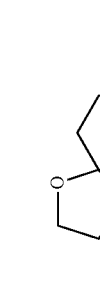 | 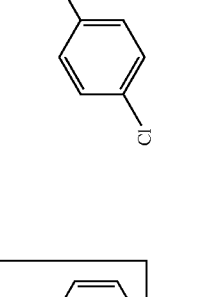 | 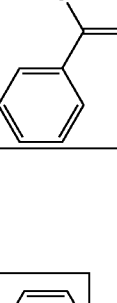 |  |
| 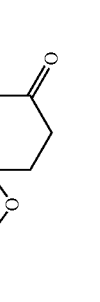 |  | 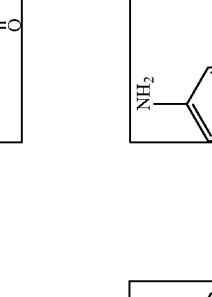 |  |
| 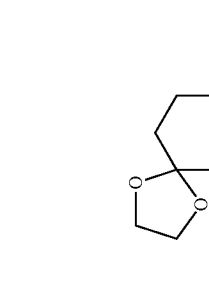 |  | 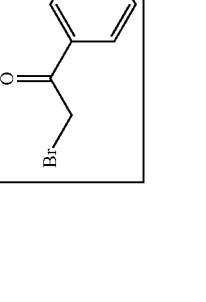 |  |

TABLE 6-continued

Compounds of the Invention and Starting Materials

| ketone SM | α-bromo ketone SM | aniline/amine |
|---|---|---|

TABLE 6-continued

Compounds of the Invention and Starting Materials

| product structure | ketone SM | α-bromo ketone SM | aniline/amine |

TABLE 6-continued

Compounds of the Invention and Starting Materials

| product structure | ketone SM | α-bromo ketone SM | aniline/amine |
|---|---|---|---|
| 233 | | | |
| 234 | | | |

TABLE 6-continued
Compounds of the Invention and Starting Materials
| product structure | ketone SM | α-bromo ketone SM | aniline/amine |
|---|---|---|---|
|  |  | 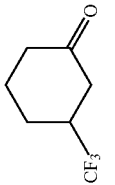 | 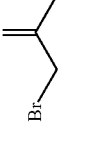 |
| 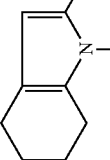 | 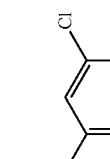 | 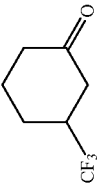 | 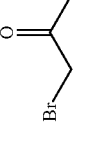 |
|  | 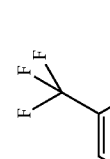 | 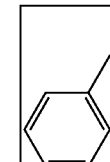 | 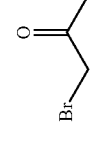 |

TABLE 6-continued
Compounds of the Invention and Starting Materials
| product structure | ketone SM | α-bromo ketone SM | aniline/amine |
|---|---|---|---|
| 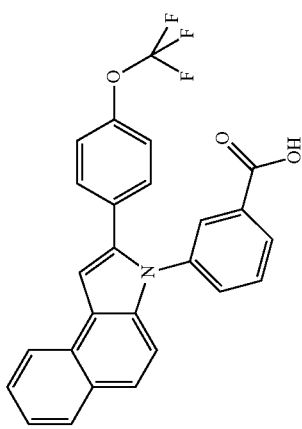 | 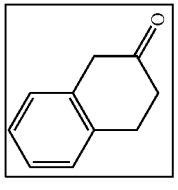 | 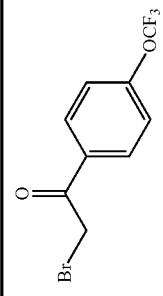 | 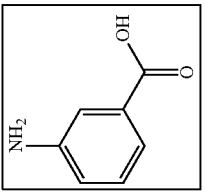 |
| 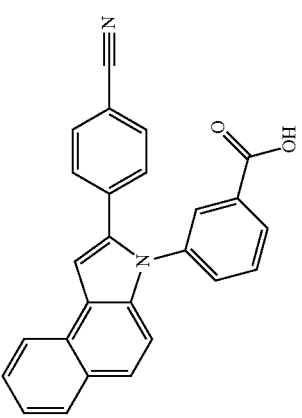 | 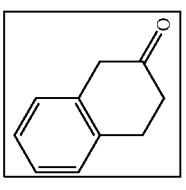 | 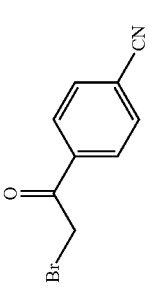 | 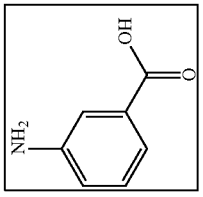 |
| 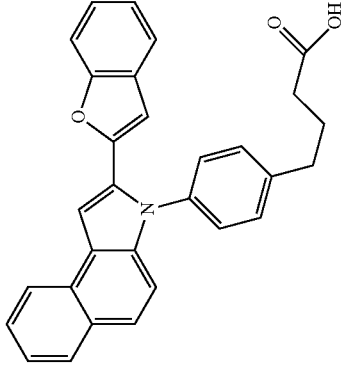 | 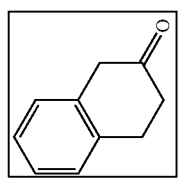 | 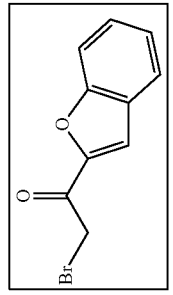 | 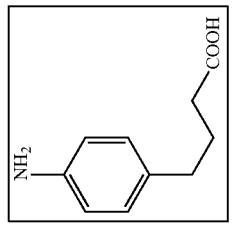 |

TABLE 6-continued

Compounds of the Invention and Starting Materials

| product structure | ketone SM | α-bromo ketone SM | aniline/amine |
|---|---|---|---|

TABLE 6-continued

Compounds of the Invention and Starting Materials

| product structure | ketone SM | α-bromo ketone SM | aniline/amine | |
|---|---|---|---|---|
| (structure) | (structure) | (structure) | (structure) | 241 |
| (structure) | (structure) | (structure) | (structure) | 242 |

TABLE 6-continued

Compounds of the Invention and Starting Materials

TABLE 6-continued

Compounds of the Invention and Starting Materials

| product structure | ketone SM | α-bromo ketone SM | aniline/amine |
|---|---|---|---|

TABLE 6-continued

Compounds of the Invention and Starting Materials

TABLE 6-continued

Compounds of the Invention and Starting Materials

| ketone SM | α-bromo ketone SM | aniline/amine | product structure |
|---|---|---|---|
| 2-tetralone | 2-bromo-1-(3,4-dichlorophenyl)ethanone | 4-(4-aminophenyl)butanoic acid | 4-(4-(2-(3,4-dichlorophenyl)-3H-benzo[e]indol-3-yl)phenyl)butanoic acid |
| 4-tert-butylcyclohexanone | 2-bromo-1-(4-(trifluoromethyl)phenyl)ethanone | 3-aminobenzoic acid | 3-(5-tert-butyl-2-(4-(trifluoromethyl)phenyl)-4,5,6,7-tetrahydro-1H-indol-1-yl)benzoic acid |

TABLE 6-continued

Compounds of the Invention and Starting Materials

| product structure | ketone SM | α-bromo ketone SM | aniline/amine |
|---|---|---|---|

TABLE 6-continued

Compounds of the Invention and Starting Materials

| ketone SM | α-bromo ketone SM | aniline/amine | product structure |
|---|---|---|---|
| 2-tetralone | 2-bromo-1-(4-(trifluoromethyl)phenyl)ethanone | 4-(4-aminophenyl)butanoic acid | 4-(4-(2-(4-(trifluoromethyl)phenyl)-3H-benzo[e]indol-3-yl)phenyl)butanoic acid |
| 2-tetralone | 1-(benzofuran-2-yl)-2-bromoethanone | 3-aminobenzoic acid | 3-(2-(benzofuran-2-yl)-1-((dimethylamino)methyl)-3H-benzo[e]indol-3-yl)benzoic acid |

TABLE 6-continued

Compounds of the Invention and Starting Materials

| ketone SM | α-bromo ketone SM | aniline/amine |
|---|---|---|

TABLE 6-continued

Compounds of the Invention and Starting Materials

| ketone SM | α-bromo ketone SM | aniline/amine |
|---|---|---|

TABLE 6-continued
Compounds of the Invention and Starting Materials
| product structure | ketone SM | α-bromo ketone SM | aniline/amine |
|---|---|---|---|
| 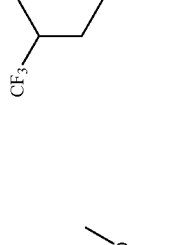 | 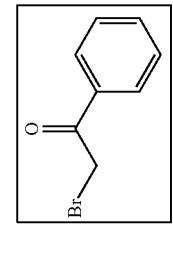 | 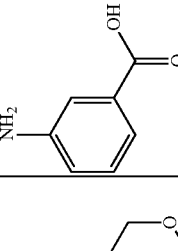 | 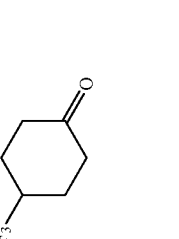 |
| 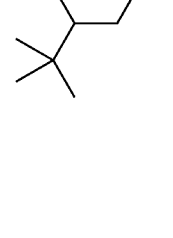 | 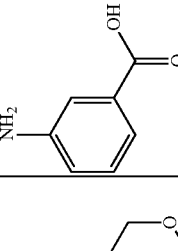 | 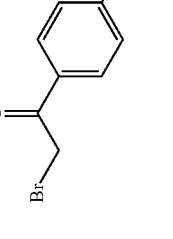 | 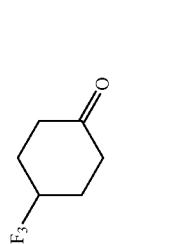 |
| 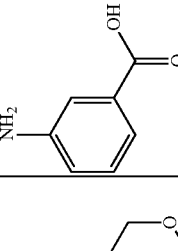 | 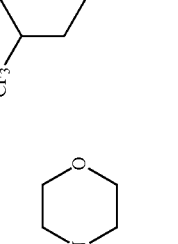 | 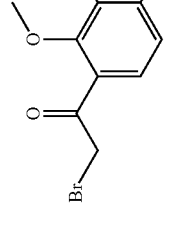 | 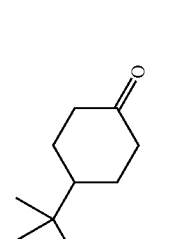 |

TABLE 6-continued

Compounds of the Invention and Starting Materials

| ketone SM | α-bromo ketone SM | aniline/amine |
|---|---|---|
| (2-tetralone) | 4'-chloro-α-bromoacetophenone | 5-amino-2-chlorobenzoic acid |
| 1,4-dioxaspiro[4.5]decan-8-one | α-bromoacetophenone | 3-aminobenzoic acid |
| 1,4-dioxaspiro[4.5]decan-8-one | α-bromoacetophenone | 3-aminobenzoic acid | product structure shown for each row.

TABLE 6-continued
Compounds of the Invention and Starting Materials
| product structure | ketone SM | α-bromo ketone SM | aniline/amine |
|---|---|---|---|
| 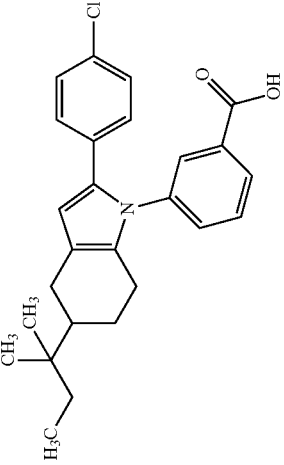 |  | 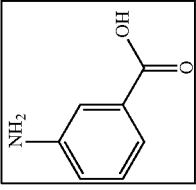 | 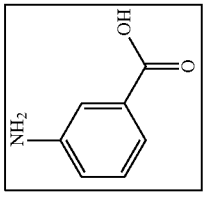 |
| 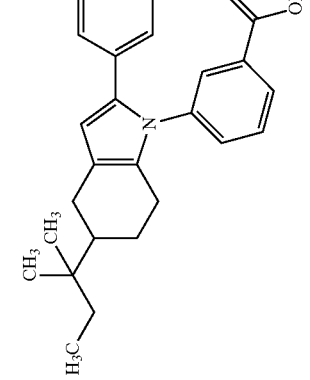 |  | 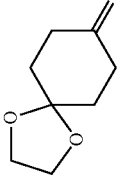 | 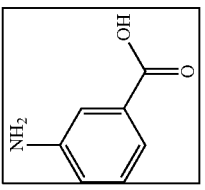 |
| 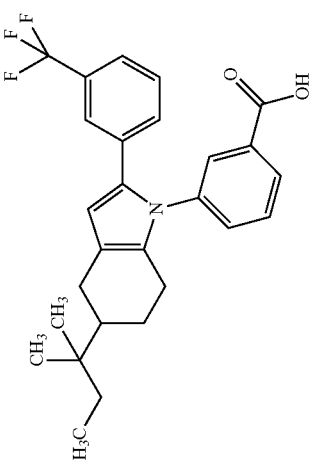 | 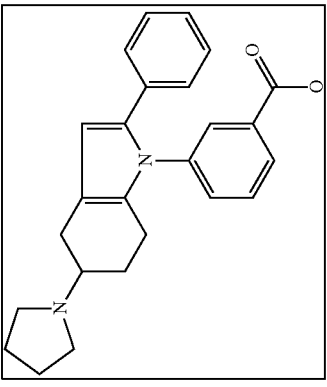 | 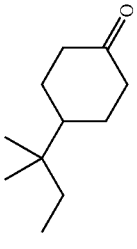 | 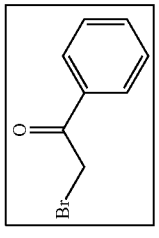 |

TABLE 6-continued

Compounds of the Invention and Starting Materials

| product structure | ketone SM | α-bromo ketone SM | aniline/amine |
|---|---|---|---|

TABLE 6-continued

Compounds of the Invention and Starting Materials

| product structure | ketone SM | α-bromo ketone SM | aniline/amine |
|---|---|---|---|

TABLE 6-continued
Compounds of the Invention and Starting Materials
| product structure | ketone SM | α-bromo ketone SM | aniline/amine |
|---|---|---|---|
| | 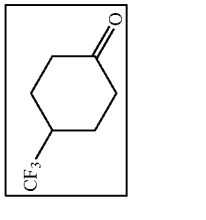 | 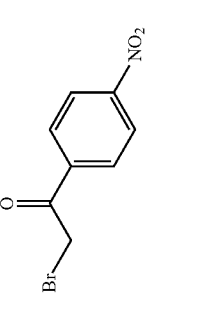 | 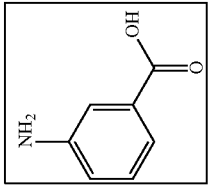 |
|  | 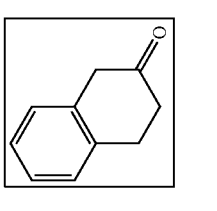 | 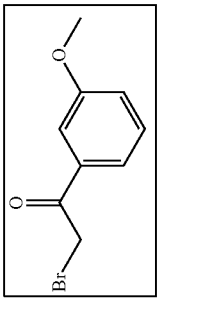 | 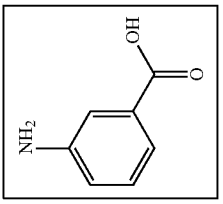 |
| 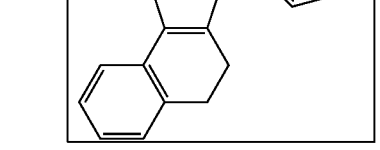 | 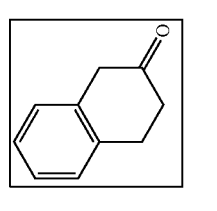 | 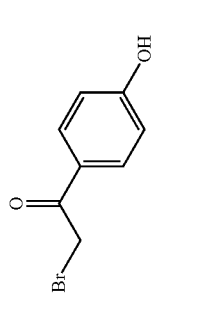 | 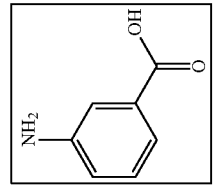 |

TABLE 6-continued
Compounds of the Invention and Starting Materials
| product structure | ketone SM | α-bromo ketone SM | aniline/amine |
|---|---|---|---|
| 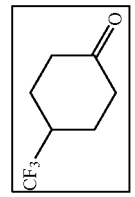 | 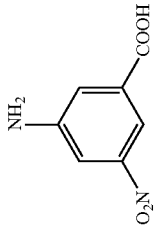 | 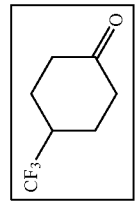 | 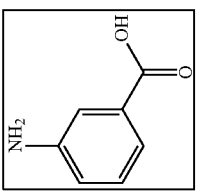 |
| 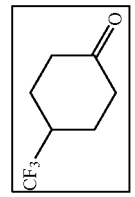 | 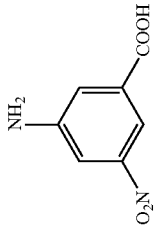 | 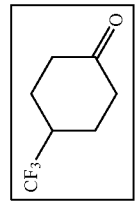 | 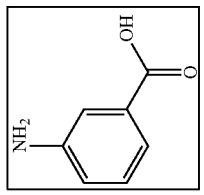 |
| 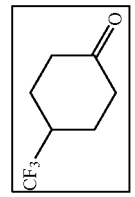 | 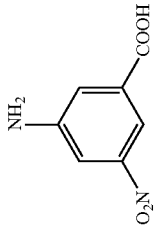 | 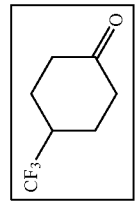 | 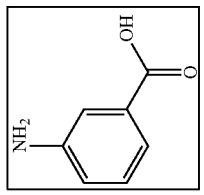 |

TABLE 6-continued
Compounds of the Invention and Starting Materials
| product structure | ketone SM | α-bromo ketone SM | aniline/amine |
|---|---|---|---|
| 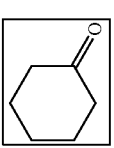 | 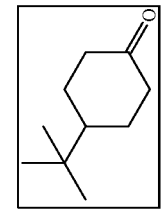 | 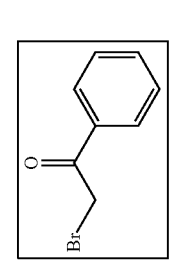 | 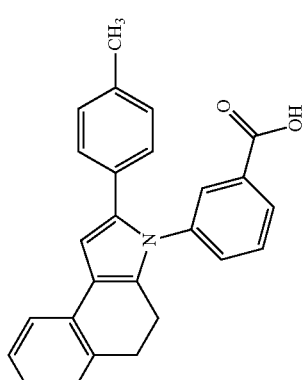 |
| 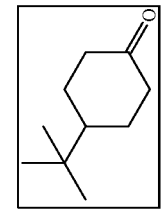 | 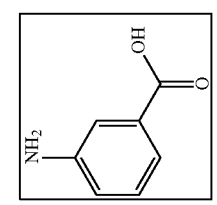 | 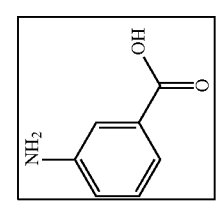 | 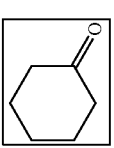 |
| 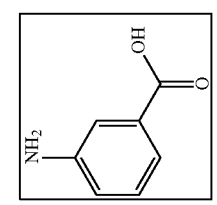 | 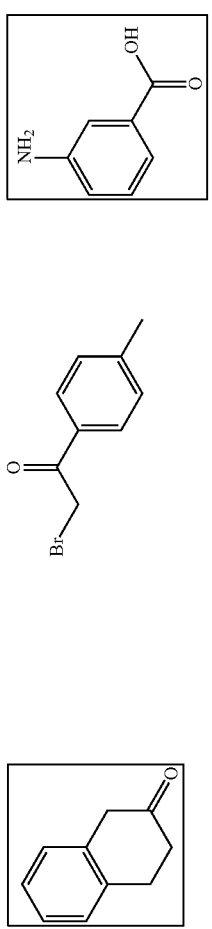 | 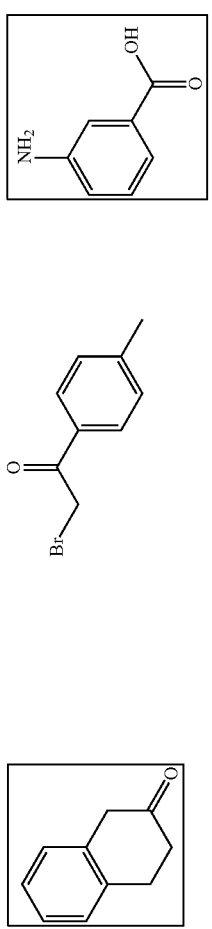 | 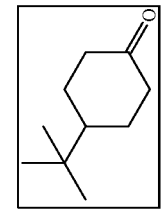 |

TABLE 6-continued
Compounds of the Invention and Starting Materials
| product structure | ketone SM | α-bromo ketone SM | aniline/amine |
|---|---|---|---|
| 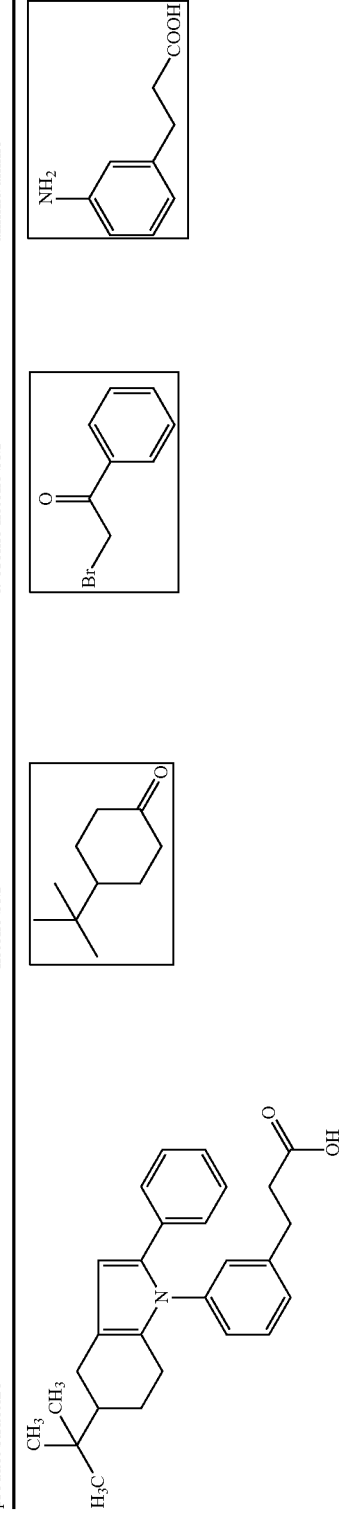 | 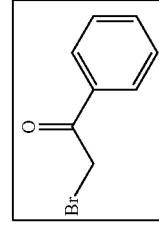 | 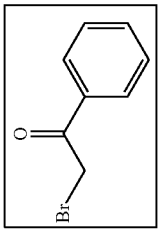 | 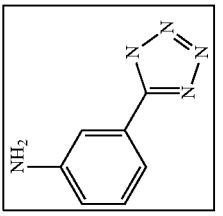 |
| 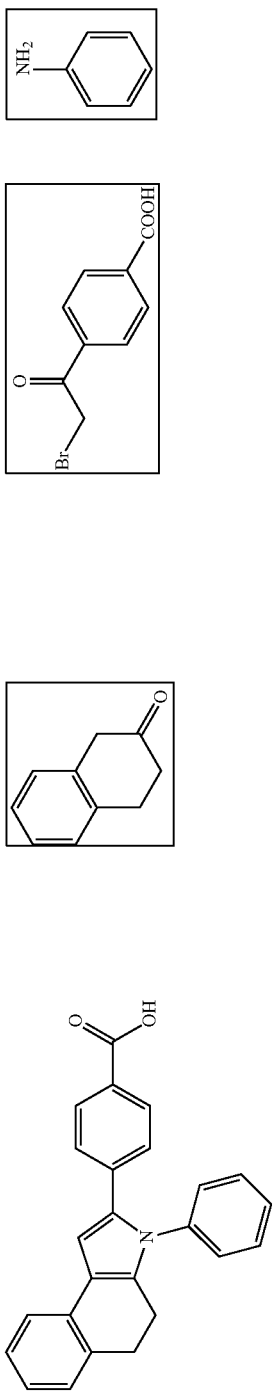 | 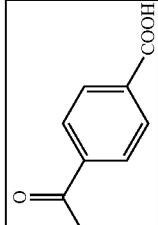 | 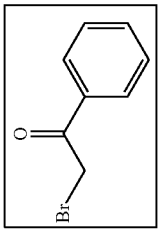 | 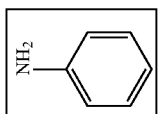 |
| 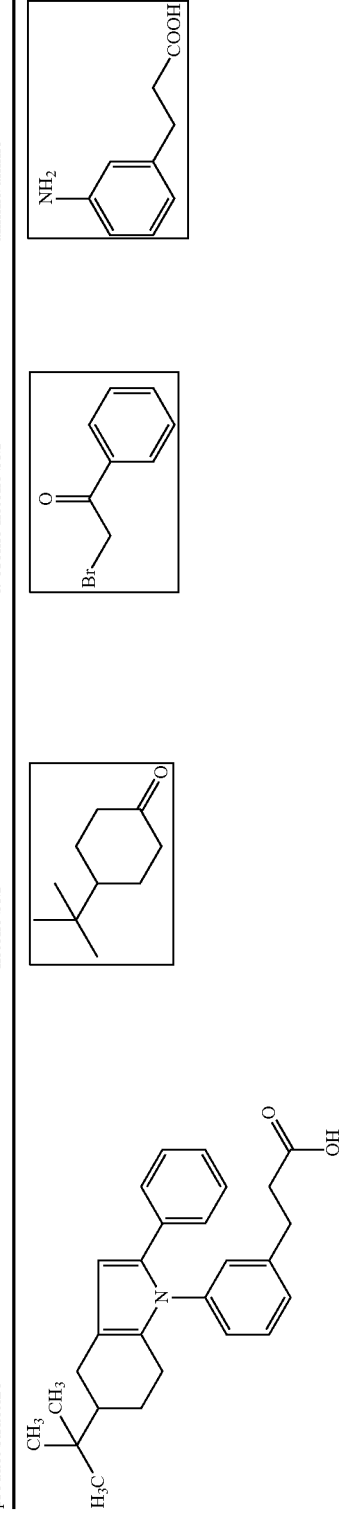 | 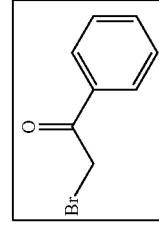 | 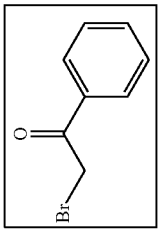 | 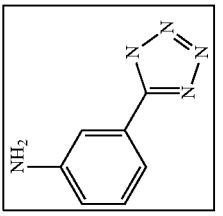 |

TABLE 6-continued

Compounds of the Invention and Starting Materials

| ketone SM | α-bromo ketone SM | aniline/amine |
|---|---|---|

TABLE 6-continued

Compounds of the Invention and Starting Materials

| ketone SM | α-bromo ketone SM | aniline/amine | product structure |
|---|---|---|---|

TABLE 6-continued

Compounds of the Invention and Starting Materials

| product structure | ketone SM | α-bromo ketone SM | aniline/amine |
|---|---|---|---|
| 2-phenyl-N-(3-carboxypropyl)-4,5-dihydrobenz[g]indole | 2-tetralone | phenacyl bromide | 4-aminobutyric acid |
| 2-phenyl-N-(3-carboxypropyl)-4,5-dihydrobenz[g]indole | 2-tetralone | phenacyl bromide | 4-aminobutyric acid |
| 2-phenyl-1-(3-carboxyphenyl)-5-phenyl-4,5,6,7-tetrahydroindole | 4-phenylcyclohexanone | phenacyl bromide | 3-aminobenzoic acid |

TABLE 6-continued

Compounds of the Invention and Starting Materials

| ketone SM | α-bromo ketone SM | aniline/amine |
|---|---|---|

TABLE 6-continued

Compounds of the Invention and Starting Materials

| product structure | ketone SM | α-bromo ketone SM | aniline/amine |
|---|---|---|---|

TABLE 7

Compounds from Table 6 and Characterization Data

| product structure | 1H NMR, δ | MS | name |
|---|---|---|---|
| 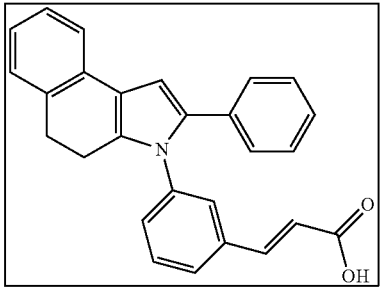 [SMILES: O=C(O)/C=C/c1cccc(-n2c(-c3ccccc3)cc3c2CCc2ccccc2-3)c1] | DMSO-d6; 7.1-7.3 (m, 16H); 6.8 (s, 1H); 2.9 (t, 2H); 2.6 (t, 2H). | pos. mode 392 (M + H), neg. mode 390 (M − 1). | 3-[3-(2-phenyl-4,5-dihydrobenzo[e]indol-3-yl)-phenyl] acrylic acid |
| 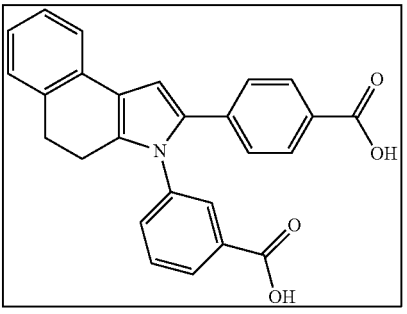 [SMILES: O=C(O)c1ccc(-c2cc3c(n2-c2cccc(C(=O)O)c2)CCc2ccccc2-3)cc1] | DMSO-d6; 8.03 (d, 1H), 7.82-7.73 (m, 3H), 7.68-7.52 (m, 3H), 7.26-7.19 (m, 4H), 7.12-7.07 (m, 2H), 2.98 (t, 2H), 2.70 (t, 2H). | pos. mode 410 (M + H); neg. mode 408 (M − H). | 3[2-(4-carboxyphenyl)-4,5-dihydrobenzo[e]indol-3-yl] benzoic acid |
| 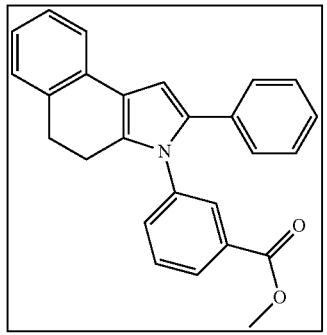 [SMILES: COC(=O)c1cccc(-n2c(-c3ccccc3)cc3c2CCc2ccccc2-3)c1] | CDCl3; 8.02 (tt, 1H), 7.93 (t, 1H); 7.46 (d, 1H), 7.42 (t, 1H), 7.28 (d, 1H); 7.24 (m, 1H), 7.21-7.05 (m, 7H), 6.74 (s, 1H), 3.92 (s, 3H), 3.0 (t, 2H), 2.72 (t, 2H). | pos. mode 380 (M + H). | methyl 3-(2-phenyl-4,5-dihydrobenzo[e]indol-3-yl) benzoate |
| 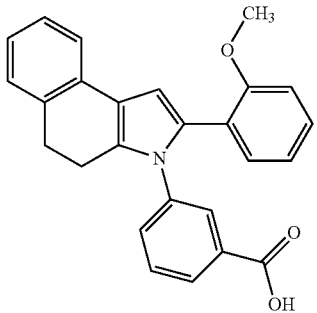 [SMILES: COc1ccccc1-c1cc2c(n1-c1cccc(C(=O)O)c1)CCc1ccccc1-2] | MeOH-d4; 7.75 (t, 1H), 7.42-7.36 (m, 3H), 7.32-7.14 (m, 5H), 7.0 (t, 1H), 6.91 (t, 1H), 6.73 (d, 1H), 6.5 (s, 1H), 3.33 (s, 3H) 2.96 (t, 2H), 2.71 (t, 2H). | pos. mode 396 (M + H). | 3-[2-(2-methoxyphenyl)-4,5-dihydrobenzo[e]indol-3-yl] benzoic acid |

TABLE 7-continued

Compounds from Table 6 and Characterization Data

| product structure | 1H NMR, δ | MS | name |
|---|---|---|---|
| | MeOH-d4; 8.3 (d, 1H); 7.99-7.94 (m, 2H); 7.88 (d, 1H); 7.59-7.38 (m, 7H); 7.33-7.28 (m, 1H); 7.21 (s, 1H), 6.99 (t, 1H); 6.81 (s, 1H); 3.38 (s, 3H). | pos. mode 394 (M + H). | 3-[2-(2-methoxyphenyl)-benzo[e]indol-3-yl] benzoic acid |
| | CDCl3: 8.0 (d, 1H); 7.9 (br. s, 1H); 7.5 (t, 1H); 7.2 (m, 1H); 7.1 (m, 5H); 6.3 (s, 1H); 2.7 (m, 1H); 2.5 (m, 1H); 2.3-2.4 (m, 2H); 2.0 (m, 1H); 1.5 (m, 1H); 1.4 (m, 1H); 1.0 (s, 9H). | pos. mode 398 (M + H). | 5-tButyl-2-phenyl-1-[3-(1H-tetrazol-5-yl) phenyl]-4,5,6,7-tetrahydro-1H-indole |
| | DMSO-d6; 7.2-8.4 (m, 16H). | pos. mode 388 (M + H). | 2-phenyl-3-[3-(2H-tetrazol-5-yl)-phenyl] 3H-benzo[e]indole |
| | CDCl3: 7.7 (dm, 1H); 7.5 (br. s, 1H); 7.4 (t, 1H); 7.3 (m, 1H); 7.0-7.2 (m, 5H); 6.2 (s, 1H); 2.7 (m, 1H); 2.6 (m, 1H); 2.4 (m, 1H); 2.2 (m, 1H); 1.9 (m, 2H); 1.4 (m, 1H); 1.1 (d, 3H). | pos. mode 331 (M + H). | 3-(5-methyl-2-phenyl-4,5,6,7-tetrahydroindol-1-yl) benzamide |
| | CDCl3: 7.0-7.2 (m, 9H); 6.2 (s, 1H); 2.7 (m, 3H); 2.5 (m, 1H); 2.4 (m, 3H); 2.2 (m, 1H); 2.0 (m, 2H); 1.9 (m, 2H); 1.4 (m, 1H); 1.0 (d, 3H). | pos. mode 374 (M + H). | 4-[4-(5-methyl-2-phenyl-4,5,6,7-tetrahydroindol-1-yl) phenyl] butyric acid |

TABLE 7-continued

Compounds from Table 6 and Characterization Data

| product structure | 1H NMR, δ | MS | name |
|---|---|---|---|
| | CDCl3: 7.8 (dm, 1H); 7.7 (br. s, 1H); 7.5 (t, 1H); 7.3 (m, 1H); 7.0-7.2 (m, 5H); 6.2 (s, 1H); 2.7 (m, 1H); 2.6 (m, 1H); 2.4 (m, 1H); 2.2 (t, 1H); 1.9 (m, 2H); 1.4 (m, 1H); 1.1 (d, 3H). | pos. mode 367 (M + H). | 3-(5-methyl-2-phenyl-4,5,6,7-tetrahydroindol-1-yl) benzenesulfonamide |
| | CD3OD: 7.44 (m, 1H), 7.41-7.36 (m, 3H), 7.30 (m, 1H), 7.20-7.08 (m, 7H), 7.00 (m, 1H), 6.77 (s, 1H), 2.97-2.92 (m, 2H), 2.67-2.48 (m, 2H), 2.44-2.34 (m, 2H), 2.25 (m, 1H), 2.04 (m, 1H). | neg. mode 392 (M − H) | 3-[2-(2-phenyl-4,5-dihydro-benzo[e]indol-3-yl)-phenyl] propionic acid |
| | CD3OD: 8.34 (m, 1H), 7.88 (m, 1H), 7.58-7.52 (m, 2H), 7.50-7.34 (m, 8H), 7.26-7.20 (m, 3H), 7.04 (m, 1H), 2.44 (m, 1H), 2.37 (m, 1H), 2.09 (m, 1H), 1.98 (m, 1H). | neg. mode 390 (M − H) | 3-[2-(2-phenyl-benzo[e]indol-3-yl)-phenyl] propionic acid |
| | CDCl3: 7.7 (dm, 1H); 7.5 (br. s, 1H); 7.4 (t, 1H); 7.2 (m, 1H); 7.0-7.1 (m, 5H); 6.2 (s, 1H); 5.9 (br. s, 1H); 3.0 (d, 3H); 2.7 (d, 1H); 2.6 (m, 1H); 2.4 (m, 2H); 2.0 (m, 1H); 1.5 (m, 1H); 1.4 (m, 1H); 1.0 (s, 9H). | pos. mode 387 (M + H). | 3-(5-tButyl-2-phenyl-4,5,6,7-tetrahydroindol-1-yl) N-methyl benzamide |

TABLE 7-continued

Compounds from Table 6 and Characterization Data

| product structure | 1H NMR, δ | MS | name |
|---|---|---|---|
| 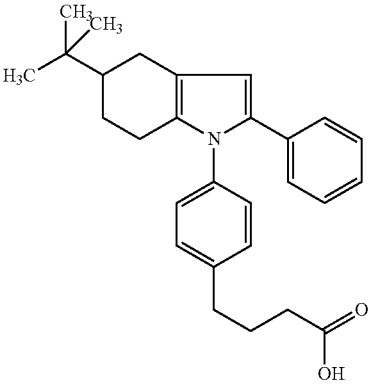 [SMILES: CC(C)(C)C1CCc2c(cc(-c3ccccc3)n2-c2ccc(CCCC(=O)O)cc2)C1] | CDCl3: 7.0-7.2 (m, 9H); 6.2 (s, 1H); 2.5 (m, 3H); 2.4-2.5 (m, 4H); 2.0 (m, 3H); 1.5 (m, 2H); 1.4 (m, 1H); 0.9 (s, 9H). | pos. mode 416 (M + H). | 4-[4-(5-tButyl-2-phenyl-4,5,6,7-tetrahydroindol-1-yl) phenyl] butyric acid |
| 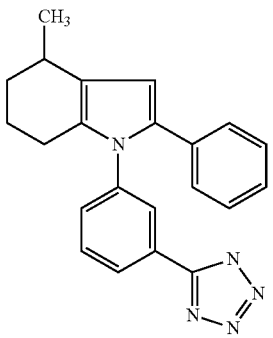 [SMILES: CC1CCCc2c1cc(-c1ccccc1)n2-c1cccc(-c2nnn[nH]2)c1] | CDCl3: 8.0 (d, 1H); 7.9 (br. s, 1H), 7.4 (m, 2H); 7.0-7.2 (m, 6H); 6.2 (s, 1H); 2.6 (m, 1H); 2.5 (m, 1H); 2.2 (m, 2H); 1.9 (m, 1H); 1.4 (m, 2H); 1.0 (d, 3H). | pos. mode 356 (M + H); neg. mode 354 (M − H). | 4-methyl-2-phenyl-1-[3-(1H-tetrazol-5-yl) phenyl]-4,5,6,7-tetrahydro-1H-indole |
| 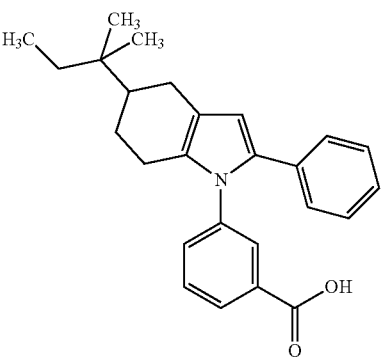 [SMILES: CCC(C)(C)C1CCc2c(cc(-c3ccccc3)n2-c2cccc(C(=O)O)c2)C1] | CDCl3; 8.00 (dt, 1H), 7.94 (br s, 1H), 7.39 (t, 1H), 7.26-7.28 (m, 1H), 7.05-7.18 (m, 5H), 6.27 (s, 1H), 2.50-2.70 (m, 2H), 2.30-2.45 (m, 2H), 1.95-2.05 (m, 1H), 1.55-1.70 (m, 1H), 1.30-1.45 (m, 3H), 0.90 (s, 3H), 0.89 (s, 3H), 0.85 (t, 3H). | pos. mode 388 (M + H). | 3-[5-(1,1-dimethylpropyl)-2-phenyl-4,5,6,7-tetrahydroindol-1-yl] benzoic acid |
| 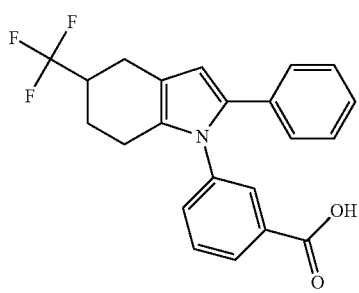 [SMILES: O=C(O)c1cccc(-n2c(-c3ccccc3)cc3c2CCC(C(F)(F)F)C3)c1] | CDCl3; 8.03 (dt, 1H), 7.93 (br s, 1H), 7.43 (t, 1H), 7.26-7.30 (m, 1H), 7.08-7.20 (m, 3H), 7.04-7.06 (m, 2H), 6.28 (s, 1H), 2.91 (dd, 1H), 2.55-2.74 (m, 2H), 2.45-2.55 (m, 2H), 2.15-2.25 (m, 1H), 1.75 (qd, 1H). | pos. mode 386 (M + H). | 3-(2-phenyl-5-trifluoromethyl-4,5,6,7-tetrahydroindol-1-yl) benzoic acid |

TABLE 7-continued

Compounds from Table 6 and Characterization Data

| product structure | 1H NMR, δ | MS | name |
|---|---|---|---|
| | CDCl3; 8.02 (d, 1H), 7.84 (br s, 1H), 7.50 (t, 1H), 7.05-7.20 (m, 6H), 6.28 (s, 1H), 2.76 (dd, 1H), 2.52-2.64 (m, 1H), 2.40-2.50 (m, 1H), 2.17-2.27 (m, 1H), 1.88-1.98 (m, 1H), 1.67 (br s, 1H), 1.32-1.50 (m, 3H), 0.99 (t, 3H). | pos. mode 370 (M + H). | 5-ethyl-2-phenyl-1-[3-(1H-tetrazol-5-yl)-phenyl]-4,5,6,7-tetrahydro-1H-indole |
| | CDCl3; 8.01 (dt, 1H), 7.97 (br s, 1H), 7.40 (t, 1H), 7.28 (br d, 1H), 7.03-7.19 (m, 5H), 6.26 (s, 1H), 3.51 (dd, 1H), 2.54 (br s, 1H), 2.41 (br d, 1H), 2.22 (dd, 1H), 1.93 (br d, 1H), 1.67 (br s, 1H), 1.33-1.49 (m, 3H), 0.99 (t, 3H). | pos. mode 346 (M + H). | 3-(5-ethyl-2-phenyl-4,5,6,7-tetrahydroindol-1-yl) benzoic acid |
| | CDCl3; 8.06 (dt, 1H), 7.90 (br s, 1H), 7.50 (t, 1H), 7.10-7.20 (m, 6H), 6.29 (s, 1H), 2.76 (dd, 1H), 2.60-2.75 (m, 2H), 2.53 (br dd, 2H), 2.21 (br d, 1H), 1.74 (qd, 1H). | pos. mode 410 (M + H). | 2-phenyl-1-[3-(1H-tetrazol-5-yl)-phenyl]-5-trifluoromethyl-4,5,6,7-tetrahydro-1H-indole |
| | CDCl3; 7.26 (t, 1H), 6.95-7.20 (m, 7H), 6.93 (br s, 1H), 6.23 (s, 1H), 2.88 (t, 2H), 2.75 (dd, 1H), 2.48-2.59 (m, 3H), 2.41 (br d, 1H), 2.22 (dd, 1H), 1.91 (br d, 1H), 1.65 (br s, 1H), 1.35-1.50 (m, 3H), 0.98 (t, 3H). | pos. mode 374 (M + H). | 3-[3-(5-ethyl-2-phenyl-4,5,6,7-tetrahydroindol-1-yl)-phenyl] propionic acid |
| | CDCl3; 8.03 (d, 1H), 7.95 (br s, 1H), 7.42 (t, 1H), 7.28 (d, 1H), 7.05-7.20 (m, 5H), 6.28 (s, 1H), 4.19 (q, 2H), 2.94 (dd, 1H), 2.85 (d, 1H), 2.72-2.81 (m, 1H), 2.59 (br s, 1H), 2.48 (br d, 1H), 2.23 (br d, 1H), 1.82-1.90 (m, 1H), 1.30 (t, 3H). | pos. mode 390 (M + H). | 3-(5-ethoxycarbonyl-2-phenyl-4,5,6,7-tetrahydroindol-1-yl) benzoic acid |

TABLE 7-continued

Compounds from Table 6 and Characterization Data

| product structure | 1H NMR, δ | MS | name |
|---|---|---|---|
| | CDCl3; 8.01 (dt, 1H), 7.97 (br s, 1H), 7.41 (t, 1H), 7.25-7.30 (m, 1H), 7.08-7.18 (m, 3H), 7.02-7.06 (m, 2H), 6.23 (s, 1H), 2.87 (dd, 1H), 2.46-2.64 (m, 3H), 1.92-2.02 (m, 1H), 1.78-1.88 (m, 2H), 0.93 (s, 9H), 0.12 (s, 3H), 0.11 (s, 3H). | pos. mode 448 (M + H); neg. mode 446 (M − H). | 3-[5-(tButyldimethylsilyl)-2-phenyl-4,5,6,7-tetrahydroindol-1-yl] benzoic acid |
| | MeOH-d4; 7.95 (t, 1H), 7.67 (t, 1H), 7.58 (t, 1H), 7.51-7.44 (m, 2H), 7.18 (d, 2H), 7.01 (d, 3H), 6.8 (d, 2H), 6.74 (s, 1H), 3.35 (s, 3H), 2.92 (t, 2H), 2.62 (t, 2H). | pos. mode 396 (M + H). | 3-[2-(4-methoxyphenyl)-4,5-dihydrobenzo[e]indol-3-yl] benaoic acid |
| | MeOH-d4; 8.4 (d, 1H), 8.03 (tt, 1H), 7.95 (d, 1H), 7.84 (t, 1H), 7.7-7.58 (m, 4H), 7.49-7.43 (m, 2H), 7.32-7.24 (m, 3H), 6.9 (m, 2H), 3.74 (s, 3H). | pos. mode 394 (M + H). | 3-[2-(4-methoxyphenyl)-benzo[e]indol-3-yl] benzoic acid |
| | CDCl3; 8.35 (d, 1H), 7.96-7.92 (m, 2H), 7.79 (t, 1H), 7.63-7.56 (m, 3H), 7.50-7.35 (m, 4H), 7.27 (s, 1H), 6.59 (dd, 1H), 6.43 (d, 1H), 3.76 (s, 3H), 3.34 (s, 3H). | pos. mode 424 (M + H). neg. mode 422 (M − H). | 3-[2-(2,4-dimethoxyphenyl)-benzo[e]indol-3-yl] benzoic acid |

TABLE 7-continued

Compounds from Table 6 and Characterization Data

| product structure | 1H NMR, δ | MS | name |
|---|---|---|---|
| (structure) | MeOH-d4; 7.96 (dt, 1H), 7.75 (br s, 1H), 7.46 (t, 1H), 7.27-7.33 (m, 1H), 7.09-7.15 (m, 2H), 7.01-7.09 (m, 3H), 6.22 (s, 1H), 2.80-2.90 (m, 1H), 2.70-2.80 (m, 2H), 2.40-2.60 (m, 2H), 2.15-2.25 (m, 1H), 1.80-1.90 (m, 1H). | pos. mode 362 (M + H); neg. mode 360 (M − H). | 3-(5-carboxyl-2-phenyl-4,5,6,7-tetrahydroindol-1-yl) benzoic acid |
| (structure) | DMSO-d6; 7.99 (tt, 1H), 7.70 (t, 1H), 7.61 (t, 1H), 7.54-7.47 (m, 2H), 7.29 (d, 2H), 7.19 (d, 2H), 7.11-7.05 (m, 3H), 6.92 (s, 1H), 2.94 (t, 2H), 2.64 (t, 2H). | pos. mode 400 (M + H). | 3-[2-(4-chlorophenyl)-4,5-dihydrobenzo[e]indol-3-yl] benzoic acid |
| (structure) | DMSO-d6; 7.71-7.48 (m, 5H), 7.22-7.18 (m, 5H), 7.07-6.95 (m, 3H), 2.94 (t, 2H), 2.64 (t, 2H). | pos. mode 400 (M + H). | 3-[2-(3-chlorophenyl)-4,5-dihydrobenzo[e]indol-3-yl] benzoic acid |
| (structure) | DMSO-d6; 6.9-7.4 (m, 9H), 6.3 (s, 1H), 4.4 (t, 1H), 2.9 (t, 2H), 2.6 (t, 2H), 3.3 (t, 2H), 1.8-0.4 (m, 10H). | pos. mode 400 (M + H); neg. mode. 398 (M − 1). | 3-cyclohexyl-3-(2-phenyl-4,5-dihydrobenzo[e]indol-3-yl) propionic acid |
| (structure) | DMSO-d6; 7.4-8.2 (m, 11H), 7.0 (s, 1H), 4.6 (s, 1H), 3.3 (t, 2H), 2.1-0.3 (m, 10H). | pos. mode 398 (M + H), neg. mode. 396 (M − 1). | 3-cyclohexyl-3-(2-phenylbenzo[e]indol-3-yl) propionic acid |

TABLE 7-continued

Compounds from Table 6 and Characterization Data

| product structure | 1H NMR, δ | MS | name |
|---|---|---|---|
| | CDCl3: 7.3 (m, 1H); 7.0-7.2 (m, 7H); 6.9 (br. s, 1H); 6.2 (s, 1H); 2.9 (t, 2H); 2.6 (m, 2H); 2.5 (m, 2H); 2.4 (m, 1H); 2.1 (m, 1H); 1.9 (m, 2H); 1.4 (m, 1H); 1.0 (d, 3H). | pos. mode 360 (M + H). | 3-[3-(4-methyl-2-phenyl-4,5,6,7-tetrahydroindol-1-yl) phenyl] propionic acid |
| | CDCl3; 8.03 (d, 1H), 7.93 (br s, 1H), 7.42 (t, 1H), 7.29 (d, 1H), 7.00-7.17 (m, 5H), 6.27 (s, 1H), 2.61 (br s, 2H), 2.21 (br s, 2H), 1.56 (t, 2H), 1.00 (s, 6H). | pos. mode 346 (M + H); neg. mode 344 (M − H). | 3-(6,6-dimethyl-2-phenyl-4,5,6,7-tetrahydroindol-1-yl) benzoic acid |
| Chiral | CDCl3; 7.27 (t, 1H), 7.10-7.16 (m, 3H), 7.02-7.10 (m, 4H), 6.92 (br s, 1H), 6.25 (s, 1H), 2.88 (t, 2H), 2.60-2.70 (m, 2H), 2.53 (t, 2H), 2.43 (dd, 1H), 2.05-2.20 (m, 1H), 1.80-1.90 (m, 2H), 1.35-1.50 (m, 1H), 1.04 (d, 3H). | pos. mode 360 (M + H); neg. mode 358 (M − H). | 3-[3-((R)-6-methyl-2-phenyl-4,5,6,7-tetrahydroindol-1-yl) phenyl] propionic acid |
| Chiral | CDCl3; 8.03 (d, 1H), 7.96 (br s, 1H), 7.42 (t, 1H), 7.29 (br d, 1H), 7.00-7.20 (m, 5H), 6.27 (s, 1H), 2.60-2.70 (m, 2H), 2.42 (dd, 1H), 2.14 (t, 1H), 1.88 (br d, 2H), 1.40-1.50 (m, 1H), 1.05 (d, 3H). | pos. mode 332 (M + H); neg. mode 330 (M − H). | 3-((R)-6-methyl-2-phenyl-4,5,6,7-tetrahydroindol-1-yl) benzoic acid |
| | CDCl3; 7.28 (t, 1H), 7.10-7.16 (m, 3H), 6.99-7.09 (m, 4H), 6.90 (t, 1H), 6.25 (s, 1H), 2.88 (t, 2H), 2.60 (t, 2H), 2.52 (t, 2H), 2.22 (s, 2H), 1.55 (t, 2H), 0.99 (s, 6H). | pos. mode 374 (M + H); neg. mode 372 (M − H). | 3-[3-(6,6-dimethyl-2-phenyl-4,5,6,7-tetrahydroindol-1-yl) phenyl] propionic acid |

TABLE 7-continued

Compounds from Table 6 and Characterization Data

| product structure | 1H NMR, δ | MS | name |
|---|---|---|---|
| | DMSO-d6; 7.2-8.2 (m, 17H), 6.6 (s, 1H). | pos. mode 390 (M + H), neg. mode. 388 (M − 1). | 3-[3-(2-phenylbenzo[e]indol-3-yl)-phenyl] acrylic acid |
| | CDCl3: 8.0 (d, 1H); 7.9 (br. s, 1H); 7.4 (t, 2H); 7.0-7.2 (m, 6H); 6.2 (s, 1H); 2.7 (m, 1H); 2.5 (m, 1H); 2.4 (m, 1H); 2.2 (m, 1H); 1.8 (m, 2H); 1.4 (m, 1H); 1.0 (d, 3H). | pos. mode 356 (M + H); neg. mode 354 (M − H). | 5-methyl-2-phenyl-1-[3-(1H-tetrazol-5-yl) phenyl]-4,5,6,7-tetrahydro-1H-indole |
| | CDCl3: 7.7 (dm, 1H); 7.5 (br. s, 1H); 7.4 (t, 1H); 7.2 (m, 1H); 7.0-7.1 (m, 5H); 6.2 (s, 1H); 5.9 (br. s, 1H); 3.0 (d, 3H); 2.7 (dd, 1H); 2.5 (m, 1H); 2.4 (m, 1H); 2.2 (m, 1H); 1.9 (m, 2H); 1.4 (m, 1H); 1.1 (d, 3H). | pos. mode 345 (M + H). | N-methyl-3-(5-methyl-2-phenyl-4,5,6,7-tetrahydroindol-1-yl) benzamide |
| | CDCl3; 8.07 (d, 1H), 7.82 (br s, 1H), 7.50 (t, 1H), 7.05-7.18 (m, 6H), 6.25 (s, 1H), 4.20 (q, 2H), 2.75-2.95 (m, 3H), 2.45-2.65 (m, 2H), 2.15-2.25 (m, 1H), 1.85-1.95 (m, 1H), 1.30 (t, 3H). | neg. mode 412 (M − H). | 3-[3-(5-ethoxycarbonyl-2-phenyl-4,5,6,7-tetrahydroindol-1-yl)-phenyl] propionic acid |

TABLE 7-continued

Compounds from Table 6 and Characterization Data

| product structure | 1H NMR, δ | MS | name |
|---|---|---|---|
| | CDCl3; 7.24-7.30 (m, 1H), 7.00-7.20 (m, 7H), 6.93 (br s, 1H), 6.26 (s, 1H), 4.19 (q, 2H), 2.79-3.00 (m, 4H), 2.68-2.78 (m, 1H), 2.20-2.45 (m, 5H), 2.15-2.25 (m, 1H), 1.29 (t, 3H). | pos. mode 418 (M + H); neg. mode 416 (M − H). | 1-[3-(2-carboxy-ethyl)-phenyl]-2-phenyl-4,5,6,7-tetrahydro-1H-indole-5-carboxylic acid ethyl ester |
| | DMSO-d6; 7.2-8.2 (m, 11H), 6.6 (s, 1H), 4.6 (s, 2H), 2.2 (s, 2H), 1.2-1.1 (m, 10H). | EM 397. | [1-(2-phenylbenzo[e]indol-3-ylmethyl)-cyclohexyl] acetic acid |
| | DMSO-d6; 7.2-8.3 (m, 10H), 5.5 (s, 1H), 2.9 (t, 2H), 2.6 (t, 2H), 2.5 (br. s, 2H). | pos. mode 361 (M + 1), neg. mode 359 (M − 1). | 2-(2-phenyl-4,5-dihydrobenzo[e]indol-3-yl) succinamic acid |
| | CDCl3; 8.01 (dt, 1H), 7.96 (br s, 1H), 7.40 (t, 1H), 7.28 (br d, 1H), 7.05-7.20 (m, 5H), 6.25 (s, 1H), 2.74 (dd, 1H), 2.50-2.60 (m, 1H), 2.41 (br d, 1H), 2.22 (dd, 1H), 1.92 (br d, 1H), 1.77 (br s, 1H), 1.30-1.50 (m, 5H), 0.94 (t, 3H). | neg. mode 358 (M − H). | 3-(2-phenyl-5-propyl-4,5,6,7-tetrahydroindol-1-yl) benzoic acid |

TABLE 7-continued

Compounds from Table 6 and Characterization Data

| product structure | 1H NMR, δ | MS | name |
|---|---|---|---|
| | CDCl3; 7.26 (t, 1H), 6.98-7.18 (m, 7H), 6.93 (br s, 1H), 6.23 (s, 1H), 2.88 (t, 2H), 2.74 (dd, 1H), 2.45-2.60 (m, 3H), 2.41 (br d, 1H), 2.21 (dd, 1H), 1.91 (br d, 1H), 1.72 (br s, 1H), 1.30-1.50 (m, 5H), 0.93 (t, 3H). | pos. mode 388 (M + H); neg. mode 386 (M − H). | 3-[3-(2-phenyl-5-propyl-4,5,6,7-tetrahydroindol-1-yl) phenyl] propionic acid |
| | acetone-d6: 8.41 (m, 1H), 7.94 (m, 1H), 7.62-7.37 (m, 10H), 7.31-7.22 (m, 3H), 7.11 (m, 1H), 3.33 (s, 2H). | pos. mode 378 (M + H) | [2-(2-phenyl-benzo[e]indol-3-yl)-phenyl] acetic acid |
| | CDCl3; 8.14 (dt, 1H), 8.09 (t, 1H), 8.00 (t, 1H), 7.54 (t, 1H), 7.37-7.46 (m, 2H), 7.33 (d, 1H), 7.20-7.32 (m, 5H), 6.89 (d, 1H). | neg. mode 380 (M − H). | 3-(2-phenyl-5-trifluoromethyl-indol-1-yl) benzoic acid |
| | CDCl3; 8.10 (s, 1H), 8.08 (t, 1H), 7.51 (s, 1H), 7.48 (t, 1H), 7.37 (d, 1H), 7.18-7.28 (m, 6H), 7.07 (dd, 1H), 6.77 (s, 1H), 2.77 (t, 2H), 1.31 (t, 3H). | pos. mode 342 (M + H); neg. mode 340 (M − H). | 3-(5-ethyl-2-phenyl-indol-1-yl) benzoic acid |
| | MeOH-d4; 8.02 (dt, 1H), 7.86-7.92 (m, 1H), 7.48-7.57 (m, 2H), 7.36-7.45 (m, 1H), 7.20-7.30 (m, 5H), 6.98-7.05 (m, 2H), 6.75 (d, 1H), 2.39 (s, 3H). | pos. mode 328 (M + H); neg. mode 326 (M − H). | 3-(6-methyl-2-phenyl-indol-1-yl) benzoic acid |

TABLE 7-continued

Compounds from Table 6 and Characterization Data

| product structure | 1H NMR, δ | MS | name |
|---|---|---|---|
| | MeOH-d4; 7.48 (d, 1H), 7.36 (t, 1H), 7.18-7.29 (m, 6H), 7.11 (t, 1H), 7.00-7.08 (m, 2H), 6.95 (ddd, 1H), 6.71 (d, 1H), 2.90 (t, 2H), 2.51 (t, 2H), 2.39 (s, 3H). | pos. mode 356 (M + H); neg. mode 354 (M − H). | 3-[3-(6-methyl-2-phenyl-indol-1-yl)-phenyl] propionic acid |
| | CDCl3; 8.03 (dt, 1H), 7.97 (t, 1H), 7.42 (t, 1H), 7.28 (ddd, 1H), 7.07-7.18 (m, 3H), 7.01-7.06 (m, 2H), 6.26 (s, 1H), 4.30-4.40 (m 1H), 3.00 (dd, 1H), 2.50-2.70 (m, 3H), 1.85-2.05 (m, 2H). | pos. mode 334 (M + H); neg. mode 332 (M − H). | 3-(5-hydroxy-2-phenyl-4,5,6,7-tetrahydroindol-1-yl) benzoic acid |
| | CDCl3: 7.5 (m, 1H); 7.4 (m, 2H); 7.0-7.2 (m, 5H); 6.8 (br. s, 1H); 6.2 (s, 1H); 3.6 (br. s, 4H); 3.2 (br. s, 2H); 2.8 (br. s, 2H); 2.7 (m, 1H); 2.5 (m, 2H); 2.2 (m, 1H); 1.9 (m, 2H); 1.4 (m, 1H); 1.1 (d, 3H). | pos. mode 401 (M + H). | [3-(5-methyl-2-phenyl-4,5,6,7-tetrahydroindol-1-yl) phenyl] morpholin-4-yl-methanone |
| | DMSO-d6; 7.2-8.3 (m, 15H), 5.6 (s, 1H), 3.8 (dd, 2H), 2.9 (t, 2H), 2.6 (t, 2H). | neg. mode 392 (M − 1). | 3-phenyl-3-(2-phenyl-4,5-dihydrobenzo[e]indol-3-yl) propionic acid |
| | DMSO-d6; 7.1-8.3 (m, 17H), 6.1 (s, 1H), 3.8-3.4 (dd, 2H). | neg. mode 390 (M − 1). | 3-phenyl-3-(2-phenylbenzo[e]indol-3-yl) propionic acid |

TABLE 7-continued

Compounds from Table 6 and Characterization Data

| product structure | 1H NMR, δ | MS | name |
|---|---|---|---|
| | MeOH-d4; 8.3 (d, 1H), 8.08-8.06 (tt, 1H), 7.96 (d, 1H), 7.87 (m, 1H), 7.6-7.2 (m, 9H), 6.82 (m, 2H), 3.75 (s, 3H). | pos. mode 394 (M + H); neg. mode 392 (M − H). | 3-[2-(3-methoxyphenyl)-benzo[e]indol-3-yl] benzoic acid |
| | MeOH-d4; 8.3 (d, 1H), 8.01-7.97 (m, 2H), 7.88 (d, 1H), 7.58-7.37 (m, 6H), 7.26-7.24 (m, 2H), 7.15-7.11 (t, 1H), 6.81 (t, 1H), 6.71 (d, 1H). | pos. mode 380 (M + H); neg. mode 378 (M − H). | 3-[2-(3-hydroxyphenyl)-benzo[e]indol-3-yl] benzoic acid |
| | DMSO-d6; 7.56 (d, 1H), 7.32 (d, 1H), 7.2 (s, 1H), 7.13 (d, 1H), 6.8-6.5 (m, 10H), 6.28-6.23 (m, 1H). | pos. mode 382 (M + H); neg. mode 380 (M − H). | 3-[2-(4-fluorophenyl)-benzo[e]indol-3-yl] benzoic acid |
| | DMSO-d6; 8.48 (d, 1H), 8.1 (tt, 1H), 8.08 (s, 1H), 8.04-8.02 (m, 2H), 7.97-7.93 (m, 3H), 7.77-7.67 (m, 4H), 7.55-7.51 (m, 1H), 7.40 (d, 1H). | pos. mode 500 (M + H); neg. mode 498 (M − H). | 3-[2-(3,5-bistrifluoromethylphenyl)-benzo[e]indol-3-yl] benzoic acid |
| | DMSO-d6; 8.4 (d, 1H), 8.07 (d, 1H), 8.0 (d, 1H), 7.87 (s, 1H), 7.72-7.60 (m, 5H), 7.5-7.44 (m, 2H), 7.4-7.33 (d, 3H), 7.2 (s, 1H). | pos. mode 398 (M + H); neg. mode 396 (M − H). | 3-[2-(3-chlorophenyl)-benzo[e]indol-3-yl] benzoic acid |

TABLE 7-continued

Compounds from Table 6 and Characterization Data

| product structure | 1H NMR, δ | MS | name |
| --- | --- | --- | --- |
| | DMSO-d6; 8.45 (d, 1H), 8.07 (tt, 1H), 8.0 (d, 1H), 7.9 (t, 1H), 7.8 (s, 1H), 7.7-7.6 (m, 6H), 7.54-7.47 (m, 3H), 7.35 (d, 1H). | pos. mode 432 (M + H); neg. mode 430 (M − H). | 3-[2-(4-trifluoromethylphenyl)-benzo[e]indol-3-yl] benzoic acid |
| | CDCl3; 8.05 (dt, 1H), 7.98 (br s, 1H), 7.44 (t, 1H), 7.37 (br d, 1H), 7.10-7.20 (m, 3H), 7.05-7.10 (m, 2H), 6.45 (s, 1H), 3.50 (sext, 1H), 2.45-2.60 (m, 1H), 2.35-2.45 (m, 1H), 1.95-2.15 (m, 2H), 1.85-1.95 (m, 1H), 1.68-1.80 (m, 1H). | pos. mode 386 (M + H); neg. mode 384 (M − H). | 3-(2-phenyl-4-trifluoromethyl-4,5,6,7-tetrahydroindol-1-yl) benzoic acid |
| | CDCl3; 8.06 (d, 1H), 7.92 (br s, 1H), 7.46 (t, 1H), 7.33 (br s, 1H), 7.08-7.20 (m, 3H), 7.02-7.08 (m, 2H), 6.27 (s, 1H), 2.80 (dd, 1H), 2.40-2.74 (m, 4H), 2.21 (br d, 1H), 1.75 (qd, 1H). | pos. mode 386 (M + H); neg. mode 384 (M − H). | 3-(2-phenyl-6-trifluoromethyl-4,5,6,7-tetrahydroindol-1-yl) benzoic acid |
| | CDCl3; 7.95-8.10 (m, 4H), 7.45 (t, 1H), 7.27-7.42 (m, 3H), 7.05-7.18 (m, 3H), 6.95-7.05 (m, 2H), 6.01 (s, 1H), 4.38 (q, 2H), 4.07-4.14 (m, 1H), 2.64 (br s, 1H), 2.45 (br d, 1H), 2.10-2.23 (m, 1H), 1.90-2.00 (m, 1H), 1.70-1.85 (m, 2H), 1.39 (t, 3H). | pos. mode 466 (M + H); neg. mode 464 (M − H). | 3-{4-[4-(ethoxycarbonyl)phenyl]-2-phenyl-4,5,6,7-tetrahydroindol-1-yl} benzoic acid |

TABLE 7-continued

Compounds from Table 6 and Characterization Data

| product structure | 1H NMR, δ | MS | name |
|---|---|---|---|
| | CDCl3; 7.95-8.05 (m, 3H), 7.92 (s, 1H), 7.40 (t, 1H), 7.25-7.35 (m, 3H), 7.05-7.20 (m, 5H), 6.32 (s, 1H), 4.35 (q, 2H), 3.00-3.13 (m, 1H), 2.79 (br s, 2H), 2.62 (br s, 2H), 1.95-2.20 (m, 2H), 1.37 (t, 3H). | pos. mode 466 (M + H); neg. mode 464 (M − H). | 3-{6-[4-(ethoxycarbonyl)phenyl]-2-phenyl-4,5,6,7-tetrahydroindol-1-yl} benzoic acid |
| | MeOH-d4; 8.3 (d, 1H), 7.9 (d, 1H), 7.75 (d, 1H), 7.56-7.26 (d, 12H), 7.18 (s, 1H). | neg. mode 362 (M − H). | 2-(3-phenyl-3H-benzo[e]indol-2-yl) benzoic acid |
| | DMSO-d6; 7.1-8.3 (m, 16H), 6.1 (s, 1H). | pos. mode 431 (M + 1), neg. mode 429 (M − 1). | 3-[2-(3-phenylisoxazol-5-yl)-benzo[e]indol-3-yl] benzoic acid |
| | DMSO-d6; 7.1-8.4 (m, 15H), 6.1 (s, 1H), 3.1 (t, 2H), 2.7 (t, 2H). | pos. mode 432 (M + 1), neg. mode 430 (M − 1). | 3-[3-(2-benzofuran-2-yl-benzo[e]indol-3-yl)-phenyl] propionic acid |
| | CDCl3; 8.22 (dt, 1H), 8.07 (t, 1H), 7.61 (t, 1H), 7.55 (ddd, 1H), 7.33-7.37 (m, 1H), 7.28-7.31 (m, 1H), 7.07-7.19 (m, 2H), 6.68 (s, 1H), 5.60 (s, 1H), 2.93 (dd, 1H), 2.65-2.75 (m, 1H), 2.40-2.58 (m, 3H), 2.19 (br d, 1H), 1.76 (qd, 1H). | neg. mode 424 (M − H). | 3-(2-benzofuran-2-yl-5-trifluoromethyl-4,5,6,7-tetrahydroindol-1-yl) benzoic acid |

TABLE 7-continued

Compounds from Table 6 and Characterization Data

| product structure | 1H NMR, δ | MS | name |
|---|---|---|---|
| | DSMO-d6; 12.9 (br s, 1H), 7.97 (dt, 1H), 7.67 (br s, 1H), 7.59 (t, 1H), 7.42 (d, 1H), 7.40-7.50 (m, 1H), 7.25 (d, 1H), 6.89 (dd, 1H), 6.48 (s, 1H), 2.81 (dd, 1H), 2.65-2.78 (m, 1H), 2.50-2.65 (m, 2H), 2.38 (dd, 1H), 2.10 (br d, 1H), 1.63 (qd, 1H). | pos. mode 454 (M + H); neg. mode 452 (M − H). | 3-[2-(3,4-dichlorophenyl)-5-trifluoromethyl-4,5,6,7-tetrahydroindol-1-yl] benzoic acid |
| | DMSO-d6; 7.1-8.3 (m, 13H), 6.2 (s, 1H), 2.9 (t, 2H), 2.6 (t, 2H). | pos. mode 433 (M + 1), neg. mode 431 (M − 1). | 3-[2-(3-phenylisoxazol-5-yl)-4,5-dihydrobenzo[e]indol-3-yl] benzoic acid |
| | CDCl3: 7.7 (m, 1H); 7.1-7.3 (m, 11H); 6.8 (s, 1H); 2.7 (t, 2H); 2.4 (t, 2H); 2.0 (m, 2H); 1.4 (m, 9H). | pos. mode 412 (M + H); neg. mode 410 (M − H). | 4-[4-(5-tButyl-2-phenyl-indol-1-yl) phenyl] butyric acid |
| | DMSO-d6; 8.4 (d, 1H), 8.1 (tt, 1H), 8.0 (d, 1H), 7.9 (t, 1H), 7.8 (s, 1H), 7.7-7.57 (m, 6H), 7.50-7.46 (t, 1H), 7.3 (d, 1H), 7.2 (dd, 1H). | pos. mode 433 (M + H); neg. mode 431 (M − H). | 3-[2-(3,4-dichlorophenyl)-benzo[e]indol-3-yl] benzoic acid |

TABLE 7-continued

Compounds from Table 6 and Characterization Data

| product structure | 1H NMR, δ | MS | name |
|---|---|---|---|
| | DMSO-d6; 6.6-8.2 (m, 16H), 4.6 (dd, 2H), 3.3 (dd, 2H), 2.07 (s, 1H). | pos. mode 430 (M + 1). | 3-(4-chlorophenyl)-4-(2-phenylbenzo[e]indol-3-yl) butyric acid |
| | CDCl3; 8.05 (d, 1H), 7.94 (s, 1H), 7.45 (t, 1H), 7.31 (d, 1H), 7.12-7.20 (m, 3H), 7.04-7.10 (m, 2H), 6.27 (s, 1H), 3.53 (s, 2H), 2.88 (t, 2H), 2.70 (t, 2H). | 331.8 (M dot) | 3-(5-oxo-2-phenyl-4,5,6,7-tetrahydroindol-1-yl) benzoic acid |
| | CDCl3; 8.02 (d, 1H), 7.99 (s, 1H), 7.40 (t, 1H), 7.29 (t, 1H), 7.08-7.25 (m, 3H), 7.00-7.06 (m, 2H), 6.24 (s, 1H), 4.03-4.10 (m, 4H), 2.89 (s, 2H), 2.70-2.60 (m, 2H), 2.02-1.95 (m, 2H). | pos. mode 376 (M + H). | 3-[2'-phenyl-4',5',6',7'-tetrahydrospiro(1,3-dioxolane-2,5'-indol)-1'-yl] benzoic acid |
| | MeOH-d4; 8.3 (d, 1H), 8.04 (t, 1H), 7.88 (m, 2H), 7.6-7.3 (m, 12H). | 363 (M dot). | 3-(3-phenyl-3H-benzo[e]indol-2-yl) benzoic acid |
| | DMSO-d6; 8.41 (d, 1H), 8.06 (tt, 1H), 7.97 (d, 1H), 7.86 (t, 1H), 7.71-7.6 (m, 5H), 7.5-7.46 (m, 1H), 7.43-7.40 (m, 2H), 7.32-7.35 (m, 3H). | 397 (M dot). | 3-[2-(4-chlorophenyl)-benzo[e]indol-3-yl] benzoic acid |

TABLE 7-continued

Compounds from Table 6 and Characterization Data

| product structure | 1H NMR, δ | MS | name |
|---|---|---|---|
| | CDCl3: 8.1 (m, 2H); 7.7 (s, 1H); 7.5 (t, 1H); 7.2-7.3 (m, 9H); 6.8 (s, 1H); 0.9 (m, 9H). | pos. mode 394 (M + H). | 5-tButyl-2-phenyl-1-[3-(1H-tetrazol-5-yl) phenyl]-1H-indole |
| | DMSO-d6; 8.4 (d, 1H), 8.0-7.91 (m, 2H), 7.78 (s, 1H), 7.68-7.38 (m, 11H), 3.37 (s, 3H). | pos. mode 422 (M + H). | 3-[2-(2-carbomethoxyphenyl)-benzo[e]indol-3-yl] benzoic acid |
| | DMSO-d6; 8.3 (d, 1H), 8.1 (m, 1H), 8.04 (m, 1H), 7.92 (m, 1H), 7.6 (m, 2H), 7.46 (m, 5H), 7.3 (m, 3H), 6.8 (s, 1H). | neg. mode 396 (M − H). | 3-[2-(2-chlorophenyl)-benzo[e]indol-3-yl] benzoic acid |
| | CDCl3; 8.01 (dt, 1H), 7.96 (br s, 1H), 7.40 (t, 1H), 7.27 (d, 1H), 7.12-7.18 (m, 2H), 7.03-7.12 (m, 3H), 6.26 (s, 1H), 2.67 (dd, 1H), 2.50-2.62 (m, 1H), 2.32-2.46 (m, 2H), 1.96 (br d, 1H), 1.72-1.84 (m, 4H), 1.68 (br d, 1H), 1.55-1.63 (m, 1H), 1.45 (quint., d, 1H), 1.00-1.36 (m, 6H). | 399 (M Dot) | 3-(5-cyclohexyl-2-phenyl-4,5,6,7-tetrahydroindol-1-yl) benzoic acid |

TABLE 7-continued

Compounds from Table 6 and Characterization Data

| product structure | 1H NMR, δ | MS | name |
|---|---|---|---|
| | CDCl3; 8.05 (dt, 1H), 8.00 (br s, 1H), 7.44 (t, 1H), 7.32 (br d, 1H), 7.00-7.17 (m, 6H), 6.31 (s, 1H), 6.21 (dd, 1H), 4.37 (qd, 2H), 4.22 (br t, 1H), 2.50-2.60 (m, 1H), 2.37-2.48 (m, 1H), 2.15-2.27 (m, 1H), 1.96-2.07 (m, 1H), 1.85-1.95 (m, 1H), 1.72-1.85 (m, 1H), 1.38 (t, 3H) | pos. mode 456 (M + H). | 5-[1-(3-carboxyphenyl)-2-phenyl-4,5,6,7-tetrahydro-1H-indol-4-yl]-furan-2-carboxylic acid ethyl ester |
| | CDCl3; 8.03 (dt, 1H), 7.93 (br s, 1H), 7.43 (t, 1H), 7.32 (br d, 1H), 7.03-7.20 (m, 6H), 6.28 (s, 1H), 6.14 (dd, 1H), 4.33 (q, 2H), 3.15-3.27 (m, 1H), 2.63-2.85 (m, 4H), 2.28-2.35 (m, 1H), 1.88-2.03 (m, 1H), 1.35 (t, 3H). | pos. mode 456 (M + H). | 5-[1-(3-carboxyphenyl)-2-phenyl-4,5,6,7-tetrahydro-1H-indol-6-yl]-furan-2-carboxylic acid ethyl ester |
| | CDCl3; 8.10 (dt, 1H), 7.94 (br s, 1H), 7.50 (t, 1H), 7.27-7.37 (m, 1H), 7.22 (d, 1H), 7.18 (d, 1H), 6.76 (dd, 1H), 6.47 (s, 1H), 3.40-3.60 (m, 1H), 2.43-2.60 (m, 1H), 2.30-2.43 (m, 1H), 1.95-2.15 (m, 2H), 1.82-1.95 (m, 1H), 1.65-1.80 (m, 1H). | pos. mode 454 (M + H). | 3-[2-(3,4-dichlorophenyl)-4-trifluoromethyl-4,5,6,7-tetrahydroindol-1-yl] benzoic acid |
| | CDCl3; 8.11 (dt, 1H), 7.88 (br s, 1H), 7.52 (t, 1H), 7.33 (br s, 1H), 7.15 (d, 1H), 7.17 (d, 1H), 6.59 (dd, 1H), 6.29 (s, 1H), 2.78 (dd, 1H), 2.40-2.70 (m, 4H), 2.15-2.25 (m, 1H), 1.73 (qd, 1H). | pos. mode 454 (M + H). | 3-[2-(3,4-dichlorophenyl)-6-trifluoromethyl-4,5,6,7-tetrahydroindol-1-yl] benzoic acid |

TABLE 7-continued

Compounds from Table 6 and Characterization Data

| product structure | 1H NMR, δ | MS | name |
| --- | --- | --- | --- |
| | DMSO-d6; 8.45 (d, 1H), 8.1-7.9 (m, 8H), 7.74-7.63 (m, 4H), 7.5 (t, 1H), 7.37 (d, 1H). | pos. mode 432 (M + H). | 3-[2-(3-trifluoromethylphenyl)-benzo[e]indol-3-yl] benzoic acid |
| | DMSO-d6; 8.5 (d, 1H), 8.1 (tt, 1H), 8.0 (d, 1H), 7.9 (t, 1H), 7.74-7.64 (m, 5H), 7.53-7.46 (m, 3H), 7.3 (m, 3H). | pos. mode 448 (M + H). | 3-[2-(4-trifluoromethoxyphenyl)-benzo[e]indol-3-yl] benzoic acid |
| | DMSO-d6; 8.45 (d, 1H), 8.10 (tt, 1H), 8.01 (d, 1H), 7.92 (t, 1H), 7.86-7.83 (m, 3H), 7.76-7.72 (m, 2H), 7.70-7.65 (m, 2H), 7.54-7.5 (m, 3H), 7.38 (d, 1H). | pos. mode 389 (M + H). | 3-[2-(4-cyanophenyl)-benzo[e]indol-3-yl] benzoic acid |
| | DMSO-d6; 7.1-8.4 (m, 15H), 5.8 (s, 1H), 2.7 (t, 2H), 2.06 (t, 2H), 1.8 (t, 2H). | pos. mode 446 (M + 1), neg. mode 444 (M − 1). | 4-[4-(2-benzofuran-2-ylbenzo[e]indol-3-yl)-phenyl] butyric acid |

TABLE 7-continued

Compounds from Table 6 and Characterization Data

| product structure | 1H NMR, δ | MS | name |
| --- | --- | --- | --- |
| | CDCl3; 7.10-7.17 (m, 4H), 7.01-7.09 (m, 5H), 6.24 (s, 1H), 2.58-2.72 (m, 3H), 2.47-2.58 (m, 1H), 2.30-2.46 (m, 4H), 1.90-2.05 (m, 3H), 1.62 (td, 1H), 1.23-1.45 (m, 3H), 0.89 (s, 3H), 0.88 (s, 3H), 0.84 (t, 3H). | neg. mode 428 (M − H). | 4-{4-[5-(1,1-dimethylpropyl)-2-phenyl-4,5,6,7-tetrahydroindol-1-yl]-phenyl} butyric acid |
| | CDCl3: 7.0-7.2 (m, 9H); 6.2 (s, 1H); 2.7 (m, 3H); 2.4 (m, 3H); 2.1 (m, 1H); 2.0 (m, 2H); 1.9 (m, 2H); 1.4 (m, 2H); 1.0 (d, 3H). | pos. mode 374 (M + H); neg. mode 372 (M − H). | 4-[4-(6-methyl-2-phenyl-4,5,6,7-tetrahydroindol-1-yl) phenyl] butyric acid |
| | CDCl3; 8.02 (dt, 1H), 7.97 (t, 1H), 7.40 (t, 1H), 7.28 (ddd, 1H), 7.07-7.18 (m, 3H), 7.01-7.06 (m, 2H), 6.26 (s, 1H), 3.45-3.80 (m, 1H), 3.46 (s, 3H), 2.99 (dd, 1H), 2.65 (dd, 1H), 2.40-2.65 (m, 2H), 2.00-2.15 (m, 1H), 1.80-2.00 (m, 1H). | pos. mode 348 (M + H); neg. mode 346 (M − H). | 3-(5-methoxy-2-phenyl-4,5,6,7-tetrahydroindol-1-yl) benzoic acid |
| | 2 rotamers, 1:1, MeOH-d4; 7.87 (dd, 0.5H), 7.85 (dd, 0.5H), 7.55 (d, 0.5H), 7.44 (d, 0.5H), 7.10 (s, 2H), 7.09 (s, 2H), 7.00-7.03 (m, 1H), 6.98 (d, 0.5H), 6.95 (d, 0.5H), 6.18 (s, 0.5H), 6.17 (s, 0.5H), 2.59 (dt, 1H), 2.20-2.50 (m, 3H), 1.85-2.00 (m, 1H), 1.45-1.62 (m, 1H), 1.25-1.45 (m, 3H), 0.92 (s, 3H), 0.91 (s, 3H), 0.87 (t, 3H). | pos. mode 404 (M + H); neg. mode 402 (M − H). | 3-[5-(1,1-dimethylpropyl)-2-phenyl-4,5,6,7-tetrahydroindol-1-yl] 4-hydroxybenzoic acid |

TABLE 7-continued

Compounds from Table 6 and Characterization Data

| product structure | 1H NMR, δ | MS | name |
| --- | --- | --- | --- |
| | CDCl3; 7.87 (d, 1H), 7.39 (d, 1H), 7.16-7.23 (m, 2H), 7.09-7.16 (m, 2H), 7.04-7.09 (m, 2H), 6.26 (s, 1H), 2.63 (dd, 1H), 2.55 (br d, 1H), 2.32-2.48 (m, 2H), 1.99 (br d, 1H), 1.63 (td, 1H), 1.26-1.46 (m, 3H), 0.90 (s, 3H), 0.89 (s, 3H), 0.86 (t, 3H) | pos. mode 422 (M + H); neg. mode 420 (M − H). | 2-chloro-5-[5-(1,1-dimethylpropyl)-2-phenyl-4,5,6,7-tetrahydroindol-1-yl] benzoic acid |
| | DMSO-d6; 7.0-8.3 (m, 14H), 6.4 (s, 1H), 3.1 (q, 4H), 2.6 (t, 2H), 2.04 (t, 2H), 1.9 (q, 4H), 1.8 (t, 2H). | pos. mode 475 (M + 1), neg. mode 473 (M − 1). | 4-{4-[2-(4-pyrrolidin-1-ylphenyl)-benzo[e]indol-3-yl]-phenyl} butyric acid |
| | CDCl3; 8.02 (dt, 1H), 7.94 (br s, 1H), 7.42 (t, 1H), 7.30 (br d, 1H), 7.11-7.18 (m, 2H), 7.02-7.11 (m, 3H), 6.26 (s, 1H), 2.54-2.74 (m, 2H), 2.44 (dd, 1H), 2.10-2.20 (m, 1H), 1.94 (br d, 1H), 1.65 (br s, 1H), 1.30-1.50 (m, 3H), 0.91 (t, 3H). | pos. mode 346 (M + H); neg. mode 344 (M − H). | 3-(6-ethyl-2-phenyl-4,5,6,7-tetrahydroindol-1-yl) benzoic acid |
| | DMSO-d6; 7.1-8.4 (m, 13H), 7.05 (s, 1H), 1.5 (dd, 4H), 1.21 (s, 6H), 0.93 (s, 6H). | pos. mode 474 (M + 1). | 3-[2-(5,5,8,8-tetramethyl-5,6,7,8-tetrahydronaphthalen-2-yl)-benzo[e]indol-3-yl] benzoic acid |

TABLE 7-continued

Compounds from Table 6 and Characterization Data

| product structure | 1H NMR, δ | MS | name |
|---|---|---|---|
| 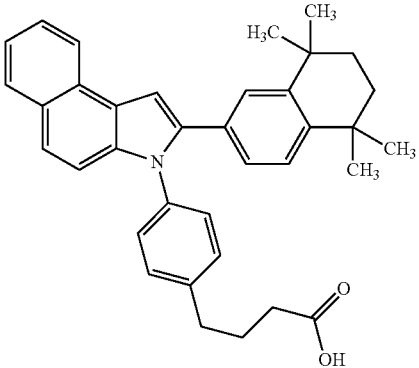 [SMILES: CC1(C)CCC(C)(C)c2cc(-c3cc4c5ccccc5ccc4n3-c3ccc(CCCC(=O)O)cc3)ccc21] | DMSO-d6; 7.2-8.3 (m, 13H), 6.9 (s, 1H), 2.6 (t, 2H), 1.9 (t, 2H), 1.7 (t, 2H), 1.5 (q, 4H), 1.21 (s, 6H), 0.9 (s, 6H). | pos. mode 516 (M + 1). | 4-{-[2-(5,5,8,8-tetramethyl-5,6,7,8-tetrahydronaphthalen-2-yl)-benzo[e]indol-3-yl]-phenyl} butyric acid |
| 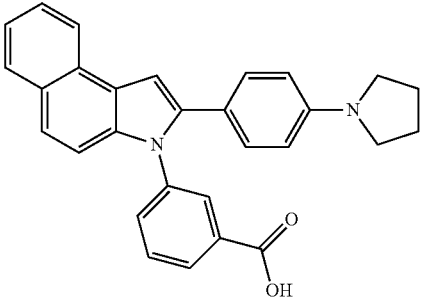 [SMILES: O=C(O)c1cccc(-n2c(-c3ccc(N4CCCC4)cc3)cc3c4ccccc4ccc32)c1] | DMSO-d6; 7.1-8.3 (m, 14H), 6.4 (s, 1H), 3.2 (q, 4H), 1.9 (q, 4H). | pos. mode 433 (M + 1), neg. mode 431 (M − 1). | 3-[2-(4-pyrrolidin-1-ylphenyl)-benzo[e]indol-3-yl] benzoic acid |
| 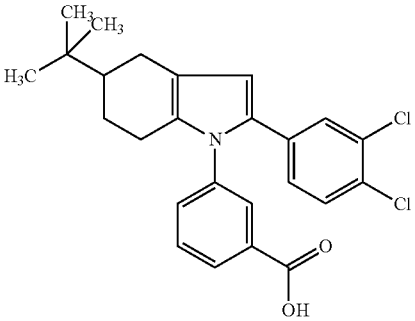 [SMILES: CC(C)(C)C1CCc2c(cc(-c3ccc(Cl)c(Cl)c3)n2-c2cccc(C(=O)O)c2)C1] | CDCl3: 8.0 (d, 1H); 7.9 (br. s, 1H); 7.4 (t, 1H); 7.2 (m, 2H); 7.1 (d, 1H); 6.7 (dd, 1H); 6.2 (s, 1H); 2.7 (m, 1H); 2.5 (m, 1H); 2.3-2.4 (m, 2H); 2.0 (m, 1H); 1.4 (m, 1H); 1.3 (m, 1H); 1.0 (s, 9H). | pos. mode 442 (M + H); neg. mode 440 (M − H). | 3-[5-tButyl-2-(3,4-dichlorophenyl)-4,5,6,7-tetrahydroindol-1-yl] benzoic acid |
| 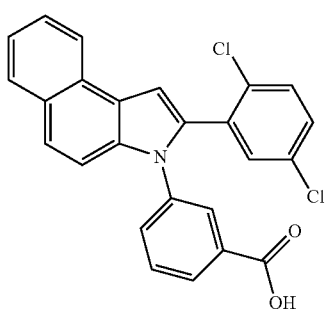 [SMILES: O=C(O)c1cccc(-n2c(-c3cc(Cl)ccc3Cl)cc3c4ccccc4ccc32)c1] | DMSO-d6; 8.38 (d, 1H), 7.98-7.92 (m, 2H), 7.84 (m, 1H), 7.7-7.66 (m, 2H), 7.62-7.56 (m, 3H), 7.51 (s, 1H), 7.48-7.4 (m, 4H). | neg. mode 430 (M − H). | 3-[2-(2,5-dichlorophenyl)-benzo[e]indol-3-yl] benzoic acid |

TABLE 7-continued

Compounds from Table 6 and Characterization Data

| product structure | 1H NMR, δ | MS | name |
|---|---|---|---|
| 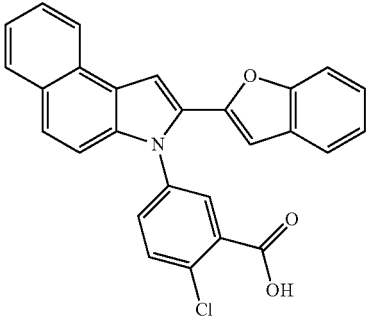 [SMILES: O=C(O)c1cc(-n2c(-c3cc4ccccc4o3)cc3c4ccccc4ccc32)ccc1Cl] | DMSO-d6; 7.1-8.4 (m, 14H), 6.09 (s, 1H). | pos. mode 438 (M + 1). | 5-(2-benzofuran-2-ylbenzo[e]indol-3-yl) 2-chlorobenzoic acid |
| 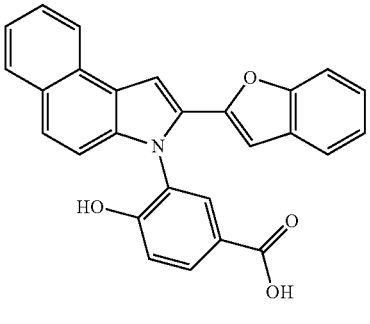 [SMILES: O=C(O)c1ccc(O)c(-n2c(-c3cc4ccccc4o3)cc3c4ccccc4ccc32)c1] | DMSO-d6; 7.1-8.4 (m, 14H), 5.9 (s, 1H). | pos. mode 420 (M + 1). | 3-(2-benzofuran-2-ylbenzo[e]indol-3-yl) 4-hydroxybenzoic acid |
| 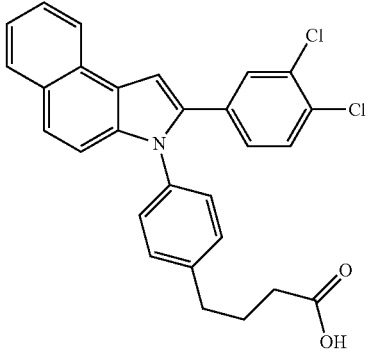 [SMILES: O=C(O)CCCc1ccc(-n2c(-c3ccc(Cl)c(Cl)c3)cc3c4ccccc4ccc32)cc1] | DMSO-d6; 8.4 (d, 1H), 7.96 (d, 1H), 7.73 (s, 1H), 7.66-7.56 (m, 3H), 7.5-7.44 (m, 2H), 7.4 (d, 2H), 7.34-7.28 (m, 3H), 7.26 (dd, 1H), 2.65 (t, 2H), 2.3 (t, 2H), 1.9 (t, 2H). | pos. mode 474 (M + H). | 4-{4-[2-(3,4-dichlorophenyl)-benzo[e]indol-3-yl]-phenyl} butyric acid |
| 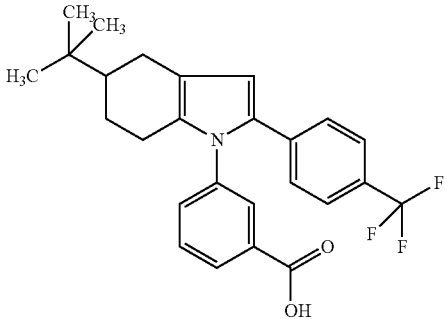 [SMILES: CC(C)(C)C1CCc2c(cc(-c3ccc(C(F)(F)F)cc3)n2-c2cccc(C(=O)O)c2)C1] | CDCl3: 8.0 (d, 1H); 7.9 (br. s, 1H); 7.4 (m, 3H); 7.2 (m, 1H); 7.1 (d, 2H); 6.4 (s, 1H); 2.7 (m, 1H); 2.5 (m, 1H); 2.3-2.4 (m, 2H); 2.0 (m, 1H); 1.5 (m, 1H); 1.4 (m, 1H); 1.0 (s, 9H). | TOF pos. mode 442 (M + H), EM 442.1994. | 3-[5-tButyl-2-(4-trifluoromethylphenyl)-4,5,6,7-tetrahydroindol-1-yl] benzoic acid |

TABLE 7-continued

Compounds from Table 6 and Characterization Data

| product structure | 1H NMR, δ | MS | name |
|---|---|---|---|
| | CDCl3; 8.02 (d, 1H), 7.96 (s, 1H), 7.33-7.45 (m, 5H), 7.25-7.32 (m, 2H), 7.08-7.18 (m, 3H), 7.00-7.08 (m, 2H), 6.25 (s, 1H), 4.67 (s, 2H), 3.86-3.92 (m, 1H), 3.02 (dd, 1H), 2.71 (dd, 1H), 2.48-2.58 (m, 2H), 2.05-2.18 (m, 1H), 1.88-2.04 (m, 1H). | pos. mode 424 (M + H); neg. mode 422 (M − H). | 3-(5-benzyloxy-2-phenyl-4,5,6,7-tetrahydroindol-1-yl) benzoic acid |
| | DMSO-d6; 8.43 (d, 1H), 7.99-7.95 (m, 2H), 7.87 (s, 2H), 7.69 (d, 1H), 7.64 (t, 1H), 7.49 (t, 1H), 7.43-7.34 (m, 6H), 2.7 (t, 2H), 2.25 (t, 2H), 1.84 (t, 2H). | pos. mode 542 (M + H); neg. mode 540 (M − H). | 4-{4-[2-(3,5-bistrifluoromethylphenyl)-benzo[e]indol-3-yl]-phenyl} butyric acid |
| | CDCl3; 8.32 (d, 1H), 7.91 (d, 1H), 7.6-7.2 (m, 13H), 2.8 (t, 2H), 2.4 (t, 2H); 2.0 (t, 2H). | pos. mode 474 (M + H); neg. mode 472 (M − H). | 4-{4-[2-(4-trifluoromethylphenyl)-benzo[e]indol-3-yl]-phenyl} butyric acid |
| | DMSO-d6; 6.8-8.7 (m, 15H), 3.9 (s, 2H), 2.27 (s, 6H). | neg. mode 459 (M − 1). | 3-(2-benzofuran-2-yl-1-dimethylaminomethylbenzo[e]indol-3-yl) benzoic acid |

TABLE 7-continued

Compounds from Table 6 and Characterization Data

| product structure | 1H NMR, δ | MS | name |
|---|---|---|---|
| | CDCl3; 8.03 (d, 1H), 7.96 (s, 1H), 7.42 (t, 1H), 7.30 (d, 1H), 7.00-7.20 (m, 5H), 6.31 (s, 1H), 2.70-2.85 (m, 1H), 2.30-2.58 (m, 4H), 1.75-2.05 (m, 5H), 1.60-1.85 (m, 2H), 1.40-1.50 (m, 1H). | pos. mode 385 (M + H). | 3-[4-(3-cyanopropyl)-2-phenyl-4,5,6,7-tetrahydroindol-1-yl] benzoic acid |
| | CDCl3; 8.04 (dt, 1H), 7.94 (br s, 1H), 7.43 (t, 1H), 7.29 (br d, 1H), 7.08-7.20 (m, 3H), 7.02-7.08 (m, 2H), 6.26 (s, 1H), 2.56-2.74 (m, 2H), 2.45 (dd, 1H), 2.33 (t, 2H), 2.12-2.23 (m, 1H), 1.90-1.98 (m, 1H), 1.75-1.85 (m, 1H), 1.62-1.75 (m, 2H), 1.40-1.61 (m, 3H) | pos. mode 385 (M + H). | 3-[6-(3-cyanopropyl)-2-phenyl-4,5,6,7-tetrahydroindol-1-yl]-benzoic acid |
| | DMSO-d6; 7.8 (d, 1H), 7.56 (s, 1H), 7.42 (t, 1H), 7.24 (d, 1H), 7.09 (d, 1H), 6.46 (d, 1H), 6.32 (s, 1H), 5.99 (s, 1H), 3.7 (s, 3H), 3.3 (s, 3H), 2.8-2.55 (m, 4H), 2.39 (d, 1H), 2.10 (d, 1H), 1.66-1.61 (m, 1H). | pos. mode 446 (M + H); neg. mode 444 (M − H). | 3-[2-(3,4-dimethoxyphenyl)-5-trifluoromethyl-4,5,6,7-tetrahydroindol-1-yl]-benzoic acid |
| | DMSO-d6; 7.91 (d, 1H), 7.63 (s, 1H), 7.56 (t, 1H), 7.44 (d, 1H), 6.78 (d, 1H), 6.57 (d, 1H), 6.51 (s, 1H), 6.24 (s, 1H), 3.67 (s, 3H), 3.35 (s, 3H), 2.81-2.55 (m, 4H), 2.36 (d, 1H), 2.10 (m, 1H), 1.66-1.61 (m, 1H). | pos. mode 446 (M + H); neg. mode 444 (M − H). | 3-[2-(2,4-dimethoxyphenyl)-5-trifluoromethyl-4,5,6,7-tetrahydroindol-1-yl] benzoic acid |

TABLE 7-continued

Compounds from Table 6 and Characterization Data

| product structure | 1H NMR, δ | MS | name |
|---|---|---|---|
| | DMSO-d6; 8.38 (d, 1H), 7.96 (d, 1H), 7.64-7.3 (m, 12H), 7.1-7.07 (tt, 1H), 2.89 (t, 2H), 2.55 (t, 2H). | pos. mode 426 (M + H), neg. mode 424 (M − H). | 3-{3-[2-(4-chlorophenyl)-benzo[e]indol-3-yl]-phenyl} propionic acid |
| | DMSO-d6; 8.39 (d, 1H), 7.97 (d, 1H), 7.73 (s, 1H), 7.67-7.33 (m, 9H); 7.19-7.12 (m, 2H); 2.9 (t, 2H); 2.55 (t, 2H). | pos. mode 460 (M + H). | 3-{3-[2-(3,4-dichlorophenyl)-benzo[e]indol-3-yl]-phenyl} propionic acid |
| | DMSO-d6; 7.92-7.89 (tt, 1H), 7.62 (s, 1H), 7.54 (t, 1H), 7.4 (d, 1H), 6.87 (d, 2H), 6.75 (d, 2H), 6.16 (s, 1H), 3.68 (t, 4H), 3.34 (s, 2H), 3.01 (t, 2H), 2.8-2.76 (dd, 1H), 2.6 (dd, 1H), 2.34 (m, 1H), 2.1 (m, 1H), 1.63 (m, 1H). | pos. mode 471 (M + H); neg. mode 469 (M − H). | 3-[2-(4-morpholin-4-yl-phenyl)-5-trifluoromethyl-4,5,6,7-tetrahydroindol-1-yl] benzoic acid |
| | CDCl3; 7.95-7.88 (m, 2H), 7.34 (t, 1H), 7.22 (d, 1H), 6.87 (d, 1H), 6.56 (d, 1H), 6.15 (s, 1H); 3.83 (s, 3H) 3.65 (s, 3H); 3.51 (s, 3H); 2.93-2.88 (dd, 1H); 2.71 (t, 2H); 2.54-2.51 (m, 2H); 2.21 (m, 1H) 1.77-1.72 (m, 1H). | pos. mode 476 (M + H); neg. mode 474 (M − H). | 3-[5-trifluoromethyl-2-(2,3,4-trimethoxyphenyl)-4,5,6,7-tetrahydroindol-1-yl] benzoic acid |
| | DMSO-d6; 6.9-7.8 (m, 9H), 3.4 (s, 2H), 2.2 (s, 3H), 1.9 (s, 3H), 1.4-1.5 (m, 2H), 0.9 (s, 9H). | neg. mode 429 (M − 1). | 3-(5-tButyl-3-dimethylaminomethyl-2-phenyl-4,5,6,7-tetrahydroindol-1-yl) benzoic acid |

TABLE 7-continued

Compounds from Table 6 and Characterization Data

| product structure | 1H NMR, δ | MS | name |
|---|---|---|---|
| | DMSO-d6; 8.4 (d, 1H); 7.97 (d, 1H); 7.85 (d, 1H); 7.76-7.46 (m, 9H); 7.39-7.33 (dd, 1H); 7.2-7.15 (td, 1H). | pos. mode 432 (M + H). | 2-chloro-5-[2-(4-chlorophenyl)-benzo[e]indol-3-yl] benzoic acid |
| | MeOH-d4; 7.99 (d, 1H), 7.77 (s, 1H), 7.48 (t, 1H), 7.28-7.33 (m, 1H), 7.10-7.20 (m, 3H), 7.00-7.10 (m, 2H), 6.28 (s, 1H), 3.75-3.88 (m, 1H), 3.37-3.50 (m, 2H), 3.23-3.35 (m, 2H), 3.07 (dd, 1H), 2.93 (dd, 1H), 2.65-2.82 (m, 1H), 2.59 (br d, 1H), 2.27 (br d, 1H), 2.03 (qd, 1H), 1.40 (t, 6H). | pos. mode 389 (M + H); neg. mode 387 (M − H) | 3-(5-diethylamino-2-phenyl-4,5,6,7-tetrahydroindol-1-yl) benzoic acid |
| | MeOH-d4; 7.99 (dt, 1H), 7.77 (br s, 1H), 7.48 (t, 1H), 7.31 (br d, 1H), 7.08-7.20 (m, 3H), 7.00-7.06 (m, 2H), 6.27 (s, 1H), 3.75-4.12 (m, 4H), 3.58-3.72 (m, 1H), 3.20-3.57 (m, 4H), 3.10-3.20 (m, 1H), 2.82-2.95 (m, 1H), 2.68-2.79 (m, 1H), 2.61 (br d, 1H), 2.40 (br d, 1H), 1.98 (qd, 1H). | pos. mode 403 (M + H); neg. mode 401 (M − H). | 3-(5-morpholin-4-yl-2-phenyl-4,5,6,7-tetrahydroindol-1-yl) benzoic acid |
| | DMSO-d6; 7.87 (d, 1H), 7.59 (br s, 1H), 7.47 (t, 1H), 7.32 (br d, 1H), 7.11-7.20 (m, 2H), 7.03-7.10 (m, 1H), 6.94-7.02 (m, 2H), 6.23 (s, 1H), 2.55-2.90 (m, 6H), 2.30-2.40 (m, 2H), 2.05-2.18 (m, 2H), 1.75 (br s, 4H), 1.57-1.70 (m, 1H). | pos. mode 387 (M + H); neg. mode 385 (M − H). | 3-(2-phenyl-5-pyrrolidin-1-yl-4,5,6,7-tetrahydroindol-1-yl) benzoic acid |

TABLE 7-continued

Compounds from Table 6 and Characterization Data

| product structure | 1H NMR, δ | MS | name |
|---|---|---|---|
| | DMSO-d6; 7.91 (d, 1H), 7.60-7.41 (m, 3H); 7.25-7.21 (m, 2H); 7.0-6.96 (m, 2H); 6.27 (s, 1H); 2.54-2.44 (m, 1H), 2.31-2.25 (m, 2H); 1.91 (m, 1H); 1.56-1.50 (m, 1H) 1.37-1.24 (m, 4H); 0.86-0.80 (m, 9H). | pos. mode 422 (M + H), neg. mode 420 (M − 1). | 3-[2-(4-chlorophenyl)-5-(1,1-dimethylpropyl)-4,5,6,7-tetrahydroindol-1-yl] benzoic acid |
| | DMSO-d6; 7.94-7.92 (dt, 1H), 7.65-7.38 (m, 5H); 7.17 (d, 2H); 6.42 (s, 1H); 2.51-2.48 (m, 1H), 2.31-2.21 (m, 2H), 1.95-1.90 (m, 1H); 1.59-1.51 (m, 1H) 1.39-1.23 (m, 4H); 0.87-0.81 (m, 9H). | pos. mode 456 (M + H); neg. mode 454 (M − 1). | 3-[5-(1,1-dimethylrpropyl)-2-(3-trifluoromethylphenyl)-4,5,6,7-tetrahydro-indol-1-yl] benzoic acid |
| | CDCl3; 8.02-7.93 (m, 2H), 7.41 (t, 1H); 7.23 (m, 1H); 7.03-6.99 (m, 2H), 6.87-6.83 (m, 2H) 6.22 (s, 1H); 2.66-2.53 (m, 2H), 2.42-2.35 (m, 2H); 1.99-1.96 (m, 1H); 1.66-1.60 (m, 1H) 1.43-1.33 (m, 3H); 0.90-0.83 (m, 9H). | pos. mode 406 (M + H), neg. mode 404 (M − 1). | 3-[5-(1,1-dimethylpropyl)-2-(4-fluoropheny)-4,5,6,7-tetrahydroindol-1-yl] benzoic acid |
| | CDCl3; 8.05-7.95 (m, 2H), 7.44 (t, 1H); 7.33-7.13 (m, 5H), 6.34 (s, 1H); 2.67-2.53 (m, 2H), 2.45-2.35 (m, 2H); 2.0-1.97 (m, 1H); 1.66-1.59 (m, 1H) 1.43-1.35 (m, 3H); 0.90-0.84 (m, 9H). | pos. mode 456 (M + H), neg. mode 454 (M − 1). | 3-[5-(1,1-dimethylpropyl)-2-(4-trifluoromethyl-phenyl)-4,5,6,7-tetrahydro-indol-1-yl] benzoic acid |
| | CDCl3; 7.27-7.38 (m, 3H), 7.01-7.18 (m, 7H), 6.25 (s, 1H), 3.72-3.80 (m, 4H), 2.75-2.90 (m, 2H), 2.46-2.74 (m, 7H), 2.07-2.17 (m, 1H), 1.70 (qd, 1H). | pos. mode 359 (M + H). | 5-morpholin-4-yl-1,2-diphenyl-4,5,6,7-tetrahydro-1H-indole |

TABLE 7-continued

Compounds from Table 6 and Characterization Data

| product structure | 1H NMR, δ | MS | name |
|---|---|---|---|
| | CDCl3; 8.04 (dd, 1H), 7.94 (br s, 1H), 7.44 (t, 1H), 7.25-7.30 (m, 1H), 7.08-7.15 (m, 1H), 6.98-7.06 (m, 2H), 6.81 (dt, 1H), 6.29 (s, 1H), 2.63 (dd, 1H), 2.48-2.58 (m, 1H), 2.30-2.46 (m, 2H), 1.98-2.20 (m, 1H), 1.56-1.68 (m, 1H), 1.30-1.44 (m, 3H), 0.90 (s, 3H), 0.89 (s, 3H), 0.85 (t, 3H). | pos. mode 422 (M + H). | 3-[2-(3-chlorophenyl)-5-(1,1-dimethylpropyl)-4,5,6,7-tetrahydroindol-1-yl] benzoic acid |
| | CDCl3; 8.08-8.05; (dt, 1H); 7.94 (s, 1H), 7.46 (t, 1H); 7.29-7.27 (m, 1H), 7.21-7.15 (m, 2H); 6.76-6.73 (dd, 1H), 6.29 (s, 1H), 2.65-2.60 (m, 1H), 2.44-2.32 (m, 2H), 1.98 (m, 1H), 1.66-1.56 (m, 1H), 1.42-1.33 (m, 4H), 0.89-0.83 (m, 9H). | pos. mode 457 (M + H). | 3-[2-(3,4-dichlorophenyl)-5-(1,1-dimethylpropyl)-4,5,6,7-tetrahydroindol-1-yl] benzoic acid |
| | CDCl3; 8.16-8.14; (m, 1H); 8.05 (m, 1H), 7.55-7.52 (m, 2H); 5.90 (s, 1H); 2.43-2.39 (m, 2H); 2.06-2.01 (m, 1H); 1.59-1.43 (m, 2H); 1.34-1.29 (m, 5H); 1.13 (s, 9H); 0.87-0.79 (m, 9H). | pos. mode 368 (M + H). | 3-[2-tert-butyl-5-(1,1-dimethylpropyl)-4,5,6,7-tetrahydroindol-1-yl] benzoic acid |
| | CDCl3; 8.03-8.09 (m, 2H), 7.42-7.52 (m, 3H), 7.30-7.42 (m, 4H), 7.17-7.29 (m, 7H), 6.94 (dd, 1H), 6.74 (d, 1H), 5.15 (s, 2H). | pos. mode 420 (M + H) | 3-(5-benzyloxy-2-phenylindol-1-yl) benzoic acid |
| | CDCl3; 8.11 (d, 1H), 8.01 (d, 2H), 7.93 (br s, 1H), 7.52 (t, 1H), 7.34 (br s, 1H), 7.14 (d, 2H), 6.48 (s, 1H), 2.92 (dd, 1H), 2.40-2.78 (m, 4H), 2.16-2.24 (m, 1H), 1.64-1.82 (m, 1H). | pos mode 431 (M + H) | 3-[2-(4-nitrophenyl)-5-trifluoromethyl-4,5,6,7-tetrahydroindol-1-yl] benzoic acid |
| | 7.95 (tt, 1H), 7.7 (t, 1H), 7.62 (t, 1H), 7.58-7.46 (m, 2H), 7.22 (d, 2H), 7.08-7.04 (m, 3H), 6.86-6.82 (m, 2H), 6.75 (s, 1H), 3.70 (s, 3H), 2.93 (t, 2H), 2.62 (t, 2H). | pos. mode 396 (M + H); neg. mode 394 (M − H). | 3-[2-(3-methoxyphenyl)-4,5-dihydrobenzo[e]indol-3-yl] benzoic acid |

TABLE 7-continued

Compounds from Table 6 and Characterization Data

| product structure | 1H NMR, δ | MS | name |
| --- | --- | --- | --- |
| | DMSO-d6; 8.3 (d, 1H), 7.9 (d, 1H), 7.75 (d, 1H), 7.56-7.26 (m, 11H), 7.18 (s, 1H). | pos. mode 382 (M + H); neg. mode 380 (M − H). | 3-[2-(4-hydroxyphenyl)-benzo[e]indol-3-yl] benzoic acid |
| | CDCl3; 7.63 (s, 1H), 7.51 (s, 1H), 7.03-7.20 (m, 5H), 6.94 (s, 1H), 6.27 (s, 1H), 2.90 (dd, 1H), 2.38-2.78 (m, 4H), 2.20 (d, 1H), 1.74 (qd, 1H). | pos. mode 401 (M + H) | 3-amino-5-(2-phenyl-5-trifluoromethyl-4,5,6,7-tetrahydroindol-1-yl) benzoic acid |
| | CDCl3; 8.02 (d, 1H), 7.93 (s, 1H), 7.41 (t, 1H), 7.25-7.30 (m, 1H), 6.80-6.90 (m, 2H), 6.44-6.52 (m, 2H), 6.16 (s, 1H), 2.89 (dd, 1H), 2.58-2.76 (m, 2H), 2.42-2.52 (m, 2H), 2.19 (br d, 1H), 1.64 (qd, 1H). | pos. mode 401 (M + H) | 3-[2-(4-aminophenyl)-5-trifluoromethyl-4,5,6,7-tetrahydroindol-1-yl] benzoic acid |
| | DMSO-d6; 7.95 (tt, 1H), 7.7 (t, 1H), 7.59 (t, 1H), 7.51-7.44 (m, 2H), 7.18 (d, 2H), 7.05-7.0 (m, 3H), 6.8 (m, 1H), 6.7 (s, 1H), 3.7 (s, 3H), 3.3 (s, 3H), 2.9 (t, 2H), 2.6 (t, 2H). | pos. mode 426 (M + H), neg. mode 424 (M − H). | 3-[2-(2,4-dimethoxyphenyl)-4,5-dihydrobenzo[e]indol-3-yl] benzoic acid |

TABLE 7-continued

Compounds from Table 6 and Characterization Data

| product structure | 1H NMR, δ | MS | name |
|---|---|---|---|
| | MeOH-d4 (mixture 55%:45% saturated:unsaturated); 8.22 (d, 2H); 7.94 (d, 2H), 7.85-7.83 (d, 2H), 7.75-7.67 (m, 4H), 7.60-7.56 (m, 4H), 7.49-7.45 (m, 1H), 7.35-7.28 (m, 4H), 7.20-7.17 (m, 5H), 7.1-7.07 (m, 2H), 7.0 (s, 2H), 3.1 (t, 2H), 2.93 (t, 2H), 2.4 (s, 3H), 2.33 (s, 3H). | neg. mode 378 (M − H). | 3-(2-p-totyl-4,5-dihydrobenzo[e]indol-3-yl) benzoic acid |
| | CDCl3; 8.1 (m, 2H); 7.7 (m, 1H); 7.5 (t, 1H); 7.4 (m, 1H); 7.2-7.3 (m, 8H, ArH); 6.8 (s, 1H). | pos. mode 314 (M + H); neg. mode 312 (M − H) | 3-(2-phenylindol-1-yl) benzoic acid |
| | CDCl3/d3-MeOD; 8.0 (m, 2H); 7.4 (t, 1H); 7.2 (m, 1H); 7.0-7.2 (m, 5H, ArH); 6.2 (s, 1H); 2.7 (m, 1H); 2.5 (m, 1H); 2.4 (m, 2H); 2.0 (m, 1H); 1.5 (m, 1H); 1.4 (m, 1H); 0.9 (s, 9H). | pos. mode 374 (M + H); neg. mode 372 (M − H) | 3-(5-tert-Butyl-2-phenyl-4,5,6,7-tetrahydroindol-1-yl) benzoic acid |
| | CDCl3; 7.2 (m, 1H); 6.9-7.1 (m, 8H, ArH); 6.2 (s, 1H); 2.9 (t, 2H); 2.7 (m, 1H); 2.5 (m, 3H); 2.4 (m, 2H); 2.0 (m, 1H); 1.5 (m, 1H); 1.4 (m, 1H); 0.9 (s, 9H). | pos. mode 402 (M + H); neg. mode 400 (M − H) | 3-[3-(5-tert-Butyl-2-phenyl-4,5,6,7-tetrahydroindol-1-yl)-phenyl] propionic acid |
| | DMSO-d6; 7.0-8.4 (13H, ArH); 6.9 (1H), 2.9 (2H, CH2), 2.5 (2H, CH2). | pos. mode 342 (M + H); neg. mode 340 (M − H) | 2-phenyl-3-[3-(2H-tetrazol-5-yl)-phenyl]-4,5-dihydro-3H-benzo[e]indole |

TABLE 7-continued

Compounds from Table 6 and Characterization Data

| product structure | 1H NMR, δ | MS | name |
|---|---|---|---|
| | DMSO-d6; 6.8-7.9 (14H, ArH), 3.0 (2H, CH2) 2.7 (2H, CH2). | neg. mode 364 (M − 1) | 4-(3-phenyl-4,5-dihydro-3H-benzo[e]indol-2-yl) benzoic acid |
| | CDCl3; 7.0-7.2 (m, 9H, ArH); 6.2 (s, 1H); 2.6 (m, 4H); 2.4 (m, 4H); 2.0 (m, 3H); 1.8 (s, 3H). | neg. mode 358 (M − H) | 4-[4-(2-phenyl-4,5,6,7-tetrahydroindol-1-yl)-phenyl] butyric acid |
| | DMSO-d6; 7.2-8.4 (16H, ArH). | pos. mode 364 (M + 1); neg. mode 362 (M − 1) | 3-(2-phenylbenzo[e]indol-3-yl) benzoic acid |
| | CDCl3; 7.3 (t, 1H); 6.9-7.1 (m, 8H, ArH); 6.2 (s, 1H); 2.9 (t, 2H); 2.7 (m, 1H); 2.5 (m, 3H); 2.4 (m, 1H); 2.2 (m, 1H); 1.9 (m, 2H); 1.4 (m, 1H); 1.0 (d, 3H). | pos. mode 360 (M + H); neg. mode 358 (M − H) | 3-[3-(5-methyl-2-phenyl-4,5,6,7-tetrahydroindol-1-yl)-phenyl] propionic acid |
| | DMSO-d6; 7.2-8.4 (16H, ArH); 2.7 (2H, CH2); 2.3 (2H, CH2); 1.9 (2H, CH2). | pos. mode 406 (M + 1); neg. mode 404 (M − 1) | 4-[4-(2-phenyl-benzo[e]indol-3-yl)-phenyl] butyric acid |

TABLE 7-continued

Compounds from Table 6 and Characterization Data

| product structure | 1H NMR, δ | MS | name |
|---|---|---|---|
| 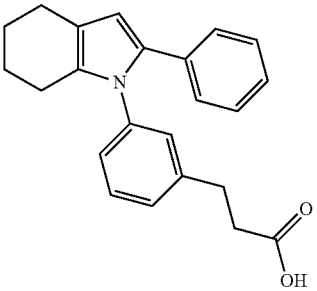 [SMILES: O=C(O)CCc1cccc(-n2c(-c3ccccc3)cc3c2CCCC3)c1] | CDCl3; 7.3 (t, 1H); 6.9-7.2 (m, 8H, ArH); 6.2 (s, 1H); 2.9 (t, 2H); 2.6 (br. s, 2H); 2.5 (t, 2H); 2.4 (br. s, 2H); 1.8 (br. s, 4H). | pos. mode 346 (M + H) | 3-[3-(2-phenyl-4,5,6,7-tetrahydroindol-1-yl)-phenyl] propionic acid |
| 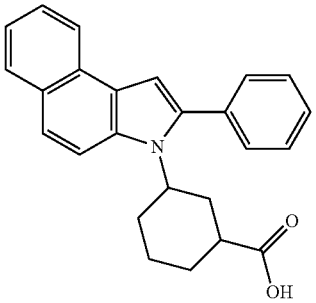 [SMILES: O=C(O)C1CCCC(n2c(-c3ccccc3)cc3c4ccccc4ccc32)C1] | CDCl3; 7.1-8.4 (11H, ArH), 6.4 (1H, ArH), 4.4 (1H, CH) 1.4-2.7 (9H, CH2). | pos. mode 372 (M + 1) | 3-(2-phenylbenzo[e]indol-3-yl) cyclohexanecarboxylic acid |
| 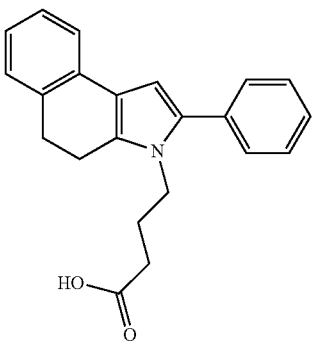 [SMILES: O=C(O)CCCn1c(-c2ccccc2)cc2c1CCc1ccccc1-2] | CD3OD-d4; 7.1-8.2 (10H, ArH), 4.0 (2H, CH2), 3.0 (2H, CH2), 2.9 (2H, CH2), 2.1 (2H, CH2), 1.9 (2H, CH2). | pos. mode 332 (M + 1) | 4-(2-phenyl-4,5-dihydrobenzo[e]indol-3-yl) butyric acid |
| 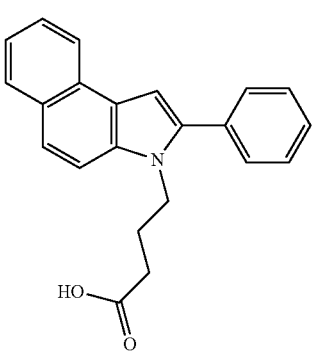 [SMILES: O=C(O)CCCn1c(-c2ccccc2)cc2c3ccccc3ccc21] | CD3OD-d4; 7.1-8.2 (12H, ArH) 4.4 (2H, CH2) 2.1 (2H, CH2) 1.9 (2H, CH2). | pos. mode 330 (M + 1) | 4-(2-phenyl-benzo[e]indol-3-yl) butyric acid |

TABLE 7-continued

Compounds from Table 6 and Characterization Data

| product structure | 1H NMR, δ | MS | name |
|---|---|---|---|
| | DMSO-d6; 7.0-7.9 (14H, ArH), 6.3 (1H, ArH), 3.0 (1H, CH), 2.8 (1H, CH2), 2.7 (2H, CH2), 2.4 (1H, CH2), 1.9 (2H, CH2). | pos. mode 394 (M + 1) | 3-(2,5-diphenyl-4,5,6,7-tetrahydroindol-1-yl) benzoic acid |
| | CDCl3; 8.0 (m, 1H); 7.9 (m, 1H); 7.4 (t, 1H); 7.0-7.3 (m, 6H, ArH); 6.2 (s, 1H); 2.6 (m, 1H), 2.5 (br. s, 1H); 2.4 (m, 1H); 2.1 (m, 1H); 1.9 (m, 2H); 1.4 (m, 1H); 1.0 (d, 3H). | pos. mode 332 (M + H) | 3-(4-methyl-2-phenyl-4,5,6,7-tetrahydroindol-1-yl) benzoic acid |
| | CDCl3; 7.1-7.3 (m, 6H, ArH); 6.2 (s, 1H); 6.0 (d, 1H); 2.6 (m, 2H); 2.4-2.5 (m, 2H); 2.0 (m, 1H); 1.5 (m, 2H); 1.0 (s, 9H). | pos. mode 364 (M + H); neg. mode 362 (M − H) | 5-(5-tertButyl-2-phenyl-4,5,6,7-tetrahydroindol-1-yl) furan-2-carboxylic acid |
| | acetone-d6; 7.5 (m, 5H); 7.2 (m, 7H); 7.0 (t, 1H); 6.8 (s, 1H); 3.2 (s, 2H, CH2); 2.9 (m, 2H); 2.6 (m, 1H); 2.4 (m, 1H). | pos. mode 380 (M + H) | [2-(2-phenyl-4,5-dihydrobenzo[e]indol-3-yl)-phenyl] acetic acid |

TABLE 7-continued

Compounds from Table 6 and Characterization Data

| product structure | 1H NMR, δ | MS | name |
|---|---|---|---|
| | DMSO-d6; 7.1-8.5 (14H, ArH/NH); 5.8 (1H); 2.9 (2H, CH2); 2.6 (2H, CH2). | pos. mode 430 (M + 1); neg. mode 429 (M − 1). | 2-benzofuran-2-yl-3-[3-(2H-tetrazol-5-yl)-phenyl]-4,5-dihydro-3H-benzo[e]indole |
| | DMSO-d6; 7.0-8.2 (15H, ArH/NH); 6.3 (1H); 2.9 (2H, CH2), 2.6 (2H, CH2). | pos. mode 457 (M + 1); neg mode 455 (M − 1). | 2-(3-phenylisoxazol-5-yl)-3-[3-(2H-tetrazol-5-yl)-phenyl]-4,5-dihydro-3H-benzo[e]indole |
| | DMSO d6; 7.0-8.1 (14H, ArH); 6.2 (1H); 2.9 (2H, CH2); 2.6 (2H, CH2). | pos. mode 433 (M + 1); neg. mode 431 (M − 1). | 3-(2-phenylisoxazol-5-yl)-4,5-dihydrobenzo[e]indol-3-yl] benzoic acid |

TABLE 8

Compounds of the Invention and Starting Materials

| product structure | ketone/enamine SM | α-bromo ketone SM | aniline |
|---|---|---|---|

TABLE 8-continued

Compounds of the Invention and Starting Materials

| product structure | ketone/enamine SM | α-bromo ketone SM | aniline |
|---|---|---|---|

TABLE 8-continued
Compounds of the Invention and Starting Materials
| product structure | ketone/enamine SM | α-bromo ketone SM | aniline |
|---|---|---|---|
| 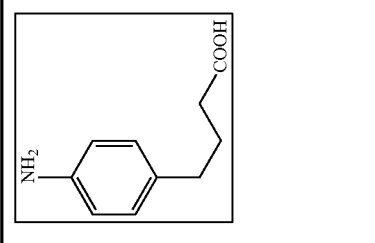 | 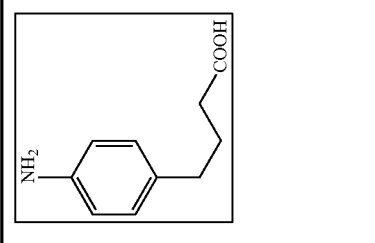 | 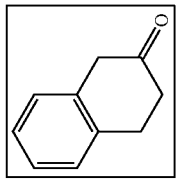 | 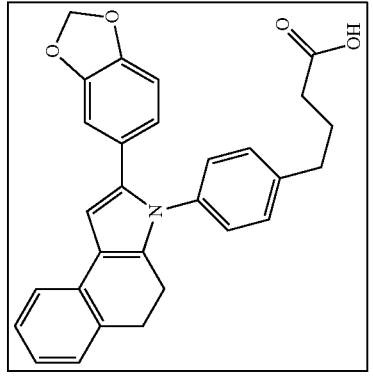 |
| 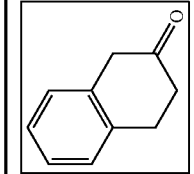 | 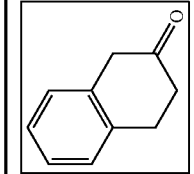 | 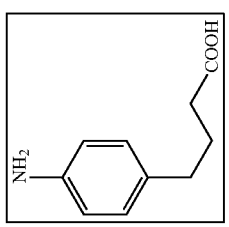 | 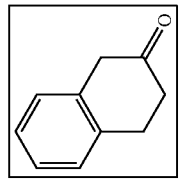 |

TABLE 8-continued

Compounds of the Invention and Starting Materials

| product structure | ketone/enamine SM | α-bromo ketone SM | aniline |
|---|---|---|---|

TABLE 8-continued

Compounds of the Invention and Starting Materials

TABLE 8-continued

Compounds of the Invention and Starting Materials

| ketone/enamine SM | α-bromo ketone SM | aniline | product structure |
|---|---|---|---|
| (2-tetralone) | 3-(2-bromoacetyl)benzoic acid | 3-aminopyridine | 3-(1-(pyridin-3-yl)-4,5-dihydro-1H-benzo[g]indol-2-yl)benzoic acid |
| (2-tetralone) | 2-bromo-1-(3-phenylisoxazol-5-yl)ethanone | 5-(aminomethyl)-4-carboxyfuran | 5-((2-(3-phenylisoxazol-5-yl)-4,5-dihydro-1H-benzo[g]indol-1-yl)methyl)furan-3-carboxylic acid |
| (2-tetralone) | 2-bromo-1-(3-phenylisoxazol-5-yl)ethanone | 5-(aminomethyl)-4-carboxyfuran | 5-((2-(3-phenylisoxazol-5-yl)-4,5-dihydro-1H-benzo[g]indol-1-yl)methyl)furan-3-carboxylic acid |

TABLE 8-continued

Compounds of the Invention and Starting Materials

| product structure | ketone/enamine SM | α-bromo ketone SM | aniline |
|---|---|---|---|

TABLE 8-continued

Compounds of the Invention and Starting Materials

| product structure | ketone/enamine SM | α-bromo ketone SM | aniline |
|---|---|---|---|

TABLE 8-continued

Compounds of the Invention and Starting Materials

| product structure | ketone/enamine SM | α-bromo ketone SM | aniline |
|---|---|---|---|

TABLE 8-continued
Compounds of the Invention and Starting Materials
| product structure | ketone/enamine SM | α-bromo ketone SM | aniline |
|---|---|---|---|
| 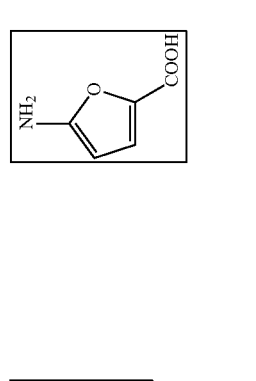 | 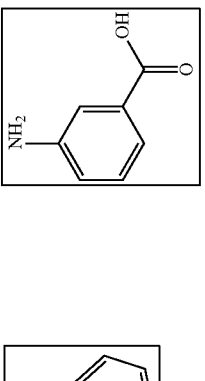 | 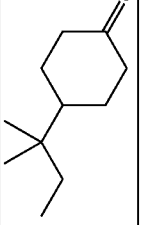 | 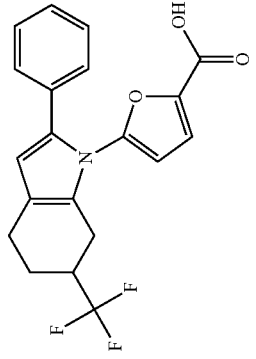 |
| 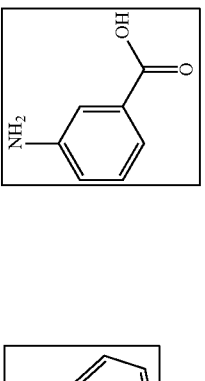 | 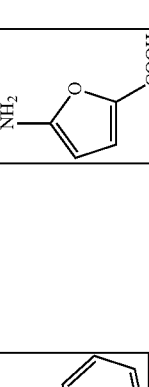 | 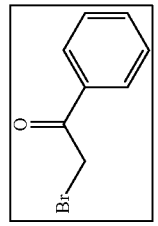 | 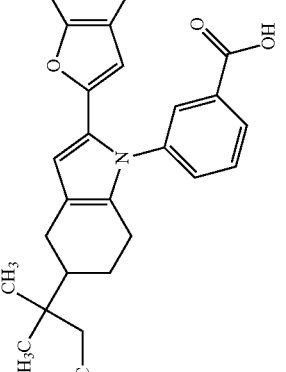 |
| 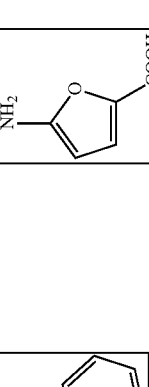 | 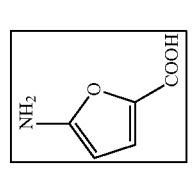 | 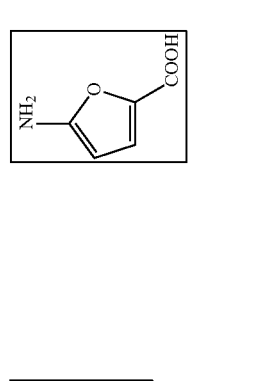 | 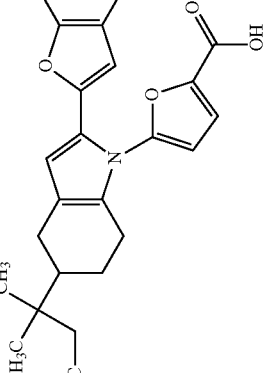 |

TABLE 8-continued
Compounds of the Invention and Starting Materials
| aniline | α-bromo ketone SM | ketone/enamine SM | product structure |
|---|---|---|---|
| 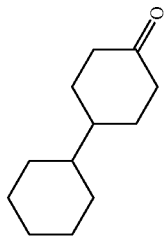 | 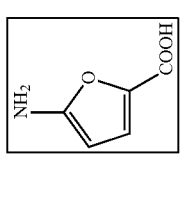 | 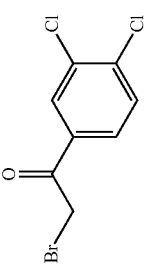 | 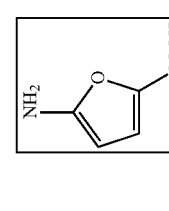 |
| 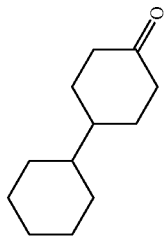 | 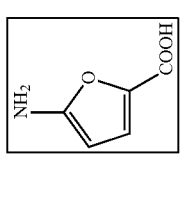 | 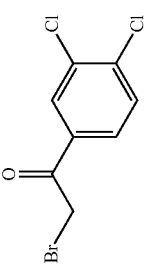 | 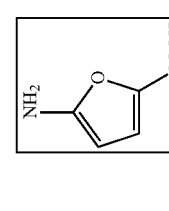 |
| 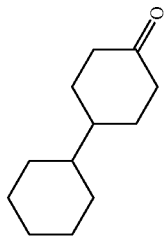 | 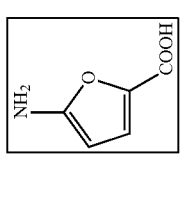 | 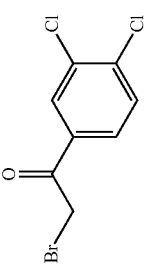 | 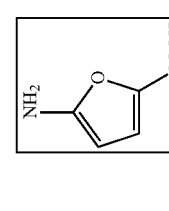 |

TABLE 8-continued

Compounds of the Invention and Starting Materials

| product structure | ketone/enamine SM | α-bromo ketone SM | aniline |
|---|---|---|---|
| (benzofuran-indole-furan-COOH with CF3) | 4-(trifluoromethyl)cyclohexanone | 2-(bromoacetyl)benzofuran | 5-amino-furan-2-carboxylic acid |
| (phenyl-indole-furan-COOH with CH3) | 3-methylcyclohexanone | 2-bromo-1-phenylethanone | 5-amino-furan-2-carboxylic acid |
| (benzofuran-benzindole-furan-COOH) | 2-tetralone (3,4-dihydronaphthalen-2(1H)-one) | 2-(bromoacetyl)benzofuran | 5-amino-furan-2-carboxylic acid |

TABLE 8-continued

Compounds of the Invention and Starting Materials

| product structure | ketone/enamine SM | α-bromo ketone SM | aniline |
|---|---|---|---|

TABLE 8-continued
Compounds of the Invention and Starting Materials
| product structure | ketone/enamine SM | α-bromo ketone SM | aniline |
|---|---|---|---|
| 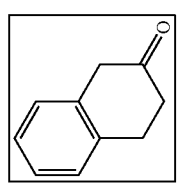 | 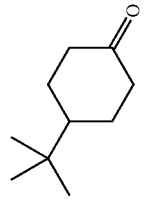 | 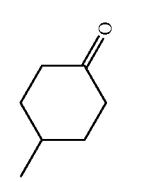 | 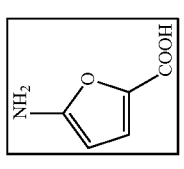 |
| 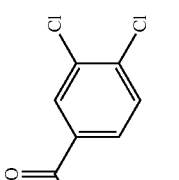 | 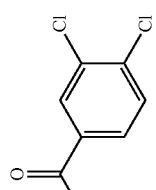 | 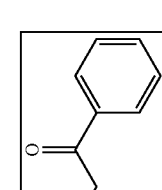 | 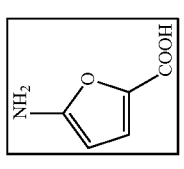 |
| 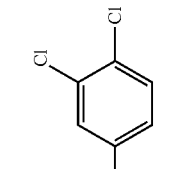 | 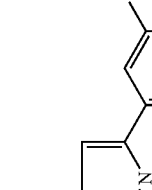 | 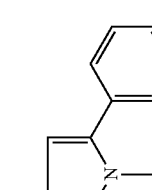 | 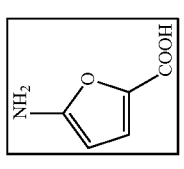 |

TABLE 8-continued

Compounds of the Invention and Starting Materials

TABLE 8-continued

Compounds of the Invention and Starting Materials

| ketone/enamine SM | α-bromo ketone SM | aniline | product structure |

TABLE 8-continued

Compounds of the Invention and Starting Materials

| | ketone/enamine SM | α-bromo ketone SM | aniline | product structure |
|---|---|---|---|---|
| 391 | 4-(trifluoromethyl)cyclohexanone | 2-bromo-1-(2,4-dimethoxyphenyl)ethanone | 2-aminothiazole-4-carboxylic acid | 2-(2,4-dimethoxyphenyl)-1-(4-carboxythiazol-2-yl)-5-(trifluoromethyl)-4,5,6,7-tetrahydroindole |
| 392 | 4-(trifluoromethyl)cyclohexanone | 2-bromo-1-(3,4-dimethoxyphenyl)ethanone | 2-aminothiazole-4-carboxylic acid | 2-(3,4-dimethoxyphenyl)-1-(4-carboxythiazol-2-yl)-5-(trifluoromethyl)-4,5,6,7-tetrahydroindole |
| | 4-(trifluoromethyl)cyclohexanone | 2-bromo-1-(4-morpholinophenyl)ethanone | 5-aminofuran-2-carboxylic acid | 2-(4-morpholinophenyl)-1-(5-carboxyfuran-2-yl)-5-(trifluoromethyl)-4,5,6,7-tetrahydroindole |

TABLE 8-continued

Compounds of the Invention and Starting Materials

| product structure | ketone/enamine SM | α-bromo ketone SM | aniline |
|---|---|---|---|

TABLE 8-continued

Compounds of the Invention and Starting Materials

| aniline | α-bromo ketone SM | ketone/enamine SM | product structure |
|---|---|---|---|
| 3-aminobenzoic acid | 1-(thiophen-3-yl)-2-bromoethanone | 3,4-dihydronaphthalen-2(1H)-one | 3-(2-(thiophen-3-yl)-benz[g]indol-1-yl)benzoic acid |
| 3-(1H-tetrazol-5-yl)aniline | 1-(thiophen-3-yl)-2-bromoethanone | 3,4-dihydronaphthalen-2(1H)-one | 1-(3-(1H-tetrazol-5-yl)phenyl)-2-(thiophen-3-yl)benz[g]indole |
| methyl 5-aminofuran-2-carboxylate | 2-bromo-1-phenylethanone | 4-tert-butylcyclohexan-1-one | 5-(5-tert-butyl-2-phenyl-4,5,6,7-tetrahydroindol-1-yl)furan-2-carboxylic acid |

TABLE 8-continued

Compounds of the Invention and Starting Materials

| aniline | α-bromo ketone SM | ketone/enamine SM | product structure |
|---|---|---|---|
| 3-(tetrazol-5-yl)aniline | 2-(bromoacetyl)benzofuran | 2-tetralone | benzofuran-pyrrole-tetrazolyl-phenyl product |
| 3-(triazol-5-yl)aniline | 2-bromo-1-(3-phenylisoxazol-5-yl)ethanone | 2-tetralone | isoxazole-pyrrole-triazolyl-phenyl product |
| 3-aminobenzoic acid | 2-bromo-1-(3-phenylisoxazol-5-yl)ethanone | 2-tetralone | isoxazole-pyrrole-benzoic acid product |

TABLE 8-continued

Compounds of the Invention and Starting Materials

| product structure | ketone/enamine SM | α-bromo ketone SM | aniline |
|---|---|---|---|

TABLE 8-continued

Compounds of the Invention and Starting Materials

| | product structure | ketone/enamine SM | α-bromo ketone SM | aniline |
|---|---|---|---|---|
| 401 | | | | |
| 402 | | | | |

TABLE 8-continued
Compounds of the Invention and Starting Materials
| | product structure | ketone/enamine SM | α-bromo ketone SM | aniline |
|---|---|---|---|---|
| 403 | 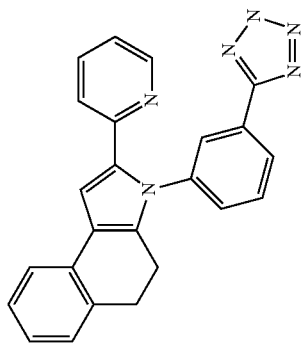 | 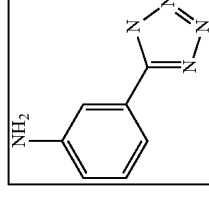 | 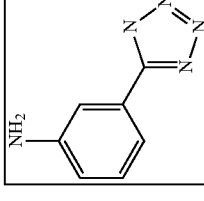 | 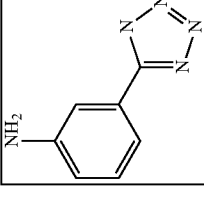 |
| 404 | 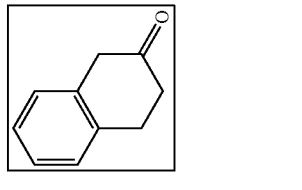 | 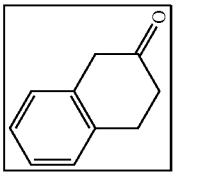 | 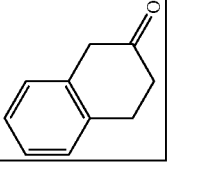 | 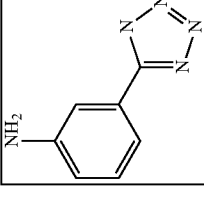 |
| | 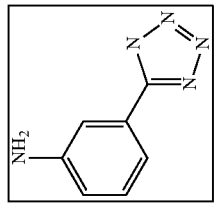 | 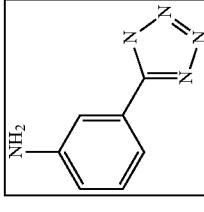 | 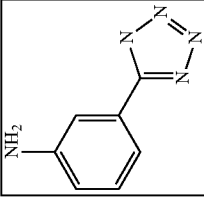 | 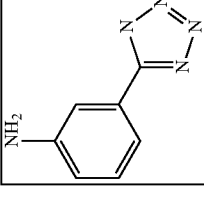 |

TABLE 8-continued

Compounds of the Invention and Starting Materials

| product structure | ketone/enamine SM | α-bromo ketone SM | aniline |
|---|---|---|---|
| (pyridinyl-phenyl-pyrazole-benzoic acid) | 1,3-diphenyl-1,3-propanedione | none | 3-hydrazinylbenzoic acid |
| (phenyl-tetrazolyl-phenyl-dihydrobenzoindole) | 2-tetralone | phenacyl bromide | 3-(tetrazol-5-yl)aniline |
| (phenyl-tetrazolyl-phenyl-tetrahydroindole) | cyclohexanone | phenacyl bromide | 3-(tetrazol-5-yl)aniline |

TABLE 9

Compounds from Table 8 and Characterization Data

| product structure | 1H NMR, δ | MS | name | Aβ42 IC50 (uM) |
|---|---|---|---|---|
| | DMSO-d6; 7.1-8.6 (m, 14H), 6.2 (t, 2H), 2.9 (t, 2H). | pos. mode 391 (M + 1), neg. mode 389 (M − 1). | 2-pyridin-4-yl-3-[3-(2H-tetrazol-5-yl)-phenyl]-4,5-dihydro-3H-benzo[e]indole | 73 |
| | DMSO-d6; 6.5-8.4 (m, 13H), 5.9 (s, 2H), 2.9 (t, 2H), 2.6 (t, 2H). | pos. mode 434 (M + 1), neg. mode 432 (M − 1). | 2-benzo[1,3]dioxol-5-yl-3-[3-(2H-tetrazol-5-yl)-phenyl]-3H-benzo[e]indole | 56 |
| | DMSO-d6; 7.3-8.6 (m, 14H), 2.9 (t, 2H), 2.7 (t, 2H). | pos. mode 391 (M + 1), neg. mode 389 (M − 1). | 2-pyridin-3-yl-3-[3-(2H-tetrazol-3-yl)-phenyl]-4,5-dihydro-3H-benzo[e]indole | >100 |
| | DMSO-d6; 6.7-8.3 (m, 12H), 6.2 (s, 2H), 2.9 (t, 2H), 2.6 (t, 2H). | pos. mode 410 (M + 1). | 3-(2-benzo[1,3]dioxol-5-yl-4,5-dihydrobenzo[e]indol-3-yl) benzoic acid | 18 |

TABLE 9-continued

Compounds from Table 8 and Characterization Data

| product structure | 1H NMR, δ | MS | name | Aβ42 IC50 (uM) |
|---|---|---|---|---|
| | DMSO-d6; 6.7-8.3 (m, 14H), 6.2 (s, 2H). | pos. mode 408 (M + 1). | 3-(2-benzo[1,3]dioxol-5-yl-benzo[e]indol-3-yl) benzoic acid | 20 |
| | DMSO-d6; 6.7-8.3 (m, 14H), 5.9 (s, 2H), 2.6 (t, 2H), 2.0 (t, 2H), 1.8 (t, 2H). | pos. mode 450 (M + 1). | 4-[4-(2-benzo[1,3]dioxol-5-yl-benzo[e]indol-3-yl)-phenyl] butyric acid | 8.9 |
| | DMSO-d6; 6.5-7.5 (m, 12H), 5.9 (s, 2H), 2.8 (t, 2H), 2.66 (t, 2H), 2.6 (t, 2H), 2.04 (t, 2H), 1.8 (t, 2H). | pos. mode 452 (M + 1). | 4-[4-(2-benzo[1,3]dioxol-5-yl-4,5-dihydrobenzo[e]indol-3-yl)-phenyl] butyric acid | 8.8 |
| | DMSO-d6; 7.0-6.7 (m, 14H), 2.9 (t, 2H), 2.6 (t, 2H), 2.43 (s, 3H), 2.5 (t, 2H), 2.1 (t, 2H), 1.73 (t, 2H). | pos. mode 489 (M + 1), neg. mode 487 (M − 1). | 4-{4-[2-(5-methyl-3-phenylisoxazol-4-yl)-4,5-dihydrobenzo[e]indol-3-yl]-phenyl} butyric acid | 1.5 |

TABLE 9-continued

Compounds from Table 8 and Characterization Data

| product structure | 1H NMR, δ | MS | name | Aβ42 IC50 (uM) |
|---|---|---|---|---|
| | DMSO-d6; 7.0-6.7 (m, 16H), 2.56 (t, 2H), 2.43 (s, 3H), 2.17 (t, 2H), 1.7 (t, 2H). | pos. mode 487 (M + 1). | 4-{4-[2-(5-methyl-3-phenylisoxazol-4-yl)-benzo[e]indol-3-yl]-phenyl} butyric acid | 1 |
| | DMSO, 7.1-8.5 (m, 13H), 2.9 (t, 2H), 2.6 (t, 2H). | pos. mode 367 (M + 1). | 3-(2-pyridin-4-yl-4,5-dihydrobenzo[e]indol-3-yl) benzoic acid | 65 |
| | DMSO-d6; 7.1-8.5 (m, 15H). | pos. mode 365 (M + 1). | 3-(2-pyridin-4-yl-benzo[e]indol-3-yl) benzoic acid | 81 |
| | DMSO-d6; 7.1-6.8 (m, 16H), 2.41 (s, 3H). | pos. mode 445 (M + 1), neg. mode 443 (M − 1). | 3-[2-(5-methyl-3-phenylisoxazol-4-yl)-benzo[e]indol-3-yl] benzoic acid | 40 |

TABLE 9-continued

Compounds from Table 8 and Characterization Data

| product structure | 1H NMR, δ | MS | name | Aβ42 IC50 (uM) |
|---|---|---|---|---|
| | DMSO-d6; 6.6-7.4 (m, 16H), 2.50 (s, 3H). | pos. mode 469 (M + 1). | 2-(5-methyl-3-phenylisoxazol-4-yl)-3-[3-(2H-tetrazol-5-yl)-phenyl] 3H-benzo[e]indole | 31 |
| | DMSO-d6; 8.6 (d, 1H), 8.5 (s, 1H), 7.8 (d, 3H), 7.59-7.53 (m, 2H), 7.27-7.21 (m, 4H), 7.12-7.08 (m, 2H), 3.0 (t, 2H), 2.7 (t, 2H). | pos. mode 367 (M + H). | 4-(3-pyridin-3-yl-4,5-dihydro-3H-benzo[e]indol-2-yl) benzoic acid | >100 |
| | DMSO-d6; 8.4 (s, 1H), 7.84-7.74 (m, 4H), 7.6-7.55 (m, 2H), 7.4 (t, 1H), 7.3 (d, 1H), 7.25 (d, 2H), 7.1 (t, 1H), 7.0 (s, 1H), 2.99 (t, 2H), 2.71 (t, 2H). | pos. mode 367 (M + H); neg. mode 365 (M − H). | 3-(3-pyridin-3-yl-4,5-dihydro-3H-benzo[e]indol-2-yl) benzoic acid | >100 |
| | DMSO-d6; 7.1-8.3 (m, 15H), 5.5 (s, 2H). | pos. mode 435 (M + 1), neg. mode 433 (M − 1). | 5-[2-(3-phenylisoxazol-5-yl)-benzo[e]indol-3-ylmethyl] furan-3-carboxylic acid | >100 |

TABLE 9-continued

Compounds from Table 8 and Characterization Data

| product structure | 1H NMR, δ | MS | name | Aβ42 IC50 (uM) |
|---|---|---|---|---|
| | DMSO-d6; 7.1-8.3 (m, 13H), 5.5 (s, 2H), 2.9 (t, 2H), 2.6 (t, 2H). | pos. mode 437 (M + 1), neg. mode 435 (M − 1). | 5-[2-(3-phenylisoxazol-5-yl)-4,5-dihydrobenzo[e]indol-3-ylmethyl] furan-3-carboxylic acid | >100 |
| | DMSO-d6; 6.8-8.5 (m, 15H). | pos. mode 421 (M + 1), neg. mode 419 (M − 1). | 5-[2-(3-phenylisoxazol-5-yl)-benzo[e]indol-3-yl] furan-2-carboxylic acid | 33 |
| | DMSO-d6; 7.2-8.4 (m, 16H), 6.1 (s, 1H), 2.7 (t, 2H), 2.08 (t, 2H), 1.8 (t, 2H). | pos. mode 473 (M + 1), neg. mode 471 (M − 1). | 4-{4-[2-(3-phenylisoxazol-5-yl)-benzo[e]indol-3-yl]-phenyl} butyric acid | 4.5 |
| | CDCl3; 7.10-7.30 (m, 6H), 6.21 (s, 1H), 5.95 (d, 1H), 2.56-2.64 (m, 2H), 2.54 (d, 1H) 2.32 (t, 1H), 2.00 (br d, 1H), 1.59 (td, 1H), 1.30-1.48 (m, 3H), 0.89 (s, 3H), 0.86 (s, 3H), 0.84 (t, 3H). | pos. mode 378 (M + H); neg. mode 376 (M − H). | 5-[5-(1,1-dimethylpropyl)-2-phenyl-4,5,6,7-tetrahydroindol-1-yl]-furan-2-carboxylic acid | 5.1 |

TABLE 9-continued

Compounds from Table 8 and Characterization Data

| product structure | 1H NMR, δ | MS | name | Aβ42 IC50 (uM) |
|---|---|---|---|---|
| | CDCl3; 7.20-7.32 (m, 4H), 7.14 (d, 2H), 6.23 (s, 1H), 5.99 (d, 1H), 2.84 (dd, 1H), 2.58-2.73 (m, 3H), 2.46 (br s, 1H), 2.20-2.38 (m, 1H), 1.70-1.85 (m, 1H). | pos. mode 376 (M + H). | 5-(2-phenyl-5-trifluoromethyl-4,5,6,7-tetrahydroindol-1-yl)-furan-2-carboxylic acid | 16.5 |
| | DMSO-d6; 9.2 (s, 1H), 8.8 (s, 1H), 8.4 (d, 1H), 8.1-7.4 (m, 9H), 6.92 (s, 1H), 6.6 (s, 1H). | pos. mode 354 (M + H). | 3-(3-furan-3-yl-3H-benzo[e]indol-2-yl) benzoic acid | >100 |
| | DMSO-d6; 8.8 (s, 1H), 8.4 (d, 1H), 8.0-7.92 (m, 3H), 7.78-7.67 (m, 3H), 7.62-7.49 (m, 4H), 6.9 (s, 1H), 6.6 (s, 1H). | pos. mode 354 (M + H). | 4-(3-furan-3-yl-3H-benzo[e]indol-2-yl) benzoic acid | >100 |
| | DMSO-d6; 6.7-8.4 (m, 13H), 6.5 (s, 1H). | 353 (M dot). | 5-(2-phenylbenzo[e]indol-3-yl) furan-2-carboxylic acid | 22 |

TABLE 9-continued

Compounds from Table 8 and Characterization Data

| product structure | 1H NMR, δ | MS | name | Aβ42 IC50 (uM) |
|---|---|---|---|---|
| | CDCl3; 7.40-7.48 (m, 2H), 7.38 (d, 1H), 7.12-7.24 (m, 2H), 6.62 (s, 1H), 6.49 (d, 1H), 5.97 (s, 1H), 2.45-2.82 (m, 5H), 2.15-2.30 (m, 1H), 1.72 (qd, 1H). | pos. mode 416 (M + H). | 5-(2-benzofuran-2-yl-6-trifluoromethyl-4,5,6,7-tetrahydroindol-1-yl)-furan-2-carboxylic acid | 23 |
| | CDCl3; 7.19-7.32 (m, 4H), 7.05-7.18 (m, 2H), 6.22 (s, 1H), 6.07 (d, 1H), 2.45-2.80 (m, 5H), 2.20 (br d, 1H), 1.72 (qd, 1H). | pos. mode 376 (M + H). | 5-(2-phenyl-6-trifluoromethyl-4,5,6,7-tetrahydroindol-1-yl)-furan-2-carboxylic acid | 25 |
| | CDCl3; 8.20 (dt, 1H), 8.09 (t, 1H), 7.52-7.62 (m, 2H), 7.32-7.36 (m, 1H), 7.26-7.30 (m, 1H), 6.60-7.17 (m, 2H), 6.66 (s, 1H), 5.60 (s, 1H), 2.65 (dd, 1H), 2.25-2.45 (m, 3H), 1.96 (br d, 1H), 1.22-1.44 (m, 3H), 0.90 (s, 6H), 0.85 (t, 3H). | pos. mode 428 (M + H). | 3-[2-benzofuran-2-yl-5-(1,1-dimethylpropyl)-4,5,6,7-tetrahydroindol-1-yl] benzoic acid | 3.7 |
| | CDCl3; 7.35-7.44 (m, 3H), 7.12-7.22 (m, 2H), 6.60 (s, 1H), 6.41 (d, 1H), 5.97 (d, 1H), 2.58 (dd, 1H), 2.51 (br d, 2H), 2.27-2.35 (m, 1H), 1.99 (br d, 1H), 1.58 (td, 1H), 1.25-1.47 (m, 3H), 0.90 (s, 3H), 0.89 (s, 3H), 0.84 (t, 3H). | pos. mode 418 (M + H). | 5-[2-benzofuran-2-yl-5-(1,1-dimethylpropyl)-4,5,6,7-tetrahydroindol-1-yl]-furan-2-carboxylic acid | 18 |

TABLE 9-continued

Compounds from Table 8 and Characterization Data

| product structure | 1H NMR, δ | MS | name | Aβ42 IC50 (uM) |
|---|---|---|---|---|
| | CDCl3; 7.15-7.28 (m, 6H), 6.20 (s, 1H), 5.97 (d, 1H), 2.54-2.60 (m, 2H), 2.20-2.40 (m, 1H), 1.80-2.00 (m, 1H), 1.35-1.85 (m, 8H), 0.95-1.35 (m, 6H). | pos. mode 390 (M + H). | 5-(5-cyclohexyl-2-phenyl-4,5,6,7-tetrahydroindol-1-yl)-furan-2-carboxylic acid | 40 |
| | CDCl3; 7.24-7.33 (m, 3H), 6.89 (dd, 1H), 6.26 (s, 1H), 6.10 (d, 1H), 2.83 (dd, 1H), 2.55-2.70 (m, 3H), 2.37-2.53 (m, 1H), 2.23 (br d, 1H), 1.70-1.83 (m, 1H) | pos. mode 444 (M + H). | 5-[2-(3,4-dichlorophenyl)-3-trifluoromethyl-4,5,6,7-tetrahydroindol-1-yl]-furan-2-carboxylic acid | 1.6 |
| | DMSO-d6; 8.44 (d, 1H), 8.03 (d, 1H), 7.98 (tt, 1H), 7.9 (t, 1H), 7.76-7.74 (m, 2H), 7.66-7.61 (m, 3H), 7.57 (s, 1H), 7.32 (m, 2H), 7.46 (d, 1H). | 421 (M dot). | 5-[2-(4-trifluoromethylphenyl)-benzo[e]indol-3-yl]-furan-2-carboxylic acid | 21 |
| | CDCl3; 7.36-7.47 (m, 3H), 7.13-7.24 (m, 2H), 6.63 (s, 1H), 6.45 (d, 1H), 6.00 (d, 1H), 2.86 (dd, 1H), 2.55-2.70 (m, 3H), 2.40-2.55 (br s, 1H), 2.23 (br d, 1H), 1.70-1.85 (m, 1H). | pos. mode 416 (M + H). | 5-(2-benzofuran-2-yl-5-trifluoromethyl-4,5,6,7-tetrahydroindol-1-yl)-furan-2-carboxylic acid | 44 |

TABLE 9-continued

Compounds from Table 8 and Characterization Data

| product structure | 1H NMR, δ | MS | name | Aβ42 IC50 (uM) |
|---|---|---|---|---|
| | CDCl3: 7.1-7.3 (m, 6H); 6.2 (s, 1H); 6.0 (d, 1H); 2.5-2.6 (m, 3H); 2.2 (m, 1H); 1.9 (m, 2H); 1.4 (m, 1H); 1.1 (d, 3H). | pos. mode 322 (M + H), TOF EM 322.1449 (M + H). | 5-(6-methyl-2-phenyl-4,5,6,7-tetrahydroindol-1-yl) furan-2-carboxylic acid | >100 |
| | DMSO-d6; 7.2-8.5 (m, 13H), 6.0 (s, 1H). | pos. mode 394 (M + 1), neg. mode 392 (M − 1). | 3-(2-benzofuran-2-yl-benzo[e]indol-3-yl) furan-2-carboxylic acid | 22 |
| | CDCl3; 7.22-7.30 (m, 3H), 7.16-7.22 (m, 2H), 6.96 (X of ABX, 1H), 6.22 (s, 1H), 3.83 (A of AB X, 1H), 3.81 (B of ABX, 1H), 2.64-2.74 (m, 2H), 2.57 (dd, 1H), 2.28-2.38 (m, 1H), 1.98-2.06 (m, 1H), 1.60 (tdd, 1H), 1.30-1.46 (m, 3H), 0.89 (s, 3H), 0.89 (s, 3H), 0.84 (t, 3H). | pos. mode 409 (M + H); neg. mode 407 (M − H). | {2-[5-(1,1-dimethylpropyl)-2-phenyl-4,5,6,7-tetrahydroindol-1-yl]-thiazol-4-yl} acetic acid | 6.5 |
| | DMSO-d6; 7.1-8.4 (m, 15H), 6.0 (s, 1H), 2.7 (t, 2H), 2.03 (t, 2H), 1.8 (t, 2H). | pos. mode 541 (M + 1), neg. mode 539 (M + 1). | 4-(4-{2-[5-(2,4-dichlorophenyl)-furan-2-yl]-benzo[e]indol-3-yl}-phenyl) butyric acid | 17 |

TABLE 9-continued

Compounds from Table 8 and Characterization Data

| product structure | 1H NMR, δ | MS | name | Aβ42 IC50 (uM) |
|---|---|---|---|---|
| | DMSO-d6; 7.1-8.4 (m, 15H), 6.0 (s, 1H). | pos. mode 499 (M + 1), neg. mode 497 (M − 1). | 3-{2-[5-(2,4-dichlorophenyl)-furan-2-yl]-benzo[e]indol-3-yl} benzoic acid | 33 |
| | MeOH-d4; 8.32 (d, 1H), 7.92 (d, 1H), 7.7 (d, 1H), 7.62-7.44 (m, 6H), 7.38 (d, 1H), 7.3 (dd, 1H), 6.55 (d, 1H). | pos. mode 422 (M + H). | 5-[2-(3,4-dichlorophenyl)-benzo[e]indol-3-yl]-furan-2-carboxylic acid | 7 |
| | CDCl3: 7.3 (m, 2H); 6.9 (dd, 2H); 6.2 (s, 1H); 6.0 (d, 1H); 2.5-2.6 (m, 4H); 2.3 (m, 1H); 2.0 (m, 1H); 1.4 (m, 1H); 1.0 (s, 9H). | pos. mode 432 (M + H); TOF EM 432.1122 (M + H). | 5-[5-tButyl-2-(3,4-dichlorophenyl)-4,5,6,7-tetrahydroindol-1-yl] furan-2-carboxylic acid | 11.7 |
| | CDCl3: 7.1-7.3 (m, 6H); 6.1 (s, 1H); 6.0 (d, 1H); 2.5-2.7 (m, 3H); 2.1 (m, 1H); 1.9 (m, 2H); 1.4 (m, 1H); 1.0 (d, 3H). | pos. mode 322 (M + H); TOF EM 322.1476 (M + H). | 5-(5-methyl-2-phenyl-4,5,6,7-tetrahydroindol-1-yl) furan-2-carboxylic acid | >100 |

TABLE 9-continued

Compounds from Table 8 and Characterization Data

| product structure | 1H NMR, δ | MS | name | Aβ42 IC50 (uM) |
|---|---|---|---|---|
| | CDCl3; 8.86-8.92 (m, 1H), 8.15-8.22 (m, 1H), 7.75-8.10 (m, 3H), 7.55-7.68 (m, 2H), 7.35 (t, 1H), 7.02-7.23 (m, 5H), 6.28 (s, 1H), 3.60-3.73 (m, 1H), 2.65-3.03 (m, 4H), 2.20-2.30 (m, 1H), 2.05-2.20 (m, 1H). | pos. mode 395 (M + H). | 3-(2-phenyl-6-pyridin-2-yl-4,5,6,7-tetrahydroindol-1-yl) benzoic acid | 70.8 |
| | CDCl3; 7.26-7.34 (m, 3H), 6.90 (dd, 1H), 6.43 (s, 1H), 6.17 (d, 1H), 3.40-3.50 (m, 1H), 2.45-2.65 (m, 2H), 1.95-2.15 (m, 2H), 1.70-1.95 (m, 2H). | pos. mode 444 (M + H). | 5-[2-(3,4-dichlorophenyl)-4-trifluoromethyl-4,5,6,7-tetrahydroindol-1-yl]-furan-2-carboxylic acid | 7.36 |
| | DMSO-d6; 13.4 (br s, 1H), 7.54 (d, 1H), 7.30-7.38 (m, 2H), 7.02 (dd, 1H), 6.73 (d, 1H), 6.56 (s, 1H), 2.81 (br s, 1H), 2.45-2.70 (m, 4H), 2.05-2.15 (m, 1H), 1.63 (qd, 1H) | pos. mode 444 (M + H). | 5-[2-(3,4-dichlorophenyl)-6-trifluoromethyl-4,5,6,7-tetrahydroindol-1-yl]-furan-2-carboxylic acid | 8.9 |
| | CDCl3: 8.0 (s, 1H); 7.2-7.3 (m, 5H); 6.2 (s, 1H); 2.7 (m, 2H); 2.6 (m, 1H); 2.2 (m, 1H); 1.9 (m, 2H); 1.5 (m, 1H); 1.0 (d, 3H). | TOF pos. mode 339 (M + H); EM 339.1175 (M + H). | 2-(5-methyl-2-phenyl-4,5,6,7-tetrahydroindol-1-yl) thiazole-4-carboxylic acid | >100 |

TABLE 9-continued

Compounds from Table 8 and Characterization Data

| product structure | 1H NMR, δ | MS | name | Aβ42 IC50 (uM) |
|---|---|---|---|---|
| | CDCl3: 7.5 (d, 2H); 7.1-7.3 (m, 3H); 6.3 (s, 1H); 6.0 (d, 1H); 2.5-2.6 (m, 3H); 2.3 (m, 1H); 2.0 (m, 1H); 1.4 (m, 1H); 1.0 (s, 9H). | TOF pos. mode 432 (M + H); EM 432.1783 (M + H). | 5-[5-tButyl-2-(4-trifluoromethylphenyl)-4,5,6,7-tetrahydroindol-1-yl] furan-2-carboxylic acid | 14 |
| | CDCl3: 8.1 (br. s., 1H); 8.0 (m, 0.4H); 7.7 (tt, 0.2H); 7.5 (tt, 0.3H); 7.1-7.2 (m, 5H); 6.2 (s, 1H), 2.5-2.6 (m, 3H); 2.3 (m, 1H); 2.0 (m, 1H); 1.4-1.5 (m, 2H); 1.0 (d, 9H). | pos. mode 321 (M + H); neg. mode 319 (M − H). | 5-tButyl-2-phenyl-1-(4H-[1,2,4]triazol-3-yl)-4,5,6,7-tetrahydro-1H-indole | 63 |
| | DMSO-d6; 7.27 (s, 1H), 6.87 (d, 1H), 6.68 (m, 2H), 6.25 (s, 1H), 3.7 (s, 3H), 3.6 (s, 3H), 2.79-2.55 (m, 5H), 2.36 (s, 1H), 2.12 (d, 1H). | neg mode 452 (M dot). | 2-[2-(2,4-dimethylphenyl)-5-trifluoromethyl-4,5,6,7-tetrahydroindol-1-yl]-thiazole-4-carboxylic acid | >100 |
| | CDCl3; 7.18 (d, 1H), 6.54 (d, 1H); 6.48 (dd, 1H), 6.35 (d, 1H), 6.1 (s, 1H), 3.82 (s, 3H), 3.5 (s, 3H), 2.96-2.8 (m, 4H), 2.68-2.60 (m, 1H), 2.24-2.18 (m, 1H), 1.8-1.68 (m, 1H). | pos. mode 423 (M + H − OMe). | 2-[2-(3,4-dimethoxyphenyl)-5-trifluoromethyl-4,5,6,7-tetrahydroindol-1-yl]-thiazole-4-carboxylic acid | >100 |

TABLE 9-continued

Compounds from Table 8 and Characterization Data

| product structure | 1H NMR, δ | MS | name | Aβ42 IC50 (uM) |
|---|---|---|---|---|
| | DMSO-d6; 7.27 (s, 1H); 6.97 (d, 2H); 6.84 (d, 2H); 6.51 (s, 1H); 6.22 (s, 1H); 3.7 (t, 4H); 3.1 (t, 4H); 2.73 (m, 2H); 2.5 (m, 3H); 2.12 (m, 1H); 2.12 (m, 1H); 1.64 (m, 1H). | pos. mode 461 (M + H); neg. mode 459 (M − H). | 5-[2-(4-morpholin-4-yl-phenyl)-5-trifluoromethyl-4,5,6,7-tetrahydroindol-1-yl]-furan-2-carboxylic acid | 68 |
| | CDCl3; 7.10-7.22 (m, 3H), 7.02 (s, 1H), 6.60-7.01 (m, 1H), 6.24 (s, 1H), 3.83 (s, 1H), 2.60-2.70 (m, 2H), 2.54 (dd, 1H), 2.20-2.38 (m, 1H), 1.96-2.08 (m, 1H), 1.55-1.65 (m, 1H), 1.32-1.46 (m, 3H), 0.89 (s, 3H), 0.88 (s, 3H), 0.84 (t, 3H). | pos. mode 443 (M + 1). | {2-[2-(3-chlorophenyl)-5-(1,1-dimethylpropyl)-4,5,6,7-tetrahydroindol-1-yl]-thiazol-4-yl} acetic acid | na |
| | CDCl3; 7.1-7.3 (m, 6H, ArH); 6.2 (s, 1H); 6.0 (d, 1H); 3.9 (s, 3H); 2.6 (m, 3H); 2.3 (m, 1H); 2.0 (m, 1H); 1.3-1.5 (m, 2H); 1.0 (s, 9H). | pos. mode 378 (M + H). | 5-(5-tertButyl-2-phenyl-4,5,6,7-tetrahydroindol-1-yl) furan-2-carboxylic acid methyl ester | >100 |
| | DMSO-d6; 6.6-8.4 (14H, ArH), | pos. mode 370 (M + 1) | 3-(2-thiophen-3-yl-benzo[e]indol-3-yl) benzoic acid | 13.2 |

TABLE 9-continued

Compounds from Table 8 and Characterization Data

| product structure | 1H NMR, δ | MS | name | Aβ42 IC50 (uM) |
|---|---|---|---|---|
| | DMSO-d6; 6.6-8.4 (13H, ArH), 2.9 (2H, CH2), 2.6 (2H, CH2) | pos. mode 396 (M + 1); 394 (M − 1). | 3-[3-(2H-tetrazol-5-yl)-phenyl]-2-thiophen-3-yl-3H benzo[e]indole | 31 |
| | CDCl3; 7.1-7.3 (m, 6H, ArH); 6.2 (s, 1H); 6.0 (d, 1H); 2.6 (m, 2H); 2.4-2.5 (m, 2H); 2.0 (m, 1H); 1.5 (m, 2H); 1.0 (s, 9H). | pos. mode 364 (M + H); neg. mode 362 (M − H) | 5-(5-tertButyl-2-phenyl-4,5,6,7-tetrahydroindol-1-yl) furan-2-carboxylic acid | 3.7 |
| | DMSO-d6; 7.1-8.5 (14H, ArH/NH); 5.8 (1H); 2.9 (2H, CH2); 2.6 (2H, CH2). | pos. mode 430 (M + 1); neg. mode 429 (M − 1). | 2-benzofuran-2-yl-3-[3-(2H-tetrazol-5-yl)-phenyl]-4,5-dihydro-3H-benzo[e]indole | 9.3 |
| | DMSO-d6; 7.0-8.2 (15H, ArH/NH); 6.3 (1H); 2.9 (2H, CD2); 2.6 (2H, CH2). | pos. mode 457 (M + 1); neg mode 455 (M − 1). | 2-(3-phenylisoxazol-5-yl)-3-[3-(2H-tetrazol-5-yl)-phenyl]-4,5-dihydro-3H-benzo[e]indole | 9.6 |

TABLE 9-continued

Compounds from Table 8 and Characterization Data

| product structure | 1H NMR, δ | MS | name | Aβ42 IC50 (uM) |
|---|---|---|---|---|
| | DMSO d6; 7.0-8.1 (14H, ArH); 6.2 (1H); 2.9 (2H, CH2); 2.6 (2H, CH2). | pos. mode 433 (M + 1); neg. mode 431 (M − 1). | 3-(2-phenylisoxazol-5-yl)-4,5-dihydrobenzo[e]indol-3-yl] benzoic acid | 2.2 |
| | DMSO-d6; 7.3-8.8 (15H, ArH). | pos. mode 365 (M + 1). | 3-(2-pyridin-3-yl-benzo[e]indol-3-yl) benzoic acid | >100 |
| | DMSO-d6; 7.0-8.6 (13H, ArH), 2.9 (2H, CH2), 2.6 (2H, CH2). | pos. mode 367 (M + 1). | 3-(2-pyridin-3-yl-4,5-dihydrobenzo[e]indol-3-yl) benzoic acid | >100 |
| | DMSO-d6; 7.2-8.5 (15H, ArH). | pos. mode 365 (M + 1). | 3-(2-pyridin-2-yl-benzo[e]indol-3-yl) benzoic acid | 79 |

TABLE 9-continued

Compounds from Table 8 and Characterization Data

| product structure | 1H NMR, δ | MS | name | Aβ42 IC50 (uM) |
|---|---|---|---|---|
| | DMSO-d6; 6.9-8.5 (13H, ArH), 2.9 (2H, CH2), 2.6 (2H, CH2). | pos. mode 367 (M + 1); 365 (M + 1). | 3-(2-pyridin-2-yl-4,5-dihydrobenzo[e]indol-3-yl) benzoic acid | 70 |
| | DMSO-d6; 7.1-8.2 (16H, ArH). | pos. mode 404 (M + 1). | 3-(2-benzofuran-2-yl-benzo[e]indol-3-yl) benzoic acid | 1.17 |
| | DMSO-d6; 7.0-8.1 (14H, ArH), 2.9 (2H, CH2), 2.6 (2H, CH2). | pos. mode 406 (M + 1). | 3-(2-benzofuran-2-yl-4,5-dihyrobenzo[e]indol-3-yl) benzoic acid | 0.56 |
| | DMSO-d6; 7.0-8.6 (14H, ArH), 2.9 (2H, CH2), 2.6 (2H, CH2). | pos. mode 391 (M + 1). | 2-pyridin-2-yl-3-[3-(2H-tetrazol-5-yl)-phenyl]-4,5-dihydro-3H-benzo[e]indole | 43 |
| | DMSO-d6; 7.4-8.6 (16H, ArH). | pos. mode 389 (M + 1). | 2-pyridin-3-yl-3-[3-(2H-tetrazol-5-yl)-phenyl]-3H-benzo[e]indole | 46 |

TABLE 9-continued

Compounds from Table 8 and Characterization Data

| product structure | 1H NMR, δ | MS | name | Aβ42 IC50 (uM) |
|---|---|---|---|---|
| | DMSO-d6; 7.2-8.4 (16H, ArH). | pos. mode 389 (M + 1). | 2-pyridin-2-yl-3-[3-(2H-tetrazol-5-yl)-phenyl]-3H-benzo[e]indole | 32 |
| | DMSO-d6; 13.27 (s(br), CO2H), 7.98-7.90 (m, 4H, Ar-H), 7.58-7.50 (m, 2H, Ar-H), 7.47 (m, 2H, Ar-H), 7.44-7.31 (m, 6H, Ar-H), 7.23 (s, 1H, pyr-H). | pos. mode 341 (M + H); neg. mode 339 (M − H) | 3-(3,5-diphenyl-pyrazol-1-yl)-benzoic acid | >100 |
| | DMSO-d6; 7.0-8.4 (13H, ArH); 6.9 (1H), 2.9 (2H, CH2), 2.52 (2H, CH2). | neg. mode 388 (M − H) | 2-phenyl-3-[3-(2H-tetrazol-5-yl)-phenyl]-4,5-dihydro-3H-benzo[e]indole | 24 |
| | CDCl3; 8.0 (d, 1H); 7.9 (s, 1H); 7.5 (t, 1H); 7.0-7.3 (7H, ArH); 6.3 (1H), 2.6 (2H, CH2), 2.5 (2H, CH2); 1.5-1.9 (4H). | pos. mode 342 (M + H); neg. mode 340 (M − H) | 2-phenyl-1-[3-(1H-tetrazol-5-yl)-phenyl]-4,5,6,7-tetrahydro-1H-indole | 100 |

In further aspects, the invention provides compounds of Formulae I-XVI for use in treating and/or preventing disorders associated with axonal transport defects. In some aspects, the invention provides for the use of compounds of Formulae I-XVI for treating and/or preventing disorders characterized by, or associated with, a defect in vesicular transport, including axonal transport.

In an aspect, the invention provides a method of treating a disease chosen from amyotrophic lateral sclerosis (ALS), Charcot-Marie-Tooth Disease 2 (CMT2), spinal muscular atrophy (SPA), spinal muscular atrophy (SMA), Parkinson's Disease (PD), hereditary sensory motor neuropathy, Optic neuropathies (e.g., Leber's hereditary optic neuropathy (LHON) and Cuban epidemic of optic neuropathy (CEON)), Niemann-Pick type C disease (NPC), Down syndrome, Dementia with Lewy Bodies (DLB), Parkinson's disease, Tauopathies (e.g., progressive supranuclear palsy, corticobasal degeneration, Pick's disease, argyrophilic grain disease, and frontotemporal dementia and parkinsonism linked to chromosome 17 (FTDP-17)), miscellaneous motor neuron disorders (e.g., Primary lateral sclerosis (PLS)), Hereditary spastic paraplegia, spinal muscular atrophy, multiple sclerosis, Guillain-Barr syndrome, traumatic brain injury, spinal cord injury, and polyQ diseases (e.g., Huntington disease, spinobulbar muscular atrophy, dentatorubral-pallidoluysian atrophy, Kennedy's disease (also called spinobulbar muscular atrophy [SBMA]), spinocerebellar ataxia 1, spinocerebellar ataxia 2, spinocerebellar ataxia 3, spinocerebellar ataxia 6, spinocerebellar ataxia 7, and spinocerebellar ataxia 17) comprising administering to a patient in need of such treatment, a pharmaceutical composition having one or more compounds of Formulae I-XVI.

Methods of Prevention and Treatment

In one embodiment of the invention, a method for treating (and/or preventing) a disorder associated with a defect in vesicular transport (including axonal transport), in an individual in need of such treatment, is provided that includes the step of administering an effective amount of a compound of Formulae I-XVI as described above.

While not wishing to be bound by theory, it is believed that the compound of Formulae I-XVI acts in vivo to treat and/or prevent certain by modulating a biochemical pathway associated with a vesicular transport pathway (e.g., axonal transport). Such disease include, but are not limited to, amyotrophic lateral sclerosis (ALS), Charcot-Marie-Tooth Disease 2 (CMT2), spinal muscular atrophy (SPA), spinal muscular atrophy (SMA), Parkinson's Disease (PD), and hereditary sensory motor neuropathy, Optic neuropathies (e.g., Leber's hereditary optic neuropathy (LHON) and Cuban epidemic of optic neuropathy (CEON)), Niemann-Pick type C disease (NPC), Down syndrome, Dementia with Lewy Bodies (DLB), Parkinson's disease, Tauopathies (E.G., progressive supranuclear palsy, corticobasal degeneration, Pick's disease, argyrophilic grain disease, and frontotemporal dementia and parkinsonism linked to chromosome 17 (FTDP-17)), Miscellaneous motor neuron disorders (e.g., Primary lateral sclerosis (PLS)), Hereditary spastic paraplegia, spinal muscular atrophy, multiple sclerosis, Guillain-Barr syndrome, traumatic brain, spinal cord injury, and polyQ diseases (e.g., Huntington disease, spinobulbar muscular atrophy, dentatorubral-pallidoluysian atrophy, Kennedy's disease (also called spinobulbar muscular atrophy [SBMA]), spinocerebellar ataxia 1, spinocerebellar ataxia 2, spinocerebellar ataxia 3, spinocerebellar ataxia 6, spinocerebellar ataxia 7, and spinocerebellar ataxia 17).

The following section providers a brief description of disorders associated with a defect in vesicular transport.

PolyQ disease. The expansion of CAG repeats encoding glutamine is known to cause several late-onset progressive neurodegenerative disorders: Huntington disease, spinobulbar muscular atrophy, dentatorubral-pallidoluysian atrophy, Kennedy's disease (also called spinobulbar muscular atrophy [SBMA]), spinocerebellar ataxia 1, spinocerebellar ataxia 2, spinocerebellar ataxia 3, spinocerebellar ataxia 6, spinocerebellar ataxia 7, and spinocerebellar ataxia 17. These polyQ disorders commonly exhibit defects in axonal transport (Neuron. 40:1, 2003; Neuron 40:25, 2003; Neuron 40:41, 2003). Indeed, evidence suggests that perturbations in transport pathways are an early event in polyQ disease (Arch Neurol. 62:46, 2005).

Traumatic brain and spinal cord injury. Traumatic brain injury (TBI) is marked by rapid and long-term accumulation of proteins, including beta-amyloid precursor protein. TBI is also an epigenetic risk factor for developing neurodegenerative disorders, such as Alzheimer's disease and Parkinson's disease (Neuromolecular Med. 4:59, 2003).

Hereditary spastic paraplegia and spinal muscular atrophy. These motor neuron diseases exhibit clear cytoskeletal abnormalities that suggest the involvement of axonal transport in the pathogenesis of the diseases (Trends Neurosci. 25:532, 2002).

Multiple sclerosis. Inflammation is the cause of much neural damage in multiple sclerosis, resulting in disruption of axonal transport (Curr Opin Neurol. 16:267, 2003). These observations admit the possibility that the neurodegeneration experienced by MS patients may be attenuated by agents that enhance axonal transport. In a similar vein, diseases such as Guillain-Barr syndrome, an inflammatory disorder of the peripheral nerves, may be amenable to therapeutic intervention with agents that enhance axonal transport.

Miscellaneous motor neuron disorders. Primary lateral sclerosis (PLS) is a rare degenerative disorder of the upper motor neuron, whose classification is controversial (J Neurol Sci. 170:5, 1999). In fact, a recent study has concluded that PLS is not a discrete nosological entity but represents one end of a continuous spectrum of motor neuron disease (Brain 124:1989, 2001). A therapeutic that successfully treats one motor neuron dysfunction is therefore a candidate for treatment of other motor neuron disorders.

Tauopathies. Aberrant functions of the microtubule-associated proteins collectively called tau can lead to neurodegenerative disorders like progressive supranuclear palsy, corticobasal degeneration, Pick's disease, argyrophilic grain disease, and frontotemporal dementia and parkinsonism linked to chromosome 17 (FTDP-17) (Biochim Biophys Acta. 1739:240, 2005; Brain Res Brain Res Rev. 33:95, 2000). One feature of tauopathies is their disruption of axonal transport that accompanies them.

Dementia with Lewy Bodies. Dementia with Lewy Bodies (DLB) is characterized by the presence of cytoplasmic inclusions of alpha-synuclein in the cerebral cortex and in the nuclei of the brain stem Arch Gerontol Geriatr 39:1, 2004). Protein aggregates, whether they are aggregates of tau, $A\beta$, prions or other proteins, apparently disrupt vesicle transport. A therapy that treats dysfunctional vesicle transport is a candidate regimen for treatment of DLB.

Down syndrome. Nearly all individuals with Down syndrome develop amyloid plaques and the attendant neuropathologic lesions by the age of 45 (Arch Neurol 46:849, 1989). This admits the possibility that $A\beta42$-lowering compounds such as certain fendosal derivatives may moderate or delay the onset of the dementia of Down syndrome.

Niemann-Pick type C disease (NPC). The primary lesion of NPC appears to be impaired cholesterol trafficking and excessive glycosphingolipid storage. One consequence of this impairment is abnormal vesicle trafficking in neural tissue, which likely contributes to the neurodegeneration characteristic of the disease (Neurobiol Aging 26:373, 2005). A recent study indicates that the abnormal vesicle trafficking contributes to increased deposition of $A\beta42$ in brain tissue of NPC patients (Am J. Pathol. 164:975, 2004), which suggests that $A\beta$ peptides may participate in the neurodegeneration.

Optic neuropathies. Histological evidence suggests impaired axonal transport of mitochondria in Leber's hereditary optic neuropathy (LHON) and in Cuban epidemic of optic neuropathy (CEON). Since mitochondria are transported along microtubules by mechanisms similar to microtubule-directed transport of vesicles.

Parkinson's disease. (Acta. Neuropathol. (Berl) 98:157-164, 1999).

Amyotrophic lateral sclerosis. (J. Neurol. Sci. 63:241-250, 1984; Acta. Neuropathol. (Berl) 94:294-299, 1997).

In another embodiment, the invention provides a method of treating a disorder associated with a defect in axonal transport, by identifying a patient in need of such treatment, and administering to the patient a therapeutically effective amount of a pharmaceutical composition having one or more compounds of Formulae I-XVI. Administration of a compound of Formulae I-XVI for at least 4 weeks, preferably at least 4 months, and more desirably at least 8 months, can provide an improvement or lessening in decline of cognitive function as characterized by clinically acceptable tests, biochemical disease marker progression, and/or pathology. The pharmaceutical composition for use in the invention is formulated with one or more pharmaceutically acceptable excipients, salts, or carriers. The pharmaceutical composition for use in the invention is delivered orally, preferably in a tablet or capsule dosage form.

In yet another embodiment, the invention provides a method for prophylaxis against a disorder associated with a defect in axonal transport, by identifying a patient in need of or desiring such treatment, and administering to the patient a prophylactically effective amount of a pharmaceutical composition having one or more compounds of Formulae I-XVI. Preferred compounds for use in this embodiment of the invention include those in Tables 1-6. Administration of a compound of Formulae I-XVI for at least 4 weeks, preferably at least 4 months, and more desirably at least 8 months, can delay the onset of the disorder or slow the rate of onset of symptoms of the disorder.

The skilled artisan readily recognizes that the invention includes the use of compounds of Formulae I-XVI, pharmaceutically acceptable salts, metabolites and prodrugs thereof in each of the described embodiments.

Example 13

We generated a stock of *Drosophila* that is heterozygous for both KHC and KLC, which encodes proteins that associate to form functional kinesin-I, also called conventional kinesin. As a result of the approximately 50% reduction in the level of kinesin-I, these khc/+; klc/+ larvae exhibit a motor defect termed "tail-flipping". Specifically, the mutant larvae exhibit loss of motor activity in the ventral posterior segments that causes an imbalance in body wall contractions; as a result, the larvae rhythmically flip their tails upward during locomotion. In preliminary studies we found that the penetrance of the tail-flipping phenotype was less than 100%; that is, not all khc/+; klc/+ larvae show the phenotype. We identified a number of factors that contribute to this incomplete penetrance:
1. The flipper phenotype of a given animal appears to be suppressed by the number of larvae that precede the animal in development. That is, if a larva is among the first to develop in a vial of eggs, it is more likely to show the flipper phenotype than if it is one of the last emerging larvae.
2. The flipper phenotype appears to be less robust on hard than on soft media.
3. The phenotype is diminished by physically disturbing the larvae.
4. The clearest expression of the flipper phenotype is restricted to that phase of the 3rd instar stage of development that follows appearance of spiracles.

We attempted to accommodate these observations in order to optimize penetrance of the phenotype. Specifically:
1. Virgin females and males were confined to a single vial for only 2 days; the flies were then transferred to fresh vials for an additional 2 days; and this process was repeated to minimize the number of larvae that would emerge in each vial.
2. Efforts were taken to minimize handling of the larvae.
3. We attempted to score the phenotype late in the 3rd instar stage of development.

After optimization, the penetrance of the phenotype appeared to be consistent with literature values (Mol Cel Bio 10:3717 (1999)).

Example 14

In a blinded experiment we tested the compound below for its ability to suppress the flipper phenotype of khc/+; klc/+ *Drosophila* larvae (as described in Example 13). When results are expressed in terms of the number of flies exhibiting no observable motor dysfunction (Non-Flipper) relative to the number with some degree of dysfunction (Flipper), the compound is seen to suppress the flipper phenotype, in a statistical significant manner as compared to flies treated with vehicle alone.

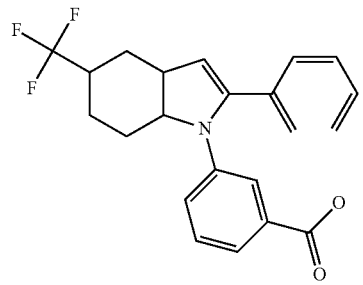 [SMILES: C=C/C=C\C(=C)C1=CC2CC(C(F)(F)F)CCC2N1c1cccc(C(=O)O)c1]

The flipper phenotype of khc/+; klc/+ *Drosophila* larvae is considered to be a model of some human motor neuropathies (e.g., disease associated with a defect in vesicular transport), including certain forms of amyotrophic lateral sclerosis (ALS) (Genetics 144:1075, 1996). Indeed, the relevance of the *Drosophila* model to ALS is supported by a recent report using the SOD1G93A mouse model of ALS (J Cell Biol 169:561, 2005). This report showed amelioration of disease when the ALS-prone mice were made mutant for the dynein heavy chain. This result, which is paradoxical on several grounds, was anticipated by dynein mutations in *Drosophila* models of ALS (Neuron 32:389, 2001). In view of the predictive power of *Drosophila* for interventions that ameliorate ALS, we anticipate the use of the compounds of the invention for treating ALS, and other disorders. Thus it is believed that the compounds of the invention can be used to modulate vesicular transport and treat disease associated with defects in vesicular transport.

NEUROTROPHIC AND AXONOTROPHIC AGENTS

Figure 1:
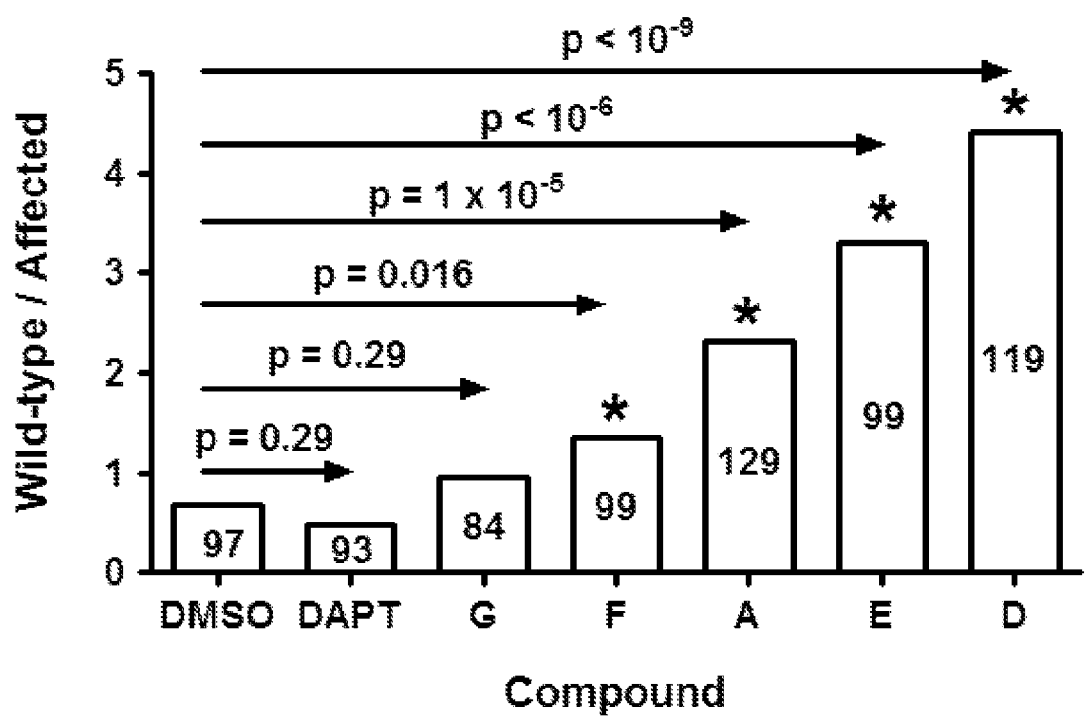
FIG. 1 illustrates the pharmacologic suppression of the locomotion defect of kinesin-deficient *Drosophila* larvae in the presence of exemplary compounds.

The present disclosure provides compounds, compositions and methods of synthesizing compounds that are effective against neurodegenerative diseases and disorders, including their action as neurotrophic and axonotrophic agents, as disclosed herein. Exemplary neurodegenerative diseases and disorders include spinal muscular atrophy (SMA), Charcot-Marie-Tooth Type 2 disease (CMT2), hereditary spastic paraplegia (HSP), amyotrophic lateral sclerosis (ALS), Huntington's disease, Parkinson's disease, spinocerebellar ataxia 3 (SCA3), spinocerebellar ataxia 6 (SCA6), spinocerebellar ataxia 5 (SCA5), spinobulbar muscular atrophy (SBMA), dystonia musculorum, frontotemporal dementia with parkinsonism linked to chromosome 17 (FTDP-17), multiple sclerosis (MS), frontotemporal lobar degeneration (FTLD)/frontotemporal dementia (FTD), spinal cord injury (SCI), and Alzheimer's disease. Also disclosed are methods of using the described compounds and compositions to treat such neurodegenerative diseases and disorders. The disclosure herein specifically addresses relevance of the claimed neurotrophic and axonotrophic agents to the motor neuropathy SMA, which is presented as an illustrative exemplary disease.

Proximal spinal muscular atrophy (SMA), a common inherited motor neuropathy for which there is no effective treatment, results from inadequate levels of the ubiquitously expressed survival motor neuron protein (SMN) (Monani, Neuron 2005, 48(6):885-896). Given the expression of SMN throughout the body, it is paradoxical that its deficiency preferentially affects motor neurons in the anterior horn of the spinal cord (Burghes et al, Nat Rev Neurosci 2009, 10(8):597-609). This suggests that some distinguishing and essential features of spinal motor neurons are particularly vulnerable to SMN deficiency. One such feature is the neuromuscular junction a highly specialized structure that develops where the motor axon terminates on muscle and that is dependent on the proper function of the distal motor axon and its terminus (Murray et al, Neuropathol Appl Neurobiol 2010, 36(2):133-156). It is possible, then, that a primary consequence of SMN deficiency is dysfunction of distal motor axons and their termini. Indeed, SMN deficiency is reported to disrupt processing of pre-mRNAs encoding subunits of kinesin and dynein (viz., Kif17, Klc4, and Dyne 1 hl; Zhang et al, Cell 2008, 133(4):585-600), which drive transport of diverse cargoes in axons (Hirokawa Science 1998, 279(5350):519-526). The function and viability of distal axons and termini of spinal motor neurons, given their exceptional lengths, will be particularly dependent on the activities of these motors.

Another transcript that suffers disrupted processing as a result of SMN deficiency encodes Stasimon, whose resulting deficiency alters neurotransmitter release at motor axon termini (Lotti et al, Cell 2012, 151(2):440-454). Inadequate SMN levels also compromise the formation of messenger ribonucleoproteins (mRNPs), which are complexes that that regulate mRNA transport, stability, and local translation in axons. The consequently reduced levels of the encoded proteins in axons and their growth cones can severely affect the function of axon termini (Akten et al, Proc Natl Acad Sci USA 2011, 108(25):10337-10342; Fallini et al, J eurosci 2011, 31(10):3914-3925; Rossoll et al, J Cell Biol 2003, 163(4):801-812). Yet other mechanisms by which reduced SMN levels can adversely affect axonal function involve the interaction of SMN with both plastin 3, which promotes axonogenesis via its effects on actin (Delanote et al, Acta Pharmacol Sin 2005, 26(7):769-779; Oprea et al, Science 2008, 320 (5875):524-527), and profilin II, which influences growth cone motility via its effects on actin and ROCK (Bernard Int J Biochem Cell Biol 2007, 39(6):1071-1076; Da Silva et al, J Cell Biol 2003, 162(7):1267-1279; Tang Neurochem Int 2003, 42(3):189-203; Gutsche-Perelroizen et al, J Biol Chem 1999, 274(10):6234-6243; Witke et al, EMBO J. 1998, 17(4):967-976; Bito et al, Neuron 2000, 26(2):431-441; Bowerman et al, Mol Cell Neurosci 2009, 42(1):66-74; Bowerman et al, J Mol Neurosci 2007, 32(2):120-131; Kim et al, J Neurobiol 2001, 47(1):26-38; Wills et al, Neuron 1999, 22(2):291-299). Through all of these disparate mechanisms, low SMN levels can compromise the function of the distal motor axon and its terminus and thereby contribute to SMA pathology. Accordingly, agents that enhance the growth, development, and performance of motor axons (i.e., axonotrophic agents) may be therapeutic for SMA.

Such axonotrophic agents may be found among compounds that affect the processing of amyloid precursor protein (APP), as there is an association between the processing of APP and intracellular membrane trafficking. For example, kinesin deficiency in mice is reported to alter γ-secretase-mediated processing of APP (Stokin et al, Science 2005, 307(5713):1282-1288). Specifically, deletion of one copy of the kinesin light chain increased the levels of the APP-derived peptides Aβ42 and Aβ40 in brains of mice that express APP mutants associated with Alzheimer's disease. Thus, kinesin function and metabolism of Aβ peptides may be mechanistically coupled. Given the importance of kinesin for the growth, development, and function of motor axons (Hurd et al, Genetics 1996, 144(3):1075-1085), agents that modulate Aβ metabolism may therefore have axonotrophic activities.

To evaluate this possibility, three classes of compounds were tested for rescue of locomotion of khc/+; klc/+ larvae, which lack one copy of the genes encoding the heavy and light chains of kinesin-1. One class of tested compounds consists of various exemplary compounds claimed herein, specifically compounds A, D, E and F (the structures and chemical names of which are shown in Table 10), each of which has been disclosed to lower Aβ42 production (U.S. Pat. No. 7,678, 823). The second class consists of one compound, Compound G, which is chemically similar to the exemplary compounds A, D, E and F, but fails to lower Aβ42 production. The third class consists of the compound DAPT (N—[N-(3,5-difluorophenacetyl-L-alanyl)]—S-phenylglycine t-butyl ester), which is chemically dissimilar to the exemplary compounds and which inhibits production not only of Aβ42, but of all other products of γ-secretase (Qi-Takahara et al, J Neurosci 2005, 25(2):436-445; Dovey et al, J Neurochem 2001, 76(1):173-181; Zhao et al, J Neurochem 2007, 100(5):1234-1246). Each of the exemplary compounds described herein, and previously disclosed to lower Aβ42 production, rescued locomotion of the mutant larvae (FIG. 1). In contrast, neither Compound G nor DAPT significantly affected the fraction of mutant larvae with motor dysfunction (FIG. 1). The lack of effect of DAPT cannot be explained in terms of inadequate concentrations of the compound, since the tested concentration has previously been reported to alter Notch-dependent phenotypes in Drosophila (Zhou et al, Proc Natl Acad Sci USA 2011, 108(6):2349-2354; Micchelli et al, FASEB J 2003, 17(1):79-81).

Figure 2:
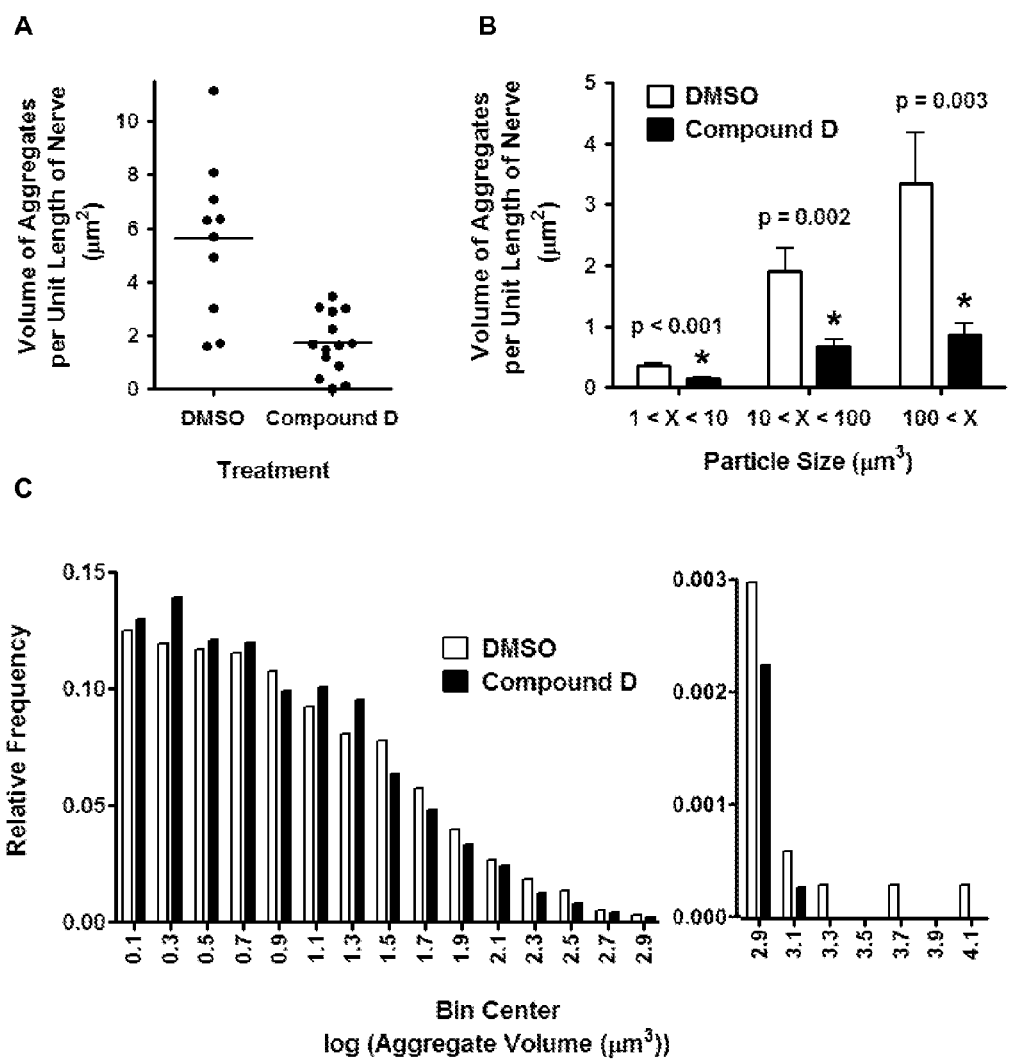
FIG. 2 shows the reduction of neuronal aggregates in segmental nerves of *Drosophila* larvae by an exemplary compound.

The aberrant locomotion of kinesin mutants is highly correlated with the accumulation in axons of membranous debris derived from vesicles, mitochondria, synaptic membranes, and pre-lysosomal organelles (Hurd 1996; Horiuchi et al, Curr Biol 2005, 15(23):2137-2141). Compounds that suppress the locomotion defect may also suppress the appearance of these membranous aggregates. Treatment of larvae with exemplary Compound D reduced the total volume of axonal aggregates to 30% of the level seen in vehicle-treated controls (FIG. 2A). Reduction of the mass of membranous accumulations was not restricted to a particular size of aggregate. Thus, when aggregates were classified as small ($1\mu^3$<volume<$10\mu^3$), medium ($10\mu^3$<volume<$100\mu^3$), or large ($100\mu^3$<volume), reductions were observed for all three classes (FIG. 2B). This effect of Compound D is also indicated by a compound-induced shift in the frequency distribution of aggregate sizes towards smaller values (FIG. 2C).

The high levels of compounds in the medium on which larvae are raised (viz., 0.5 mM) are typical of Drosophila studies that explore drug effects (Micchelli 2003; Steffan et al, Nature 2001, 413(6857):739-743; Ferrante et al, J Neurosci 2003, 23(28):9418-9427; Pollitt et al, Neuron 2003, 40(4): 685-694; Moore et al, Cell 1998, 93(6):997-1007; Kang et al, Proc Natl Acad Sci USA 2002, 99(2):838-843; Pendleton et al, J Pharmacol Exp Ther 2002, 300(1):91-96; Mudher et al, Mol Psychiatry 2004, 9(5):522-530; Morfini et al, EMBO J. 2002, 21(3):281-293). Still, it is possible that the levels of compounds used in the experiments result in very high concentrations in the animals. To address this possibility, the levels of Compound D in hemolymph of larvae raised on media containing 0.5 mM compound were assayed by liquid chromatography-tandem mass spectrometry (LC-MS/MS). This concentration of Compound D suppressed motor dysfunction in 69% of khc/+; klc/+ larvae (FIG. 1) and reduced by 70% the mass of membranous aggregates in their segmental nerves (FIG. 2A). No trace of Compound D was observed in the hemolymph of larvae treated with DMSO vehicle, indicating negligible background signal in the LC-MS/MS assay. The concentration of Compound D in the hemolymph of compound-treated larvae averaged 228 nM; concentrations in the independently collected duplicate samples were 207 and 248 nM. That is, the concentration in hemolymph was less than $\frac{1}{2,000}^{th}$ the nominal concentration in the media. There existed an apparent metabolite of Compound D of greater molecular weight, suggesting modification (e.g., oxidation) of the parent compound. The signal from this single metabolite was equivalent to Compound D. Thus, the suppressor effects of Compound D and, by inference, its analogs, are determined to be observed at pharmacologically reasonable concentrations of compounds.

Compound D is one of several exemplary compounds that were tested for suppression of kinesin deficiency in Drosophila larvae, all of which showed positive effects (FIG. 1), suggesting that the compounds affect anterograde transport in motor axons. Since extension and maintenance of axons and their growth cones depend on anterograde transport of membrane-bound organelles, protein complexes, and mRNA-containing particles (Mochida Neurosci Res 2011, 70(1):16-23; Goldstein et al, Curr Opin Neurobiol 2008, 18(5):495-503), these exemplary compounds may promote neurite outgrowth of motor neurons. This was tested using motor neurons isolated from embryonic rat spinal cords.

Of the exemplary compounds that were shown to suppress the locomotion defect of kinesin-deficient Drosophila larvae, Compound A exhibited superior PK (pharmacokinetic) and ADMET (absorption, distribution, excretion, metabolism, toxicity) properties in rats and mice. Because of its attractive PK and ADMET properties, Compound A was further evaluated by examining the compound's effects on neurite outgrowth of rat spinal motor neurons. Two additional exemplary compounds that likewise exhibit attractive PK and ADMET properties, Compounds B and C, were tested alongside Compound A. Motor neurons isolated from spinal cords of E15 rat embryos were cultured for 3 days in the presence of the three exemplary compounds and morphometrically analyzed to quantify neurite lengths. All three compounds significantly stimulated axon outgrowth from the isolated motor neurons (FIG. 3); that is, the compounds exhibited axonotrophic activity.

Figure 4:
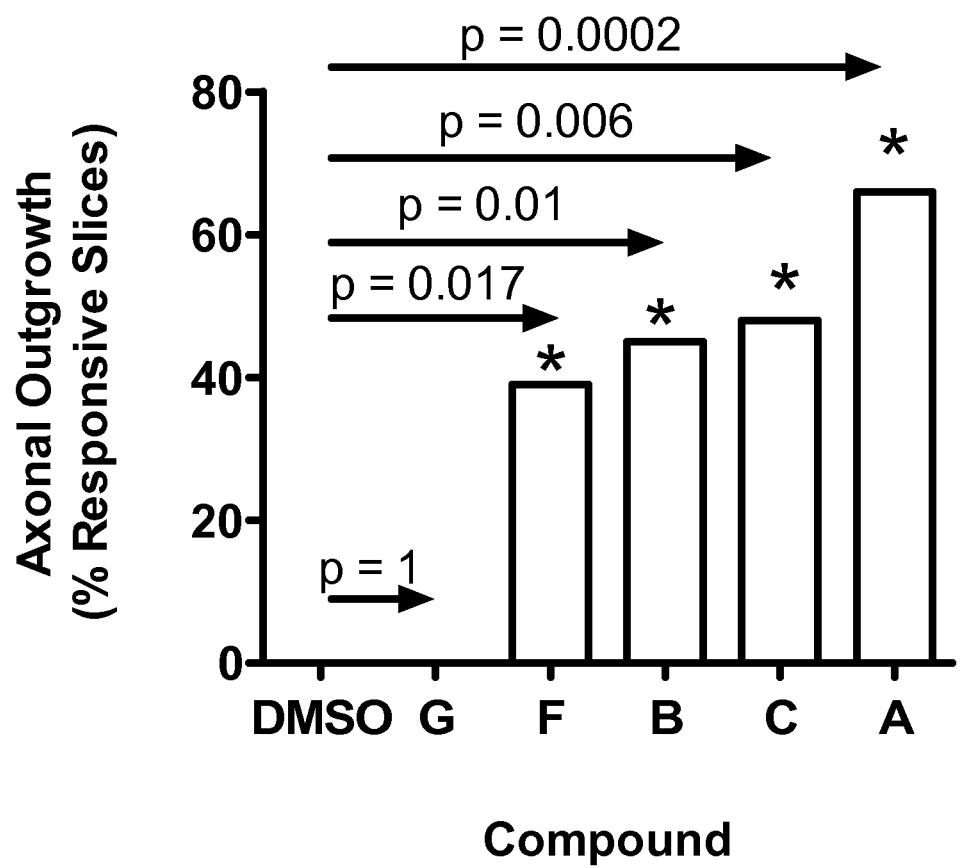
FIG. 4 illustrates the stimulatory effect of exemplary compounds on axonal outgrowth of motor neurons in cultured sections of rat spinal cord.

To evaluate the axonotrophic activity of the compounds on motor neurons in a more native biological context, organotypic spinal cord slices were treated with the same three exemplary compounds. Specifically, transverse sections of 8-day-old rat spinal cords were exposed to: exemplary Compounds A, B, or C; Compound G, which does not lower Aβ42 production or rescue locomotion of kinesin-deficient Drosophila larvae (FIG. 1); or DMSO vehicle. At least 15 individual spinal cord slices were treated with each compound. While no compound affected all slices treated with the compound, the exemplary compounds stimulated motor neuron outgrowth in a fraction of the treated slices (FIG. 4). In contrast, the DMSO vehicle and Compound G failed to affect any slice. Thus, each of the exemplary compounds exhibited detectable axonotrophic activity on motor neurons that reside in their native tissue environment. This result is particularly compelling given the inhibitory effects of the myelin component of spinal cord tissue on outgrowth of motor axons (Hannila and Filbin, Exp Neurol 2008 209(2):321-32).

SMA is caused by low levels of SMN protein (Monani, 2005), which can be modeled in zebrafish using antisense morpholino oligonucleotide (AMO) to decrease expression of Smn, the zebrafish homolog of human SMN protein (McWhorter et al, J Cell Biol 2003, 162(5):919-931). AMO-mediated reduction of Smn levels in zebrafish embryos results in motor axon defects such as truncation and aberrant branching, defects that are rescued by heterologous expression of human SMN. Such results indicate that the motor axon defects are indicative of low Smn levels and suggest that motor neuron development is abnormal when Smn levels are low (McWhorter 2003; Carrel et al, J Neurosci 2006, 26(43): 11014-11022; Beattie et al, J Child Neurol 2007, 22(8):995-1003). To evaluate the effects of the exemplary compounds on motor axon development in Smn-deficient zebrafish embryos, a known scoring algorithm was applied, in which individual embryos are classified according to the number of defective motor axons and the severity of the defects (Carrel 2006). Thus, an embryo is classified as severe, moderate, mild, or unaffected on the basis of its motor axon defects (Akten 2011).

Figure 5:
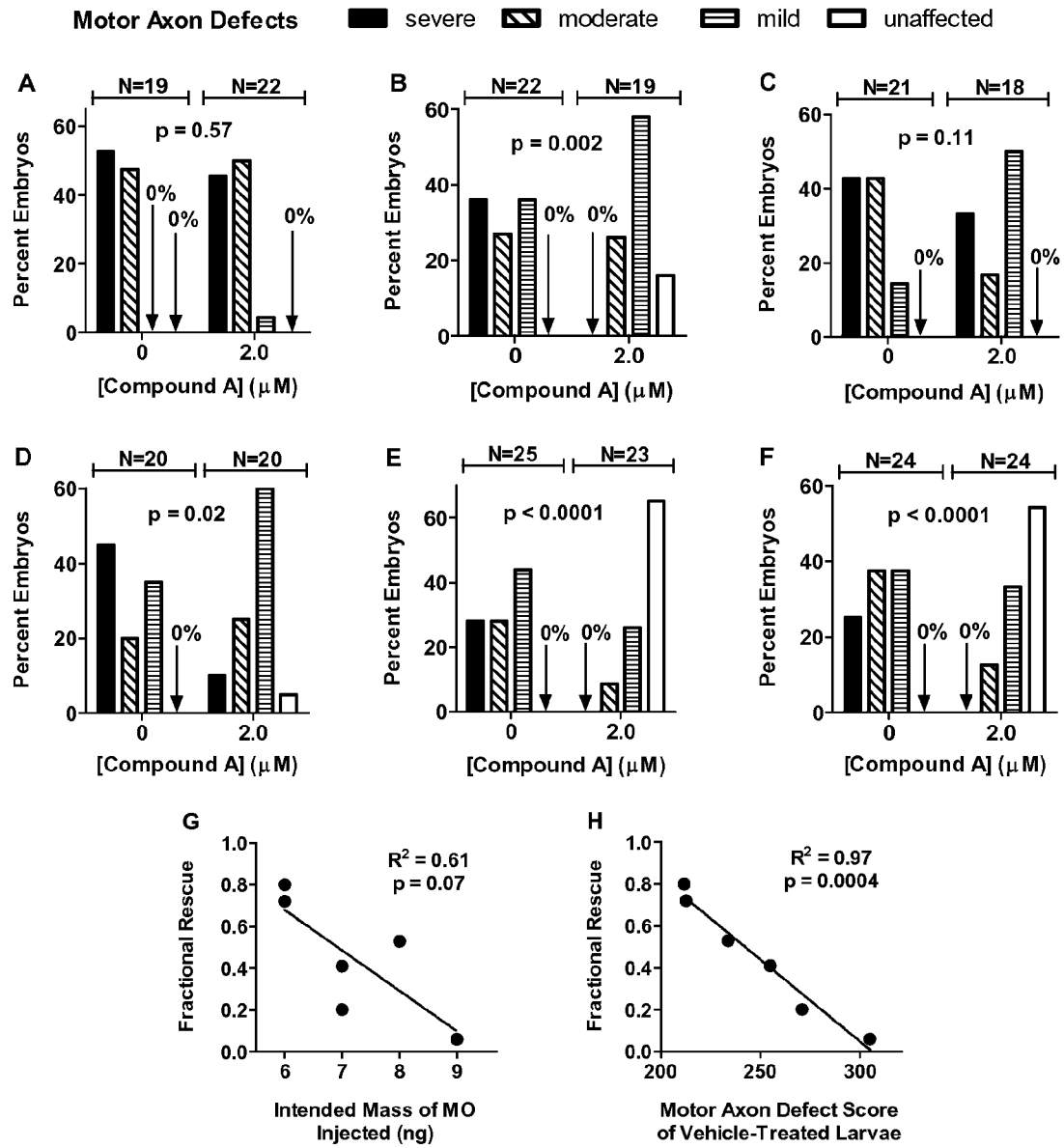
FIG. 5 illustrates the rescue of motor axon development in Smn-deficient zebrafish embryos by an exemplary compound.
Figure 6:
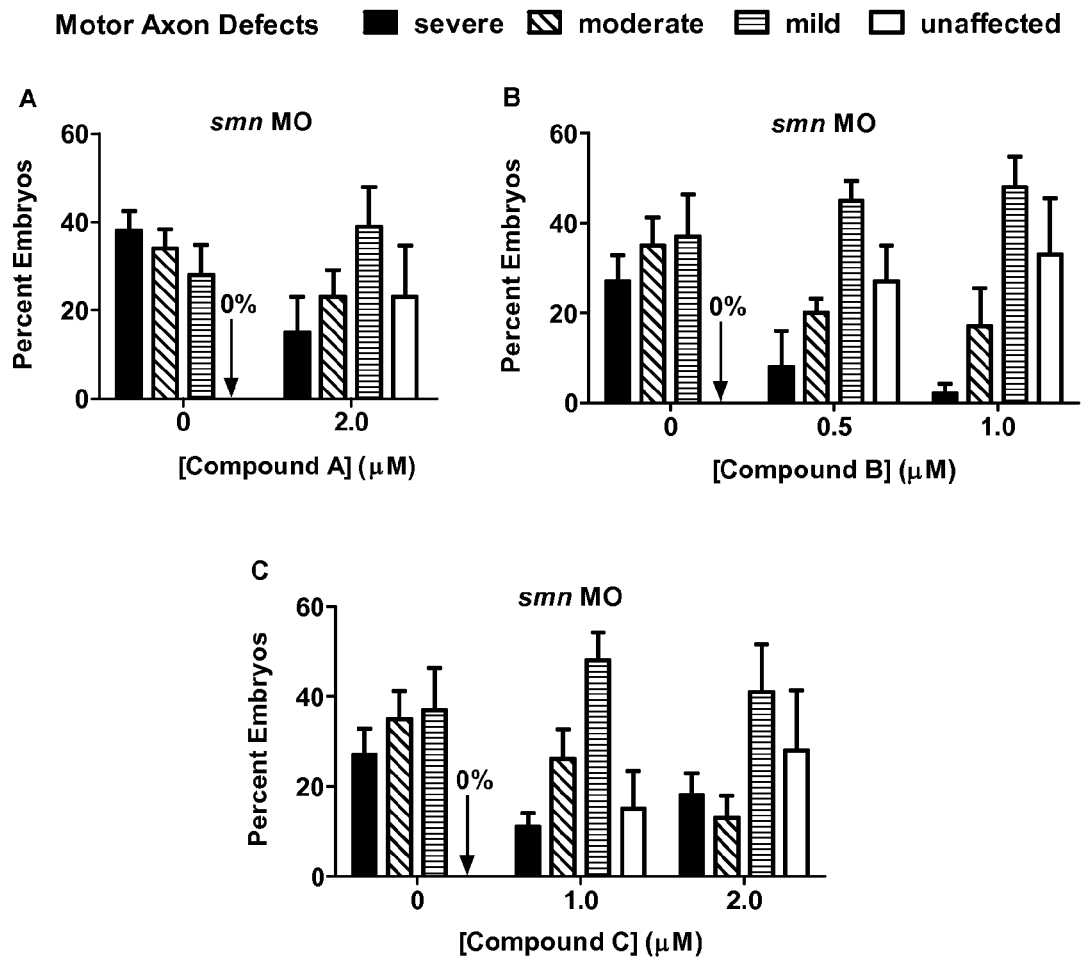
FIG. 6 illustrates the rescue of motor axon development in Smn-deficient zebrafish embryos by exemplary compounds.

The ability of exemplary Compound A to rescue normal development of motor axons in Smn-deficient embryos is illustrated in FIGS. 5 and 6. FIGS. 5A-F show results of the 6 experiments in which embryos were injected with Smn-reducing antisense morpholino (designated smn AMO) and allowed to develop in fish water containing either DMSO vehicle or Compound A from 10 to 28 hours post fertilization (hpf). In 4 of the 6 experiments, exposure of embryos to 2 μM Compound A resulted in a statistically significant redistribution of embryos among the severe, moderate, mild, or unaffected classes. Results averaged from the six experiments indicate that the compound significantly rescued the normal development of motor axons (FIG. 6A). The compound's effects are highlighted by considering embryos that were unaffected by Smn knockdown: among the 6 experiments, none of the 131 embryos exposed to DMSO vehicle were completely free of motor axon defects; in contrast 25% of compound-treated embryos (32 of 126) were unaffected.

To look at these data in more detail, a metric, Motor Axon Defect Score, was constructed to quantify the severity of motor axon defects. Motor Axon Defect Scores, in turn, were used to calculate the effectiveness of candidate suppressors, which were expressed as Fractional Rescue. A Fractional Rescue of 1 indicates the absence of any motor axon defects among compound-treated Smn-deficient embryos (that is, full rescue); a Fractional Rescue of 0 indicates equal motor axon defects between vehicle-treated and compound-treated Smn-deficient embryos (that is, no rescue). The Fractional Rescue was used to determine whether rescue was correlated with the dose of AMO or with the severity of the motor axon defects. The nominal amount of smn AMO injected into embryos varied from 6 to 9 ng among the experiments of FIGS. 5A-F. FIG. 5G plots the Fractional Rescue for Compound A as a function of the amount of smn AMO that was delivered in each experiment. Although there is a suggestion of an inverse correlation between the suppressor effect of Compound A and the nominal amount of smn AMO delivered, the slope of the linear regression is not significantly different from zero (p=0.07). Several factors, such as aging-dependent changes in AMO concentration and differing efficacies among batches of AMO, could obscure a relationship between suppression and the amount of AMO delivered. A stronger association exists between the suppressor effect of Compound A and the Motor Axon Defect Score of vehicle-treated embryos (FIG. 5H). This analysis indicates that 97% of the variance in the suppressor effect of Compound A among the experiments in FIG. 5A-F can be attributed to various severities of smn AMO-induced motor axon defects. Importantly, the analysis also indicates that the greater the severity of the smn AMO-induced motor axon defects, the less effective the compound is in suppressing those defects.

Exemplary compounds B and C, which are analogs of Compound A that likewise show axonotrophic activities on spinal motor neurons (FIGS. 3 and 4), were also tested for rescue of Smn knockdown. Compound C was tested at both 1 and 2 µM; Compound B, because of its lower maximum nontoxic dose in zebrafish, was tested at 0.5 and 1 µM. As shown in FIGS. 6B-C, both compounds rescued motor axon development. Again, the suppressor effects of the compounds are illustrated by considering the AMO-injected embryos that were completely free of motor axon defects: no such unaffected embryos were among the 99 embryos exposed to DMSO vehicle; in contrast 30% of embryos treated with 1 µM Compound B (29 of 95) and 31% of embryos treated with 2 µM Compound C (27 of 88) were free of motor axon defects. Taken together, these data show that all three exemplary compounds alleviate the motor axon defects caused by low levels of Smn.

The exemplary compounds that rescued motor axon development in the zebrafish SMA model are modifiers of Aβ metabolism (U.S. Pat. No. 7,678,823). One likely target of the compounds is γ-secretase, the enzyme complex responsible for production of Aβ peptides by proteolysis of APP. Since Notch, a protein critical for tissue development and homeostasis (Penton et al, *Semin Cell Dev Biol* 2012, 23(4):450-457), is another substrate of γ-secretase, compounds that target γ-secretase can have teratogenic or carcinogenic effects (Barten et al, *Drugs R D* 2006, 7(2):87-97). For this reason, developers of pharmaceuticals for Alzheimer's disease have expended efforts to identify compounds that modify γ-secretase-mediated processing of APP without affecting the enzyme's processing of Notch (Bulic et al, *Curr Neuropharmacol* 2011, 9(4):598-622). The pediatric nature of SMA magnifies concerns of the exemplary compounds' potential for detrimental effects on development.

The formation of somite borders in zebrafish larvae requires proper processing of Notch by γ-secretase, and the regularity of these somite boundaries provides a sensitive, in vivo indicator of accurate Notch processing (Holley *Dev Dyn* 2007, 236(6):1422-1449; Julich et al, *Dev Biol* 2005, 286(2): 391-404; Jiang et al, *Nature* 2000, 408(6811):475-479; Gossler et al, *Curr Top Dev Biol* 1998, 38:225-287). At the concentrations that rescued motor axon development in Smn-deficient embryos, no effect of Compounds A, B and C on the somite borders of normal larvae was found. Indeed, irregular somite boundaries were never observed at concentrations below their toxic thresholds, which are at least twice the concentrations tested on Smn-deficient embryos. In contrast, treatment with 32 µM DAPT, which has been shown to alter Notch processing in zebrafish (Geling et al, *EMBO Rep* 2002, 3(7):688-694), consistently disrupted the regularity of somite boundaries. Thus, the exemplary compounds' rescue of motor axon development is not associated with altered Notch processing.

Agents that discriminately modify the processing of APP by γ-secretase without affecting its activity on Notch have been designated γ-secretase modulators (Wolfe *J Neurochem* 2012, 120 Suppl 1:89-98). Thus, γ-secretase modulators are pharmacologically distinct from conventional γ-secretase inhibitors such as DAPT, which affect processing of all γ-secretase substrates. If Compounds A, B and C were γ-secretase modulators, it would reconcile the compounds' inactivity on Notch processing in zebrafish with their disclosed effects on Aβ metabolism (U.S. Pat. No. 7,678,823). It would also rationalize the results shown in FIG. 1, where the compounds and DAPT have qualitatively different effects on locomotion of kinesin-deficient *Drosophila* larvae. In summary, these observations are consistent with the exemplary suppressor compounds behaving as γ-secretase modulators.

These results collectively indicate that the exemplary compounds promote the growth and function of motor axons. Of specific relevance to motor neuropathies, three of the exemplary compounds rescued development of motor axons in a zebrafish model of SMA. These findings suggest that the exemplary compounds may be useful as candidate SMA therapeutics in particular and more generally as axonotrophic agents for the treatment of additional neuropathies.

*Drosophila* larvae that are deficient in functional kinesin are relevant to human motor neuropathies (Djagaeva et al, *Genetics* 2012 192(1):173-83). Mutations in Kif5A, the human ortholog of *Drosophila* Khc, can cause both CMT2 and the SPG10 form of HSP (Blair et al, *Neurogenetics* 2006, 7(1):47-50; Crimella et al, *Clin Genet.* 2012, 82(2):157-164; Fichera et al, *Neurology* 2004, 63(6):1108-1110; Reid et al, *Am J Hum Genet.* 2002, 71(5):1189-1194; Salinas et al, *Lancet Neurol* 2008, 7(12):1127-1138). Like kinesin-deficient *Drosophila*, patients who suffer from CMT2 or the SPG10 form of HSP exhibit dystrophic axon termini, reduced axonal transport, and accumulation of axonal aggregates, all of which precede distal neuropathy (Hurd 1996; Salinas 2008; Saxton et al, *Cell* 1991, 64(6):1093-1102; Gho et al, *Science* 1992, 258(5080):313-316; Tarrade et al, *Hum Mol Genet.* 2006, 15(24):3544-3558). Clearly, kinesin-deficient *Drosophila* models these diseases.

The relevance of kinesin-deficient *Drosophila* to motor neuropathies extends beyond diseases caused by mutant kinesin to other diseases in which axonal transport is compromised and axonal swellings are observed. These diseases include ALS (Delisle et al, *J Neurol Sci* 1984, 63(2):241-250; De Vos et al, *Hum Mol Genet.* 2007, 16(22):2720-2728; Takahashi et al, *Acta Neuropathol* 1997, 94(3):294-299; Rao et al, *Neurochem Res* 2003, 28(7):1041-1047; Okamoto et al, *Acta Neuropathol* 1990, 80(2):222-226; Magrané et al, *Antioxid Redox Signal.* 2009, 11(7):1615-26; Perlson et al, *Trends*

Neurosci 2010, 33(7):335-44), Huntington's disease (Morfini et al, *Nat Neurosci* 2009, 12(7):864-871; Gunawardena et al, *Arch Neurol* 2005, 62(1):46-51; Trushina et al, *Mol Cell Biol* 2004, 24:8195-8209; Perlson 2010), Parkinson's disease (Chung et al, *J Neurosci* 2009, 29(11):3365-3373; Mattila et al, *Acta Neuropathol* 1999, 98(2):157-164; Perlson 2010), forms of HSP in addition to SPG10 (Tarrade 2006; Kasher et al, *J Neurochem* 2009, 110(1):34-44; Salinas 2008), SMA (Dale et al, *Acta Neuropathol* 2011, 122(3):331-341; McGovern et al, *Hum Mol Genet.* 2008, 17(18):2900-2909; Martinez-Hernandez et al, *J Pathol* 2012, 229(1):49-61; Rao 2003), SCA3 (Seidel et al, *Acta Neuropathol* 2010 120(4): 449-60; Gunawardena 2005; Gunawardena et al, *Neuron* 2003 40(1):25-40; Feany and La Spada *Neuron* 2003 40(1): 1-2), SCA6 (Takahashi et al, *Neuropathology* 2012 32(6): 595-603; Ishiguro et al, *Acta Neuropathol* 2010 119(4):447-64; Seidel et al, *Clin Neuropathol* 2009 28(5):344-9; Ishikawa et al, *Neurology* 2001 56(12):1753-6), SCA5 (Dick et al, *Handb Clin Neurol* 2012, 103:451-9; Lorenzo et al, *J Cell Biol* 2010 189(1):143-58), SBMA (Katsuno et al, *Prog Neurobiol* 2012, 99(3):246-56; Kemp et al, *Hum Mol Genet.* 2011, 20(22):4475-90; Kikuchi et al, *Acta Neuropathol* 2000, 99(1):63-6), dystonia musculorum (De Repentigny et al, *PLoS One* 2011, 6(6):e21093; Bernier et al, *Dev Genet.* 1998, 22(2):160-8), FTDP-17 (Zhang et al, *J Neurosci* 2004 24(19): 4657-67; Hong et al, *Science* 1998 282(5395):1914-7), MS (Ferguson et al, *Brain* 1997, 120(Pt 3):393-399; Anderson et al, *Brain* 2008, 131(Pt 7):1736-1748; Shriver and Dittel, *Am J Pathol* 2006, 169(3):999-1011), FTLD/FTD (Ghazi-Noori et al, *Brain* 2012, 135(Pt 3):819-832; Ittner et al, *Proc Natl Acad Sci USA* 2008 105(41):15997-6002; Martinaud et al, *Acta Neuropathol* 2005, 110(1):84-92), SCI (Beirowski et al, *J Neuropathol Exp Neurol* 2010, 69(5):455-72; Nashmi and Fehlings, *Neuroscience* 2001, 104(1):235-51), and Alzheimer's disease (Rao 2003; Dickson et al, *Exp Neurol* 1999, 156(1):100-110; Stokin et al, *Science* 2005, 307(5713):1282-1288; Perlson 2010). It is notable that, while Alzheimer's disease, multiple sclerosis, and frontotemporal lobar degeneration are not conventionally classified as motor neuropathies, they often have some degree of motor involvement. Such considerations emphasize the relevance of kinesin-deficient *Drosophila*, with their motor dysfunction, axonal swellings, and compromised axonal transport, to all of the diseases listed above.

Further, the axonotrophic characteristics of the exemplary compounds suggest they can be used as therapeutics for spinal cord injury (SCI). Particularly relevant to their potential as SCI therapeutics is ability of the compounds to stimulate growth of motor axons in spinal cord slices (Example 17 and FIG. 4), where the presence of myelin normally inhibits axonal growth (Chaudhry et al, *J Cereb Blood Flow Metab,* 2007 27(6):1096-107). The inhibitory effect of myelin on axonal growth is a factor responsible for the inability of axons to regenerate after SCI. Without being bound by theory, the compounds herein disclosed appear to block the inhibitory effect of myelin on axonal growth. This characteristic, together with their ability to stimulate neurite outgrowth from isolated motor neurons (Example 16 and FIG. 3), indicates their potential to promote recovery from the neurological damage of SCI.

Disclosed herein is evidence that certain of the exemplary compounds rescue normal locomotion of kinesin-deficient *Drosophila* larvae, promote neurite outgrowth of isolated spinal motor neurons, stimulate motor neuron growth in cultured spinal cord sections, and rescue motor axon development in Smn-deficient zebrafish. These findings have particular relevance for the development of SMA therapeutics and general relevance for the treatment of neuropathies that involve dysfunctional motor neurons.

Compounds and Methods of Treatment

In an embodiment, exemplary compounds include compounds having the structure shown below in Formula (XVII):

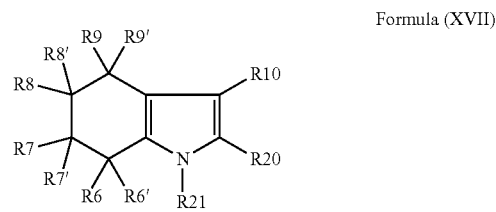

Formula (XVII)

In Formula (XVII), the bonds from the saturated ring to the substituents R6, R6', R7, R7', R8, R8', R9 and R9' are not intended to show any chirality unless otherwise noted, although they each may independently be chiral. All chiral conformations and combinations thereof are included in the compounds of Formula (XVII). For example, the R-group pair R6 and R6' are both attached to the same carbon in the saturated ring, but no chirality is indicated. When different substituents are recited for the R-group pairs, there is no chirality assumed or intended by the order of recitation, although all conformations are included. Some of the compounds of Formula (XVII) for use in the invention may exist as single stereoisomers (i.e., essentially free of other stereoisomers), racemates, and/or mixtures of enantiomers and/or diastereomers. All such single stereoisomers, racemates and mixtures thereof are intended to be within the scope of the present invention. Furthermore, some of the compounds for use in the invention can exist as cis and trans geometric isomers, and all such isomers and mixtures thereof are intended to be within the scope of the present invention.

In the compounds of Formula (XVII), the groups labeled R6-R10 are independently selected from at least one of hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$ alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, and —NO$_2$. For example, R6 and R6' may be hydro; R7 and R7' may independently be hydro, methyl, ethyl or trifluoromethyl; R8 and R8' may independently be hydro, methyl, tert-butyl, 1,1-dimethylpropyl, trifluoromethyl, cyclohexyl or methyl; R9 and R9' may independently be hydro or trifluoromethyl, and R10 may be hydro.

In certain embodiments, R6 and R6' are hydro, R7, R7', R8 and R8' are independently selected from at least one of hydro, alkyl and haloalkyl, R9 is alkyl or haloalkyl, R9' is hydro, and R10 is hydro. In further embodiments, R6, R6', R7, R7', R8, R9, R9' and R10 may be hydro and R8' is 1,1-dimethylpropyl or trifluoromethyl.

In the compounds of Formula (XVII), the group labeled R20 is aryl or heteroaryl, each of which may be optionally substituted. For example, R20 may be phenyl, 3,4-dichlorophenyl, 4-morpholin-4-yl-phenyl, 2-benzofuran-2-yl, 4-trifluoromethylphenyl, 2,4-dimethoxyphenyl, 3,4-dimethoxyphenyl, or 3-chlorophenyl. In an embodiment, R20 is aryl or benzofuranyl. In an embodiment, R20 is phenyl or 3,4-dichlorophenyl.

In the compounds of Formula (XVII), the group labeled R21 is heteroaryl, which optionally may be substituted, and which may be joined to the nitrogen atom via any appropriate position of the heteroaryl ring. For example, R21 may be furan-2-carboxylic acid, thiazol-4-yl acetic acid, picolinic acid, nicotinic acid, isonicotinic acid, pyrimidine-4-carboxylic acid, 1H-pyrrole-2-carboxylic acid, furan-2-carboxylic acid methyl ester, thiazole-4-carboxylic acid, or 4H-[1,2,4]triazol-3-yl. In an embodiment, R21 is heteroaryl substituted with a carboxy or a carboxyalkyl. In certain embodiments, R21 is furan-2-carboxylic acid or thiazol-4-yl acetic acid.

The compounds of Formula (XVII) include pharmaceutically-acceptable salts thereof.

In certain embodiments, when R9 is OH, R9' is hydro, and R7 and R7' are each methyl, R21 is not 3-pyridyl. Particularly, R9 can be OH, R9' can be hydro, and R7 and R7' can each be methyl in the compounds of Formula XVII, with the proviso that when R9 is OH, R9' is hydro, and R7 and R7' are each methyl, the compound of Formula XVII is not 6,6-dimethyl-2-phenyl-1-(pyridin-3-yl)-4,5,6,7-tetrahydro-1H-indol-4-ol.

In certain embodiments, when R6, R6', R7, R7', R8, R8', R9, R9' and R10 are all hydro and R20 is unsubstituted phenyl, R21 is not 3-pyridyl. Particularly, R6, R6', R7, R7', R8, R8', R9, R9' and R10 can all be hydro and R20 can be unsubstituted phenyl in the compounds of Formula XVII, with the proviso that when R6, R6', R7, R7', R8, R8', R9, R9' and R10 are all hydro and R20 is unsubstituted phenyl, the compound of Formula XVII is not 2-phenyl-1-(pyridin-3-yl)-4,5,6,7-tetrahydro-1H-indole.

In an embodiment, exemplary compounds include compounds having the structure of Formula (XVII) wherein R6, R6' and R10 are hydro, R7, R7', R8 and R8' are independently selected from at least one of hydro, alkyl and haloalkyl, R9 is alkyl or haloalkyl, R9' is hydro, R20 is aryl or benzofuranyl, and R21 is heteroaryl. In certain embodiments, exemplary compounds include compounds having the structure of Formula (XVII) wherein R6, R6', R7, R7', R8, R9, R9' and R10 are hydro, R8' is 1,1-dimethylpropyl or trifluoromethyl, R20 is phenyl or 3,4-dichlorophenyl, and R21 is furan-2-carboxylic acid or thiazol-4-yl acetic acid.

Exemplary compounds of Formula (XVII) and analogs thereof include the compounds shown in Table 10.

TABLE 10

Exemplary compounds of Formula (XVII) and analogs thereof

| compound structure | compound name | ref. to earlier Tables | compound abbrev. |
|---|---|---|---|
| 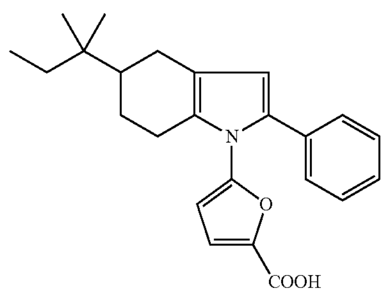 [SMILES: CCC(C)(C)C1CCc2c(cc(-c3ccccc3)n2-c2ccc(C(=O)O)o2)C1] | 5-[5-(1,1-dimethyl-propyl)-2-phenyl-4,5,6,7-tetrahydro-indol-1-yl]-furan-2-carboxylic acid | 8, 9 | A |
| 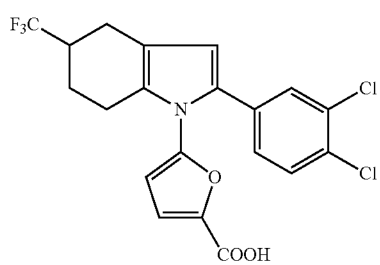 [SMILES: O=C(O)c1ccc(-n2c(-c3ccc(Cl)c(Cl)c3)cc3c2CCC(C(F)(F)F)C3)o1] | 5-[2-(3,4-dichloro-phenyl)-5-trifluoromethyl-4,5,6,7-tetrahydro-indol-1-yl]-furan-2-carboxylic acid | 8, 9 | B |
| 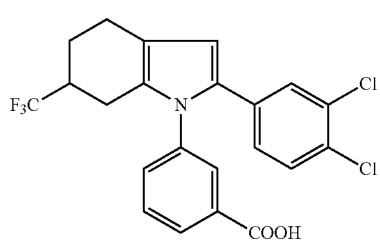 [SMILES: O=C(O)c1cccc(-n2c(-c3ccc(Cl)c(Cl)c3)cc3c2CC(C(F)(F)F)CC3)c1] | 3-[2-(3,4-dichloro-phenyl)-6-trifluoromethyl-4,5,6,7-tetrahydro-indol-1-yl]-benzoic acid | 6, 7 | C |

TABLE 10-continued

Exemplary compounds of Formula (XVII) and analogs thereof

| compound structure | compound name | ref. to earlier Tables | compound abbrev. |
|---|---|---|---|
| 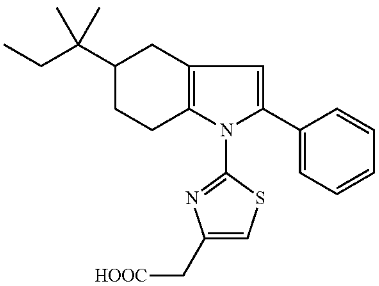 [SMILES: CCC(C)(C)C1CCc2c(cc(-c3ccccc3)n2-c2nc(CC(=O)O)cs2)C1] | {2-[5-(1,1-dimethylpropyl)-2-phenyl-4,5,6,7-tetrahydroindol-1-yl]-thiazol-4-yl}acetic acid | 8, 9 | D |
| 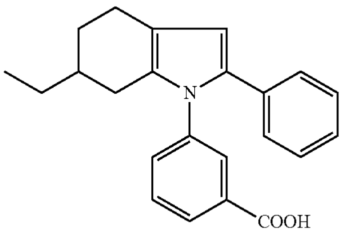 [SMILES: CCC1CCc2cc(-c3ccccc3)n(-c3cccc(C(=O)O)c3)c2C1] | 3-(6-ethyl-2-phenyl-4,5,6,7-tetrahydroindol-1-yl)benzoic acid | 6, 7 | E |
| 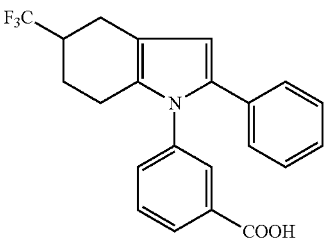 [SMILES: O=C(O)c1cccc(-n2c(-c3ccccc3)cc3c2CCC(C(F)(F)F)C3)c1] | 3-(2-phenyl-5-trifluoromethyl-4,5,6,7-tetrahydroindol-1-yl)benzoic acid | 6, 7 | F |
| 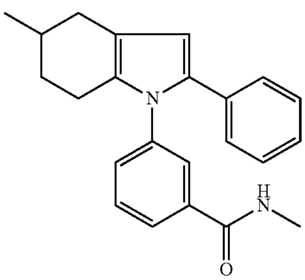 | N-methyl-3-(5-methyl-2-phenyl-4,5,6,7-tetrahydroindol-1-yl)benzamide | 6, 7 | G |
| 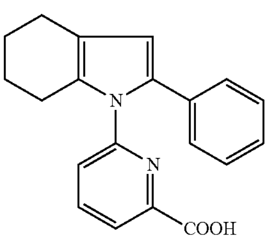 [SMILES: O=C(O)c1cccc(-n2c(-c3ccccc3)cc3c2CCCC3)n1] | 6-(2-phenyl-4,5,6,7-tetrahydro-1H-indol-1-yl)picolinic acid | 3 | H |
| 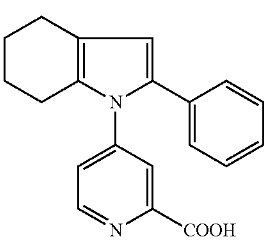 [SMILES: O=C(O)c1cc(-n2c(-c3ccccc3)cc3c2CCCC3)ccn1] | 4-(2-phenyl-4,5,6,7-tetrahydro-1H-indol-1-yl)picolinic acid | 3 | I |

TABLE 10-continued

Exemplary compounds of Formula (XVII) and analogs thereof

| compound structure | compound name | ref. to earlier Tables | compound abbrev. |
|---|---|---|---|
| 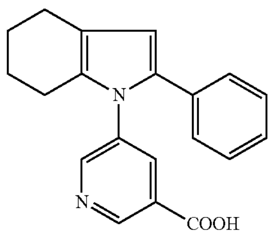 [SMILES: O=C(O)c1cncc(-n2c(-c3ccccc3)cc3c2CCCC3)c1] | 5-(2-phenyl-4,5,6,7-tetrahydro-1H-indol-1-yl) nicotinic acid | 3 | J |
| 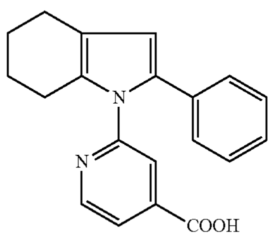 [SMILES: O=C(O)c1ccnc(-n2c(-c3ccccc3)cc3c2CCCC3)c1] | 2-(2-phenyl-4,5,6,7-tetrahydro-1H-indol-1-yl) isonicotinic acid | 3 | K |
| 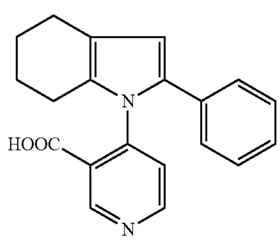 [SMILES: O=C(O)c1cnccc1-n1c(-c2ccccc2)cc2c1CCCC2] | 4-(2-phenyl-4,5,6,7-tetrahydro-1H-indol-1-yl) nicotinic acid | 3 | L |
| 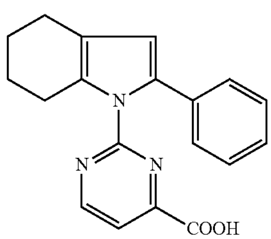 | 2-(2-phenyl-4,5,6,7-tetrahydro-1H-indol-1-yl) pyrimidine-4-carboxylic acid | 3 | M |
| 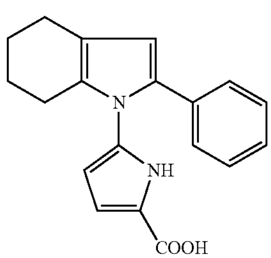 [SMILES: O=C(O)c1ccc(-n2c(-c3ccccc3)cc3c2CCCC3)[nH]1] | 5-(2-phenyl-4,5,6,7-tetrahydro-1H-indol-1-yl)-1H-pyrrole-2-carboxylic acid | 3 | N |
| 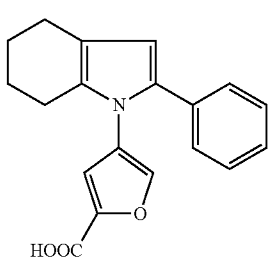 [SMILES: O=C(O)c1cc(-n2c(-c3ccccc3)cc3c2CCCC3)co1] | 4-(2-phenyl-4,5,6,7-tetrahydro-1H-indol-1-yl) furan-2-carboxylic acid | 3 | O |

TABLE 10-continued

Exemplary compounds of Formula (XVII) and analogs thereof

| compound structure | compound name | ref. to earlier Tables | compound abbrev. |
|---|---|---|---|
| 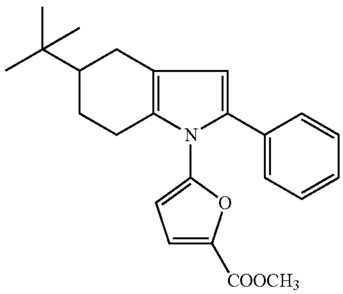 [SMILES: COC(=O)c1ccc(-n2c(-c3ccccc3)cc3c2CCC(C(C)(C)C)C3)o1] | 5-(5-tert-butyl-2-phenyl-4,5,6,7-tetrahydroindol-1-yl)furan-2-carboxylic acid methyl ester | 5, cmpd 133 | P |
| 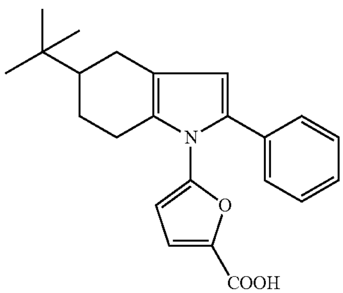 [SMILES: CC(C)(C)C1CCc2c(cc(-c3ccccc3)n2-c2ccc(C(=O)O)o2)C1] | 5-(5-tert-butyl-2-phenyl-4,5,6,7-tetrahydroindol-1-yl)furan-2-carboxylic acid | 5, cmpd 136; 6, 7 | Q |
| 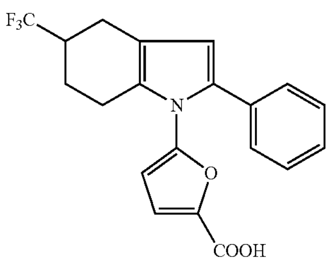 [SMILES: O=C(O)c1ccc(-n2c(-c3ccccc3)cc3c2CCC(C(F)(F)F)C3)o1] | 5-(2-phenyl-5-trifluoromethyl-4,5,6,7-tetrahydroindol-1-yl)-furan-2-carboxylic acid | 8, 9 | R |
| 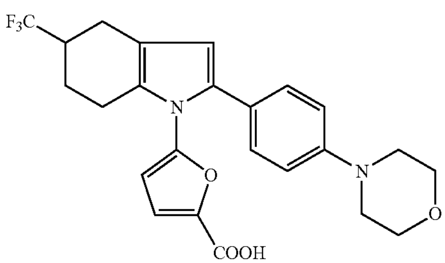 [SMILES: O=C(O)c1ccc(-n2c(-c3ccc(N4CCOCC4)cc3)cc3c2CCC(C(F)(F)F)C3)o1] | 5-[2-(4-morpholin-4-yl-phenyl)-5-trifluoromethyl-4,5,6,7-tetrahydroindol-1-yl]-furan-2-carboxylic acid | 8, 9 | S |
| 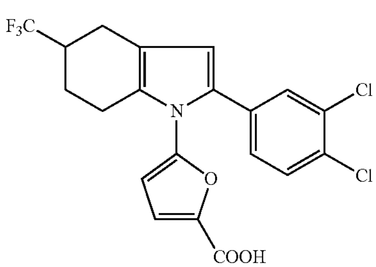 [SMILES: O=C(O)c1ccc(-n2c(-c3ccc(Cl)c(Cl)c3)cc3c2CCC(C(F)(F)F)C3)o1] | 5-[2-(3,4-dichlorophenyl)-5-trifluoromethyl-4,5,6,7-tetrahydroindol-1-yl]-furan-2-carboxylic acid | 8, 9 | T |

TABLE 10-continued

Exemplary compounds of Formula (XVII) and analogs thereof

| compound structure | compound name | ref. to earlier Tables | compound abbrev. |
|---|---|---|---|
| 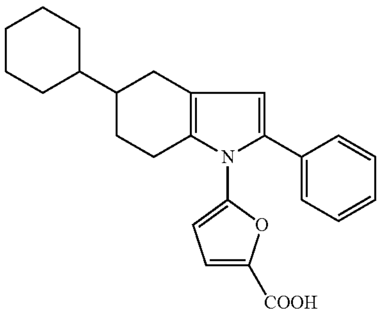 [SMILES: O=C(O)c1ccc(-n2c(-c3ccccc3)cc3c2CCC(C2CCCCC2)C3)o1] | 5-(5-cyclohexyl-2-phenyl-4,5,6,7-tetrahydroindol-1-yl)-furan-2-carboxylic acid | 8, 9 | U |
| 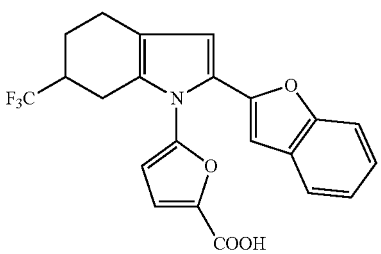 [SMILES: O=C(O)c1ccc(-n2c(-c3cc4ccccc4o3)cc3c2CC(C(F)(F)F)CC3)o1] | 5-(2-benzofuran-2-yl-6-trifluoromethyl-4,5,6,7-tetrahydroindol-1-yl)-furan-2-carboxylic acid | 8, 9 | V |
| 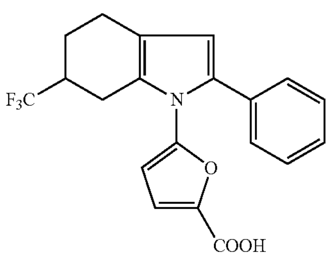 [SMILES: O=C(O)c1ccc(-n2c(-c3ccccc3)cc3c2CC(C(F)(F)F)CC3)o1] | 5-(2-phenyl-6-trifluoromethyl-4,5,6,7-tetrahydroindol-1-yl)-furan-2-carboxylic acid | 8, 9 | W |
| 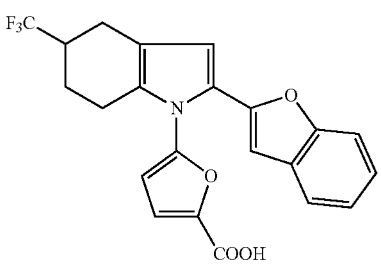 [SMILES: O=C(O)c1ccc(-n2c(-c3cc4ccccc4o3)cc3c2CCC(C(F)(F)F)C3)o1] | 5-(2-benzofuran-2-yl-5-trifluoromethyl-4,5,6,7-tetrahydroindol-1-yl)-furan-2-carboxylic acid | 8, 9 | X |
| 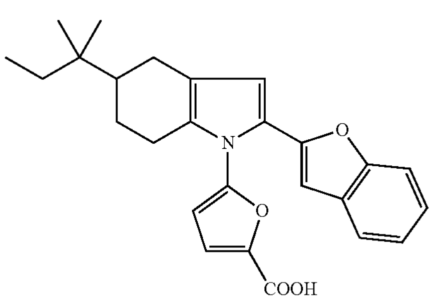 [SMILES: CCC(C)(C)C1CCc2c(cc(-c3cc4ccccc4o3)n2-c2ccc(C(=O)O)o2)C1] | 5-[2-benzofuran-2-yl-5-(1,1-dimethylpropyl)-4,5,6,7-tetrahydroindol-1-yl]-furan-2-carboxylic acid | 8, 9 | Y |

TABLE 10-continued

Exemplary compounds of Formula (XVII) and analogs thereof

| compound structure | compound name | ref. to earlier Tables | compound abbrev. |
|---|---|---|---|
| 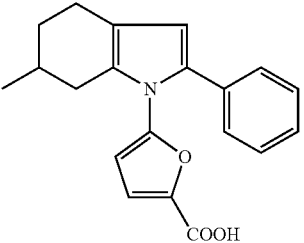 [SMILES: CC1CCc2cc(-c3ccccc3)n(-c3ccc(C(=O)O)o3)c2C1] | 5-(6-methyl-2-phenyl-4,5,6,7-tetrahydroindol-1-yl)furan-2-carboxylic acid | 8, 9 | Z |
| 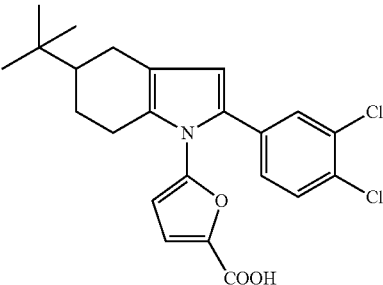 [SMILES: CC(C)(C)C1CCc2c(cc(-c3ccc(Cl)c(Cl)c3)n2-c2ccc(C(=O)O)o2)C1] | 5-[5-tert-butyl-2-(3,4-dichlorophenyl)-4,5,6,7-tetrahydroindol-1-yl]furan-2-carboxylic acid | 8, 9 | AA |
| 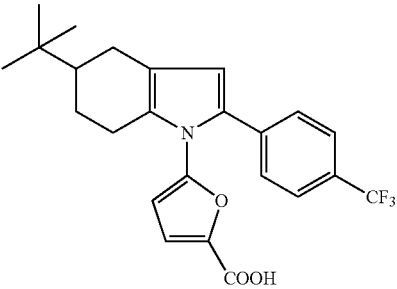 [SMILES: CC(C)(C)C1CCc2c(cc(-c3ccc(C(F)(F)F)cc3)n2-c2ccc(C(=O)O)o2)C1] | 5-[5-tert-butyl-2-(4-trifluoromethylphenyl)-4,5,6,7-tetrahydroindol-1-yl]furan-2-carboxylic acid | 8, 9 | AB |
| 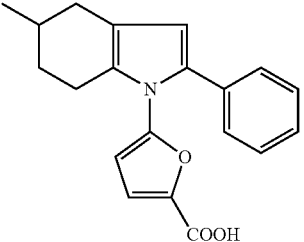 [SMILES: CC1CCc2c(cc(-c3ccccc3)n2-c2ccc(C(=O)O)o2)C1] | 5-(5-methyl-2-phenyl-4,5,6,7-tetrahydroindol-1-yl)furan-2-carboxylic acid | 8, 9 | AC |
| 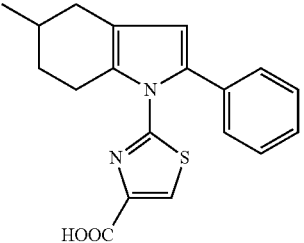 [SMILES: CC1CCc2c(cc(-c3ccccc3)n2-c2nc(C(=O)O)cs2)C1] | 2-(5-methyl-2-phenyl-4,5,6,7-tetrahydroindol-1-yl)thiazole-4-carboxylic acid | 8, 9 | AD |

TABLE 10-continued

Exemplary compounds of Formula (XVII) and analogs thereof

| compound structure | compound name | ref. to earlier Tables | compound abbrev. |
|---|---|---|---|
| 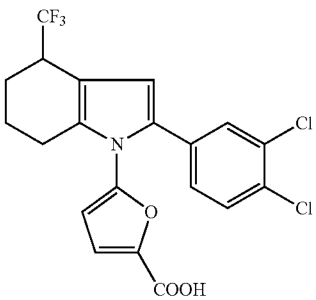 [SMILES: O=C(O)c1ccc(-n2c(-c3ccc(Cl)c(Cl)c3)cc3c2CCCC3C(F)(F)F)o1] | 5-[2-(3,4-dichlorophenyl)-4-trifluoromethyl-4,5,6,7-tetrahydroindol-1-yl]-furan-2-carboxylic acid | 8, 9 | AE |
| 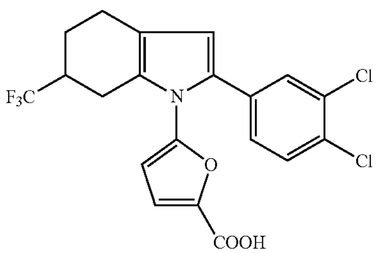 [SMILES: O=C(O)c1ccc(-n2c(-c3ccc(Cl)c(Cl)c3)cc3c2CC(C(F)(F)F)CC3)o1] | 5-[2-(3,4-dichlorophenyl)-6-trifluoromethyl-4,5,6,7-tetrahydroindol-1-yl]-furan-2-carboxylic acid | 8, 9 | AF |
| 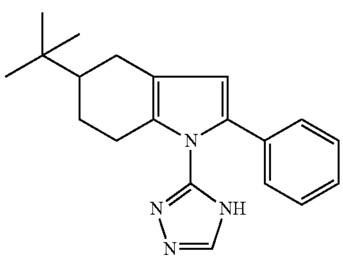 [SMILES: CC(C)(C)C1CCc2c(cc(-c3ccccc3)n2-c2nnc[nH]2)C1] | 5-tert-butyl-2-phenyl-1-(4H-[1,2,4]triazol-3-yl)-4,5,6,7-tetrahydro-1H-indole | 8, 9 | AG |
| 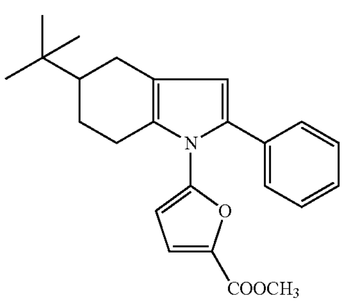 [SMILES: COC(=O)c1ccc(-n2c(-c3ccccc3)cc3c2CCC(C(C)(C)C)C3)o1] | 5-(5-tert-butyl-2-phenyl-4,5,6,7-tetrahydroindol-1-yl)furan-2-carboxylic acid methyl ester | 8, 9 | AH |
| 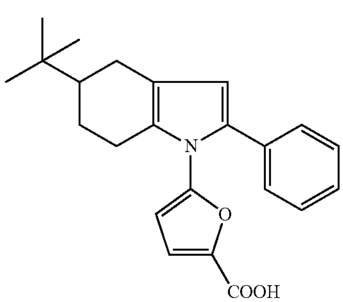 [SMILES: CC(C)(C)C1CCc2c(cc(-c3ccccc3)n2-c2ccc(C(=O)O)o2)C1] | 5-(5-tert-butyl-2-phenyl-4,5,6,7-tetrahydroindol-1-yl)furan-2-carboxylic acid | 8, 9 | AI |

TABLE 10-continued

Exemplary compounds of Formula (XVII) and analogs thereof

| compound structure | compound name | ref. to earlier Tables | compound abbrev. |
|---|---|---|---|
| (structure) | 2-[2-(2,4-dimethoxyphenyl)-5-trifluoromethyl-4,5,6,7-tetrahydroindol-1-yl]-thiazole-4-carboxylic acid | 8, 9 | AJ |
| (structure) | 2-[2-(3,4 dimethoxyphenyl)-5-trifluoromethyl-4,5,6,7-tetrahydroindol-1-yl]-thiazole-4-carboxylic acid | 8, 9 | AK |
| (structure) | {2-[2-(3-chlorophenyl)-5-(1,1-dimethylpropyl)-4,5,6,7-tetrahydroindol-1-yl]-thiazol-4-yl}acetic acid | 8, 9 | AL |

In an embodiment, exemplary compounds include
3-[2-(3,4-dichloro-phenyl)-6-trifluoromethyl-4,5,6,7-tetrahydro-indol-1-yl]-benzoic acid;
3-(6-ethyl-2-phenyl-4,5,6,7-tetrahydroindol-1-yl) benzoic acid;
3-(2-phenyl-5-trifluoromethyl-4,5,6,7-tetrahydroindol-1-yl) benzoic acid; and
N-methyl-3-(5-methyl-2-phenyl-4,5,6,7-tetrahydroindol-1-yl) benzamide, and pharmaceutically-acceptable salts of any of the foregoing.

In an embodiment, exemplary compounds include
5-[5-(1,1-dimethyl-propyl)-2-phenyl-4,5,6,7-tetrahydro-indol-1-yl]-furan-2-carboxylic acid;
5-[2-(3,4-dichloro-phenyl)-5-trifluoromethyl-4,5,6,7-tetrahydro-indol-1-yl]-furan-2-carboxylic acid;
{2-[5-(1,1-dimethylpropyl)-2-phenyl-4,5,6,7-tetrahydroindol-1-yl]-thiazol-4-yl}acetic acid;
6-(2-phenyl-4,5,6,7-tetrahydro-1H-indol-1-yl) picolinic acid;
4-(2-phenyl-4,5,6,7-tetrahydro-1H-indol-1-yl) picolinic acid;
5-(2-phenyl-4,5,6,7-tetrahydro-1H-indol-1-yl) nicotinic acid;
2-(2-phenyl-4,5,6,7-tetrahydro-1H-indol-1-yl) isonicotinic acid;
4-(2-phenyl-4,5,6,7-tetrahydro-1H-indol-1-yl) nicotinic acid;
2-(2-phenyl-4,5,6,7-tetrahydro-1H-indol-1-yl) pyrimidine-4-carboxylic acid;
5-(2-phenyl-4,5,6,7-tetrahydro-1H-indol-1-yl)-1H-pyrrole-2-carboxylic acid;
4-(2-phenyl-4,5,6,7-tetrahydro-1H-indol-1-yl) furan-2-carboxylic acid;
5-(5-tert-butyl-2-phenyl-4,5,6,7-tetrahydroindol-1-yl) furan-2-carboxylic acid methyl ester;
5-(5-tert-butyl-2-phenyl-4,5,6,7-tetrahydroindol-1-yl) furan-2-carboxylic acid;
5-(2-phenyl-5-trifluoromethyl-4,5,6,7-tetrahydroindol-1-yl)-furan-2-carboxylic acid;
5-[2-(4-morpholin-4-yl-phenyl)-5-trifluoromethyl-4,5,6,7-tetrahydroindol-1-yl]-furan-2-carboxylic acid;
5-[2-(3,4-dichlorophenyl)-5-trifluoromethyl-4,5,6,7-tetrahydroindol-1-yl]-furan-2-carboxylic acid;
5-(5-cyclohexyl-2-phenyl-4,5,6,7-tetrahydroindol-1-yl)-furan-2-carboxylic acid;
5-(2-benzofuran-2-yl-6-trifluoromethyl-4,5,6,7-tetrahydroindol-1-yl)-furan-2-carboxylic acid;
5-(2-phenyl-6-trifluoromethyl-4,5,6,7-tetrahydroindol-1-yl)-furan-2-carboxylic acid;
5-(2-benzofuran-2-yl-5-trifluoromethyl-4,5,6,7-tetrahydroindol-1-yl)-furan-2-carboxylic acid;
5-[2-benzofuran-2-yl-5-(1,1-dimethylpropyl)-4,5,6,7-tetrahydroindol-1-yl]-furan-2-carboxylic acid;

5-(6-methyl-2-phenyl-4,5,6,7-tetrahydroindol-1-yl) furan-2-carboxylic acid;
5-[5-tert-butyl-2-(3,4-dichlorophenyl)-4,5,6,7-tetrahydroindol-1-yl]furan-2-carboxylic acid;
5-[5-tert-butyl-2-(4-trifluoromethylphenyl)-4,5,6,7-tetrahydroindol-1-yl]furan-2-carboxylic acid;
5-(5-methyl-2-phenyl-4,5,6,7-tetrahydroindol-1-yl) furan-2-carboxylic acid;
2-(5-methyl-2-phenyl-4,5,6,7-tetrahydroindol-1-yl) thiazole-4-carboxylic acid;
5-[2-(3,4-dichlorophenyl)-4-trifluoromethyl-4,5,6,7-tetrahydroindol-1-yl]-furan-2-carboxylic acid;
5-[2-(3,4-dichlorophenyl)-6-trifluoromethyl-4,5,6,7-tetrahydroindol-1-yl]-furan-2-carboxylic acid;
5-tert-butyl-2-phenyl-1-(4H-[1,2,4]triazol-3-yl)-4,5,6,7-tetrahydro-1H-indole;
5-(5-tert-butyl-2-phenyl-4,5,6,7-tetrahydroindol-1-yl) furan-2-carboxylic acid methyl ester;
5-(5-tert-butyl-2-phenyl-4,5,6,7-tetrahydroindol-1-yl) furan-2-carboxylic acid;
2-[2-(2,4-dimethoxyphenyl)-5-trifluoromethyl-4,5,6,7-tetrahydroindol-1-yl]-thiazole-4-carboxylic acid;
2-[2-(3,4-dimethoxyphenyl)-5-trifluoromethyl-4,5,6,7-tetrahydroindol-1-yl]-thiazole-4-carboxylic acid;
{2-[2-(3-chlorophenyl)-5-(1,1-dimethylpropyl)-4,5,6,7-tetrahydroindol-1-yl]-thiazol-4-yl}acetic acid;
and pharmaceutically-acceptable salts of any of the foregoing.

In an embodiment, the exemplary compounds may be used in a method of treating a neurodegenerative disease or disorder associated with a defect in motor axonal growth or transport in a human patient comprising, identifying a patient in need of such treatment, and administering to said patient a therapeutically effective amount of the said exemplary compound. In some embodiments, the neurodegenerative disease or disorder associated with a defect in motor axonal growth or transport is SMA, CMT2, HSP, ALS, Huntington's disease, Parkinson's disease, SCA3, SCA6, SCA5, SBMA, dystonia musculorum, FTDP-17, MS, FTLD/FTD, and Alzheimer's disease. In certain embodiments, the neurodegenerative disease or disorder associated with a defect in motor axonal growth or transport is SMA.

Protected derivatives of the disclosed compounds also are contemplated. A variety of suitable protecting groups for use with the inventive compounds are disclosed. Other conventional protecting groups can be selected by those of skill in the art in consultation with Greene and Wuts, Protective Groups in Organic Synthesis; 3rd Ed.; John Wiley & Sons, New York, 1999.

The compounds of the present invention may be prepared in a variety of ways known to one skilled in the art of organic synthesis. The compounds of the present invention can be synthesized using the methods as described herein, together with synthetic methods known in the art of synthetic organic chemistry or variations thereon as appreciated by those skilled in the art.

The specific examples included herein are for illustrative purposes only and are not to be considered as limiting to this disclosure. Any active agents and reagents used in the following examples are either commercially available or can be prepared according to standard literature procedures by those skilled in the art of organic synthesis. In light of this disclosure, those of skill in the art will recognize that variations of these examples and other examples of the disclosed method would be possible without undue experimentation.

Example 15

Construction of *Drosophila* Strains: Reductions of kinesin function in *Drosophila* can result in a larval locomotion defect characterized by a rhythmic elevation of the tail due to paralysis of muscles in ventral posterior segments (Hurd et al, *Genetics* 1996, 142(1):195-204; Bowman et al, *Cell* 2000, 103(4):583-594). The phenotype is observed in animals with mutations in either the heavy or the light chains of kinesin-1 (formerly termed conventional kinesin), encoded by Khc and Klc, respectively. The severity and penetrance of the phenotype depends on the combination of mutant alleles carried by the larvae (Martin et al, *Mol Biol Cell* 1999, 10(11):3717-3728). Thus, khc/+; klc/+ double heterozygotes exhibit phenotypes that are intermediate between khc/khc or klc/klc homozygotes and single khc or klc heterozygotes. Furthermore, the severity of the phenotype of khc/+; klc/+ double heterozygotes depends on the particular alleles of Khc and Klc. A khc/+; klc/+ heterozygote was constructed that exhibits a penetrance of approximately 70%; it was presumed that the severity of the phenotype would be sufficiently low to be pharmacologically suppressible yet sufficiently high to allow discrimination of rescues with different efficacies. Such an intermediate penetrance also allows the formal possibility of identifying agents that exacerbate the locomotion defect. Thus, publicly available stocks of b[1] pr[1] Khc[8]/CyO cy and y[1] w[*]; T(2:3)B3 CyO; TM6B Tb[1]/Pin[88K] were used to obtain female b[1] pr[1] Khc[8]; T(2:3)B3 CyO; TM6B Tb[1] that were mated to male w[*]; Df(3L)8ex25/TM6B Tb[1] animals. The female wild-type Khc allele can be followed using the larval marker Tubby to distinguish it from the amorphic Khc[8] (http://flybase.org). The male wild-type Klc allele, which encodes the kinesin light chain, is also marked by Tubby, allowing it to be distinguished from the deletion that includes the Klc locus. The b[1] pr[1] Khc[8]; Df(3L)8ex25 larval progeny from this cross, identified by their normal (non-tubby) body shape, are the experimental khc/+; klc/+ double heterozygotes that are scored herein. Fly stocks were crossed and maintained at 25° C.; phenotypic assays were scored at room temperature.

Scoring of *Drosophila* Motor Phenotype: Experimental larvae were raised on Instant *Drosophila* Medium (Carolina Biological Supply, Burlington, N.C.) supplemented with 0.1% bromophenol blue and containing dimethyl sulfoxide (DMSO) alone or with test compounds dissolved in the DMSO vehicle. None of the test compounds had a discernible effect on larval development at the concentrations reported herein. The locomotion phenotype of non-tubby wandering third instar larvae was scored as either wild-type or uncoordinated, based on visual detection of the characteristic tail-flipping exhibited by kinesin-1 mutants (Hurd et al, *Genetics* 1996, 144(3):1075-1085). The person scoring the locomotion phenotype was unaware of the compound treatment of the animals.

As seen in FIG. 1, the results of khc/+; klc/+ larvae grown in the presence of vehicle alone (DMSO) or 0.5 mM of the indicated compounds were scored for motor dysfunction. The number of larvae scored for each treatment is indicated within the relevant bar. Results are expressed in terms of the number of larvae exhibiting no observable motor dysfunction (Wild-type) relative to the number with some degree of dysfunction (Affected). The extent of suppression of motor dysfunction is reflected by the heights of the bars relative to DMSO treatment. The Wild-type/Affected ratio for the vehicle condition reflects 60% penetrance of the locomotion defect. p values, calculated by application of Fisher's exact test to each experimental condition vs. DMSO, are shown. With the sequential Bonferroni method described by Holland (*Psychological Bulletin* 1988, 104(1):145-149) and Holm (*Scand J Stat* 1979, 6:65-67) to determine significance (*) at $\alpha=0.05$ (thereby accommodating multiple testing issues), the results indicate with 95% confidence that exemplary Compounds A, D, E and F rescue coordinated locomotion.

Measurements of Intraneuronal Aggregates: Immunostaining of segmental nerves of *Drosophila* larvae was performed as described (Hurd et al, *Genetics* 1996, 144(3):1075-1085). Experimental larvae were grown on Instant *Drosophila* Medium containing 0.5 mM Compound D or DMSO vehicle until the wandering third instar stage, when they were dissected in calcium-free buffer (128 mM NaCl, 2 mM KCl, 1 mM EGTA, 4 mM $MgCl_2$, 5 mM HEPES (pH 7.1)) and fixed in several changes of 4% paraformaldehyde. Larval pelts were then permeabilized with several washes of phosphate buffered saline (137 mM NaCl, 2.7 mM KCl, 10 mM $Na_2HPO_4$, 2 mM $KH_2PO_4$, pH7.4) containing 0.1% Triton X-100; stained overnight at 4° C. with rabbit anti-synaptotagmin (Santa Cruz Biotechnology, Santa Cruz, Calif.); labeled with fluorescein (FITC)-conjugated anti-rabbit antibody (Molecular Probes, Eugene, Oreg.); and mounted for confocal microscopy. Synaptotagmin labels synaptic vesicles, which can accumulate at sites within dysfunctional axons where membranous material is deposited to form structures that are variously termed axonal swellings, axonal spheroids, and neuritic beads. These synaptotagmin-marked, intraneuronal aggregates were imaged using FluoView® software on an Olympus FV1000 confocal laser scanning microscope (Olympus, Center Valley, Pa.). Images were taken from segmental nerves passing through larval segment A4 for standardization. A 60× oil immersion objective was used along with a 488 nm excitation laser optimized for detection of the FITC fluorophore. Z-series stacked images were obtained at a step size of 0.5 μm over a 10-30 μm range for each field. Raw z-stacks were then processed using Volocity® 3D Image Analysis Software (v 2.5, Improvision (PerkinElmer) Waltham, Mass.) to render 3-D images and calculate the volumes of synaptotagmin-positive objects. Only individual, distinct swellings that were also larger than 1 $\mu m^3$ were processed.

FIG. 2(A) depicts the volume of aggregates per unit length of nerve plotted for khc/+; klc/+ larvae raised on media containing DMSO(N=10 larvae) or 0.5 mM Compound D (N=14 larvae). Each data point represents one animal. The variance in the DMSO condition likely reflects incomplete penetrance (typical penetrance is about 0.7). Despite this variance, the mean values differ significantly (p<0.001, unpaired t test).

FIG. 2(B) shows the mean volumes of aggregates per unit length of nerve for three classes of aggregate sizes in DMSO-treated (N=10; white bars) and Compound D-treated (N=14; black bars) larvae. Aggregate volumes per length of nerve are significantly (*) lower in Compound D-treated larvae regardless of size class (t test with Bonferroni method to determine significance (Holland 1988; Holm 1979)).

FIG. 2(C) presents histograms of the volumes of the intraneuronal aggregates, with aggregates greater than 1 $\mu m^3$ distributed among 0.2 log unit-wide bins. The frequency distribution of the aggregates is shown for DMSO-treated (white bars; 3,359 objects) and Compound D-treated larvae (black bars; 3,551 objects). The differently scaled y-axis for bins containing the largest aggregates allows visual discrimination of histograms throughout the entire range of aggregate volumes. Exemplary Compound D significantly shifts the size distribution of aggregates to smaller volumes (Mann Whitney test; p<0.001).

Measurements in Hemolymph: Wild-type *Drosophila* larvae were raised on media containing 0.5 mM Compound D or DMSO (vehicle). Wandering third instar larvae that had recently (within 60 minutes) climbed from the media were collected, washed three times in phosphate buffered saline (PBS) containing 0.1% Tween 20 to remove compound that may adhere to the cuticle, and rinsed three times in PBS to remove both any remaining compound and residual Tween 20 from the washes. Washing steps consumed less than 20 minutes in total. Larvae were then dissected individually for collection of about 0.25 μl hemolymph per animal. Since their food was stained with bromophenol blue, larvae could be dissected without damaging the clearly visible gut, thus avoiding contamination of collected hemolymph with intestinal contents. The visible presence of food in the gut indicated that a reservoir of compound- or vehicle-containing media existed within the gut throughout the procedure. Approximately 50 μl of hemolymph were collected from experimental and from control larvae, diluted to 200 μl in PBS, and stored at −20 C until thawed for mass spectroscopic analysis. This was done with independent duplicate samples for both the experimental and control conditions, yielding a total of 4 samples that represented about 800 dissected larvae. Hemolymph samples were fortified with an internal standard, extracted with ethyl acetate, reconstituted, and subjected to liquid chromatography-tandem mass spectrometry (LC-MS/MS) analysis as follows. Extracted samples were injected onto a reversed phased liquid chromatography system (Shimadzu LC-10 with an Agilent Zorbax C-18, 50 mm×4.6 mm column) serving an AB Sciex API4000 QTrap mass spectrometer. The mass spectrometer operated a multiple reaction monitoring method in positive ion mode with an electrospray ionization source. Synthetic standards were used to generate a calibration curve and quality control samples in a PBS surrogate matrix. The quantitation range was 1-1000 ng/ml based on the analysis of 50 μl of diluted hemolymph. Back-calculated values for each calibration standard and quality control sample were within 15% of the theoretical concentration, and the coefficients of determination for the calibration curves were >0.99.

Example 16

Neurite Outgrowth of Rat Spinal Motor Neurons. Pregnant Wistar rats were sacrificed at 15 days gestation by cervical dislocation, fetuses were removed, and fetal spinal cords were dissected into ice-cold medium of Leibovitz (L15, Gibco), where their meninges were carefully removed. The spinal cords were dissociated by treatment with trypsin (Gibco) for 30 minutes at 37° C. in the presence of DNAse I (Boehringer Mannheim, France); proteolysis was terminated by addition of DMEM containing 10% fetal bovine serum (Gibco). The suspension was triturated using a 10 ml pipette and a needle syringe followed by centrifugation at 580×g for 10 min at room temperature (RT). The pellet of dissociated cells was resuspended in L15 medium, and the resulting suspension was centrifuged for 10 min at 180×g at RT on a layer of 3.5% solution of bovine serum albumin in L15 medium. The supernatant was discarded, the pellet was resuspended in L15 supplemented with 1% DNAase I, the suspension was layered on a cushion of Optiprep® (Abcys, France), and the preparation was centrifuged at 400×g for 25 min at RT. The upper phase, containing purified spinal motor neurons, was collected, resuspended in L15, and centrifuged at 800×g for 10 min at RT. The cell pellet was finally resuspended in a defined culture medium consisting of Neurobasal Medium® (Gibco) supplemented with 2% B27® Supplements (Gibco) and 5 mM L-glutamine (Gibco). Viable cells were counted in a Neubauer cytometer using the Trypan Blue exclusion test (Sigma-Aldrich). Approximately 30,000 purified rat spinal motor neurons were seeded on 35 mm dishes (Nunc) coated with poly-L-lysine, allowed to adhere for 2 hours, and treated for three days with the compounds, brain-derived neurotrophic factor (BDNF) as positive control, or DMSO vehicle at 37° C. in a humidified incubator with 5% $CO_2$-95% atmospheric air. The length of the longest unbranched neurite was determined for each of ~80 neurons for each condition. The 13 kd neurotrophin BDNF was tested at a concentration (3.7 nM) that has near-maximal effects on neurite outgrowth.

Figure 3:
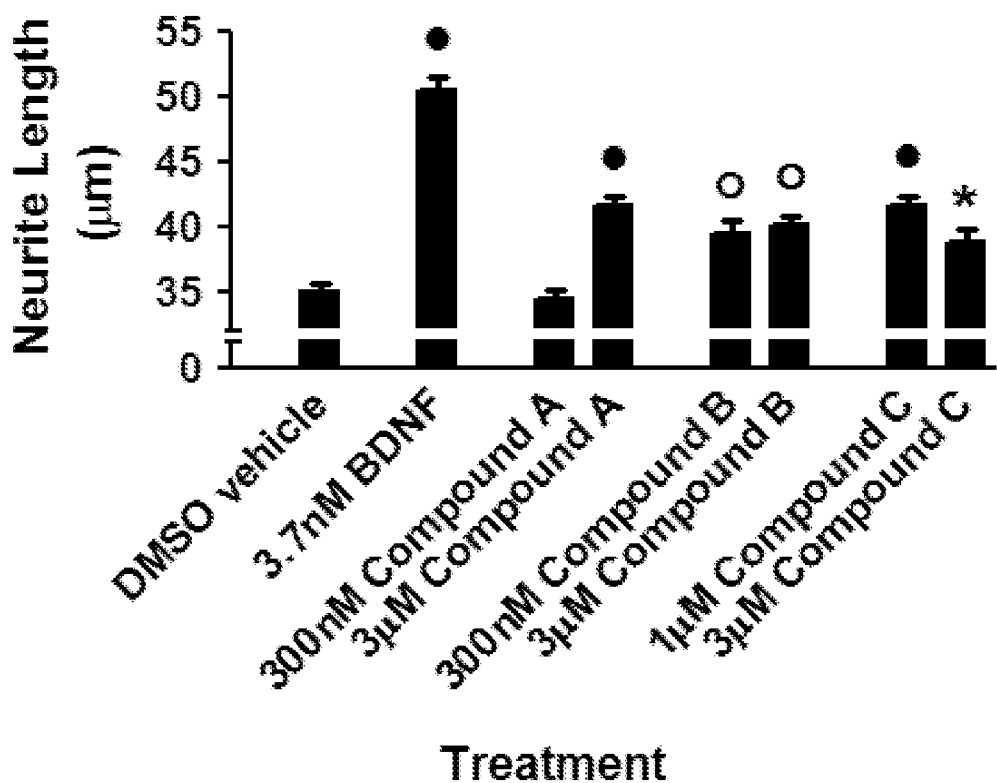
FIG. 3 illustrates the stimulation of neurite outgrowth in isolated rat spinal motor neurons in the presence of exemplary compounds.

FIG. 3 illustrates the stimulation of neurite outgrowth in rat spinal motor neurons in the presence of exemplary compounds. Primary cultures of rat embryonic spinal motor neurons were treated with BDNF at 3.7 nM and with Compounds A, B and C at the two indicated concentrations of each compound. One-way ANOVA with Dunnett's post test indicates that the positive control BDNF and each compound enhanced neurite outgrowth relative to DMSO vehicle (N=3 cultures; ●p<0.001; o p<0.01; * p<0.05).

Example 17

Organotypic Spinal Cord Slices. Spinal cord organotypic slice cultures were prepared from 8-day-old Sprague Dawley rats. Animals were euthanized and spinal cords removed under sterile conditions and placed in Gey's balanced salt solution (Sigma-Aldrich). Spinal cords were cut into 250 μm sections using a McIlwain Tissue Chopper, and the freshly cut spinal cords were placed into 0.4 μm tissue culture plate inserts (Millicell) inside 6 well plates pre-incubated with 1 mL of organotypic growth media [50% MEM (Gibco), 25% Hanks balanced salt solution (Gibco), 25% heat-inactivated horse serum (Gibco), 0.8% Hepes Buffer Solution (Gibco) supplemented with penicillin and streptomycin]. Cultures were maintained for 1 week (with 2 media changes) prior to treatment. The treatment groups were: no treatment, control (DMSO vehicle), and compound alone at a final concentration of 100 μM (10 μt of 10 mM stock into 1 mL of media) over 10 days. At least 3 wells (15 spinal cord slices) were used for each treatment. Over the 10 day treatment period, cultures were replenished with fresh media and/or compound 3 times. After 10 days of treatment, cultures were fixed in 4% paraformaldehyde, washed in PBS, and immunostained with antibody SMI-31, which stains a phosphorylated epitope in neurofilaments H and M, in order to visualize motor neurons. Culture slices were assessed for the morphology of axons of motor neurons (specifically axon lengths). Slices that showed evidence of motor axon extension were scored as responsive to treatment.

The fraction of spinal cord slices that were responsive to each treatment is shown in FIG. 4. Exemplary Compounds A, B, C, and F were observed to stimulate the extension of motor axon bundles in about 40% to about 60% of spinal cord slices. Notably, the structural analog Compound G, which failed to rescue locomotion of kinesin-deficient Drosophila (FIG. 1) and which does not lower Aβ42 production, resembled DMSO in showing no enhanced extension of the motor neurons in treated spinal cord slices. p values, calculated by application of Fisher's exact test to each experimental condition vs. DMSO, are shown. The effects of Compounds A, B, C, and F are statistically significant (*) at α=0.05 (Holland 1988).

Example 18

Selection of Test Concentrations in Zebrafish (Danio rerio). Selection of concentrations of small molecules for treating D. rerio Tg(mnx1:GFP) embryos that had been injected with antisense morpholino oligonucleotides (AMO) was guided by determinations of their maximum nontoxic concentrations (MTDs) in wild-type AB/Tübingen embryos and larvae. These MTDs were determined by exposing embryos to compound dissolved in egg water containing 0.25% DMSO or to the DMSO vehicle alone beginning at 4, 11, and 25 hours post-fertilization (hpf) and continuing exposure for 7 days; media was replaced with fresh media every 48 hours after initiation of exposure. The following parameters were monitored throughout the treatment period: morphology (gross body shape), viability (strength of escape reflex), growth (larval length), somite boundaries (regularity of borders between somites), swim bladder development (inflation of swim bladder), and pigmentation (level of pigmentation of yolk sac and yolk sac extension). Observed MTDs were not noticeably affected by dechorionation of the embryos. Based on these observations in wild-type embryos and larvae, AMO-injected Tg(mnx1: GFP) embryos with intact chorions were treated for a total of 18 hours, from 10 to 28 hpf, with Compounds A and C at 2 μM and with the slightly less tolerated Compound B at 1 μM. Compounds B and C were also tested at 50% lower concentrations (viz., 0.5 μM and 1 μM, respectively). As expected from the toxicity testing in wild-type embryos, these concentrations appeared nontoxic to AMO-injected Tg(mnx1: GFP) embryos.

Zebrafish Motor Axon Morphology: Zebrafish and embryos were maintained at 28.5° C. and staged by hours post-fertilization (hpf) (Westerfield, The Zebrafish Book. A Guide for the Laboratory Use of Zebrafish (Danio rerio), 3rd ed. Eugene, Oreg.: University of Oregon Press; 1995). Transgenic Tg(mnx1:0.6hsp70:GFP)os26 zebrafish embryos that express GFP in ventrally projecting motor axons (Dalgin et al, Development 2011, 138(21):4597-4608), referred to as Tg(mnx1: GFP) embryos, were used for all knockdown experiments. Specifically, using an MPPI-2 Pressure Injector (Applied Scientific Instrumentation, Eugene, Oreg.) and according to previous protocols (Carrel 2006), Tg(mnx1: GFP) embryos were injected at the one- to two-cell stage with the AMO CGACATCTTCTGCACCATTGGC (Gene Tools, Philomath, Oreg.) to knock down Smn as previously described (McWhorter 2003). At 10 hpf injected embryos were placed in egg water (60 μg/ml Instant Ocean® sea salts) containing compound or DMSO (0.25%) vehicle and incubated at 28.5° C. To visualize motor axons in GFP transgenic animals, Tg(mnx1: GFP) embryos at 28 hpf were anesthetized with tricaine and fixed overnight at 4° C. in 4% formaldehyde/PBS. After removing embryos from fix, their yolks and heads were removed and their trunks were mounted on glass coverslips for observation under a Zeiss Axioplan microscope. Motor axons innervating the mid-trunk (myotomes 6-15) on both sides of the fish were scored as described (Carrel 2006), which allowed each embryo to be classified as severe, moderate, mild, or unaffected according to previously described criteria based on the number and types of motor axon abnormalities (Akten 2011). The effectiveness of a compound in suppressing the aberrant motor axon morphologies is assessed as the compound's effect on the distribution of embryos among the severe, moderate, mild, or unaffected classes.

FIG. 5 shows the rescue of motor axon development in Smn-deficient zebrafish embryos by Compound A. In FIGS. 5A-F, zebrafish embyros that had been injected with Smn-reducing antisense morpholino (designated smn AMO) and treated with either DMSO vehicle or 2 μM Compound A were classified by degree of motor axon abnormalities. Distributions of embryos among the 4 classes of severity of motor axon dysmorphism are shown for the vehicle and Compound A conditions for each of 6 experiments. The p values comparing the two distributions were calculated for the individual experiments by the Mann-Whitney U test and are indicated in each graph along with the numbers of vehicle- and compound-treated embryos scored in that experiment. For any single embryo, approximately 20 axons were evaluated, resulting in about 400 axons scored for each of the control and experimental conditions in each experiment. The nominal mass of smn AMO injected varied among experiments: Expt. A: 9 ng; Expt.B: 8 ng; Expt.C: 7 ng; Expt.D: 7 ng; Expt.E: 6 ng; Expt.F: 6 ng. In FIGS. 5G-H, suppression of motor axon abnormalities in embryos injected with smn AMO by 2 µM Compound A is expressed in terms of Fractional Rescue, as described herein. The Fractional Rescues for the 6 individual experiments shown in FIGS. 5A-F are plotted as a function of two different measures of the amount of smn AMO delivered to the embryos: FIG. 5G shows the nominal, intended mass of injected AMO; FIG. 5H shows an amount of smn AMO reflected by the Motor Axon Defect score, a metric of the severity of motor axon abnormalities, of vehicle-treated embryos. Parameters of the linear regressions in each graph are indicated. The two experiments associated with the lowest Fractional Rescues (values of 0.2 and 0.06, corresponding to panels A and C, respectively) failed to show significant rescue of motor axon development by Compound A. FIG. 6 illustrates the rescue of motor axon development by axonotrophic compounds. The results with 2 µM Compound A were averaged across the experiments in FIGS. 5A-F for both the control (vehicle-treated embryos) and experimental conditions, and mean values are plotted along with SEM (N=6) in FIG. 6A. Compound A significantly reduced the severity of motor axon defects (p<0.0001, N=6; Mann-Whitney U test). FIG. 6B shows the suppression of Smn knockdown by Compound B, which was tested in 5 experiments, each of which examined 3 conditions: 0.5 µM Compound B (95 embryos scored among the 5 experiments, with about 20 embryos per experiment), 1 µM Compound B (95 embryos), and DMSO vehicle (99 embryos). Both concentrations of Compound B significantly reduce the severity of motor neuron dysmorphism (p<0.0001, N=5; Kruskal-Wallis one-way ANOVA). FIG. 6C shows the suppression of Smn knockdown by Compound C, which was tested in 5 experiments, each of which examined 3 conditions: 1 µM Compound C (88 embryos), 2 µM Compound C (88 embryos), and DMSO vehicle (99 embryos). Both concentrations of Compound C significantly reduce the severity of motor neuron dysmorphism (p<0.0001, N=5; Kruskal-Wallis one-way ANOVA).

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference. The mere mentioning of the publications and patent applications does not necessarily constitute an admission that they are prior art to the instant application.

Although the foregoing invention has been described in some detail by way of illustration and example for purposes of clarity of understanding, it will be obvious that certain changes and modifications may be practiced within the scope of the appended claims.

The invention claimed is:
1. A compound with the structure of Formula (XVII):

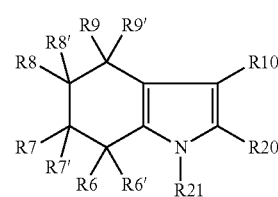

Formula (XVII)

wherein R6, R6', R7, R7', R8, R8', R9, R9' and R10 are independently selected from at least one of hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$ alkyl), —S(=O)$_2$NH$_2$, —S(=O)$_2$N (C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$;
R20 is aryl or heteroaryl; and
R21 is heteroaryl; or a pharmaceutically-acceptable salt thereof,
with the proviso that when R6, R6', R7, R7', R8, R8', R9, R9' and R10 are all hydro and R20 is unsubstituted phenyl, the compound is not 2-phenyl-1-(pyridin-3-yl)-4,5,6,7-tetrahydro-1H-indole; and
with the proviso that when R9 is OH, R9' is hydro, R7 and R7' are each methyl, and the compound is not 6,6-dimethyl-2-phenyl-1-(pyridin-3-yl)-4,5,6,7-tetrahydro-1H-indol-4-ol.

2. The compound of claim 1, wherein
R6, R6' and R10 are hydro,
R7, R7', R8 and R8' are independently selected from at least one of hydro, alkyl and haloalkyl,
R9 is alkyl or haloalkyl,
R9' is hydro,
R20 is aryl or benzofuranyl, and
R21 is heteroaryl.

3. The compound of claim 1, wherein
R6, R6', R7, R7', R8, R9, R9' and R10 are hydro,
R8' is 1,1-dimethylpropyl or trifluoromethyl,
R20 is phenyl or 3,4-dichlorophenyl, and
R21 is furan-2-carboxylic acid or thiazol-4-yl acetic acid.

4. The compound of claim 1, wherein the compound is selected from at least one of:
5-[5-(1,1-dimethylpropyl)-2-phenyl-4,5,6,7-tetrahydro-indol-1-yl]-furan-2-carboxylic acid;
5-[2-(3,4-dichloro-phenyl)-5-trifluoromethyl-4,5,6,7-tetrahydro-indol-1-yl]-furan-2-carboxylic acid; and
{2-[5-(1,1-dimethylpropyl)-2-phenyl-4,5,6,7-tetrahydroindol-1-yl]-thiazol-4-yl}acetic acid.

5. A composition comprising at least one compound of claim 1 and a pharmaceutically acceptable excipient.

6. A compound with the structure of Formula (XVII):

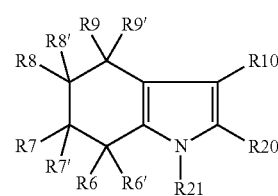

Formula (XVII)

wherein R6 and R6' are hydro;
R7, R7', R8, R8', R9 and R9' are independently selected from at least one of hydro, alkyl, haloalkyl, —CHF$_2$, —OCF$_3$, —OCHF$_2$, —SCF$_3$, —CF$_3$, —CN, —NH$_2$, and —NO$_2$;
R10 is hydro;
R20 is aryl or heteroaryl; and
R21 is heteroaryl; or a pharmaceutically-acceptable salt thereof,
with the proviso that when R6, R6', R7, R7', R8, R8', R9, R9' and R10 are all hydro and R20 is unsubstituted phenyl, the compound is not 2-phenyl-1-(pyridin-3-yl)-4,5,6,7-tetrahydro-1H-indole.

7. The compound of claim 6, wherein
R6, R6' and R10 are hydro,
R7, R7', R8 and R8' are independently selected from at least one of hydro, alkyl and haloalkyl,
R9 is alkyl or haloalkyl,
R9' is hydro,
R20 is aryl or benzofuranyl, and
R21 is heteroaryl.

8. The compound of claim 6, wherein
R6, R6', R7, R7', R8, R9, R9' and R10 are hydro,
R8' is 1,1-dimethylpropyl or trifluoromethyl,
R20 is phenyl or 3,4-dichlorophenyl, and
R21 is furan-2-carboxylic acid or thiazol-4-yl acetic acid.

9. The compound of claim 6, wherein the compound is selected from at least one of:
   5-[5-(1,1-dimethylpropyl)-2-phenyl-4,5,6,7-tetrahydro-indol-1-yl]-furan-2-carboxylic acid;
   5-[2-(3,4-dichloro-phenyl)-5-trifluoromethyl-4,5,6,7-tetrahydro-indol-1-yl]-furan-2-carboxylic acid; and
   {2-[5-(1,1-dimethylpropyl)-2-phenyl-4,5,6,7-tetrahydroindol-1-yl]-thiazol-4-yl}acetic acid.

10. A composition comprising at least one compound of claim 6 and a pharmaceutically acceptable excipient.

11. A method of treating a neurodegenerative disease or disorder associated with a defect in motor axonal growth or transport in a human patient comprising,
   identifying a patient in need of such treatment, and
   administering to said patient a therapeutically effective amount of a compound of claim 1,
   wherein the disease or disorder is selected from at least one of spinal muscular atrophy, Charcot-Marie-Tooth Type 2 disease, hereditary spastic paraplegia, amyotrophic lateral sclerosis, Huntington's disease, Parkinson's disease, spinocerebellar ataxia 3, spinocerebellar ataxia 6, spinocerebellar ataxia 5, spinobulbar muscular atrophy, dystonia musculorum, frontotemporal dementia with parkinsonism linked to chromosome 17, multiple sclerosis, frontotemporal lobar degeneration/frontotemporal dementia, spinal cord injury, or Alzheimer's disease.

12. A method of treating a neurodegenerative disease or disorder associated with a defect in motor axonal growth or transport in a human patient comprising,
   identifying a patient in need of such treatment, and
   administering to said patient a therapeutically effective amount of a compound of claim 6,
   wherein the disease or disorder is selected from at least one of spinal muscular atrophy, Charcot-Marie-Tooth Type 2 disease, hereditary spastic paraplegia, amyotrophic lateral sclerosis, Huntington's disease, Parkinson's disease, spinocerebellar ataxia 3, spinocerebellar ataxia 6, spinocerebellar ataxia 5, spinobulbar muscular atrophy, dystonia musculorum, frontotemporal dementia with parkinsonism linked to chromosome 17, multiple sclerosis, frontotemporal lobar degeneration/frontotemporal dementia, spinal cord injury, or Alzheimer's disease.

13. The method of claim 11, wherein said neurodegenerative disease or disorder associated with a defect in motor axonal growth or transport is spinal muscular atrophy.

14. The method of claim 12, wherein said neurodegenerative disease or disorder associated with a defect in motor axonal growth or transport is spinal muscular atrophy.

15. A method of treating a neurodegenerative disease or disorder associated with a defect in motor axonal growth or transport in a human patient comprising,
   identifying a patient in need of such treatment, and
   administering to said patient a therapeutically effective amount of a compound, wherein the compound is selected from at least one of:
   3-[2-(3,4-dichloro-phenyl)-6-trifluoromethyl-4,5,6,7-tetrahydro-indol-1-yl]-benzoic acid;
   3-(6-ethyl-2-phenyl-4,5,6,7-tetrahydroindol-1-yl) benzoic acid;
   3-(2-phenyl-5-trifluoromethyl-4,5,6,7-tetrahydroindol-1-yl) benzoic acid;
   N-methyl-3-(5-methyl-2-phenyl-4,5,6,7-tetrahydroindol-1-yl) benzamide;
   5-[5-(1,1-dimethyl-propyl)-2-phenyl-4,5,6,7-tetrahydro-indol-1-yl]-furan-2-carboxylic acid;
   5-[2-(3,4-dichloro-phenyl)-5-trifluoromethyl-4,5,6,7-tetrahydro-indol-1-yl]-furan-2-carboxylic acid;
   {2-[5-(1,1-dimethylpropyl)-2-phenyl-4,5,6,7-tetrahydroindol-1-yl]-thiazol-4-yl}acetic acid;
   6-(2-phenyl-4,5,6,7-tetrahydro-1H-indol-1-yl) picolinic acid;
   4-(2-phenyl-4,5,6,7-tetrahydro-1H-indol-1-yl) picolinic acid;
   5-(2-phenyl-4,5,6,7-tetrahydro-1H-indol-1-yl) nicotinic acid;
   2-(2-phenyl-4,5,6,7-tetrahydro-1H-indol-1-yl) isonicotinic acid;
   4-(2-phenyl-4,5,6,7-tetrahydro-1H-indol-1-yl) nicotinic acid;
   2-(2-phenyl-4,5,6,7-tetrahydro-1H-indol-1-yl) pyrimidine-4-carboxylic acid;
   5-(2-phenyl-4,5,6,7-tetrahydro-1H-indol-1-yl)-1H-pyrrole-2-carboxylic acid;
   4-(2-phenyl-4,5,6,7-tetrahydro-1H-indol-1-yl) furan-2-carboxylic acid;
   5-(5-tert-butyl-2-phenyl-4,5,6,7-tetrahydroindol-1-yl) furan-2-carboxylic acid methyl ester;
   5-(5-tert-butyl-2-phenyl-4,5,6,7-tetrahydroindol-1-yl) furan-2-carboxylic acid;
   5-(2-phenyl-5-trifluoromethyl-4,5,6,7-tetrahydroindol-1-yl)-furan-2-carboxylic acid;
   5-[2-(4-morpholin-4-yl-phenyl)-5-trifluoromethyl-4,5,6,7-tetrahydroindol-1-yl]-furan-2-carboxylic acid;
   5-[2-(3,4-dichlorophenyl)-5-trifluoromethyl-4,5,6,7-tetrahydroindol-1-yl]-furan-2-carboxylic acid;
   5-(5-cyclohexyl-2-phenyl-4,5,6,7-tetrahydroindol-1-yl)-furan-2-carboxylic acid;
   5-(2-benzofuran-2-yl-6-trifluoromethyl-4,5,6,7-tetrahydroindol-1-yl)-furan-2-carboxylic acid;
   5-(2-phenyl-6-trifluoromethyl-4,5,6,7-tetrahydroindol-1-yl)-furan-2-carboxylic acid;
   5-(2-benzofuran-2-yl-5-trifluoromethyl-4,5,6,7-tetrahydroindol-1-yl)-furan-2-carboxylic acid;
   5-[2-benzofuran-2-yl-5-(1,1-dimethylpropyl)-4,5,6,7-tetrahydroindol-1-yl]-furan-2-carboxylic acid;
   5-(6-methyl-2-phenyl-4,5,6,7-tetrahydroindol-1-yl) furan-2-carboxylic acid;

5-[5-tert-butyl-2-(3,4-dichlorophenyl)-4,5,6,7-tetrahydroindol-1-yl]furan-2-carboxylic acid;

5-[5-tert-butyl-2-(4-trifluoromethylphenyl)-4,5,6,7-tetrahydroindol-1-yl]furan-2-carboxylic acid;

5-(5-methyl-2-phenyl-4,5,6,7-tetrahydroindol-1-yl)furan-2-carboxylic acid;

2-(5-methyl-2-phenyl-4,5,6,7-tetrahydroindol-1-yl) thiazole-4-carboxylic acid;

5-[2-(3,4-dichlorophenyl)-4-trifluoromethyl-4,5,6,7-tetrahydroindol-1-yl]-furan-2-carboxylic acid;

5-[2-(3,4-dichlorophenyl)-6-trifluoromethyl-4,5,6,7-tetrahydroindol-1-yl]-furan-2-carboxylic acid;

5-tert-butyl-2-phenyl-1-(4H-[1,2,4]triazol-3-yl)-4,5,6,7-tetrahydro-1H-indole;

5-(5-tert-butyl-2-phenyl-4,5,6,7-tetrahydroindol-1-yl)furan-2-carboxylic acid methyl ester;

5-(5-tert-butyl-2-phenyl-4,5,6,7-tetrahydroindol-1-yl)furan-2-carboxylic acid;

2-[2-(2,4-dimethoxyphenyl)-5-trifluoromethyl-4,5,6,7-tetrahydroindol-1-yl]-thiazole-4-carboxylic acid;

2-[2-(3,4-dimethoxyphenyl)-5-trifluoromethyl-4,5,6,7-tetrahydroindol-1-yl]-thiazole-4-carboxylic acid;

{2-[2-(3-chlorophenyl)-5-(1,1-dimethylpropyl)-4,5,6,7-tetrahydroindol-1-yl]-thiazol-4-yl} acetic acid;

and pharmaceutically-acceptable salts of any of the foregoing, and wherein the disease or disorder is selected from at least one of spinal muscular atrophy, Charcot-Marie-Tooth Type 2 disease, hereditary spastic paraplegia, amyotrophic lateral sclerosis, Huntington's disease, Parkinson's disease, spinocerebellar ataxia 3, spinocerebellar ataxia 6, spinocerebellar ataxia 5, spinobulbar muscular atrophy, dystonia musculorum, frontotemporal dementia with parkinsonism linked to chromosome 17, multiple sclerosis, frontotemporal lobar degeneration/frontotemporal dementia, spinal cord injury, or Alzheimer's disease.

* * * * *